United States Patent
Appaiah et al.

(10) Patent No.: US 11,236,314 B2
(45) Date of Patent: Feb. 1, 2022

(54) CHIMERIC LYSM POLYPEPTIDES

(71) Applicant: GangaGen, Inc., Newark, CA (US)

(72) Inventors: Chemira B. Appaiah, Bengaluru (IN); Vivek Daniel Paul, Bengaluru (IN); Rajagopalan Sanjeev Saravanan, Bengaluru (IN)

(73) Assignee: Bactoclear Holdings PTE. Ltd, Singapore (SG)

( * ) Notice: Subject to any disclaimer, the term of this patent is extended or adjusted under 35 U.S.C. 154(b) by 20 days.

(21) Appl. No.: 15/940,578

(22) Filed: Mar. 29, 2018

(65) Prior Publication Data

US 2020/0017843 A1  Jan. 16, 2020

Related U.S. Application Data

(60) Provisional application No. 62/479,028, filed on Mar. 30, 2017.

(51) Int. Cl.
| | |
|---|---|
| *A61K 38/00* | (2006.01) |
| *C12N 9/36* | (2006.01) |
| *C07K 19/00* | (2006.01) |
| *C12N 15/74* | (2006.01) |

(52) U.S. Cl.
CPC ............ *C12N 9/2462* (2013.01); *C07K 19/00* (2013.01); *C12N 15/74* (2013.01); *C12Y 302/01017* (2013.01)

(58) Field of Classification Search
None
See application file for complete search history.

(56) References Cited

U.S. PATENT DOCUMENTS 9,622,486 B2 * 4/2017 Padmanabhan ...... C12N 9/2462

OTHER PUBLICATIONS

Garvey, Nucleic Acids Res. 14, 10001-10008, 1986 (Year: 1986).*
Saedi, Proc. Natl. Acad. Sci. USA, vol. 84, pp. 955-958, Feb. 1987 (Year: 1987).*
Saedi, STN search note citatioon, 3 pages, Jun. 10, 2020 (Year: 2020).*
Schumann, Science 249 (4975), 1429-1431, 1990 (Year: 1990).*
Buist, et al. "LysM, a widely distributed protein motif for binding to (peptido) glycans." Molecular microbiology 68, No. 4 (2008): 838-847.
Hu, et al. "Characterization of a novel LysM domain from Lactobacillus fermentum bacteriophage endolysin and its use as an anchor to display heterologous proteins on the surfaces of lactic acid bacteria." Applied and environmental microbiology 76, No. 8 (2010): 2410-2418.
Mesnage, et al. "Molecular basis for bacterial peptidoglycan recognition by LysM domains." Nature communications 5 (2014): 4269.
Wong, et al. "An intermolecular binding mechanism involving multiple LysM domains mediates carbohydrate recognition by an endopeptidase." Acta Crystallographica Section D: Biological Crystallography 71, No. 3 (2015): 592-605.
Altschul et al. Basic local alignment search tool. Journal of molecular biology. Oct. 5, 1990;215(3):403-10.
Baba et al. Targeting of muralytic enzymes to the cell division site of Gram-positive bacteria: repeat domains direct autolysin to the equatorial surface ring of *Staphylococcus aureus*. The EMBO journal. Aug. 17, 1998;17(16):4639-46.
Loessner, Bacteriophage endolysins—current state of research and applications. Current opinion in microbiology. Aug. 1, 2005;8(4):480-7.
Piuri et al. A peptidoglycan hydrolase motif within the mycobacteriophage TM4 tape measure protein promotes efficient infection of stationary phase cells. Molecular microbiology. Dec. 2006;62(6):1569-85.
Salazar et al. Enzymatic lysis of microbial cells. Biotechnology letters. Jul. 1, 2007;29(7):985-94.
Vollmer et al. Peptidoglycan structure and architecture. FEMS microbiology reviews. Mar. 1, 2008;32(2):149-67.

* cited by examiner

*Primary Examiner* — Satyanarayana R Gudibande
(74) *Attorney, Agent, or Firm* — Kilpatrick Townsend & Stockton LLP

(57) ABSTRACT

Provided herein are antibacterial compositions and methods of making and using the compositions.

20 Claims, 35 Drawing Sheets

Specification includes a Sequence Listing.

| Bactericidal activity of P617 on A. baumannii in LB with and without L-Arginine | | | | |
|---|---|---|---|---|
| Samples | P617 (pH 4.0) | Log kill | P617 (pH 7.0) | Log kill |
| Cell control- 0 hr | 6.0E+05 | 0 | 6.0E+05 | 0 |
| Cell control- 2hr | 2.0E+06 | 0 | 2.0E+07 | 0 |
| Cell control + L-Arg - 2hr | 1.0E+06 | 0 | 1.0E+06 | 0 |
| P617-100 µg/ml | 8.0E+03 | 2 logs | 1.0E+04 | 1.5 log |
| P617-100 µg/ml + L-Arg | 1.0E+01 | 4.5 logs | 1.0E+01 | 4.5 logs |
| P617-200 µg/ml | 1.0E+03 | 2.5 log | 2.0E+03 | 2.5 logs |
| P617-200 µg/ml + L-Arg | 1.0E+01 | 4.5 logs | 1.0E+01 | 4.5 logs |

| Bactericidal activity of P617 on P. aeruginosa in LB with and without L-Arginine | | | | |
|---|---|---|---|---|
| Samples | P617 (pH 4.0) | Log kill | P617 (pH 7.0) | Log kill |
| Cell control- 0 hr | 3.0E+05 | 0 | 6.0E+05 | 0 |
| Cell control- 2hr | 5.0E+05 | 0 | 1.0E+06 | 0 |
| Cell control + L-Arg - 2hr | 4.0E+05 | 0 | 3.0E+05 | 0 |
| P617-100 µg/ml | 2.0E+05 | 0 | 2.0E+04 | 1 log |
| P617-100 µg/ml + L-Arg | 1.0E+02 | 3 logs | 1.0E+02 | 3 logs |
| P617-200 µg/ml | 2.0E+03 | 2 logs | 3.0E+03 | 2 logs |
| P617-200 µg/ml + L-Arg | 8.0E+01 | 3.5 logs | 1.0E+01 | 4 logs |

| Bactericidal activity of P617 on *A. baumannii* in IF with and without L-Arginine ||| 
|---|---|---|
| Samples | P617 (pH 4.0) | Log kill |
| Cell control- 0 hr | 9.0E+05 | 0 |
| Cell control- 2hr | 1.0E+07 | 0 |
| Cell control + L-Arg - 2hr | 1.0E+07 | 0 |
| P617- 50 µg/ml | 1.0E+06 | 0 |
| P617- 50 µg/ml + L-Arg | 2.0E+06 | 0 |
| P617-100 µg/ml | 2.0E+04 | 2 logs |
| P617-100 µg/ml + L-Arg | 1.0E+01 | 5 logs |
| P617-200 µg/ml | 2.0E+03 | 1.5 log |
| P617-200 µg/ml + L-Arg | 1.0E+01 | 5 logs |

| Dose ranging activity of P601 on *A. baumannii* in FCS | | | | |
|---|---|---|---|---|
| Samples | FCS | Log kill | LB broth | Log kill |
| Cell control | 4.30E+06 | 0 | 4.60E+06 | 0 |
| P601-100 µg/ml | 3.50E+06 | 0 | 1.10E+06 | 0 |
| P601-200 µg/ml | 5.54E+05 | 1 log | 2.00E+01 | 5 logs |
| P601-400 µg/ml | 1.51E+03 | 3 logs | 2.00E+01 | 5 logs |

Bactericidal activity of P617 on P. aeruginosa PA01

| Samples | Cell control | P617 (pH 4.0) | Log kill | P617 (pH7.0) | Log kill | P601 (pH 4.0) | Log kill |
|---|---|---|---|---|---|---|---|
| HEPES | 8.0E+06 | 1.0E+01 | 5 logs | 1.0E+01 | 5 logs | 1.0E+02 | 5 logs |
| HEPES + 150mM NaCl | 8.0E+06 | 7.0E+02 | 4 logs | 1.0E+01 | 5 logs | 3.0E+03 | 3.5 logs |

| Bactericidal activity of P617 on A. baumannii in IF with and without L-Arginine ||| 
| Samples | P617 (pH 4.0) | Log kill |
| --- | --- | --- |
| Cell control- 0 hr | 9.0E+05 | 0 |
| Cell control- 2hr | 1.0E+07 | 0 |
| Cell control + L-Arg - 2hr | 1.0E+07 | 0 |
| P617- 50 µg/ml | 1.0E+06 | 0 |
| P617- 50 µg/ml + L-Arg | 2.0E+06 | 0 |
| P617-100 µg/ml | 2.0E+04 | 2 logs |
| P617-100 µg/ml + L-Arg | 1.0E+01 | 5 logs |
| P617-200 µg/ml | 2.0E+03 | 1.5 log |
| P617-200 µg/ml + L-Arg | 1.0E+01 | 5 logs |

| CFU reduction assay of P663 on *A. baumannii* | | | | | | | |
|---|---|---|---|---|---|---|---|
| *A. baumannii* (MHB) | Cell control (0 hr) | Cell control (2 hrs) | P663 100 µg/ml Cell control | P663 100 µg/ml | Log cell killing | P663 200 µg/ml Cell control | P663 200 µg/ml | Log cell killing |
| P663 | 3.20E+06 | 3.80E+07 | 1.10E+07 | 3.40E+05 | 3 | 1.12E+06 | 2.00E+01 | 5 |

| Dose ranging activity of P630 | | | |
|---|---|---|---|
| Cell control- 0 hr | 2.20E+06 | - | 2.20E+06 | - |
| Cell control- 2hr | 5.80E+06 | - | 1.23E+08 | - |
| P630-50 µg/ml | 1.90E+08 | 0 | 1.04E+08 | 0 |
| P630-100 µg/ml | 5.60E+06 | 0 | 1.44E+07 | 0 |
| P630-200 µg/ml | 4.00E+01 | 5 | 1.20E+02 | 5 |

US 11,236,314 B2

CHIMERIC LYSM POLYPEPTIDES

CROSS-REFERENCES TO RELATED APPLICATIONS

This application claims the benefit of U.S. Provisional Application No. 62/479,028, filed Mar. 30, 2017, the entire contents of which is incorporated herein by reference.

SEQUENCE LISTING

The instant application contains a Sequence Listing which has been submitted electronically in ASCII format and is hereby incorporated by reference in its entirety. Said ASCII copy, created on Jun. 12, 2019, is named 088675-1083091-002310US_SL.txt and is 95,571 bytes in size.

FIELD OF INVENTION

The present invention provides methods and compositions to reduce growth of microbial colonies, including infections, and includes therapeutic compositions, methods for treatment of infections, and methods for identifying additional such compositions.

BACKGROUND OF THE INVENTION

Bacteria are ubiquitous, ecologically diverse, and find unusual niches for survival. They are present throughout the environment, e.g., soil, dust, water, and on virtually all surfaces.

Pathogenic bacteria can cause infectious diseases in humans, other animals, and plants. Some bacteria can only infect or cause problems for a particular host, while others have a broader host specificity, and can cause trouble in a number of hosts. Diseases caused by bacteria are almost as diverse as the bacteria themselves, e.g., food poisoning, tooth decay, anthrax, general infectious diseases, and even certain forms of cancer.

Certain bacteria are normally innocuous, but become pathogenic at the appropriate opportunity, or become problematic upon introduction to an abnormal site or situation. Persons lacking effective immune systems are most vulnerable, and certain bacteria use weakened hosts to proliferate and disperse throughout the population.

Antibiotics have revolutionized clinical medicine over the last half century. Since the original discovery of antibiotic phenomenon, the mechanism of action and development of this class of remarkable therapeutic entities has made enormous progress. See, e.g., Therrien and Levesque (2000) *FEMS Microbiol Rev.* 24:251-62; (Burgess) Durgess (1999) *Chest* 115(3 Suppl):19S-23S; Medeiros (1997) *Clin. Infect. Dis.* 24(Suppl 1):S19-45; Jones (1996) *Am. J. Med.* 100 (6A):3S-12S; Ford and Hait (1993) *Cytotechnology* 12(1-3):171-212; and Liu (1992) *Compr. Ther.* 18:35-42. Antibiotics had about $32B worldwide sales in 2002.

Yet the widespread appearance of antibiotic-resistant bacteria has emphasized the vulnerability of current antimicrobial treatments to bacterial adaptation. See, e.g., Walsh (1992) *Antibiotics: Actions, Origins, Resistance* Amer. Soc. Microbiol.; Cunha (1992) *Antibiotic Essentials* (Physicians Press); Amyes (2003) *Magic Bullets, Lost Horizons: The rise and Fall of Antibiotics* (Taylor & Francis); Axelsen (2001) *Essentials of Antimicrobial Pharmacology: A Guide to Fundamentals for Practice* (Humana Press); and Mainous and Pomeroy (eds. 2001) *Management of Antimicrobials in Infectious Diseases: Impact of Antibiotic Resistance* (Humana Press). Multiple resistance plasmid NDM-1 has been reported (Kumarasamy, et al. (2010) *Lancet Infectious Diseases* 10:597-602; and Walsh, et al. (2011) *Lancet Infectious Diseases*, Early Online Publication, 7 Apr. 2011, doi: 10.1016/S1473-3099(11)70059-7).

Thus, improved methods for decreasing bacterial growth and survival, or limiting bacterial pathogenicity find great utility, especially for antibiotic resistant bacteria, which are most commonly Gram-negative. Antimicrobial effects are applicable to environmental, local, topical, and particularly in vivo colonization. The present invention addresses these and other significant issues.

BRIEF DESCRIPTION OF THE DRAWINGS

FIG. 17B shows cells treated with P340 appeared to be bacterial ghosts that contained intact bacterial envelope, devoid of cytoplasmic contents.

BRIEF SUMMARY OF THE INVENTION

Figure 1:
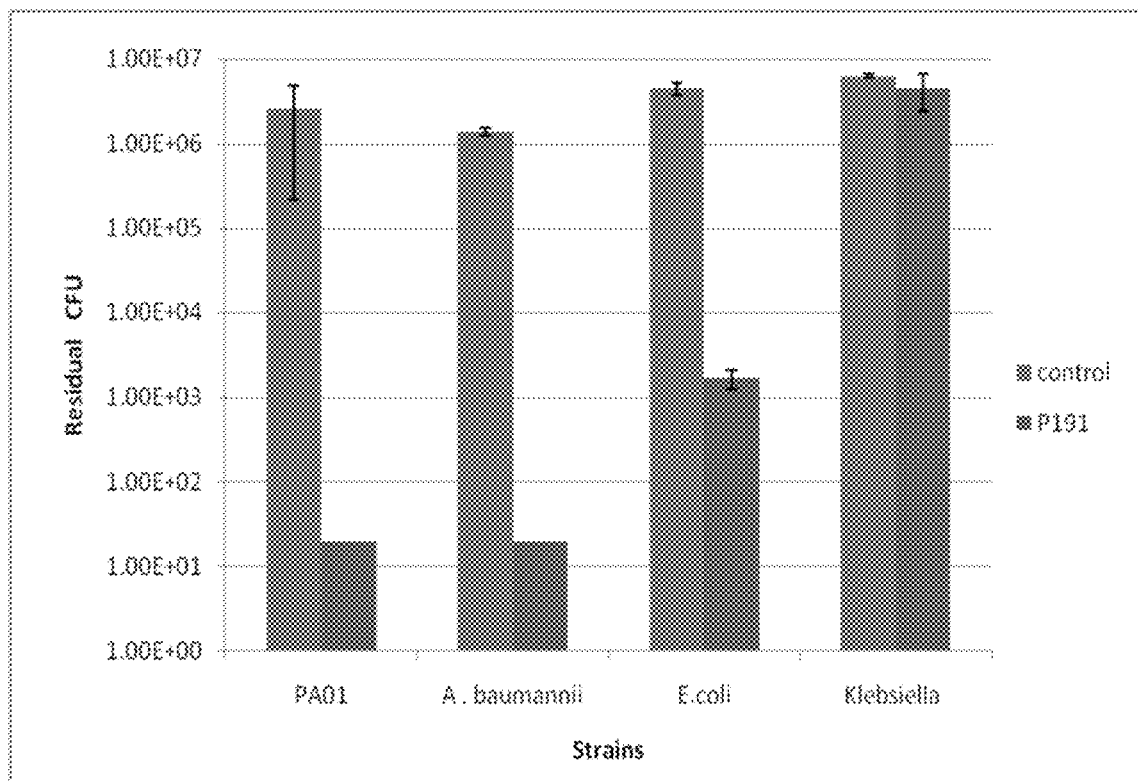
FIG. 1 shows killing of bacteria by a construct of the invention.

Provided herein are antibacterial chimeric polypeptides comprising a component for traversing the outer membrane of a Gram-negative bacteria (i.e., a membrane traversing segment, e.g., the LysM segment), as described. The invention is based, in part, upon the discovery that the LysM segment (derived from the Phi29 endolysin) has, by itself, cell binding and cell killing activity on Gram-negative bacteria. The activity was localized to a partial segment, and could be enhanced by the attachment of additional heterologous segments. The LysM appears to be able to assist attached segments to access the periplasmic space from outside the outer membrane, i.e., to help such segment to penetrate or traverse the outer membrane. The heterologous segments included, e.g., muralytic segments (acting on the peptidoglycan layer found in the periplasmic space), other peptide motifs such as Lipopolysaccharide Binding Proteins (LBP) and WLBU2 peptide (an AMP), and others. Besides the bactericidal activity of the LysM peptide segment, the capability of targeting the peptide to the cell and accessing the periplasmic space has valuable utility.

Various proteins have demonstrated activity on a variety of Gram-negative bacteria, including various drug-resistant *Escherichia*, *Pseudomonas*, *Acinetobacter*, and *Klebsiella* isolates.

Provided are chimeric polypeptides comprising these LysM segments. In some embodiments, the chimeric polypeptide reduces CFU of a culture of Gram-negative bacteria compared to an untreated control culture. In some embodiments, 1-100 nmol of the chimeric polypeptide lyses at least 50% of $10^7$ Gram-negative bacteria in a CFU drop assay. In some embodiments, the bacteria are selected from the group consisting of *Pseudomonas aeruginosa*, *Klebsiella pneumoniae*, *Escherichia coli*, *Acinetobacter baumannii*, *Salmonella typhimurium*, *Salmonella infantis*, *Shigella*, *Proteus mirabilis*, and *Burkholderia thailandensis*.

In one embodiment, the invention provides a chimeric polypeptide, the polypeptide decreases the rate of growth of a Gram-negative bacteria, comprising: (i) a LysM polypeptide segment exhibiting at least about 70% identity to SEQ ID NO: 2; and (ii) a heterologous polypeptide sequence exhibiting at least about 10% lower identity to the LysM polypeptide segment. In various forms, e.g., the decreasing rate of growth is essentially no growth; or the decreasing rate of growth also results in decrease in population of the Gram-negative bacteria; or the heterologous polypeptide comprises sequence derived from a polypeptide from a different organism from the LysM polypeptide; or the Gram-negative bacteria is from a genus selected from *Klebsiella*, *Acinetobacter*, *Pseudomas*, or *Escherichia*. In certain preferred versions of the invention, the at least about 70% identity to SEQ ID NO: 2 is at least about 80% and the heterologous polypeptide sequence exhibiting less than about 70% identity to the LysM polypeptide segment; or the at least about 70% identity to SEQ ID NO: 2 is at least about 90%, and the heterologous polypeptide sequence exhibiting less than about 80% identity to the LysM polypeptide segment. In other versions, the heterologous polypeptide sequence is derived from: (a) a phage endolysin; (b) a phage structure associated muralytic enzyme (ectolysin); (c) a lipopolysachharide binding protein (LBP); (d) an AntiMicrobial Peptide (AMP); or (e) a bactericidal permeability increasing protein (BPI); and may comprise 6×His (SEQ ID NO: 9) or a segment from one or more of: GP36CD, phi29 endolysin, BPI TMD, LBP, WLBU2, phiKZ GP144, phiKZ GP181 lysozyme, phi6 P5, BP7 lysozyme, or SUSHI peptide.

In other preferred embodiments, the invention will comprise a composition with the chimeric polypeptide and a pharmaceutically acceptable excipient, carrier, or buffer; or with another pharmaceutical composition or antimicrobial agent. The invention also provides an isolated cell comprising the protein, or an isolated nucleic acid encoding the protein, or an isolated cell comprising the nucleic acid encoding the protein.

Further provided are methods, e.g., of reducing the growth rate of a susceptible target Gram-negative bacteria, the method comprising contacting the bacteria with the chimeric polypeptide. This will often further accomplish reducing the population of a susceptible target Gram-negative bacteria.

The invention alternatively provides a chimeric polypeptide, the polypeptide accesses the periplasmic space of a Gram-negative bacterium from outside of the cell, comprising:(i) a LysM polypeptide segment exhibiting at least about 70% identity to SEQ ID NO: 2; and (ii) a heterologous polypeptide sequence exhibiting at least about 10% lower identity to the LysM polypeptide segment. Similarly, in various embodiments, at least some portion of the polypeptide accesses the periplasmic space of the Gram-negative bacteria, and the access of the polypeptide will often result in a decrease in rate of growth of the bacteria; or the decrease in rate of growth of the bacteria results in decrease in population of the Gram-negative bacteria. In preferred versions, the heterologous polypeptide comprises sequence derived from a polypeptide from a different organism from the LysM polypeptide; or the Gram-negative bacteria is from a genus selected from *Klebsiella*, *Acinetobacter*, *Pseudomonas*, or *Escherichia*. In preferred embodiments, the at least about 70% identity to the LysM polypeptide segment is at least about 80%, and the heterologous polypeptide sequence exhibits less than about 70% identity to that setment; or the at least about 70% identity to the LysM polypeptide segment is at least about 90%, and the heterologous polypeptide sequence exhibits less than about 80% identity to the LysM polypeptide segment. In certain versions, the heterologous polypeptide sequence is derived from: (a) a phage endolysin; (b) a phage structure associated muralytic enzyme (ectolysin); (c) a lipopolysachharide binding protein (LBP); (d) an AntiMicrobial Peptide (AMP); or (e) a bactericidal permeability increasing protein (BPI); and in preferred versions, the heterologous polypeptide sequence comprises 6×His (SEQ ID NO: 9) or a segment from one or more of: GP36CD, phi29 endolysin, BPI TMD, LBP, WLBU2, phiKZ GP144, phiKZ GP181 lysozyme, phi6 P5, BP7 lysozyme, or SUSHI peptide.

The inventions provide compositions comprising the chimeric polypeptide with a pharmaceutically acceptable excipient, carrier, or buffer; or with another pharmaceutical composition or antimicrobial agent. Also provided are cells comprising the chimeric polypeptide, and various nucleic acids encoding the chimeric polypeptides. Cells comprising these nucleic acids are also provided.

Methods are provided, e.g., of reducing the growth rate of a susceptible target Gram-negative bacteria, by contacting the bacteria with the chimeric polypeptides. The reduction of growth rate may further accomplish reducing the population of a susceptible target Gram-negative bacteria.

DETAILED DESCRIPTION OF THE INVENTION

I. Introduction

The outer membrane of a Gram-negative bacterium is a lipopolysaccharide bilayer which serves as one of various permeability barriers which separate the outside of the cell from the inside of the bacterial cell. Another of the permeability barriers include the peptidoglycan (murein) sacculus, which is a structural component of the cell wall of most bacteria. Made of glycan strands cross-linked by short peptides, the sacculus forms a closed, bag-shaped structure surrounding the bacterial cytoplasmic membrane. The sacculus must withstand up to 25 atmospheres of osmotic pressure. The sacculus is flexible, allowing reversible expansion under pressure, which allows diffusion of even large protein molecules. See, e.g., Silhavy, et al. (2010) *CSH Persp. Biol.*, 2:a000414; Vollmer, et al. (2008) *FEMS Microbiol. Revs* 32:149-167; Bos, et al. (2007) *Ann. Rev. Microbial.* 61:191-214; and Costerton, et al. (1974) *Bact. Revs.* 38:87-110.

Many antibiotics act on the peptidoglycan layer of a target bacterial species. This structure is thus a critical component in the survival of a bacterial target. Attack of the peptidoglycan is a rational strategy for killing target bacterial hosts. Although the peptidoglycan layer is typically about 1-3 layers thick, the outer membrane serves as a permeability barrier that prevents externally applied muralytic enzymes from reaching their substrate.

However, the outer membrane is a critical structural component which distinguishes the Gram-negative group of bacteria from the Gram-positive group. The Gram-positive group tend to have a more accessible peptidoglycan layer which is more accessible to staining with the Gram stain, while the Gram-negative bacteria do not tend to stain as readily because the outer membrane prevents accessibility of the peptidoglycan layer to the stain. In addition, the outer membrane of Gram-negative bacteria further provides an additional barrier which makes the periplasmic space a more effective barrier to access of molecules to the cell membrane from outside the outer membrane.

The present invention is directed to various chimeric proteins comprising various LysM segments which function to access more readily the periplasmic space of a Gram-negative bacteria from outside the outer membrane to the periplasmic space. This accessibility may be due to either some portion of the polypeptide traversing the outer membrane, while other portions of the polypeptide may remain associated with the outer membrane lipid bilayer, or the entire protein may traverse the outer membrane bilayer and pass from outside to inside. In the latter case, other components or domains of the polypeptide may be selected which might act in the periplasmic space to affect the physiology of the Gram-negative bacterium.

Thus, in certain embodiments, a muralytic or other function is linked to the LysM outer membrane permeability function to achieve a new entity. The LysM segment allows the segment with muralytic activity to be transferred across the bacterial outer membrane, i.e., moving the muralytic activity from outside of the bacterial outer membrane to the inside, and allowing contact between the enzyme and its peptidoglycan substrate. In some embodiments, the LysM traversing segment might direct the chimeric polypeptide to the outer leaflet of the outer membrane, and the polypeptide flips from the outer leaflet of the outer membrane to the inner leaflet, thereby delivering the other functional segment to the periplasmic space. In other embodiments, the polypeptide might become soluble in the periplasmic space, e.g., due to different solubility factors therein. The chimeric (and linked) constructs described herein combine a peptidoglycan degrading enzyme activity with the LysM segment providing the membrane traversing function. Other functions may include, e.g., AntiMicrobial Peptide (AMP) segments transferred into the periplasmic space, or Lipopolysaccharide (LPS) Binding Proteins, or Bactericidal Permeability Increasing Protein (BPI), among others.

II. Murein-Degrading Enzymes; Lysozymes and Lysins

The present application incorporates by reference Appaiah, et al. (2013) Chimeric Antibacterial Polypeptides U.S. Ser. No. 14/111,531 filed Oct. 11, 2013, which describes various murein degrading domains of relevance to the present invention and various methodologies useful in screening and assaying effects of chimeric constructs on bacteria.

Muralytic domains (also called catalytic domains herein) include, e.g., lysozyme proteins (Salazar and Asenjo (2007) *Biotechnol. Lett.* 29:985-94). Breakdown of the peptidoglycan structure occurs naturally in at least four contexts. One is biosynthesis of the structure; as the bacterial cell grows and divides, it must necessarily must break down the structure. See, e.g., Vollmer (2008) *FEMS Microbiol Rev.* 32:287-306; Scheurwater, et al. (2008) *Int. J. Biochem. Cell Biol.* 40:586-91; Keep, et al. (2006) *Trends Microbiol.* 14:271-276, and Baba and Schneewind (1998) *EMBO J.* 117:4639-4646. There are additional situations when the cell itself must rearrange or modify structure which was synthesized earlier. These activities can be derived from the bacteria themselves. Second, eukaryotic hosts degrade the structure upon clearing of an infection, e.g., using mutanolysin or lysozymes. See, e.g., Callewaert and Michiels (2010) *J. Biosci.* 35:127-60; Harder, et al. (2007) *Endocr. Metab. Immune Disord. Drug Targets* 7:75-82; and Lichtman, et al. (1992) *J. Clin. Invest.* 90:1313-1322. These activities will typically be derived from eukaryote hosts in or on which the bacteria live or can colonize. A third area is in phage replication, where the phage typically employs an endolysin to release the replicated phages and lyse the bacterial host cell. See, e.g., Srividhya and Krishnaswamy (2007) *J. Biosci.* 32:979-90; and Loessner (2005) *Curr. Opin. Microbiol.* 8:480-487. These activities will typically be found in the bacteriophage genome. This is a lysis of the peptidoglycan layer of cells from within. A fourth context is where phage infection requires that the peptidoglycan barrier be traversed, as described in Padmanabhan, et al. WO2007/130655. This is degradation of the peptidoglycan layer from the exterior of the cell. These activities will be found as a component of the phage virion, and will typically be encoded in the phage genome.

Each of these mechanisms involves some means to disassemble the peptidoglycan structure. Thus, muralytic activities are found in genomes of eukaryotic hosts for bacteria, in bacterial genomes themselves, and in phage (and related prophages) which target bacteria as hosts. Muralytic domains can be found by homology to any of these sources, and informatics can be used to identify candidate genes with their respective canonical motifs.

Peptidoglycan "degrading activities" can be converted into highly effective bactericidal activities for use against Gram-negative bacterial pathogens under therapeutic conditions, and can include muraminidase, glucosaminidase, amidase, or endopeptidase activities. Exemplary muralytic domains can be identified, incorporated into chimeric constructs to be delivered to the peptidoglycan substrate, produced, purified, and confirmed to have bactericidal activity against bacterial hosts with an outer membrane. Recombinant constructs comprising such activities have significant advantageous properties as antimicrobial compositions and formulations. Many of the peptidoglycan degrading activities of the invention are directed to Gram-negative bacteria, or bacteria which possess an outer membrane, but others will have target specificity which may include either or both Gram-negative and Gram-positive bacteria. The peptidoglycan structures of the two types of bacteria share certain linkages and structures, which may be susceptible to a selected muralytic activity. Thus, muralytic domains which can hydrolyze shared linkages may have broader target range than those which do not.

An example of the linked polypeptides of the invention uses a fragment comprising a lysozyme domain from *Pseudomonas* phage P134, which is closely related to phage phiKMV. The ORF36 in phage P134 that corresponds to that in phiKMV lyses Gram-negative bacterial cells whose outer membrane has been removed. Contacting the construct to a variety of different Gram-negative bacteria after the outer membrane was removed resulted in the cells being broken down. These results demonstrate that the peptidoglycans from different Gram-negative bacteria species are susceptible to the muralytic activity. See also Appaiah, et al. (2013) Chimeric Antibacterial Polypeptides U.S. Ser. No. 14/111,521, which is incorporated herein by reference.

Sequence homology searches identify various other similar domains which can be used as alternative sources for peptidoglycan degrading activities. The small size of the polypeptides exhibiting these activities affords efficient large scale production. Accessibility to relevant cell wall target components, e.g., peptidoglycans, at the bacterial target is provided, as are pharmacological distribution upon in vivo administration.

Relevant muralytic activities can be found within the lysozyme-like superfamily, lytic transglycosylase (LT), goose egg white lysozyme (GEWL); the Superfamily Cl00442 containing Lysozyme like domain, which contains several members including the Soluble Lytic Transglycosylases (SLT), Goose Egg-White Lysozymes (GEWL), Hen Egg-White Lysozymes (HEWL), Chitinases, Bacteriophage lambda lysozymes, Endolysins, Autolysins, Chitosanases. All these members are involved in the hydrolysis of beta-1,4-linked polysaccharides. The Cysteine Histidine dependent Amidohydrolase/Peptidase (CHAP) domain is found in phage endolysins and bacterial autolysins. Most proteins containing a CHAP domain function as peptidoglycan hydrolases and are commonly associated with amidases. See Bateman and Rawlings (2003) *Trends Biochem. Sci.* 5:234-237; and Pritchard, et al. (2004) *Microbiology* 150:2079-2087. See also the Carbohydrate-Active enzymes Database found at cazy.org. The CAZY database describes the families of structurally related catalytic and carbohydrate-binding modules (or functional domains) of enzymes that degrade, modify, or create glycosidic bonds. Another source for endopeptidases is the database from the website found at merops.sanger.ac.uk/cgi-bin/clan_index?type=P. Table A provides an exemplary list of enzymes having peptidoglycan degrading activities that can be used in the present invention. Additional similar or analogous activities may be found which are similarly annotated, share characteristic motifs with, or are homologous to members of the list. Likewise, Table B provides a list of exemplary AntiMicrobial Peptides (AMPseXAMPLES) which may be used in the present invention, along with similar or analogous activities, including homologs to segments on the list.

TABLE A

Muralytic Domain (MD) sources

| Description | Details |
|---|---|
| Phage lysozyme | Lysozyme helps to release mature phage particles from the cell wall by breaking down the peptidoglycan. The enzyme hydrolyses the 1,4-beta linkages between N-acetyl-D-glucosamine and N-acetylmuramic acid in peptidoglycan heteropolymers of prokaryotic cell walls. |
| C-type lysozyme/alpha-lactalbumin family | C-type lysozymes are secreted bacteriolytic enzymes that cleave the peptidoglycan of bacterial cell walls. Structure is a multi-domain, mixed alpha and beta fold, containing four conserved disulfide bonds. |
| Gene 25-like lysozyme | This family includes the phage protein Gene 25 from T4 which is a structural component of the outer wedge of the baseplate that has acidic lysozyme activity |
| A1 propeptide | Most eukaryotic endopeptidases (Merops Family A1) are synthesized with signal and propeptides. The animal pepsin-like endopeptidase propeptides form a distinct family of propeptides, which contain a conserved motif approximately 30 residues long. |
| Prophage endopeptidase tail | This family is of prophage tail proteins that are probably acting as endopeptidases. (e.g.: prophage tail protein gp18 (NP_465809.1) from Listeria monocytogenes |
| Reprolysin (m12b) family zinc metalloprotease | The members of this family are enzymes that cleave peptides. These proteases require zinc for catalysis. Members of this family are also known as adamalysins. Most members of this family are snake |

TABLE A-continued

Muralytic Domain (MD) sources

| Description | Details |
|---|---|
| | venom endopeptidases, but there are also some mammalian proteins such as P78325 and fertilin. |
| Mutanolysin | Muramidase derived from *Streptomyces globisporus* |
| Virion associated muralytic enzymes from phages (VAMEs) | |
| Peptidoglycan hydrolases e.g.: Mur-1 N-acetylmuramidase, Mur-2 N-acetylglucosaminidase | From *Enterococcushirae* ATCC9790 |
| Phage PhiKMV | gp36; Protein domain: Lysozyme like superfamily |
| Phage LKD16 | orf3; Protein domain: Lysozyme like superfamily |
| Phage LKD19 | gp36; Protein domain: Lysozyme like superfamily |
| Phage phikF77 | gp40; Protein domain: Lysozyme like superfamily |
| Phage PT2 | gp42; Protein domain: Lysozyme like superfamily |
| Phage PT4 | gp40; Protein domain: Lysozyme like superfamily |
| Phage 201 | gp276; Protein domain: Lytic Transglycosylase (LT) or Goose Egg White Lysozyme (GEWL) |
| Phage F8 | orf38; Protein domain: Lytic Transglycosylase (LT) or Goose Egg White Lysozyme (GEWL) |
| Phage 14-1 | gp39; Protein domain: Lytic Transglycosylase (LT) or Goose Egg White Lysozyme (GEWL) |
| Phage LBL3 | gp36; Protein domain: Lytic Transglycosylase (LT) or Goose Egg White Lysozyme (GEWL) |
| Phage LMA2 | gp38; Protein domain: Lytic Transglycosylase (LT) or Goose Egg White Lysozyme (GEWL) |
| Phage PB1 | gp39; gp40; Protein domain: Lytic Transglycosylase (LT) or Goose Egg White Lysozyme (GEWL) |
| Phage SN | |
| Phage phiKZ | orf181; Protein domain: Lytic Transglycosylase (LT) or Goose Egg White Lysozyme (GEWL) |
| Phage phiKZ | GP144; endolysin; |
| Phage Phi29 | Lysozyme from phi29 phage endolysin |
| Phage BP7 | Lysozyme from BP7 endolysin |
| Phage Phi6 | Protein P5; putative peptidase; Lytic Transglycosylase |

TABLE B

Antimicrobial peptides (AMPs) for fusion to LysM (also homolog counterparts)

| SI no | Antimicrobial peptide | SEQ ID NO: | Amino acid Sequence | Salient features | Reference |
|---|---|---|---|---|---|
| 1 | WLBU2 | SEQ ID NO: 10 | RRWVRRVRRWV RRVVRVVRRWV RR | de novo design of modular cationic amphipathic peptides (CAPs) reported to be active in human serum | Deslouches, et al. (2005) Activity of the De Novo Engineered Antimicrobial Peptide WLBU2against *Pseudomonas aeruginosa* in Human Serum and Whole Blood: Implications for Systemic Applications Antimicrobial Agents and Chemother. 49:3208-3216 |
| 2 | Cathelicidin related antimicrobial peptide (CRAMP) | SEQ ID NO: 11 | GLLRKGGEKIGE KLKKIGQKIKNFF QKLVPQPEQ | Derived from mouse analogue of cathlelicidin antimicrobial peptide (CAP) | Mishra, et al. (2015) Evaluation of the antibacterial and antibiofilm activities of novel CRAMP-vancomycin conjugates with diverse linkers Org. Biomol. Chem. 13(27):7477-86 |
| 3 | Sushi | SEQ ID NO: 12 | HAEHKVKIGVEQ KYGQFPQGTEVT YTCSGNYFLM | Corresponds to residues 268 to 301 of the factor C Sushi 3 domain designated S3 | Li, et al. (2004) Perturbation of Lipopolysaccharide (LPS) Micelles By Sushi 3 (S3) Antimicrobial Peptide J. Biol. Chem. 279:50150-50156. |
| 4 | RI18 | SEQ ID NO: 13 | RKKTRKRLKKIG KVLKWI | Derived from Porcine myeloid antimicrobial peptide-36 (PMAP-36) | Lyu, et al. (2016) Antimicrobial activity, improved cell selectivity and mode of action of short PMAP-36-derived peptides against bacteria and *Candida* Scientific Reports, article number: 27258 |

TABLE B-continued

Antimicrobial peptides (AMPs) for fusion to LysM (also homolog counterparts)

| SI no | Antimicrobial peptide | SEQ ID NO: | Amino acid Sequence | Salient features | Reference |
|---|---|---|---|---|---|
| 5 | Cecropin-bee melittin hybrid peptide (CEME) | SEQ ID NO: 14 | KWKLFKKIGIGAV LKVLTTGLPALIS | Resistant to salt up to 300 mM | Friedrich, et al. (1999) Salt-Resistant Alpha-Helical Cationic Antimicrobial Peptides Antimicrobial Agents and Chemotherapy 43:1542-1548 |
| 6 | Synthetic peptide hLF1-11 | SEQ ID NO: 15 | GRRRRSVQWCA | Corresponds to the N-terminal eleven residues of human lactoferrin | Brouwer, et al. (2011) Discovery and development of a synthetic peptide derived from lactoferrin for clinical use Peptides 32:1953-1963. |
| 7 | Magainin | SEQ ID NO: 16 | GIGKFLHSAKKF GKAFVGEIMNS | Isolated from *Xenopus* skin, have broad spectra of antimicrobial activity and low toxicities to normal eukaryotic cells | Matsuzaki, et al. (1997) Interactions of an Antimicrobial Peptide, Magainin 2, With Outer and Inner Membranes of Gram-Negative Bacteria Biochim. Biophys. Acta 1327:119-130 |
| 8 | Omiganan | SEQ ID NO: 17 | ILRWPWWPWRR K | Isolated from the cytoplasmic granules of bovine neutrophils | Sader, et al. (2004) Omiganan Pentahydrochloride (Mbi 226), A Topical 12-Amino-Acid Cationic Peptide: Spectrum of Antimicrobial Activity and Measurements of Bactericidal Activity Antimicrob Agents Chemother. 48(8):3112 |
| 9 | Arenicin-3 | SEQ ID NO: 18 | GFCWYVCYRNG VRVCYRRCN | Isolated from the lugworm *Arenicola marina*. Exhibit potent, rapid antimicrobial activity in vitro against a broad range of multi-resistant pathogenic Gram-negative bacteria | Andra, et al. (2008) Structure and Mode of Action of the Antimicrobial Peptide Arenicin Biochem J. 410(1):113-22 |
| 10 | LBP peptide | SEQ ID NO: 19 | SDSSIRVQGRWK VRASFFKLQGSF DVSVKG | Corresponds to the N terminal region of lipopolysaccharide binding protein (LBP) that has high affinity to Lipopolysaccharide (LPS) | Taylor, et al. (1995) Lipopolysaccharides Neutralizing Peptides Reveal a Lipid A Binding Site of LPS Binding Protein J. Biol. Chem. 270:17934-17938 |
| 11 | Protamine | SEQ ID NO: 20 | PRRRRSSSRPV RRRRRPRVSRR RRRRGGRRRR | A polycationic peptide found in the nuclei of sperm of different animal species | Aspedon, et al. (1996) The Antibacterial Action of Protamine: Evidence for Disruption of Cytoplasmic Membrane Energization in *Salmonella Typhimurium* Microbiology 142:3389-3397 |
| 12 | Apidaecins | SEQ ID NO: 21 | GNNRPVYIPQPR PPHPRL | Proline-rich AMPs expressed in insects as part of the innate immune system. They are very active against Gram-negative bacteria, especially *Enterobactericeae* members | Czihal, et al. (2009) Mapping of Apidaecin Regions Relevant for Antimicrobial Activity and Bacterial Internalization Internatl J. Peptide Res. and Therapeutics 15(2):57-164 |
| 13 | Sheep myeloid antimicrobial peptide (SMAP29) | SEQ ID NO: 22 | RGLRRLGRKIAH GVKKYGPTVLRII RIAG | α-helical cathelicidin derived peptide deduced from sheep myeloid mRNA | Skerlavaj, et al. (1999) Smap-29: A Potent Antibacterial and Antifungal Peptide from Sheep Leukocytes FEBS Letters 463:58-62 |

III. LysM Outer Membrane Traversing Domain

A particular domain of critical importance here is the LysM domain derived from the phi29 endolysin. See ID YP_002004544. Phi29 endolysin is a natural fusion of a lysozyme domain with (comprising) LysM domain. Although LysM domains are reported to bind to bacterial peptidoglycan, they have not been reported to possess or exhibit Gram-negative bacterial outer membrane penetrating or traversing function. However, we found that LysM domains could bind to the outer membrane of Gram-negative bacteria. Moreover, we have observed that truncated fragments of the complete phi29 endolysin protein, in particular significantly truncated smaller fragments comprising portions of the LysM domain also bind to the OM. The truncated segments retaining this function are described further herein.

In addition, while the original phi29 endolysin sequence possesses various of these functions, other related homologous sequences have also been tested and shown to also possess them. Thus, segments having less than complete identity of sequence retain such combinations of functions, and the divergence of sequence may reach as low as 65%, 70%, 75%, 80%, 85%, 90%, or 95% identity, depending upon what portion of the sequence is used and what divergence of sequence is selected. In particular, it is expected that mostly conservative amino acid substitutions in these regions, within these ranges, will typically retain these functions. And the functional combinations can be routinely screened and tested, to identify particularly advantageous variants. The variants may be optimized, e.g., for production efficiency, pharmacological or biophysical properties, therapeutic properties, or other advantageous features. This lysozyme domain, besides having a muralytic activity as described above, was observed to also exhibit an interesting property of being able to kill Gram-negative bacteria, suggesting the ability to traverse the outer membrane. Further investigating this feature, we have determined that the entire protein is not necessary, but that only a shorter segment containing the LysM domain is sufficient.

Because the bacterial outer membrane is a contiguous bilayer, it serves as a barrier to larger molecules accessing the periplasmic space. The outer membrane is a selective semipermeable barrier that can protect the cell from harmful compounds in the environment, including antibiotics, and efficiently excludes larger proteins (e.g., a muralytic enzyme or perhaps an AMP) from the periplasmic space. It also serves to sequester a special periplasmic space environment close to the cell, as an intermediate zone of protection between the cell and outside the outer membrane. Thus, the Gram-negative cell has a semi-regulated environment in the periplasmic space, and the mediated composition and effects therein may moderate temporal changes of the external environment. However, changes in the periplasmic space environment may accomplish effects on the metabolism or physiology of the cell itself, e.g., affecting its internal health or antibiotic resistance.

Rates of transfer across the outer membrane can be measured by a number of methods. One method is to indirectly evaluate the results of transfer, e.g., the effects of a muralytic segment reaching its periplasmic substrate. The criteria of measurement can be release of measurable cell contents, substrate release, or cell lysis. Cell killing can also be a surrogate measure of peptidoglycan digestion. See Examples section below describing binding of product to cell.

A more direct method is to track the number of molecules transferred into the periplasmic space, e.g., using a detectable label. The efficiency of transfer of a particular transfer segment will often be evaluated by measuring an amount of passenger segment transferred. A detectable label can be used to differentiate between the periplasmic space conditions (more oxidizing than outside the OM) and the extracellular environment. See Rajarao, et al. (2002) *FEMS Microbiology Letters* 215:267-272.

An efficient membrane transfer segment will effect at least a 3 fold increase in the level of killing of target host by the muralytic domain, or at least a 3-fold increase in the level of transfer, as compared to absence of the membrane transfer segment. In some embodiments, the membrane transfer segment will increase the level of killing or transfer by at least 5, 7, 10, 15, 20, 30, 50, 80, 100, 150, 250 or more fold compared to the absence of the membrane transfer segment. The assay is typically carried out under conditions which approximate the concentrations which might be used according to the application. The assay will typically measure transfer over a time period ranging from minutes, e.g., 1, 2, 5, 10, 15, or 30 minutes, to an hour or two.

IV. Linkers Connecting Segments; Chemical Conjugation

The invention includes chimeric proteins which comprise, e.g., two distinct segments or domains from heterologous sources. In many embodiments, the two segments or domains are part of a single polypeptide as a contiguous (chimeric) protein. The two segments might be connected in either order, with the muralytic domain N-proximal to the LysM transfer domain (LysMTD) or vice versa. The segments might be linked directly or with a linker (peptide or non-peptide). The function may be more passive in the biophysical features of thermodynamic interaction of the peptide with the hydrophobic membrane bilayer, or may be interacting with an active process of serving as a segment which interacts with an active transport process, e.g., as the recognition component of an active transport mechanism which transfers the entity from outside to inside the bacterial outer membrane of a Gram-negative bacteria.

In some embodiments, the LysMTD can also transfer the muralytic segment across the inner membrane of a prokaryotic production host. In some embodiments, the LysMTD does not transfer the MD across the inner membrane, while retaining LysMTD activity for the outer membrane of a Gram-negative bacteria. In some embodiments, the constructs described herein can be produced instead in a eukaryotic cell system.

In some embodiments, the component segments are produced separately and linked chemically. In some cases, synthetic polymerization methods are used to add peptides to existing sequences.

Chemical linkages or bioconjugation technologies may be used. See, e.g., Niemeyer (ed. 2010) *Bioconjugation Protocols: Strategies and Methods (Methods in Molecular Biology)* Humana Press; Hermanson (2008) *Bioconjugate Techniques* (2d ed.) Academic Press; Lahann (ed. 2009) *Click Chemistry for Biotechnology and Materials Science* Wiley; Rabuka (2010) "Chemoenzymatic methods for site-specific protein modification" *Curr. Opin. Chem. Biol.* 14:790-96. Epub 2010 Oct. 26; Tiefenbrunn and Dawson (2010) "Chemoselective ligation techniques: modern applications of time-honored chemistry" *Biopolymers* 94:95-106; Nwe and Brechbiel (2009) "Growing applications of "click chemistry" for bioconjugation in contemporary biomedical research" *Cancer Biother. Radiopharm.* 24:289-302; de Graaf, et al. (2009) "Nonnatural amino acids for site-specific protein conjugation" *Bioconjug. Chem.* 20:1281-95; the journal *Bioconjugate Chemistry* (ACS); and Thordarson, et al. (2006) "Well-defined protein-polymer conjugates—synthesis and potential applications" *Applied Microbiology and Biotechnology* 73:243-254, DOI: 10.1007/s00253-006-0574-4. For example, specific amino acids can be incorporated or added at either end, perhaps to constructs which have removed non-critical like residues, e.g., for cysteine residues. Accessible cysteine residues can be used to connect the segments by disulfide linkages. Cysteine residues can also be linked with bifunctional maleimide linkers with thioether bonds. The linkers can also have a hydrocarbon spacer of appropriate length, e.g., 6, 9, 12, 15, 18, 21, 25, 29, 35, or more carbon chains.

Constructs might be generated having accessible cysteines, e.g., in the functional region, at either or both the N-terminus and C-terminus. These can be used to attach a variety of other chemical moieties. Longer non-peptide hydrophobic molecules can be attached to a Cys residue, including palmityl or similar groups, e.g., using an alkyl or acyl halide, e.g., palmityl bromide, or acyl chloride. The alkyl form will provide a stable thioether linkage while the acyl form will provide a less stable thioester link. The alkyl or acyl hydrocarbon can integrate into the outer membrane outer leaflet, which will flip to the inner leaflet at a detectable rate, e.g., increasing with temperature.

V. Definitions

A "cell wall degrading activity" is an enzymatic activity that degrades, breaks down, disintegrates, or diminishes or reduces the integrity of a bacterial cell wall (peptidoglycan layer). Unless indicated otherwise, e.g., by context, the term "muralytic" is used generically to mean "cell wall degrading." Most wall degrading catalytic activities are hydrolytic. Thus, much of the terminology used refers to "muralytic" even if the catalytic mechanism does not involve hydrolysis. Degradation of defined or artificial substrates can be used to measure muralytic or static activity on a populational basis for the target. "Cell wall muralytic activity" in a phage context is usually a characterization assigned to a structure based upon testing under artificial conditions, but such characterization can be specific for bacterial species, families, genera, or subclasses (which may be defined by sensitivity). Therefore, a "bacterium susceptible to a cell wall degrading activity" describes a bacterium whose cell wall is degraded, broken down, disintegrated, or that has its cell wall integrity diminished or reduced by a particular cell wall degrading activity or activities. As explained herein, other cell wall degrading activities originate from the host bacterial cells, or on the phage structure (e.g., to serve in penetration, but abortive to phage replication if destructive to the host cell before intact phage are ready to be released). The structures useful in the penetration steps are particularly relevant to the present invention in that these activities operate on normal hosts from the exterior.

In some circumstances, a prophage sequence can be detected in a bacterial genome. The prophage is often the remnants of an integrated phage genome which may have lost certain essential functions, and thus is embedded therein reflecting past biological function. See, e.g., Kropinski, et al. (2007) *Methods Mol. Biol.* 394:133-75; Canchaya, et al. (2004) *Mol. Microbiol.* 53:9-18; Canchaya, et al. (2003) *Microbiol. Mol. Biol. Rev.* 67:238-76; and Casjens (2003) *Mol. Microbiol.* 149:277-300. Although a prophage can encode a substantial portion of the functions of a lytic phage genome, the prophage normally does not pass through a lytic cycle. Many of the structural components of a lytic phage have equivalent or counterpart forms discoverable from a prophage sequence. Informatics analysis can typically determine the difference between a sequence which once encoded the lytic activity used for infection as compared to an endolysin activity used to lyse the target host cell after phage assembly.

A "binding segment" refers to a targeting motif, which can recognize specific structures on the bacterial outer surface. In Gram-positive bacteria, the outer surface of the bacteria is typically the murein layer (cell wall). Thus, a binding segment for Gram-positive bacteria can target a cell surface entity, e.g., protein, lipid, sugar, or combination. Binding segments from lysozymes, endolysins, and such are known and can be used. Other proteins which bind to bacteria include the PGRPs described below, the TLRs, flagellum and pili binding entities, and phage tail proteins involved in target recognition. In Gram-negative bacteria, the outer membrane presents various structures which can be targets for specific binding. The outer leaflet of the lipid bilayer or lipopolysaccharide can be exposed to the external environment.

A "LysM transfer domain (LysMTD)," refers to a molecular entity, e.g., a polypeptide domain comprising at least about 65%, 70%, 75%, 80%, 85%, 90%, or 95% identity to the relevant portion of the LysM segment identified which exhibits the function as described, which is able to provide transfer accessibility of the linked segment across the outer membrane of the Gram-negative bacteria from outside to access the periplasmic space of the bacteria. Such domain may itself have the ability to translocate the associated segment across the membrane, or be recognized by an endogenous translocation system which will effect transport of the linked catalytic segment. The translocation may be flipping of the segment from the outer leaflet to the inner leaflet, or may be translocation of the entire protein across the lipid bilayer. The chimeric polypeptide can be transferred intact across the membrane, or be modified during translocation. In some embodiments, the LysMTD does not significantly penetrate the inner membrane of an expression host. In some embodiments, the LysMTD does not significantly penetrate the cell membrane of a eukaryotic cell which typically has a different composition and properties from the outer membrane of a bacterial cell.

Although the outer membrane of Gram-negative bacteria protects cells from many external agents, it is possible to weaken it specifically by various agents, collectively called permeabilizers, which help to disintegrate the LPS layer and increase the permeability of the OM to hydrophobic agents. Permeabilizers are compounds that weaken the OM and can thus increase the activity of antimicrobials by facilitating entry of external substances capable of inhibiting or destroying cellular functions. This entry may be across the OM into the periplasmic space and perhaps ultimately into the cell cytoplasm. Permeabilizers themselves may not be bactericidal, but may potentiate the activity of other compounds, thus providing the possibility of synergistic action. The classical example of permeabilizers is the chelator EDTA, which sequesters divalent cations that contribute to the stability of the OM by providing electrostatic interactions with proteins and LPS. Treatment with EDTA releases a large proportion of LPS from the OM, exposing hydrophobic phospholipids and creating a hydrophobic pathway for certain substances. This is noticeable as an increased susceptibility to hydrophobic agents. Permeabilizers may not be applicable in therapeutic contexts since at high concentrations they are often toxic to cells. In other contexts, they may be useful, e.g., in surface or device sterilization applications. At lower concentrations they are able to act in permeabilizing the outer membrane thus allowing access for molecules to reach the peptidoglycan. Often permeabilizers may promote or facilitate the transfer function of the chimeric polypeptide.

tongue, pancreas, spleen, thyroid, etc. In vivo environments include tissues, such as gums, nervous tissue, lymph tissue, glandular tissue, and biological fluids, e.g., blood, sputum, etc. Catheter, tubing, implant, and monitoring or treatment devices which are introduced into or attached to the body may be sources of infection under normal usage. Environments also include the surface of food, e.g., fish, meat, or plant materials. Meats include, e.g., beef, pork, chicken,

TABLE C

Agents with outer membrane disrupting activity

| Designation | Agent | Mode of action |
|---|---|---|
| A | Chelators | |
| 1 | Ethylenediaminetetraacetic acid | Removes stabilizing cations from the OM, notably $Ca^{2+}$ and $Mg^{2+}$. |
| | | Releases LPS to the external medium and creates a hydrophobic pathway. |
| 2 | Na-hexametaphosphate | Removes stabilizing cations from the OM, notably $Ca^{2+}$ and $Mg^{2+}$. |
| | | Increases sensitivity to hydrophobic antibiotics. |
| 3 | Na2-pyrophosphate, Na-orthophosphate | Destabilizes OM. Sensitizes cells to nisin |
| 4 | Nitrilotriacetic acid | Disintegrates the OM. Increases sensitivity to hydrophobic antibiotics. |
| B | Polycationic agents | |
| 1 | Polymyxins | Displaces cations from the OM, causes membrane damage. |
| | Tris (high concentrations) | Binds to OM and increases sensitivity to hydrophobic antibiotics |
| 2 | Polymyxin B nonapeptide | Permeabilizes the OM without significant release of LPS. Increases the cell surface hydrophobicity. |
| 3 | Poly-L-ornithine, Poly-L-lysine | Permeabilises the OM to hydrophobic antibiotics and releases LPS. |
| 4 | L-Ascorbate, Acetylsalicylate | Destabilizes the OM |
| 5 | Lactoferrin, transferrin | Releases LPS, increases sensitivity to rifampin |
| 6 | Cationic detergents, e.g. benzalkonium chloride | Destabilizes hydrophobic interactions in OM |
| 7 | Polyethyleneimine | Intercalates in the OM and increases the membrane surface area without liberation of LPS-associated cell material. Sensitizes target cells to hydrophobic antibiotics and to detergents; causes the formation of vesicular structures on the surface of OM. |
| C | Membrane-perturbing proteins and peptides | |
| 1 | Synthetic cationic peptides Cationic amphiphilic peptides | Disorganization of LPS by interaction of the peptide with the anionic and hydrophobic lipid A. |
| D | Terpenoid and phenolic compounds found in berries and herb plants | |
| 1 | Thymol, carvacrol | Destabilizes the OM and causes LPS release |
| 2 | Gallic acid | Displaces cations from the OM, causes membrane damage and LPS release. |
| 3 | Phenolic berry extracts (cloudberry and raspberry) | Displaces cations from the OM, causes membrane damage and LPS release. |
| E | Organic acids and their salts | |
| 1 | Citric acid | cations from the OM, notably $Ca^{2+}$ and $Mg^{2+}$, induces release of LPS. |
| 2 | Succinate, acetate, citrate | Weakly increases membrane permeability |
| F | Other compounds | |
| 1 | Chitosan (polymeric β-1,4-N-Acetylglucosamine | Binds to OM resulting in the loss of barrier function |
| 2 | Quinolones Low amounts (0.25 × MIC) | Increases the sensitivity of Gram-negative bacteria to antimicrobial peptides by interacting with the OM by removal of stabilizing divalent cations from LPS-binding sites. |

An "environment" of a bacterium can include an in vitro or an in vivo environment. In vitro environments can include a reaction vessel, e.g., holding isolated or purified bacteria, a surface to be sterilized (e.g., in a public health facility), equipment, surfaces in animal quarters, or public health facilities such as water, septic, or sewer facilities. Other in vitro conditions can provide mixed species populations, e.g., including a number of symbiotically or interacting species in close proximity. An in vivo environment can be a host organism infected by a target bacterium. In vivo environments include organs, such as bladder, kidney, lung, skin, heart and blood vessels, stomach, fur, intestine, liver, brain or spinal cord, sensory organs, such as eyes, ears, nose, turkey or other poultry. Plant materials include vegetable, fruits, or juices made from fruits and/or vegetables, or may include clothing or shelter. In some embodiments, surfaces that have come in contact with a bacterially-infected food product are treated with a protein of the invention, including a VAME construct or chimera, e.g., P617. Sucrose and/or sorbitol may be useful to increases the osmotic pressure to make targets more susceptible to degradation of peptidoglycan layer.

"Introducing" a composition to an environment includes applying or administering a compound or composition, and such that a targeted bacteria is exposed to the compound or composition. Introducing said compound or composition can be effected by live or dead bacteria or cells which may produce or release such.

A "cell wall degradingprotein" is a protein that has detectable, e.g., substantial, degrading activity on an accessible cell wall or components thereof "Muralytic" activity can be a result of the degrading activity. Exemplary degrading polypeptides include, e.g., GP36 CD segment or P617 products, and functional structurally related entities, mutant and variants thereof. Examples of cell wall degrading proteins are described in the Examples. Similar degrading domains can be identified by motif analysis, their gene locations in the phage genome (or analogous prophage sequence), their structural location on the phage (or prophage counterpart) structure, e.g., tails or contact points of natural phage, similar motifs from mutated phage remnants (e.g., pyocins), or encoded by prophage sequences. Cell wall degrading domains can be derived, e.g., from the tail plates of myoviridae phage or ends of tails from siphoviridae phage, and other phage virion muralytic polypeptides.

A "LysM polypeptide segment" or grammatical variant thereof, refers to a polypeptide sequence exhibiting lytic (bacteriostatic) activity, typically encoded by a fragment of the phi29 phage sequence SEQ ID NO: 2 provides the sequence of a truncated segment of phi29 LysM which possesses both Gram-negative peptidoglycan binding function and outer membrane traversing function. Exemplary variant LysM polypeptide segments include polypeptide polymorphic variants, alleles, mutants, and interspecies homologs that: (1) have an amino acid sequence that has greater than about 60% amino acid sequence identity, preferably at least about 65%, 70%, 75%, 80%, 85%, 90%, e.g., 91%, 92%, 93%, 94%, 95%, 96%, 97%, 98% or 99% or greater amino acid sequence identity, preferably over one or more regions corresponding to that of SEQ ID NO: 2, e.g., of at least about 80, 90, 100, 110, 120, 135, 150, 175, 200, or more amino acids, to an amino acid sequence encoded by the LysM sequence, (2) bind to antibodies, e.g., polyclonal antibodies, raised against a substantially purified immunogen comprising an amino acid sequence of an active fragment of LysM polypeptide, and conservatively modified variants thereof; or (3) specifically hybridize under stringent hybridization conditions to an anti-sense strand corresponding to a natural nucleic acid sequence encoding the LysM polypeptide, and conservatively modified variants thereof; or (4) have a nucleic acid sequence that has greater than about 65%, 70%, 75%, 80%, 85%, 90%, or 95%, preferably greater than about 96%, 97%, 98%, 99%, or higher nucleotide sequence identity, preferably over a region of at least about 25, 50, 100, 150, 200, 250, 300, 400, 500, 600, 700, etc., or more nucleotides, to the LysM encoding nucleic acid or a nucleic acid encoding fragment thereof. The phi29 sequence described comprises this LysM segment within it. The nucleic acids and proteins of the invention include both natural or recombinant molecules. The LysM polypeptide and truncated fragments thereof can be tested for membrane translocation function, peptidoglycan binding and degradative activity, and cell killing function, as described, to determine boundaries critical for desired properties. In preferred embodiments, LysM polypeptide and chimeric proteins of the invention with catalytic domains have bacteriostatic or bactericidal activity against various *Pseudomonas, Escherichia, Klebsiella, Acinetobacter, Salmonella, Proteus, Shigella,* and *Burkholderia* bacteria. Some embodiments may also exhibit activity on Gram-positive bacteria, such as *Bacillus,* which lack the outer membrane. The concentration, time of action, temperature, and conditions may be optimized to have such activity on broader range of Gram-negative targets, and perhaps also Gram-positive targets.

"Traverse the outer membrane" refers to the physical traversal of a polypeptide across the Gram-negative bacterial outer membrane. Typically, this will be from outside the cell, e.g., the cell medium, into the periplasmic space. This may be transfer from a soluble form in the extracellular milieu to a soluble form in the periplasmic space, but may include situations where the protein is not freely soluble in either or both compartments, but may be associated with other proteins or molecules. For example, as the solution compositions in the two regions are different, the solubility behavior of a protein may be different. It is more likely that the protein will be associated with other components within the periplasmic space, as the concentrations and solvent conditions there are often much more likely to cause molecular associations. Both direct and indirect means for determining spatial localization are available to determine amounts and efficiencies to transfer of specific proteins between the two compartments. In other situations, the protein may become associated with the outer membrane bilayer, and the protein may flip between the outer and inner leaflet, providing accessibility of particular portions of the protein to the periplasmic space from the outside medium. Again, labeling and other means are available to determine amounts, rates, and efficiencies of accessibility under particular conditions.

Nucleic acids encoding cell wall degrading polypeptides can be amplified using PCR primers based on the sequence of described cell wall degrading polypeptides. For example, nucleic acids encoding GP36 CD polypeptide variants and fragments thereof, as well as likely wall degrading activity candidates, can be amplified using primers. See, e.g., Vybiral, et al. (2003) *FEMS Microbiol. Lett.* 219:275-283. Thus, cell wall degrading polypeptides and fragments thereof include polypeptides that are encoded by nucleic acids that are amplified by PCR based on the sequence of the identified cell wall degrading polypeptides. In a preferred embodiment, a bacteriostatic polypeptide or fragment thereof is encoded by a nucleic acid that is amplified by primers relevant to the GP36 CD sequences described.

A "phage particle component" refers to, e.g., a head or tail component of a phage, e.g., phage phiKMV. The invention provides that many different phage types can be sources of the muralytic activity ascribed to the phage components. See, e.g., Piuri and Hatfull (2006) *Molecular Microbiology* 62:1569-1585. Related sequences can be found in prophages or incomplete phage genomes, typically found integrated into the bacterial host chromosome. Tail components typically mediate the recognition and attachment of the phage to the target host, and can possess cell wall degrading activities which assist in penetration of phage components into the host.

"GMP conditions" refers to good manufacturing practices, e.g., as defined by the Food and Drug Administration of the United States Government. Analogous practices and regulations exist in Europe, Japan, and most developed countries.

The term "substantially" in the above definitions of "substantially pure" generally means at least about 60%, at least about 70%, at least about 80%, or more preferably at least about 90%, and still more preferably at least about 92%, 95%, 97%, or 99% pure, whether protein, nucleic acid, or other structural or other class of molecules.

Likewise, "essentially no growth" typically means that the growth of bacteria is decreased significantly. Generally, the target bacteria population growth rate will be decreased by at least about 50%, but will preferably be decreased by more, e.g., to below about 20%, 10%, 5%, or less. In certain cases, the rate will be down near the detectable growth rate, depending upon how accurately growth rate may be quantitated.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analog refers to a compound that has the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain a basic chemical structure as a naturally occurring amino acid. Amino acid mimetic refers to a chemical compound that has a structure that is different from the general chemical structure of an amino acid, but that functions in a manner similar to a naturally occurring amino acid.

"Protein", "polypeptide", or "peptide" refers to a polymer in which most or all of the monomers are amino acids and are joined together through amide bonds, alternatively referred to as a polypeptide. When the amino acids are α-amino acids, either the L-optical isomer or the D-optical isomer can be used. Additionally, unnatural amino acids, e.g., β-alanine, phenylglycine, and homoarginine, are also included. Amino acids that are not gene-encoded may also be used in the present invention. Furthermore, amino acids that have been modified to include appropriate structure or reactive groups may also be used in the invention. The amino acids used in the present invention may be the D- or L-isomer, or mixtures thereof. The L-isomers are generally preferred. In addition, other peptidomimetics are also useful in the present invention. For a general review, see, Spatola, A. F., in Weinstein, et al. (eds. 1983) *Chemistry and Biochemistry of Amino Acids, Peptides and Proteins*, Marcel Dekker, New York, p. 267.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. In particular, fusions of sequence may be generated, e.g., incorporating an upstream secretion cassette upstream of desired sequence to generate secreted protein product.

"fusion protein," "chimeric protein," "protein conjugate," and like terms refer to a protein comprising amino acid sequences that are in addition to, in place of, less than, and/or different from the amino acid sequences encoding the original or native full-length protein or subsequences thereof. More than one additional domain can be added to a cell wall muralytic protein as described herein, e.g., an epitope tag or purification tag, or multiple epitope tags or purification tags. Additional domains may be attached, e.g., which may add additional muralytic activities (on the target or associated organisms of a mixed colony or biofilm), targeting functions, or which affect physiological processes, e.g., vascular permeability or integrity of biofilm. Alternatively, domains may be associated to result in physical affinity between different polypeptides to generate multi-chain polymer complexes. The segments may be as short as about 5 to 10 residues, but will usually be at least about 15, 20, 25, or 30 residues long. Thus, "chimeric protein" refers to an artificial construct where a single protein is made from linking segments to one another which are normally not contiguous, e.g., from the original source organism, or typically where two or more different source organisms provide segments fused together. Thus, where segments of selected function are combined into a single protein, e.g., linking the LysM polypeptide segment to a purification tag such as 6×His (SEQ ID NO: 9), produces a chimeric polypeptide. It also refers to a construct where two different functions are combined into a single protein which normally, e.g., in nature, are not found adjacent to one another, which applies to situations where selection processes are used to generate such constructs in vivo by using an organism manipulated to produce significant recombination of gene sequences.

The term "nucleic acid" refers to a deoxyribonucleotide, ribonucleotide, or mixed polymer in single- or double-stranded form, and, unless otherwise limited, encompasses known analogues of natural nucleotides that hybridize to nucleic acids in a manner similar to naturally occurring nucleotides. Unless otherwise indicated or by context, a particular nucleic acid sequence includes the complementary sequence thereof.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes typically include at least promoters and/or transcription termination signals. Typically, the recombinant expression cassette includes a nucleic acid to be transcribed (e.g., a nucleic acid encoding a desired polypeptide), and a promoter. Additional factors for effecting expression can be included. In certain embodiments, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette. In certain embodiments, a recombinant expression cassette encoding an amino acid sequence comprising a muralytic activity on a cell wall is expressed in a bacterial host cell.

"heterologous sequence" or a "heterologous nucleic acid", as used herein, is one that originates from a source foreign to the particular host cell, or, if from the same source, is modified from its original form. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence. In other contexts, "heterologous" in relation to the LysM can mean that the flanking sequences of the LysM polypeptide segment are derived from sequences different from the corresponding segments of the LysM polypeptide, if aligned. Alternatively, the flanking segments outside the LysM polypeptide segment boundaries exhibit substantially less, e.g., more than about 10% less of the identity as the LysM polypeptide segment identity inside those boundaries. Thus, where the protein comprises sequence outside the LysM polypeptide segment derived from a completely different source, the construct has heterologous sequence. A completely different source will often be derived from an organism from a different genus as the LysM polypeptide, or different classification family, order, or class.

The term "isolated" refers to material that is substantially or essentially free from components which interfere with the activity of an enzyme. For a saccharide, protein, or nucleic acid of the invention, the term "isolated" refers to material that is substantially or essentially free from components which normally accompany the material as found in its native state. Typically, an isolated saccharide, protein, or nucleic acid of the invention is at least about 80% pure, usually at least about 90%, or at least about 95% pure as measured by band intensity on a silver stained gel or other method for determining purity. Purity or homogeneity can be indicated by a number of means well known in the art. For example, a protein or nucleic acid in a sample can be resolved by polyacrylamide gel electrophoresis, and then the protein or nucleic acid can be visualized by staining. For certain purposes high resolution of the protein or nucleic acid may be desirable and, e.g., HPLC or mass spectroscopy or a similar means for purification may be utilized.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The terms "identical" or percent "identity," in the context of two or more nucleic acids or protein sequences, refer to two or more sequences or subsequences that are the same or have a specified percentage of amino acid residues or nucleotides that are the same, when compared and aligned for maximum correspondence, as measured using one of the sequence comparison algorithms or by visual inspection. In certain alignments of identity, no gaps are permitted, while in other algorithms, gaps are allowed with appropriate penalty measures.

The phrase "substantially identical," in the context of two nucleic acids or proteins, refers to two or more sequences or subsequences that have, over the appropriate segment, at least greater than about 60% nucleic acid or amino acid sequence identity, 65%, 70%, 75%, 80%, 85%, 90%, preferably about 91%, 92%, 93%, 94%, 95%, 96%, 97%, 98% or 99% nucleotide or amino acid residue identity, when compared and aligned for maximum correspondence, as measured using one of the following sequence comparison algorithms or by visual inspection. Preferably, the substantial identity exists over one or more region of the sequences that corresponds to at least about 13, 15, 17, 23, 27, 31, 35, 40, 50, or more amino acid residues in length, more preferably over a region of at least about 60, 70, 80, or 100 residues, and most preferably the sequences are substantially identical over at least about 150 residues, or over the entire length of the reference sequence. It will be noted that three of the constructs specifically described have high hydrophobic stretches of 23, 23, and 30 amino acids, and data is presented that at least 3 of 23 amino acid residues may be substituted with nonconservative residues while maintaining activity.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these and related algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel, et al., eds., *Current Protocols*, a joint venture between Greene Publishing Associates, Inc. and John Wiley & Sons, Inc. (1995 and Supplements) (Ausubel)).

Examples of algorithms that are suitable for determining percent sequence identity and sequence similarity are the BLAST and BLAST 2.0 algorithms, which are described in Altschul, et al. (1990) *J. Mol. Biol.* 215:403-410 and Altschuel, et al. (1977) *Nucleic Acids Res.* 25:3389-3402, respectively. Software for performing BLAST analyses is publicly available through the National Center for Biotechnology Information (ncbi.nlm.nih.gov) or similar sources.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given protein. For instance, the codons CGU, CGC, CGA, CGG, AGA, and AGG all encode the amino acid arginine. Thus, at each position where an arginine is specified by a codon, the codon can be altered to another of the corresponding codons described without altering the encoded protein. Such nucleic acid variations are "silent variations," which are one species of "conservatively modified variations." Each polynucleotide sequence described herein which encodes a protein also describes possible silent variations, except where otherwise noted. One of skill will recognize that each codon in a nucleic acid (except AUG, which is ordinarily the only codon for methionine, and UGG which is ordinarily the only codon for tryptophan) can be modified to yield a functionally identical molecule by standard techniques. Accordingly, each "silent variation" of a nucleic acid which encodes a protein is typically implicit in each described sequence.

Those of skill recognize that many amino acids can be substituted for one another in a protein without affecting the function of the protein, e.g., a conservative substitution can be the basis of a conservatively modified variant of a protein such as the disclosed cell wall muralytic proteins. An incomplete list of conservative amino acid substitutions follows. The following eight groups each contain amino acids that are normally conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V), Alanine (A); 6) Phenylalanine (F), Tyrosine (Y), Tryptophan (W); 7) Serine (S), Threonine (T), Cysteine (C); and 8) Cysteine (C), Methionine (M) (see, e.g., Creighton (1984) *Proteins*).

Furthermore one of skill will recognize that individual substitutions, deletions, or additions which alter, add, or delete a single amino acid or a small percentage of amino acids (typically less than 5%, more typically less than 1%) in an encoded sequence are effectively "conservatively modified variations" where the alterations result in the substitution of an amino acid with a chemically similar amino acid. Conservative substitution tables providing functionally similar amino acids are well known in the art.

One of skill will appreciate that many conservative variations of proteins, e.g., cell wall muralytic proteins, and nucleic acids which encode proteins yield essentially identical products. For example, due to the degeneracy of the genetic code, "silent substitutions" (e.g., substitutions of a nucleic acid sequence which do not result in an alteration in an encoded protein) are an implied feature of each nucleic acid sequence which encodes an amino acid. As described herein, sequences are preferably optimized for expression in a particular host cell used to produce the cell wall muralytic proteins (e.g., yeast, human, and the like). Similarly, "conservative amino acid substitutions," in one or a few amino acids in an amino acid sequence are substituted with different amino acids with highly similar properties, are also readily identified as being highly similar to a particular amino acid sequence, or to a particular nucleic acid sequence which encodes an amino acid. Such conservatively substituted variations of any particular sequence are a feature of the present invention. See also, Creighton (1984) *Proteins*, W.H. Freeman and Company. In addition, individual substitutions, deletions or additions which alter, add or delete a single amino acid or a small percentage of amino acids in an encoded sequence generally are also "conservatively modified variations".

The practice of this invention can involve the construction of recombinant nucleic acids and the expression of genes in host cells, preferably bacterial host cells. Optimized codon usage for a specific host will often be applicable. Molecular cloning techniques to achieve these ends are known in the art. A wide variety of cloning and in vitro amplification methods suitable for the construction of recombinant nucleic acids such as expression vectors are well known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology*, F. M. Ausubel, et al., eds., *Current Protocols*, a joint venture between Greene Publishing Associates, Inc. and John Wiley & Sons, Inc., (1999 Supplement) (Ausubel). Suitable host cells for expression of the recombinant polypeptides are known to those of skill in the art, and include, for example, prokaryotic cells, such as *E. coli*, and eukaryotic cells including insect (baculovirus), mammalian (CHO cells), fungal cells (e.g., yeast, *Pichia, Aspergillus niger*), and bacteriophage expression systems. Note that the N terminal MET is often removed in prokaryotic productions hosts. The presently described chimeric polypeptides include those with and without an N-terminal methionine on any or all of the peptide components.

Examples of protocols sufficient to direct persons of skill through in vitro amplification methods, including the polymerase chain reaction (PCR), the ligase chain reaction (LCR), Qβ-replicase amplification and other RNA polymerase mediated techniques are found in Berger, Sambrook, and Ausubel, as well as Mullis, et al. (1987) U.S. Pat. No. 4,683,202; *PCR Protocols A Guide to Methods and Applications* (Innis, et al. eds) Academic Press Inc. San Diego, Calif. (1990) (Innis); Arnheim and Levinson (Oct. 1, 1990) *C&EN* 36-47; *The Journal Of NIH Research* (1991) 3:81-94; Kwoh, et al. (1989) *Proc. Natl. Acad. Sci. USA* 86:1173; Guatelli, et al. (1990) *Proc. Natl. Acad. Sci. USA* 87:1874; Lomeli, et al. (1989) *J. Clin. Chem.* 35:1826; Landegren, et al. (1988) *Science* 241:1077-1080; Van Brunt (1990) *Biotechnology* 8:291-294; Wu and Wallace (1989) *Gene* 4: 560; and Barringer, et al. (1990) *Gene* 89:117. Improved methods of cloning in vitro amplified nucleic acids are described in Wallace, et al., U.S. Pat. No. 5,426,039.

VI. Commercial Applications

Various applications of the polypeptides described herein can be immediately recognized. Many medical conditions result from bacterial infections, described further in infectious disease and medical microbiology textbooks. See, e.g., Kasper and Fauci (2010) *Harrison's Infectious Diseases* McGraw-Hill Professional, ISBN-10: 0071702938, ISBN-13: 978-0071702935; Mandel (2008) Mandell, Douglas, and Bennett's Principles and Practice of Infectious Diseases: Expert Consult Premium Edition (7th Ed.) Churchill Livingstone, ISBN-10: 0443068399, ISBN-13: 978-0443068393; Schlossberg (ed. 2008) *Clinical Infectious Disease* Cambridge University Press, ISBN-10: 0521871123. ISBN-13: 978-0521871129; Bauman (2011) *Microbiology with Diseases by Body System* (3d ed.) Benjamin Cummings, ISBN-10: 0321712714, ISBN-13: 978-0321712714; and Murray, et al. (2008) *Medical Microbiology* (with Student Consult Online Access, 6th ed.) Mosby, ISBN-10: 0323054706, ISBN-13: 978-0323054706. Therapeutic applications for these polypeptide constructs will be appreciated.

The presently described outer membrane traversing, muralytic chimeric proteins can be used for antibacterial treatment of articles which may be contaminated in normal use. Locations, surfaces, equipment, or environments where target bacteria are public health hazards can be treated using the chimeric polypeptides described herein. Locations of interest include public health facilities where target bacteria containing materials exist. These materials may include waste products, e.g., liquid, solid, or air. Aqueous waste treatment plants may incorporate the muralytic polypeptides to eliminate target bacteria from effluent, whether by treatment with the muralytic polypeptides or cells that express and release the muralytic polypeptides. Solid waste sites can introduce the muralytic polypeptides to minimize possibility of target host outbreaks.

Food preparation areas and equipment can be regularly treated using the muralytic polypeptide compositions, thereby providing means to effectively eliminate target bacteria. Medical and other public environments subject to contamination can use similar means to minimize growth and spread of target microorganisms. The present methods can be used in contexts where elimination of target bacteria is desired, including air filtration systems, e.g., for an intensive care unit.

The chimeric muralytic proteins can be used as a protein stabilizer or a preservative, i.e., where the target bacteria are destabilizing agents. Such compositions can be used as part of the formulation for drugs, or preservative for meat or other food products. In some embodiments, the muralytic polypeptides can be used in aquatic food products, e.g., as a stabilizer or as a component of preservative formulations. Such applications are particularly useful for materials that must be kept antiseptic but cannot contain classical antibiotics.

Alternative applications include use in a veterinary or medical context. Means to determine the presence of particular bacteria, or to identify specific targets may utilize the effect of selective agents on the population or culture. Inclusion of bacteriostatic activities to cleaning agents, including washing of animals and pets, may be desired.

The muralytic polypeptides described herein can be used to treat bacterial infections of, e.g., humans, animals, and plants. The muralytic polypeptides can be administered to a subject prophylactically or where the subject has a bacterial infection. In addition, the present methods can be applied to display (e.g., zoo or performing), companion (e.g., dogs, cats, other pets), racing (e.g., horses), or farm (e.g., dairy and beef cattle, sheep, goats, pigs, chicken, fish, shrimp, lobster, and the like) animals where the composition is applied to reduce the presence of bacteria. The muralytic polypeptides can be used to treat infections caused by bacteria that replicate slowly, as the killing mechanism does not depend upon host cell replication. Many current antibacterial agents, e.g., antibiotics, are most useful against replicating bacteria. For example, the muralytic polypeptides can be used to target bacteria that replicate with doubling times of, e.g., 1-72 hours, 1-48 hours, 1-24 hours, 1-12 hours, 1-6 hours, 1-3 hours, or 1-2 hours.

Medically relevant Gram-negative cocci species include *Neisseria gonorrhoeae* and spirochaetes (causing a sexually transmitted disease); *Neisseria meningitides* (causing meningitis); and *Moraxella catarrhalis* (causing respiratory symptoms). Relevant Gram-negative bacilli species include *Haemophilus influenza, Klebsiella pneumoniae, Legionella pneumophila, Burkholderia,* and *Pseudomonas aeruginosa* (respiratory problems); *Escherichia coli, Proteus mirabilis, Enterobacter cloacae,* and *Serratia marcescens* (urinary problems), and *Helicobacter pylori, Salmonella enteritidis, Salmonella typhi* (gastrointestinal problems), and spirochaetes (sexually transmitted disease). Gram-negative bacteria associated with nosocomial infections include *Acinetobacter baumannii,* which cause bacteremia, secondary meningitis, and ventilator-associated pneumonia, e.g., in intensive-care units of hospital establishments.

Other relevant bacteria that can be targeted using the present muralytic polypeptides include Gram-negative species include *Stenotrophomonas, Bdellovibrio,* acetic acid bacteria, and alpha-proteobacteria such as *Wolbachia,* the cyanobacteria, spirochaetes, green sulfur and green non-sulfur bacteria.

Gram-variable organisms, which may have an outer membrane under certain conditions (display a Gram-variable pattern with Gram staining), can also be targeted using the present muralytic polypeptides. Gram-variable bacteria include, e.g., the genera *Actinomyces, Arthobacter, Corynebacterium, Mycobacterium,* and *Propionibacterium,* which have cell walls particularly sensitive to breakage during cell division, and display Gram-negative staining. In cultures of *Bacillus, Butyrivibrio,* and *Clostridium,* a decrease in peptidoglycan thickness during growth coincides with an increase in the number of cells that stain Gram-negative. In addition, the age of the bacterial culture can influence the results of the Gram stain.

VII. Administration

The route of administration and dosage of the muralytic polypeptides described herein vary with the infecting bacteria strain(s), the site and extent of infection (e.g., local or systemic), and the subject being treated. The routes of administration include but are not limited to: oral, aerosol or other device for delivery to the lungs, nasal spray, intravenous (IV), intramuscular, intraperitoneal, intrathecal, intraocular, vaginal, rectal, topical, lumbar puncture, intrathecal, and direct application to the brain and/or meninges. Excipients which can be used as a vehicle for the delivery of the therapeutic will be apparent to those skilled in the art. For example, the muralytic polypeptide can be in lyophilized form and dissolved (resuspended) prior to administration (e.g., by IV injection). The dosage is contemplated to be in the range of 0.03, 0.1, 0.3, 1, 3, 10, 30, 100, 300, 1000, 3000, 10000 or more muralytic polypeptide molecules per bacterium in the host infection. Depending upon the size of the protein, which may itself be tandemly associated, or in multiple subunit form (dimer, trimer, tetramer, pentamer, etc.) or in combination with one or more other entities, e.g., enzymes or fragments of different specificity, the dose may be about 1 million to about 10 trillion/per kg/per day, and preferably about 1 trillion/per kg/per day, and may be from about $10^6$ killing units/kg/day to about $10^{13}$ killing units/kg/day.

Methods to evaluate killing capacity may be similar to methods used by those of skill to evaluate intact replicating phage, e.g., plaque forming units or pfu, though killing units may be better evaluated by determining the number of surviving bacteria after titration of the killing units. Quantification of killing is distinct, since non-replicating phage will not form plaques on bacterial host lawns. Thus, serial dilution methods can be used to evaluate the quantity of "killing" units in place of standard pfu. Serial dilutions of bacterial cultures exposed to the killing compositions can be used to quantify killing units. Total bacterial counts can be compared with viable colony units can establish the viable fraction of bacteria and what fraction was susceptible to the killing constructs. Other means for evaluating stasis activity may include release of intracellular contents, whether natural or loaded, or enzymatic activity on defined or prepared substrates which correspond to natural cell wall structures.

The therapeutic(s) are typically administered until successful elimination of the pathogenic bacteria is achieved. The invention contemplates single dosage forms, as well as multiple dosage forms of the compositions of the invention, as well as methods for accomplishing sustained release means for delivery of such single and multi-dosages forms. Broad spectrum formulations can be used while specific diagnosis of the infecting strain is determined.

With respect to the aerosol administration to the lungs or other mucosal surfaces, the therapeutic composition is incorporated into an aerosol formulation specifically designed for administration. Many such aerosols are known in the art, and the present invention is not limited to any particular formulation. An example of such an aerosol is the Proventil™ inhaler manufactured by Schering-Plough, the propellant of which contains trichloromonofluoromethane, dichlorodifluoromethane, and oleic acid. Other embodiments include inhalers that are designed for administration to nasal and sinus passages of a subject or patient. The concentrations of the propellant ingredients and emulsifiers are adjusted if necessary based on the specific composition being used in the treatment. The number of enzyme killing units to be administered per aerosol treatment will typically be in the range of about $10^6$ to $10^{13}$ killing units, e.g., about $10^{12}$ killing units.

Typically, the killing will decrease the host replication capacity by at least 3 fold, e.g., 10, 30, 100, 300, etc., to many orders of magnitude. Slowing the rate of host replication without killing can also have significant therapeutic or commercial value. Genetic inactivation efficiencies may be 4, 5, 6, 7, 8, or more log units.

VIII. Formulations

The invention further contemplates pharmaceutical compositions comprising a described chimeric polypeptide, e.g., a LysMTD containing entity, of the invention provided in a pharmaceutically acceptable excipient. The formulations and pharmaceutical compositions of the invention thus contemplate formulations comprising an isolated polypeptide specific for a bacterial host; a mixture of two, three, five, ten, or twenty or more such entities that affect the same or different bacterial hosts; and a mixture of two, three, five, ten, or twenty or more entities that affect different bacterial hosts or different strains of the same bacterial host, e.g., a cocktail mixture of enzymes that collectively inhibit the growth of multiple Gram-negative bacterial species. In this manner, the compositions of the invention can be tailored to the needs of the patient. The compounds or compositions can be sterile or near sterile.

A "therapeutically effective dose" is a dose that produces the effects, bacteriostatic (reducing bacterial growth) or bactericidal (killing bacteria), for which it is administered. The exact dose will depend on the purpose of the treatment, and will be ascertainable by one skilled in the art using known techniques. See, e.g., Ansel, et al. (2010), *Pharmaceutical Dosage Forms and Drug Delivery*; Lieberman (1992) *Pharmaceutical Dosage Forms* (vols. 1-3), Dekker; Lloyd (1999) *The Art, Science and Technology of Pharmaceutical Compounding*; and Pickar (1999) *Dosage Calculations*. As is known in the art, adjustments for protein degradation, systemic versus localized delivery, as well as the age, body weight, general health, sex, diet, time of administration, drug interaction, and the severity of the condition may be necessary, and will be ascertainable by those skilled in the art.

Various pharmaceutically acceptable excipients are well known in the art. As used herein, "pharmaceutically acceptable excipient" includes a material which, when combined with an active ingredient of a composition, allows the ingredient to retain biological activity and without causing disruptive reactions with the subject's immune system. Such excipients include stabilizers, preservatives, salt or sugar complexes or crystals, and the like.

Exemplary pharmaceutically carriers include sterile aqueous or non-aqueous solutions, suspensions, and emulsions. Examples include, but are not limited to, standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In other embodiments, the compositions will be incorporated into solid matrix, including slow release particles, glass beads, bandages, inserts on the eye, and topical forms.

Further included are formulations for liposomal delivery, and formulations comprising microencapsulated enzymes, including sugar crystals. Compositions comprising such excipients are formulated by well known and/or conventional methods (see, e.g., *Remington's Pharmaceutical Sciences*, Chapter 43, 14th Ed., Mack Publishing Co.). The proteins may be subjected to PEGylation to achieve advantages often deriving therefrom. See, e.g., Jevsevar, et al. (2010) *Biotechnol. J.* 5:113-128; Brocchini, et al. (2008) *Adv. Drug Delivery Revs.* 60:3-12; Jain and Jain (2008) *Crit. Rev. Ther. Drug Carrier Syst.* 25:403-47, PMID: 190626331; and Shaunak, et al. (2006) *Nature Chemical Biology* 2:312-313. Alternatives exist for achieving similar stabilizing results. See, e.g., Schellenberger, et al. (2009) *Nature Biotechnology* 27:1186-1192.

In general, pharmaceutical compositions can be prepared in various forms, such as granules, tablets, pills, capsules (e.g., adapted for oral delivery), suppositories, microbeads, microspheres, liposomes, suspensions, solutions, salves, lotions, ointments, and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Formulations may incorporate stabilizing agents, wetting and emulsifying agents, salts for varying the osmotic pressure or buffers for securing an adequate pH value.

The pharmaceutical composition can comprise other components in addition to the chimeric polypeptide, e.g., more than one active ingredient, e.g., two or more, three or more, five or more, or ten or more different enzymes, where the different enzymes may be specific for the same, different, or accompanying bacteria. For example, the pharmaceutical composition can contain multiple (e.g., at least two or more) defined chimeric polypeptide of the invention, wherein at least two of the polypeptides in the composition have different bacterial host specificity or different peptidoglycan linkage specificity, such as a combination of a transglycolase and an endopeptidase. In this manner, the therapeutic composition can be adapted for treating a mixed infection of different bacteria, or may be a composition selected to be effective against various types of infections found commonly in a particular institutional environment. A select combination may result, e.g., by selecting different groups of cell wall degrading entities derived from various bacteriophage of differing specificity so as to target multiple strains present, or potentially present in the infection. As noted above, the wall degrading enzyme can be administered in conjunction with other agents, such as a conventional antimicrobial agent or a reagent which provides for efficacy against biofilm or capsule forming cultures. Various materials are described, e.g., in Davies and Marques (2009) *J. Bacteriology* 191:393-403; Kimura and Itoh (2002) *Appl. and Env. Microbiology* 69:2491-2497; Kim and Geider (2000) *Phytopathology* 90 1263-1268; Hughes, et al. (1998) *J. Appl. Microbiology* 85:583-590; and Bartell and Orr (1969) *J. Virology* 4:580-584. In some embodiments, an additive (e.g., fatty acid) or biofilm depolymerase may be added as an additional domain to the chimeric construct, as an additional component in a formulation, or administered in combination, simultaneously or sequentially, with the polypeptide.

IX. Modification of Protein Sequence for Improved Production

LysMTDfusion constructs may be hydrophobic in nature, and a chimeric protein including such a LysMTD may be insoluble when expressed in a production host such as *E. coli*. Constructs can be generated which exhibit an unexpected combination of properties. A construct can be designed to be sufficiently hydrophilic to remain soluble within the producing cell host, and fail to traverse the producing host cell inner membrane. The modified construct retains the LysMTD function to traverse the bacterial outer cell wall to effect target bacteria killing but itself does not kill the producing cell. This may be achieved because the bacterial cell membrane properties (and structure) are sufficiently different from the bacterial outer membrane.

Such improved production constructs combine three properties: (1) produced in substantially soluble form in a host cell, typically Gram-negative *E. coli*; (2) retains function of traversing the bacterial outer cell wall to access the periplasmic space where the substrate peptidoglycan is accessible to the catalytic domain; and (3) no substantial disruption of the inner membrane of the producing cell. Appropriate controls (such as the non-modified construct) will be incorporated to ensure that cell survival, expression, and catalytic activity are be quantitated or relatively assessed.

X. Modification of Protein for Improved Half-Life, Stability, Storage

Addition of a polyalkylene glycol (PAG) moiety to a polypeptide or other molecule is referred to as PAGylation. PAGylation (typically PEGylation) can improve the pharmacokinetic and pharmacodynamic properties of a polypeptide, e.g., increase in vitro and in vivo activity and stability, increase half-life, reduce proteolytic degradation, reduce immunogenicity, and improve bioavailability and biodistribution. Amino acids that are commonly targeted for PAGylation are arginine, aspartic acid, glutamic acid, tyrosine, serine, threonine, histidine, cysteine, and lysine. The ε-amino group on the side chain of lysine is commonly targeted for PAGylation.

Polyethylene glycol (PEG) is commercially available over a wide range of molecular weights from 300 g/mol to 10,000,000 g/mol. Different forms of PEG can be made using different initiators for the polymerization process, the most common of which is a monofunctional methyl ether PEG (methoxypoly(ethylene glycol)), referred to as mPEG. Lower-molecular-weight PEGs are also available as purer oligomers, referred to as monodisperse, uniform or discrete.

PEG molecules can have different geometries. Branched PEGs have three to ten PEG chains emanating from a central core group. Star PEGs have 10-100 PEG chains emanating from a central core group. Comb PEGs have multiple PEG chains normally grafted to a polymer backbone.

Melting points vary depending on the MW of the polymer. PEG has the structure:

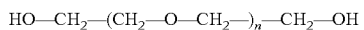

where n=9 would have an average molecular weight of approximately 400 daltons (PEG 400). Ideally, for therapeutic consistency and regulatory reasons, the PEG polymers added to the polypeptide are highly uniform (low dispersity). For a MW of about 5 KDa then n is about 100; and for the MW of about 20 KDa, n is about 400.

In addition to amino acid attachment site, considerations for the PEGylation reaction include the initiator PEGylating reagents, the PEG-to-protein ratio, pH, reaction time, and temperature (see, e.g., Seely, et al. (2005) "Making Site-specific PEGylation Work: Purification and analysis of PEGylated protein pharmaceuticals presents many challenges' *BioPharm International* 18:30-41).

Cys specific reagents include iodoacetamide or chloroacetamide chemistries, and maleimide chemistry has also been applied (Kalia and Raines (2010) *Curr. Org. Chem.* 14:138-147). PEG maleimide, PEG iodoacetate, PEG thiols, and PEG vinylsulfone are thus useful reagents which allow cysteine specific PEGylation under mild conditions.

Agents that add PEG to the N-terminal amino acid of a given polypeptide include PEG NHS ester, PEG tresylate, PEG aldehyde, PEG isothiocyanate, and several others (Nucci, et al. (1991) *Adv. Drug Del. Rev.* 6:133-151; Harris, et al. (1984) *J. Poly. Sci: Polymer Chem. Ed.* 22:341-352; Bailon and Berthold (1998) *Pharm. Sci. Technol. Today* 1:352-356). All react under mild conditions and are quite specific for amino groups. Generally the pK of the alpha-amino group is 1-2 pH units lower than the epsilon-amino group of lysine residues. By PEGylating the molecule at pH 7 or below, high selectivity for the N-terminus is attained.

PEG molecules and conditions for PEGylation are known in the art. See, e.g., Abuchowski, et al. (1984) *Cancer Biochem. Biophys.* 7:175-186; Abuchowski, et al. (1977) *J. Biol. Chem.* 252:3582-3586; Jackson, et al. (1987) *Anal. Biochem.* 165:114-127; Koide, et al. (1983) *Biochem. Biophys. Res. Commun.* 111:659-667; tresylate (Nilsson, et al. (1984) *Methods Enzymol* 104:56-69; Delgado, et al. (1990) *Biotechnol. Appl. Biochem.* 12:119-128); N-hydroxysuccinimide derived active esters (Buckmann, et al. (1981) *Makromol. Chem.* 182:1379-1384; Joppich, et al. (1979) *Makromol. Chem.* 180:1381-1384; Abuchowski, et al. (1984) *Cancer Biochem. Biophys.* 7:175-186; Katre, et al. (1987) *Proc. Natl. Acad. Sci. USA* 84:1487-1491; Kitamura, et al. (1991) *Res.* 51:4310-4315; Boccu, et al. (1983) *Z. Naturforsch.* 38C:94-99); carbonates (Zalipsky, et al. pp. 347-370 in Harris (ed. 1992) *Poly(ethylene glycol) Chemistry: Biotechnical and Biomedical Applications* Plenum Press, New York; Zalipsky, et al. (1992) *Biotechnol. Appl. Biochem.* 15:100-114; Veronese, et al. (1985) *Appl. Biochem. Biotech.* 11:141-152); imidazolyl formates (Beauchamp, et al. (1983)

*Anal. Biochem.* 131:25-33; Berger, et al. (1988) *Blood* 71:1641-1647); 4-dithiopyridines (Woghiren, et al. (1993) *Bioconjugate Chem.* 4:314-318); isocyanates (Byun, et al. (1992) *ASAIO Journal M*649-M653); and epoxides (U.S. Pat. No. 4,806,595, issued to Noishiki, et al. (1989)). Other linking groups include, e.g., the urethane linkage between amino groups and activeated PEG (Veronese, et al. (1985) *Appl. Biochem. Biotechnol.* 11:141-152).

A bifunctional PEG can be used to as a linker for the muralytic domain and LysMTD of the chimeric proteins described herein. For example, homobifunctional PEG can be used to conjugate the N-terminus of the LysMTD to the N-terminus of the catalytic domain (or vice versa). In some embodiments, a Y structure PEG derivative with one branch of the Y having an N-terminus specific group (e.g., aldehyde reactive group) and the other with a C-terminus specific group (e.g., hydrazine) is used. In some embodiments, a linear PEG with the reactive groups at either end is used.

In some embodiments, a cysteine residue is introduced on to the N or C terminus of the domains, and a heterobifunctional PEG (e.g., Thiol-PEG-Amine, a product with one end as thiol and the other end as amine) is used. Boc or Fmoc can be used to block amine groups.

Conjugation reactions can be performed in succession, and may involve purification steps to remove undesired reactants and products. The purification methods will generally be typical peptide purification methods, many of which are known in protein chemistry. These may include size exclusion chromatography, ion exchange chromatography, etc.

The PEG reacting group for a C terminus can be a hydrazine or similar specific reacting group. The reaction will typically be for 0.5-18 hr; at an appropriate reaction temperature, e.g., between 20-40° C.; with appropriate peptide concentrations, e.g., 0.5-3 mg/ml; with appropriate PEG reagent concentrations, e.g., about 1-10 fold excess of PEG to protein target; and appropriate pH, e.g., pH 4-7. The reaction can be terminated, the reactants removed, and the desired PEGylated polypeptide isolated.

The reaction linking the domain-PEG reacting group to the N terminus of the other domain can be an aldehyde or similar specific reacting group. Again, the reaction can run for an appropriate time, at an appropriate reaction temperature, with appropriate peptide concentrations, and with appropriate reagent concentrations, and appropriate pH.

Methoxypolyethylene glycol tresylate (mPEG-tresylate MW 5 kDA) can be used for lysine specific PEGylation of the target protein. Typically, mPEG-tresylate is incubated with the protein at 30° C. for 3 hr.

Methoxypolyethylene glycol maleimide (mPEG-maleimide, MW 5 kDA), a cysteine specific PEG targeting reagent, can be used to PEGylate the desired protein. Typically, mPEG-maleimide is reacted with the target proteinat 30° C. for 3 hr.

Methoxypolyethylene glycol propionaldehyde is an N terminal specific PEG targeting reagent (mPEG-aldehyde, MW 20 kDA). Typically, mPEG-aldehyde is incubated with the desired protein at 30° C. for 3-4 hr.

Standard SDS-PAGE electrophoresis is routinely employed to monitor the PEGylation reaction and the products of the derivitization. Anomalous SDS-PAGE migration as compared to molecular weight markers typically results from the non-linear nature of the PEGylated products. In particular, because the PEG provides different SDS binding compared to protein, migration of standard proteinaceous molecular weight markers does not correlate with the migration of protein derivatized with different integral numbers of PEG moieties. The stoichiometry of binding of SDS to the PEG is different from linear protein, and the charge ratio is non-linear.

The extent of PEGylation can be determined using a microfluidic based electrophoresis system, the Agilent 2100 Bioanalyzer (P230 assay). For the Bioanalyzer, protein loading and on-chip sample analysis were performed as described in the manufacturer's protocol. See Protein 230 Kit Guide, Agilent Technologies Publication Number G2938-90054. PEGylation reactions typically result in differently PEGylated protein species (un-, mono-, di-, tri-, etc.), having different numbers of PEG moieties attached.

XI. Methodology

Production and use of the presently described chimeric polypeptides involve well-known methods general clinical microbiology, general methods for handling bacteriophage, and general fundamentals of biotechnology, principles and methods. References for such methods are listed below.

A. General Clinical Microbiology

General microbiology is the study of the microorganisms. See, e.g., Sonenshein, et al. (ed. 2002) *Bacillus Subtilis and Its Closest Relatives: From Genes to Cells* Amer. Soc. Microbiol.; Alexander and Strete (2001) *Microbiology: A Photographic Atlas for the Laboratory* Benjamin/Cummings; Cann (2001) *Principles of Molecular Virology* (3d ed.); Garrity (ed. 2005) *Bergey's Manual of Systematic Bacteriology* (2 vol. 2d ed.) Plenum; Salyers and Whitt (2001) *Bacterial Pathogenesis: A Molecular Approach* (2d ed.) Amer. Soc. Microbiol.; Tierno (2001) *The Secret Life of Germs: Observations and Lessons from a Microbe Hunter* Pocket Star; Block (ed. 2000) *Disinfection, Sterilization, and Preservation* (5th ed.) Lippincott Williams & Wilkins Publ.; Cullimore (2000) *Practical Atlas for Bacterial Identification* Lewis Pub.; Madigan, et al. (2000) *Brock Biology of Microorganisms* (9th ed.) Prentice Hall; Maier, et al. (eds. 2000) *Environmental Microbiology* Academic Pr.; Tortora, et al. (2000) *Microbiology: An Introduction* including Microbiology Place™ Website, Student Tutorial CD-ROM, and Bacteria ID CD-ROM (7th ed.), Benjamin/Cummings; Demain, et al. (eds. 1999) *Manual of Industrial Microbiology and Biotechnology* (2d ed.) Amer. Soc. Microbiol.; Flint, et al. (eds. 1999) *Principles of Virology: Molecular Biology, Pathogenesis, and Control* Amer. Soc. Microbiol.; Murray, et al. (ed. 1999) *Manual of Clinical Microbiology* (7th ed.) Amer. Soc. Microbiol.; Burlage, et al. (eds. 1998) *Techniques in Microbial Ecology* Oxford Univ. Press; Forbes, et al. (1998) *Bailey & Scott's Diagnostic Microbiology* (10th ed.) Mosby; Schaechter, et al. (ed. 1998) *Mechanisms of Microbial Disease* (3d ed.) Lippincott, Williams & Wilkins; Tomes (1998) *The Gospel of Germs: Men, Women, and the Microbe in American Life* Harvard Univ. Pr.; Snyder and Champness (1997) *Molecular Genetics of Bacteria* Amer. Soc. Microbiol., ISBN: 1555811027; Karlen (1996) *ManAnd Microbes: Disease and Plagues in History and Modern Times* Touchstone Books; and Bergey (ed. 1994) *Bergey's Manual of Determinative Bacteriology* (9th ed.) Lippincott, Williams & Wilkins.

B. General Methods for Handling Bacteriophage

General methods for handling bacteriophage are well known, see, e.g., Snustad and Dean (2002) *Genetics Experiments with Bacterial Viruses* Freeman; O'Brien and Aitken (eds. 2002) *Antibody Phage Display: Methods and Protocols* Humana; Ring and Blair (eds. 2000) *Genetically Engineered Viruses* BIOS Sci. Pub.; Adolf (ed. 1995) *Methods in Molecular Genetics: Viral Gene Techniques* vol. 6, Elsevier;

Adolf (ed. 1995) *Methods in Molecular Genetics: Viral Gene Techniques* vol. 7, Elsevier; and Hoban and Rott (eds. 1988) *Molec. Biol. of Bacterial Virus Systems* (Current Topics in Microbiology and Immunology No. 136) Springer-Verlag.

C. General Fundamentals of Biotechnology, Principles and Methods

General fundamentals of biotechnology, principles and methods are described, e.g., in Alberts, et al. (2002) *Molecular Biology of the Cell* (4th ed.) Garland; Lodish, et al. (1999) *Molecular Cell Biology* (4th ed.) Freeman; Janeway, et al. (eds. 2001) *Immunobiology* (5th ed.) Garland; Flint, et al. (eds. 1999) *Principles of Virology: Molecular Biology, Pathogenesis, and Control, Am. Soc. Microbiol.*; Nelson, et al. (2000) *Lehninger Principles of Biochemistry* (3d ed.) Worth; Freshney (2000) *Culture of Animal Cells: A Manual of Basic Technique* (4th ed.) Wiley-Liss; Arias and Stewart (2002) *Molecular Principles of Animal Development*, Oxford University Press; Griffiths, et al. (2000) *An Introduction to Genetic Analysis* (7th ed.) Freeman; Kierszenbaum (2001) *Histology and Cell Biology*, Mosby; Weaver (2001) Molecular Biology (2d ed.) McGraw-Hill; Barker (1998) *At the Bench: A Laboratory Navigator* CSH Laboratory; Branden and Tooze (1999) *Introduction to Protein Structure* (2d ed.), Garland Publishing; Sambrook and Russell (2001) *Molecular Cloning: A Laboratory Manual* (3 vol., 3d ed.), CSH Lab. Press; Scopes (1994) *Protein Purification: Principles and Practice* (3d ed.) Springer Verlag; Simpson, et al. (eds. 2009) *Basic Methods in Protein Purification and Analysis: A Laboratory Manual*, CSHL Press, NY, ISBN 978-087969868-3; Friedmann and Rossi (eds. 2007) *Gene Transfer: Delivery and Expression of DNA and RNA, A Laboratory Manual*, CSHL Press, NY, ISBN 978-087969764-8; Link and LaBaer (2009) *Proteomics: A Cold Spring Harbor Laboratory Course Manual*, CSHL Press, NY, ISBN 978-087969793-8; and Simpson (2003) *Proteins and Proteomics: A Laboratory Manual*, CSHL Press, NY, ISBN 978-087969554-5, Other references directed to bioinformatics include, e.g., Mount (2004) *Bioinformatics: Sequence and Genome Analysis* (2d ed.), CSHL Press, NY, ISBN 978-087969687-0; Pevsner (2009) *Bioinformatics and Functional Genomics* (2d ed.) Wiley-Blackwell, ISBN-10: 0470085851, ISBN-13: 978-0470085851; Lesk (2008) *Introduction to Bioinformatics* (3d ed.) Oxford Univ. Press, ISBN-10: 9780199208043, ISBN-13: 978-0199208043; Zvelebil and Baum (2007) *Understanding Bioinformatics*, Garland Science, ISBN-10: 0815340249, ISBN-13: 978-0815340249; Baxevanis and Ouellette (eds. 2004) *Bioinformatics: A Practical Guide to the Analysis of Genes and Proteins* (3d ed.) Wiley-Interscience; ISBN-10: 0471478784, ISBN-13: 978-0471478782; Gu and Bourne (eds. 2009) *Structural Bioinformatics* (2d ed.), Wiley-Blackwell, ISBN-10: 0470181052, ISBN-13: 978-0470181058; Selzer, et al. (2008) *Applied Bioinformatics: An Introduction*, Springer, ISBN-10: 9783540727996, ISBN-13: 978-3540727996; Campbell and Heyer (2006) *Discovering Genomics, Proteomics and Bioinformatics* (2d ed.), Benjamin Cummings, ISBN-10: 9780805382198, ISBN-13: 978-0805382198; Jin Xiong (2006) *Essential Bioinformatics*, Cambridge Univ. Press, ISBN-10: 0521600820, ISBN-13: 978-0521600828; Krane and Raymer (2002) *Fundamental Concepts of Bioinformatics*, Benjamin Cummings, ISBN-10: 9780805346336, ISBN-13: 978-0805346336; He and Petoukhov (2011) *Mathematics of Bioinformatics: Theory, Methods and Applications* (Wiley Series in Bioinformatics), Wiley-Interscience, ISBN-10: 9780470404430, ISBN-13: 978-0470404430; Alterovitz and Ramoni (2011) *Knowledge-Based Bioinformatics: From analysis to interpretation*, Wiley, ISBN-10: 9780470748312, ISBN-13: 978-0470748312; Gopakumar (2011) *Bioinformatics: Sequence and Structural Analysis*, Alpha Science Intl Ltd., ISBN-10: 184265490X, ISBN-13: 978-1842654903; Barnes (ed. 2007) *Bioinformatics for Geneticists: A Bioinformatics Primer for the Analysis of Genetic Data* (2d ed.) Wiley, ISBN-10: 9780470026199, ISBN-13: 978-0470026199; Neapolitan (2007) *Probabilistic Methods for Bioinformatics*, Kaufmann Publishers, ISBN-10: 0123704766, ISBN-13: 978-0123704764; Rangwala and Karypis (2010) *Introduction to Protein Structure Prediction: Methods and Algorithms* (Wiley Series in Bioinformatics), Wiley, ISBN-10: 0470470593, ISBN-13: 978-0470470596; Ussery, et al. (2010) *Computing for Comparative Microbial Genomics: Bioinformatics for Microbiologists* (Computational Biology), Springer, ISBN-10: 9781849967631, ISBN-13: 978-1849967631; and Keith (ed. 2008) *Bioinformatics: Volume I: Data, Sequence Analysis and Evolution* (Methods in Molecular Biology), Humana Press, ISBN-10: 9781588297075, ISBN-13: 978-1588297075.

The following references provide additional guidance for fusion and chimeric proteins: Hammarstrom, et al. (2001) Protein Science 11:313-321; Harrison (1999) *InNovations* 11:4-7; Banerjee and Padmanabhan WO/2010/125588.

D. Mutagenesis; Site Specific, Random, Shuffling

Based upon the structural and functional descriptions provide herein, homologs and functional variants can be generated. Segments with penetration functions can be found by structural homology. Phage tail genes are typically found in particular gene arrangements, and other entities found in the corresponding arrangements can be tested for cell wall degrading function. These may also serve as the starting points to screen for variants of the structures, e.g., mutagenizing such structures and screening for those which have desired characteristics, e.g., broader substrate specificity. Standard methods of mutagenesis may be used, see, e.g., Johnson-Boaz, et al. (1994) *Mol. Microbiol.* 13:495-504; U.S. Pat. Nos. 6,506,602, 6,518,065, 6,521,453, 6,579,678.

LysM transfer segments can be similarly identified, and prevalent or specific target motifs can be screened for receptor domains which specifically interact. Targets can be surface expressed proteins, carbohydrate, or lipid containing structures found on the various target strains. Mutagenesis can be used to broaden binding selectivity or increase stability of segments or the entire construct, deletion strategies may eliminate extraneous segments.

The components of the Gram-positive bacteria cell wall can be shared with components of the Gram-negative cell wall, or with other mycobacteria or spores. Other phage derived activities can be combined to penetrate more complex Gram-negative cell wall structures if necessary. In particular, multiple functional segments can be used to provide multiple activities, which can function synergistically within a single construct or when combined with another therapeutic, e.g., antibiotic or antimicrobial.

A targeting moiety can increase a local concentration of an active moiety, but a linker of appropriate length may also increase the number of functionally active events locally. Thus, linkers compatible with the target and killing segment, or of appropriate length, can be used to increase the cell wall penetration activity leading to stasis or killing of target bacteria.

Phage have been selected to survive outside of cells, often under biologically inhospitable conditions. Thus, the structures are likely to be particularly hardy and robust, and resistant to the environmental conditions which might otherwise inactivate enzymatic or catalytic entities. Bacteria which live in inhospitable environments, e.g., extreme environments of temperature, salt, oxidizing or reactive extremes, high pressure, etc., are targeted by phage which are particularly adapted to survive those conditions. Polypeptides derived from these phage are likely to be more stable in various purification processes, storage, and pharmacological conditions of use.

E. Screening

Screening methods can be devised for evaluating mutants or new candidate functional segments. A purified preparation of phage particles can be screened for presence of such gene products on the phage structure.

Functional activity screens can use crude bacteria cultures, isolated bacterial cell wall components, peptidoglycan preparations, synthetic substrates, or purified reagents to determine the affinity and number of substrate sites on target cells. Penetration or wall degrading assays can be incorporated to evaluate integrity of the outer membranes of target strains, lawn inhibition assays, viability tests of cultures, activity on cell wall preparations or other substrates, or release of components (e.g., sugars, amino acids, polymers) of the cell wall upon muralytic action. Amidase activity may be measured by release of soluble N-acetyl hexose amines (e.g., modified Morgan-Elson reaction) or endopeptidase activity by assay for free amino groups (L-alanine for ala-gly endopeptidases, L-glycine for gly-gly endopeptidases) using a DNFB assay), all three of these assays based on Petit, et al. (1966) *Biochemistry* 5:2764-76. Gly-gly endopeptidase activity can also be measured as the release of free aminogroups from N-acetylated hexaglycine(acetyl-Gly6) (SEQ ID NO: 23), see Kline, et al. (1994) *Anal. Biochem.* 217:329-331. Lysozyme activity may be measured by using *Micrococcus bysodeikticus* cells as a substrate and measuring the decrease in absorbance at 450 nm, see Shugar (1952) *Biochimica Biophysica Acta* 8:302-309.

Linkers can be tested to compare the effects on LysM transfer or linked functions, or to compare the activities of various orientations of the active fragments. Panels of targets (e.g., Gram-negative, Gram-positive, mycobacteria and spores) can be screened using cell wall degrading fragments to determine which fragments on a broader or narrower spectrum of targets.

One method to test for a cell wall degrading activity is to treat phage with mild detergents or denaturants to release proteins associated with the virion. These proteins are further tested for wall degrading ormuralytic activity on bacterial cells. Another method is to determine cell wall degradation activity or lysis from without (LO) on a phage resistant host. A third method to assess walldegrading or muralytic activity associated with phage structural component is to perform Zymogram assays, e.g., where a pure phage preparation is electrophoresed on SDS-polyacrylamide gel incorporating autoclaved host cells. Proteins on the gels are allowed to renature in situ and then act upon the cell wall components giving rise to clear "muralytic" zones when the rest of the gel stains blue with methylene blue dye. See, e.g., Lepeuple, et al, (1998) *Appl. Environ. Microbiol.* 64:4142-428. The clear zones are visualized and the protein band from each zone is eluted. The protein can be identified, e.g., by N-terminal sequencing or by Mass spectrometry. The coding sequence for the degrading protein can then be isolated.

XII. Isolation of nucleic acids encoding LysMTDs and/or functional domains

Further provided are nucleic acids that encode the chimeric polypeptides of the invention, and additional source sequences for alternative LysM transfer or other functional segments or domains. The described sources may be directly used, may be used as segments for further homology searches, or for searching for similar functions based, e.g., on genome organization or structures where similar functions are similarly organized. Such polynucleotides may encode muralytic proteins described herein, including proteins with CHAP domains (particularly C terminal CHAP domains) and others with cell wall degrading activity, AMP, LPS binding, and other described functional segments.

Nucleic acids that encode functional polypeptide segments are relevant to the nucleic acid embodiments of the invention. These nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). Besides synthetic methodologies, a wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc.; Sambrook, et al. (1989) *Molecular Cloning—A Laboratory Manual* (2nd ed.) Vol. 1-3, Cold Spring Harbor Laboratory, Cold Spring Harbor Press; *Current Protocols in Molecular Biology*, Ausubel, et al., eds., *Current Protocols* (Greene Publishing Associates, Inc. and John Wiley & Sons, Inc., 1994 Supplement); Cashion, et al., U.S. Pat. No. 5,017,478; and Carr, European Patent No. 0246864. Although in vitro methods are typically most expedient, analogous natural or high recombination in vivo systems may generate similar constructs which may be identified and isolated.

A DNA that encodes a phi29 endolysin polypeptide can be prepared by a suitable method described above, including, e.g., cloning and restriction of appropriate sequences with restriction enzymes. Nucleic acids encoding cell wall degrading polypeptides can be isolated by routine cloning methods. An exemplary nucleotide sequence of the phi29 endolysin polypeptide, e.g., in Genbank Acc no: NC_011048.1:15457-16233, can be used to design probes that specifically hybridize to a gene; or to an mRNA, encoding the lysozyme or the LysM domain polypeptide, in a total nucleic acid sample (e.g., in a Southern or Northern blot). Once the target nucleic acid encoding the desired protein is identified, it can be isolated according to standard methods known to those of skill in the art. Further, the isolated nucleic acids can be cleaved with restriction enzymes to create nucleic acids encoding the full-length cell wall degrading polypeptide, or subsequences thereof, e.g., containing subsequences encoding at least a subsequence of a segment or domain of the polypeptide. These restriction enzyme fragments, encoding a desired polypeptide or subsequences thereof, can then be ligated, for example, to produce a nucleic acid encoding a LysM membrane traversing polypeptide segment.

Similar methods can be used to generate appropriate cell wall binding fragments, functional segments as described, or linkers between fragments.

A nucleic acid encoding an appropriate polypeptide, or a subsequence thereof, can be characterized by assaying for the expressed product. Assays based on the detection of the physical, chemical, or immunological properties of the expressed polypeptide can be used. For example, one can identify a cell wall degrading polypeptide by the ability of a polypeptide encoded by the nucleic acid to degrade or digest bacterial cells, e.g., as described herein. Assays for membrane traversing are available, as described.

Also, a nucleic acid encoding a desiredpolypeptide, or a subsequence thereof, can be chemically synthesized. Suitable methods include the phosphotriester method of Narang, et al. (1979). *Meth. Enzymol,* 68:90-99; the phosphodiester method of Brown, et al. (1979) *Meth. Enzymol.* 68:109-151; the diethylphosphoramidite method of Beaucage, et al. (1981) *Tetra. Lett.* 22:1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding a desired polypeptide, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired polypeptide or subsequence and having terminal restriction enzyme sites. This nucleic acid can then be easily ligated into a vector containing a nucleic acid encoding the second molecule and having the appropriate corresponding restriction enzyme sites. Suitable PCR primers can be determined by one of skill in the art using the sequence information provided in GenBank or other sources. Appropriate restriction enzyme sites can also be added to the nucleic acid encoding the cell wall degrading polypeptide or a polypeptide subsequence thereof by site-directed mutagenesis. The plasmid containing a cell wall degrading polypeptide-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis, et al. (1987) U.S. Pat. No. 4,683,202; *PCR Protocols A Guide to Methods and Applications* (Innis, et al., eds) Academic Press Inc. (1990); Arnheim and Levinson (Oct. 1, 1990) *C&EN* 36-47; *The Journal Of NIH Research* (1991) 3:81-94; Kwoh, et al. (1989) *Proc. Natl. Acad. Sci. USA* 86:1173; Guatelli, et al. (1990) *Proc. Natl. Acad. Sci. USA* 87:1874; Lomell, et al. (1989) *J. Clin. Chem.* 35:1826; Landegren, et al. (1988) *Science* 241:1077-1080; Van Brunt (1990) *Biotechnology* 8:291-294; Wu and Wallace (1989) *Gene* 4:560; and Barringer, et al. (1990) *Gene* 89:117.

Some nucleic acids encoding cell wall degrading polypeptides can be amplified using PCR primers based on the sequence of the identified polypeptides.

Other physical properties, e.g., of a recombinant cell wall degrading polypeptide embodiments of the proteins of this invention expressed from a particular nucleic acid, can be compared to properties of known desired polypeptides to provide another method of identifying suitable sequences or domains, e.g., of the cell wall degrading proteins that are determinants of bacterial specificity, binding specificity, and/or catalytic activity. Alternatively, a cell wall degrading polypeptide encoding nucleic acid or recombinant cell wall degrading polypeptide gene can be mutated, and its role as a cell wall degrading polypeptide, or the role of particular sequences or domains established by detecting a variation in bacterial "lysis" normally enhanced by the unmutated, naturally-occurring, or control cell wall degrading polypeptide. Those of skill will recognize that mutation or modification of cell wall degrading polypeptides of the invention can be facilitated by molecular biology techniques to manipulate the nucleic acids encoding the polypeptides, e.g., PCR. Other mutagenesis or gene shuffling techniques may be applied to the functional fragments described herein, including membrane traversing activities, wall degrading activities, wall binding properties, or linker features compatible with chimeric constructs.

Functional domains of newly identified LysM membrane traversing polypeptides can be identified by using standard methods for mutating or modifying the polypeptides and testing them for function, as described herein. The sequences of functional domains of the various cell wall traversing proteins can be used to construct nucleic acids encoding or combining functional domains of one or more traversing polypeptides. These multiple activity polypeptide fusions can then be tested for a desired bacteriostatic or bacteriolytic activity. Particular examples of sources for cell wall degrading polypeptides include prophage sequences, including incomplete remnants of functional phage genomes, or pyocin-like structures, including particles derived from phage-like genetic segments, e.g., deletion or mutated genetic remnants of phage remaining in the DNA of a bacterium, or bacterial autolyins involved in peptidoglycan remodelling.

Nucleic acids encoding membrane traversing or cell wall degrading polypeptides can be identified by alignment and comparison with known nucleic acid or amino acid sequences of previously identified polypeptides, e.g., to determine the amount of sequence identity between them. This information can be used to identify and select polypeptide domains that confer or modulate traversing or cell wall degrading polypeptide activities, e.g., target bacterial or binding specificity and/or degrading activity based on the amount of sequence identity between the polypeptides of interest. For example, domains having sequence identity between the cell wall degrading polypeptides of interest, and that are associated with a known activity, can be used to construct polypeptides containing that domain and other domains, and having the activity associated with that domain (e.g., bacterial or binding specificity and/or wall degrading activity). Similar strategies may be applied to isolate bacterial SH3 domains which bind to cell wall structures, peptidoglycan recognizing proteins (PGRPs), phage tail "muralytic" polypeptides, or to linkers for spacing between domains.

XIII. Expression of Desired Polypeptides in Host Cells

The proteins described herein can be expressed in a variety of host cells, including *E. coli*, other bacterial hosts, and yeast. The host cells can be microorganisms, such as, for example, yeast cells, bacterial cells, or filamentous fungal cells. Examples of suitable host cells include, for example, *Azotobacter* sp., (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus, Staphylococcus,* and *Klebsiella* sp., among many others. The cells can be of any of several genera, including) *Saccharomyces* (e.g., *S. cerevisiae*), *Candida* (e.g., *C. utilis, C. parapsilosis, C. krusei, C. versatilis, C. lipolytica, C. zeylandoides, C. guil-*

*liermondii, C. albicans*, and *C. humicola*), *Pichia* (e.g., *P. farinosa* and *P. ohmeri*), *Torulopsis* (e.g., *T. candida, T. sphaerica, T. xylinus, T. fannota*, and *T. versatilis*), *Debaryomyces* (e.g., *D. subglobosus, D. cantarelli, D. globosus, D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anamala* and *H. jadimi*), and *Brettanomyces* (e.g., *B. lambicus* and *B. anomalus*). Examples of useful bacteria include, but are not limited to, *Escherichia, Enterobacter, Azotobacter, Erwinia, Klebsielia, Bacillus, Pseudomonas, Proteus*, and *Salmonella*. Eukaryotic cells, e.g., CHO cells, can also be used for production.

Once expressed in a host cell, the cell wall degrading polypeptides can be used to prevent growth or kill target bacteria. In some embodiments, the various polypeptides are used to decrease growth of a Gram-negative bacterium. In some embodiments, the protein is used to decrease growth of, e.g., a *Pseudomonas*, e.g., *Pseudomonas aeruginosa*, bacterium. Fusion constructs combining such fragments can be generated, including fusion proteins comprising a plurality of wall degrading activities, including lysozymes, lytic transglycosylases, transglycosylases, peptidase, and amidase catalytic activities which degrade the peptidoglycan of Gram-negative bacteria.

Typically, a polynucleotide that encodes the membrane traversing polypeptides is placed under the control of a promoter that is functional in the desired host cell. An extremely wide variety of promoters is well known, and can be used in expression vectors of the invention, depending on the particular application. Ordinarily, the promoter selected depends upon the cell in which the promoter is to be active. Other expression control sequences such as ribosome binding sites, transcription termination sites, etc., can be included. Constructs that include one or more of these control sequences are termed "expression cassettes." Accordingly, the invention provides expression cassettes into which the nucleic acids that encode fusion proteins, e.g., combining an outer membrane traversing fragment with a cell wall degrading fragment, are incorporated for expression in a desired host cell.

Expression control sequences that are suitable for use in a particular host cell can be obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems, the tryptophan (trp) promoter system (Goeddel, et al. (1980) *Nucleic Acids Res.* 8:4057), the tac promoter (DeBoer, et al. (1983) *Proc. Natl. Acad. Sci. USA* 80:21-25); and the lambda-derived PL promoter and N-gene ribosome binding site (Shimatake, et al. (1981) *Nature* 292:128). A bacteriophage T7 promoter is used in various examples, though one of skill will recognize that the particular promoter system is not critical to the invention.

For expression of cell wall degrading polypeptides in prokaryotic cells other than *E. coli*, a promoter that functions in the particular prokaryotic production species is used. Such promoters can be obtained from genes that have been cloned from the species, or heterologous promoters can be used. For example, the hybrid trp-lac promoter functions in *Bacillus* in addition to *E. coli*.

Hyper-expression of proteins can result in inclusion body formation. The stronger the promoter, the higher is the protein yield per cell, and in some cases, a medium strength promoter results in higher yield of soluble protein compared to a strong promoter. Some examples include T7 promoter, arabinose promoters, T5 and hybrid promoters, etc. Moreover, some toxic protein has been found to be difficult to express due to leaky expression in bacterial cells. Such leaky expression can be avoided by use of promoters that are strongly regulated like arabinose promoters. See, e.g., Correa and Oppezzo (2011) *Biotechnol. J.* 6:715-730 and Alakomi (2007) "Weakening of the Gram-negative bacterial outer membrane: A tool for increasing microbiological safety" thesis, Univ. Helsinki, June 2007.

A ribosome binding site (RBS) is conveniently included in the expression cassettes of the invention. An exemplary RBS in *E. coli* consists of a nucleotide sequence 3-9 nucleotides in length located 3-11 nucleotides upstream of the initiation codon (Shine and Dalgarno (1975) *Nature* 254:34; Steitz (1979) In *Biological regulation and development: Gene expression* (ed. R. F. Goldberger), vol. 1, p. 349, Plenum Publishing, NY).

For expression of proteins in yeast, convenient promoters include GAL1-10 (Johnson and Davies (1984) *Mol. Cell. Biol.* 4:1440-1448) ADH2 (Russell, et al. (1983) *J. Biol. Chem.* 258:2674-2682), PHO5 (*EMBO J.* (1982) 6:675-680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N. E, pp. 181-209). Another suitable promoter for use in yeast is the ADH2/GAPDH hybrid promoter as described in Cousens, et al. (1987) *Gene* 61:265-275. For filamentous fungi such as, for example, strains of the fungi *Aspergillus* (McKnight, et al., U.S. Pat. No. 4,935,349), examples of useful promoters include those derived from *Aspergillus nidulans* glycolytic genes, such as the ADH3 promoter (McKnight, et al (1985) *EMBO J.* 4:2093-2099) and the tpiA promoter. An example of a suitable terminator is the ADH3 terminator (McKnight, et al.).

Either constitutive or regulated promoters can be used in the present invention. Regulated promoters can be advantageous because the host cells can be grown to high densities before expression of the fusion proteins is induced. High level expression of heterologous polypeptides slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the desired polypeptide. For *E. coli* and other bacterial host cells, inducible promoters are known to those of skill in the art. These include, for example, the lac promoter, the bacteriophage lambda PL promoter, the hybrid trp-lac promoter (Amann, et al. (1983) *Gene* 25:167; de Boer, et al. (1983) *Proc. Nat'l Acad. Sci. USA* 80:21), and the bacteriophage T7 promoter (Studier, et al. (1986) *J. Mol. Biol.*; Tabor, et al. (1985) *Proc. Nat'l. Acad. Sci. USA* 82:1074-78). These promoters and their use are discussed in Sambrook, et al., supra.

The construction of polynucleotide constructs generally requires the use of vectors able to replicate in bacteria. A plethora of kits are commercially available for the purification of plasmids from bacteria (see, e.g., EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a polypeptide, necessary for the survival or growth of transformed host cells grown in a selective culture medium. A number of selectable markers are known to those of skill in the art and are described for instance in Sambrook, et al., supra.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill.

A variety of common vectors suitable for use as starting materials for constructing the expression vectors of the invention are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

Expression vectors can be introduced into a chosen host cell using standard methods known to those of skill in the art. For example, the expression vectors can be introduced into prokaryotic cells, including $E.$ $coli$, by calcium chloride transformation, and into eukaryotic cells by calcium phosphate treatment or electroporation.

Translational coupling can be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et al. (1988) $J.$ $Biol.$ $Chem.$ 263: 16297-16302.

The various polypeptides of the invention can be expressed intracellularly, or can be secreted from the cell. Intracellular expression often results in high yields. If necessary, the amount of soluble, active fusion polypeptide may be increased by performing refolding procedures (see, e.g., Sambrook, et al., supra; Marston, et al. (1984) $Bio/Technology$ 2:800; Schoner, et al. (1985) $Bio/Technology$ 3:151). In embodiments in which the polypeptide is secreted, either into the periplasm or into the extracellular medium, the DNA sequence is often linked to a cleavable signal peptide sequence. The signal sequence directs translocation of the fusion polypeptide through the cell membrane. An example of a suitable vector for use in $E.$ $coli$ that contains a promoter-signal sequence unit is pTA1529, which has the $E.$ $coli$ phoA promoter and signal sequence (see, e.g., Sambrook, et al., supra; Oka, et al. (1985) $Proc.$ $Natl.$ $Acad.$ $Sci.$ $USA$ 82:7212; Talmadge, et al. (1980) $Proc.$ $Natl.$ $Acad.$ $Sci.$ $USA$ 77:3988; Takahara, et al. (1985) $J.$ $Biol.$ $Chem.$ 260: 2670). In another embodiment, the fusion polypeptides are fused to a subsequence of protein A or bovine serum albumin (BSA), for example, to facilitate purification, secretion, or stability. Affinity methods, e.g., using substrate for the catalytic fragment may be appropriate.

The cell wall degrading polypeptides of the invention can also be further linked to other polypeptide segments, e.g., biofilm depolymerase segments. This approach often results in high yields, because normal prokaryotic control sequences direct transcription and translation. In $E.$ $coli$, lacZ fusions are often used to express heterologous proteins. Suitable vectors are readily available, such as the pUR, pEX, and pMR100 series. For certain applications, it may be desirable to cleave extraneous sequence from the fusion polypeptide after purification. This can be accomplished by any of several methods known in the art, including cleavage by cyanogen bromide, a protease, or by Factor $X_a$ (see, e.g., Sambrook, et al., supra; Itakura, et al. (1977) $Science$ 198:1056; Goeddel, et al. (1979) $Proc.$ $Natl.$ $Acad.$ $Sci.$ $USA$ 76:106; Nagai, et al. (1984) $Nature$ 309:810; Sung, et al. (1986) $Proc.$ $Natl.$ $Acad.$ $Sci.$ $USA$ 83:561). Cleavage sites can be engineered into the gene for the fusion polypeptide at the desired point of cleavage.

More than one recombinant polypeptide may be expressed in a single host cell by placing multiple transcriptional cassettes in a single expression vector, or by utilizing different selectable markers for each of the expression vectors which are employed in the cloning strategy.

A suitable system for obtaining recombinant proteins from $E.$ $coli$ which maintains the integrity of their N-termini has been described by Miller, et al. (1989) $Biotechnology$ 7:698-704. In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

XIV. Purification of Desired Polypeptides

A crude cellular extract containing the expressed intracellular or secreted polypeptides described herein can be used in the methods of the present invention.

The polypeptides can also be purified according to standard procedures of the art, including ammonium sulfate precipitation, affinity columns, column chromatography, gel electrophoresis and the like (see, generally, R. Scopes (1982) $Protein$ $Purification$, Springer-Verlag, N.Y., Deutscher (1990) $Methods$ $in$ $Enzymology$ Vol. 182: $Guide$ $to$ $Protein$ $Purification$, Academic Press, Inc. NY.). Because the degrading segments, at least, derive from phage proteins selected for stability, purification can involve denaturation of contaminating materials. Substantially pure compositions are typically about 70, 75, 80, 85, 90, 92, 95, 98 to 99% or higher homogeneous. The purified polypeptides can also be used, e.g., as immunogens for antibody production, which antibodies may be used in immunoselection purification methods.

To facilitate purification of the polypeptides of the invention, the nucleic acids that encode them can also include a coding sequence for an epitope or "tag" for which an affinity binding reagent is available, e.g., a purification tag. Examples of suitable epitopes include the myc and V-5 reporter genes; expression vectors useful for recombinant production of fusion polypeptides having these epitopes are commercially available (e.g., Invitrogen (Carlsbad, Calif.)

vectors pcDNA3.1/Myc-His and pcDNA3.1/V5-His are suitable for expression in mammalian cells). Additional expression vectors suitable for attaching a tag to the polypeptides of the invention, and corresponding detection systems are known to those of skill in the art, and several are commercially available (e.g., FLAG, Kodak, Rochester N.Y.). Another example of a suitable tag is a polyhistidine sequence, which is capable of binding to metal chelate affinity ligands. Typically, six adjacent histidines (SEQ ID NO: 9) are used, although one can use more or fewer than six. Suitable metal chelate affinity ligands that can serve as the binding moiety for a polyhistidine tag include nitrilo-tri-acetic acid (NTA) (Hochuli (1990) *Genetic Engineering: Principles and Methods*, J. K. Setlow, Ed., Plenum Press, NY; commercially available from Qiagen (Santa Clarita, Calif.)). Purification tags also include maltose binding domains and starch binding domains. Purification of maltose binding domain proteins is known to those of skill in the art.

Other haptens that are suitable for use as tags are known to those of skill in the art and are described, for example, in the *Handbook of Fluorescent Probes and Research Chemicals* (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill will recognize that certain modifications can be made to the catalytic or functional domains of the polypeptide without diminishing their biological activity. Some modifications can be made to facilitate the cloning, expression, or incorporation of the catalytic domain into a fusion polypeptide. Such modifications are well known to those of skill in the art and include, for example, the addition of codons at either terminus of the polynucleotide that encodes the catalytic domain, e.g., a methionine added at the amino terminus to provide an initiation site, or additional amino acids (e.g., poly His) placed on either terminus to create conveniently located restriction enzyme sites or termination codons or purification sequences.

The following discussion of the invention is for the purposes of illustration and description, and is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. All publications, patents, patent applications, Genbank numbers, and websites cited herein are hereby incorporated by reference in their entireties for all purposes. More recent editions of books may provide updated techniques or approaches to accomplish many of the same objectives.

XV. Examples

Example 1. Phi29 LysM

1. Isolation and Cloning of LysM Domain into an *E. coli* Expression Vector:

The LysM domain from Phi29 endolysin was PCR amplified using specific primers and cloned into *E. coli* expression vector, pET16b for expression as N-terminal 10x-His (SEQ ID NO: 24) tag under the inducible T7 expression promoter using the T7 expression system. The plasmid DNA constructs were confirmed by restriction analysis followed by DNA sequencing. The clone was labeled as pGDC191.

2. Expression and purification of P191:

The plasmid pGDC 191 was introduced into *E. coli* ER2566 and the recombinant protein was expressed by growing the transformants in LB medium until absorbance at 600 nm reached ~0.8-1.0 followed by inducing the recombinant protein expression by addition of IPTG to final concentration of 1 mM. The induction was done at 37° C., 200 rpm for 4 hours. After 4 hours of IPTG induction, the induced whole cell lysate sample was analyzed on a 15% acrylamide gel. A hyperexpressed protein of expected 15 kDa was observed on the acrylamide gel indicating that the His-tagged protein was successfully expressed in *E. coli* ER2566 cells.

3. Sub-Cellular Localization:

The induced *E. coli* cultures were pelleted by centrifugation at 13,000 rpm for 10 minutes and the spent media was discarded. The cell pellet was resuspended in 20 mM Sodium phosphate buffer (SPB) pH 7.0 and sonicated to disrupt the cells. After the sonication cycle, samples are centrifuged to separate the supernatant, which represent the soluble fraction of the cells and pellet, which represent the inclusion bodies (IB). The supernatant and the pellet fraction were analyzed on a 15% acrylamide gel, stained with coomassie brilliant blue (CBB) stain and visualized. The P191 protein of ~15 kDa was found in the supernatant fraction of the cells indicating soluble expression in *E. coli*.

4. Purification of P191 Protein:

P191 was purified by Ni-NTA chromatography from the supernatant. The clarified supernatant was loaded on a Ni-NTA agarose column which was pre-equilibrated with 20 mM SPB, pH 7.0. After the loading was completed, the column was washed with 10 column volumes (CV) of equilibration buffer and the bound protein was eluted with step gradient containing 50, 100, and 300 mM imidazole. Appropriate fractions were collected and analyzed on a 15% acrylamide gel. Most of the P191 eluted in 100 and 300 mM imidazole and the purified protein was ~90-95% homogeneous. Fractions containing purified proteins were pooled and dialyzed against 20 mM SPB, pH 7.0 to remove the imidazole and used for testing antibacterial activity against various genera of Gram-negative bacteria.

5. Testing Antibacterial Activity of P191 Against Gram-Negative Bacteria:

Antibacterial activity was tested by a CFU drop assay in SPB pH 7.0. Briefly, Gram-negative bacteria grown in LB medium until mid-log phase ($OD_{600}$ of ~0.6) were diluted 100-fold in 20 mM SPB pH 7.0 to a final density of ~$10^6$ CFU/ml. 100 µL of cells were treated with 100 µg/mL of purified P191. The final volume of the reaction mixture was adjusted to 200 with assay buffer, SPB pH 7.0. The reaction mixture was incubated at 37° C. for 2 hours, 200 µL rpm and enumerated remaining number of viable cells by plating of appropriate dilutions on LB plate followed by overnight incubation at 37° C. The antibacterial activity was calculated by dividing initial number of untreated cells with number of residual cells in log units and tabulating the results to determine antibacterial activity.

Gram-negative bacteria tested: *Pseudomonas aeruginosa* strain PA01; *E. coli* strain B5500; *Acinetobacter baumannii* strain HER1401; *Klebsiella pneumoniae* NDM KL5.

TABLE D1

Antibacterial activity of P191 against Gram-negative bacteria

| Gram-negative bacteria | Cell control | P191 treated | Log kill |
|---|---|---|---|
| P. aeruginosa PA01 | 2.55E + 06 | 2.00E + 01 | 5 logs |
| A. baumannii HER 1401 | 1.40E + 06 | 2.00E + 01 | 5 logs |
| E. coli B5500 | 4.50E + 06 | 1.70E + 03 | 3.5 logs |
| K. pneumoniae NDM KL5 | 6.25E + 06 | 4.50E + 06 | 0 |

Result (Table D1, FIG. 1): Except *Klebsiella pneumoniae*, LysM domain killed other Gram-negative bacteria efficiently with >3 log cell killing obtained 100 μg/mL of the protein. Inference: LysM domain has potent antibacterial activity against *Pseudomonas aeruginosa, E. coli*, and *Acinetobacter baumannii*.

Example 2: WLBU2-lysin-LysM Fusion Protein

1. Generating WLBU2-GP36-LysM Fusion (Cloning Strategy):

WLBU2 was fused to the 5' end of the P203 (GP36 CD-LysM domain fusion) coding region by a PCR based method introducing appropriate cloning sites and the chimeric DNA sequence without a stop codon was cloned into *E. coli* expression vector pET26b as an NdeI-XhoI fragment, for expression of the chimeric fusion protein as a C-terminal 6x-His tag (SEQ ID NO: 9) fusion.

*E. coli* transformants were screened by PCR, plasmid DNA was isolated from the PCR positive clones and presence of the insert confirmed by restriction digestion analysis. The plasmids released the expected DNA fragment of 1100 bp demonstrating that the cloning was successful. The clones were then confirmed by DNA sequencing of the target fusion gene in the plasmids. DNA sequence of Clone #12 was confirmed and designated as pGDC 601.

Protein expression: Protein expression of P601 was performed by introducing the plasmids into *E. coli* ER2566, growing the *E. coli* transformants in LB medium until absorbance at 600 nm reached 0.8-1.0 and inducing the recombinant protein expression by addition of IPTG to final concentration of 1 mM. The induction was done at 37° C., 200 rpm for 4 hours. After 4 hours of IPTG induction, the induced whole cell lysate samples were analyzed on a 12% acrylamide gel. An hyperexpressed protein of ~40 kDa was observed on the acrylamide gel indicating that the fusion protein was successfully expressed in *E. coli* ER2566 cells.

Sub-cellular localization: The induced *E. coli* cultures were pelleted by centrifugation at 13,000 rpm for 10 minutes and the spent media was discarded. The cell pellet was resuspended in 20 mM Sodium phosphate buffer pH 7.0 and sonicated to disrupt the cells. After sonication cycle, the samples are centrifuged to separate the supernatant, which represent the soluble fraction of the cells and pellet, which represent the inclusion bodies (IB). The supernatant and the pellet fraction were analyzed on a 12% acrylamide gel, stained with coomassie brilliant blue (CBB) stain and visualized. The P601 protein of ~40 kDa was found in the pellet fraction of the cells indicating formation of insoluble inclusion bodies. P601 forms inclusion bodies upon hyperexpression in *E. coli*.

2. Purification and Refolding of P601:

Purification of P601: P601 forms inclusion bodies on expression in E P601 was solubilized, purified and refolded from the inclusion bodies to get soluble protein. Inclusion bodies were solubilized in Buffer A (6M Guanidine hydrochloride in 100 mM $NaH_2PO_4$, 10 mM TrisCl, pH 8.0) and the protein was purified by Ni-NTA chromatography. The solubilized inclusion bodies were clarified by centrifugation at 13,000 rpm for 10 minutes and the clarified sample was loaded on a Ni-NTA agarose column which was pre-equilibrated with Buffer B. After the loading is completed, the column was washed with 10 column volumes (CV) of buffer B and the bound protein was eluted with step gradient of Buffer B containing 50, 100, and 300 mM imidazole. Appropriate fractions were collected and analyzed on a 12% acrylamide gel. Most of the P601 was eluted in 300 mM imidazole and the purified protein was ~90% homogeneous.

Refolding of the P601: The 300 mM imidazole fractions containing P601 was dialyzed for 16 hrs against 10 mM Sodium acetate buffer, pH 4.0, to refold the protein by slowly removing the urea. A fraction of the refolded protein was dialyzed against 10 mM HEPES pH 7.0 buffer. After dialysis, P601 buffered at pH 4.0 and pH 7.0 were analyzed on a 12% acrylamide gel and the refolded proteins were found to be ~90-95% homogeneous. These proteins were used for further activity testing to determine their antibacterial activity.

3. Activity of Purified P601:

Two assays were done to determine the activity of the purified, refolded P601.

a) OD Fall Assay:

The catalytic activity of the GP36 CD was determined by OD fall assay using chloroform treated *P. aeruginosa* cells as substrate. 50 μg/ml of purified P601 and a positive control protein P203 were used in this assay. An active protein by OD fall assay will also suggest the correct refolding of the GP36 CD.

TABLE D2

Catalytic activity of P601 on $CHCl_3$ treated PA01

| Time | Cell control | P601 | P203 |
|---|---|---|---|
| $T_{ini}$ | 0.9405 | 0.976 | 0.978 |
| T0 | 0.886 | 0.781 | 0.483 |
| T5 | 0.899 | 0.584 | 0.3785 |
| T10 | 0.8905 | 0.526 | 0.3675 |
| T15 | 0.8795 | 0.482 | 0.328 |
| T30 | 0.8635 | 0.418 | 0.2905 |
| T60 | 0.814 | 0.3385 | 0.288 |

Result: The purified P601 is catalytically active as observed by the OD fall obtained (Table D2).

b) CFU Drop Assay:

The antibacterial activity of P601 was tested against *P. aeruginosa* strain PA01 by using the CFU drop assay. ~$10^6$ cells/mL of PA01 in buffer, buffer containing saline, FBS, LB medium and LB medium without NaCl was treated with 100 μg/ml of P601, incubated at 37° C. for 2 hours and enumerated remaining number of viable cells.

Figure 4:
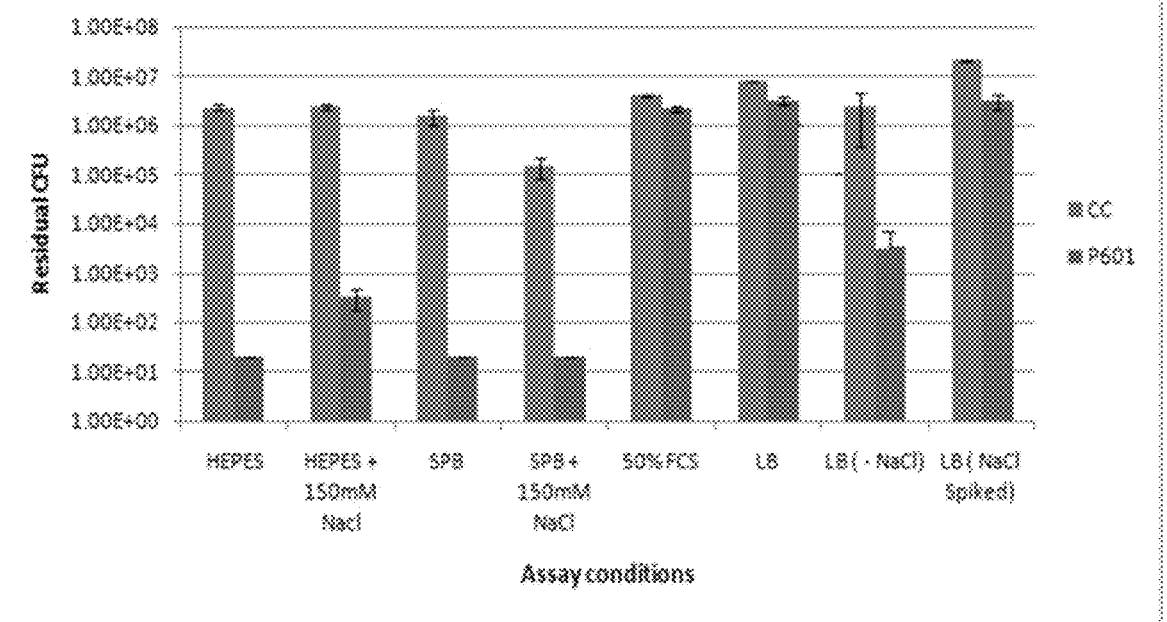
FIG. 4 shows Bactericidal activity of P601 on PA01 cells.

Result: 4-5 log cell killing was obtained in both buffer and saline, and 3 log cell-killing obtained with LB (—NaCl). Inference: The fusion protein P601 kills efficiently in both physiological buffer and buffered saline; however, no cell killing obtained in LB and FCS (FIG. 4)

4. Activity of Purified P601 on *Acinetobacter baumannii*:

For this assay, P601 refolded in 10 mM Sodium acetate pH 4.0 was used and the assay was done in both 50% LB and HEPES buffer with 150 mM NaCl. ~$10^6$ cells/mL of *A. baumannii* strain HER1401 in buffer containing saline and LB medium was treated with 100 μg/mL of P601, incubated at 37° C. for 2 hours and enumerated remaining number of viable cells.

Figure 5:
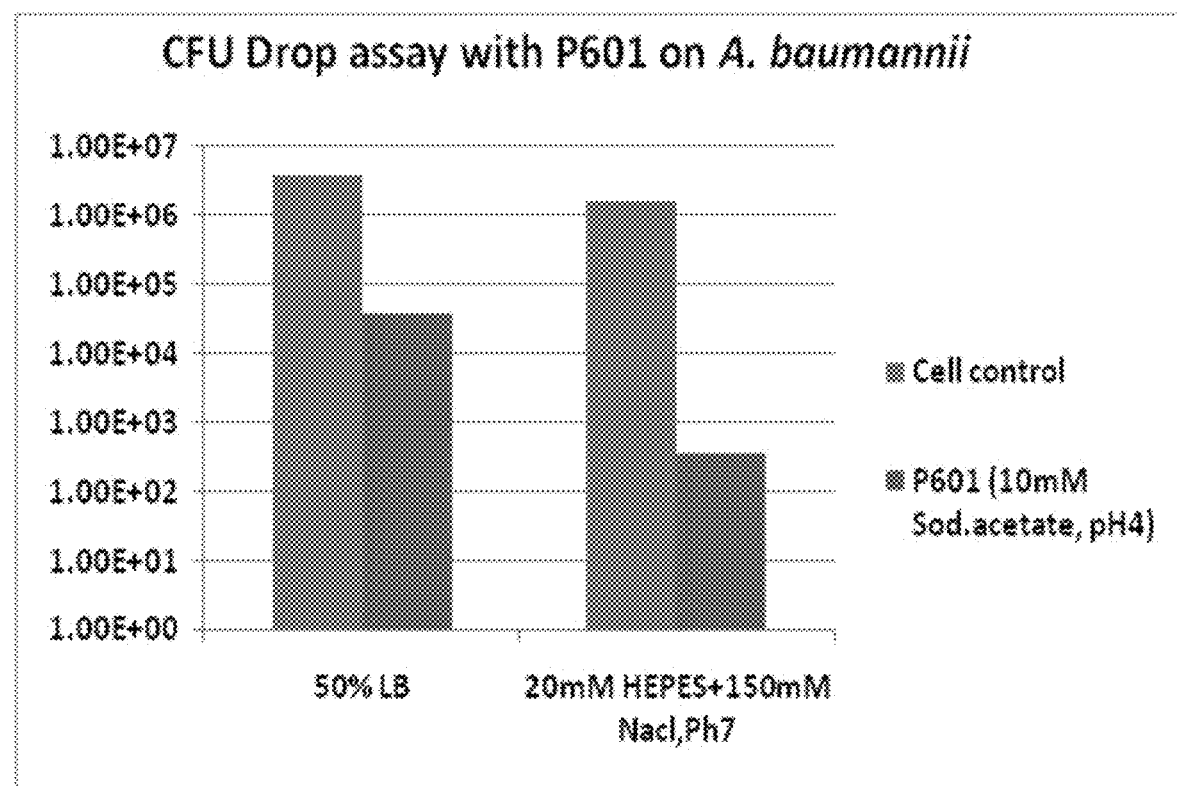
FIG. 5 shows Bactericidal activity of P601 on *A. baumannii*.

Result: 3-4 log cell killing obtained in buffer and 2 log cell-killing was obtained with LB (FIG. 5).

5. Activity of P601 on *Acinetobacter baumannii* FCS:

Having demonstrated the activity of P601 in growing conditions such as LB medium, we wanted to determine its activity in biological fluid such as serum.

For this, P601 refolded in 10 mM Sodium acetate pH 4.0 was used and the assay was done in both 50% LB broth and 50% FCS. ~$10^6$ cells/mL of *A. baumannii* strain HER1401 in LB broth and FCS was treated with 100, 200, and 400 µg/mL of P601, incubated at 37° C. for 2 hours and enumerated remaining number of viable cells.

Figure 6:
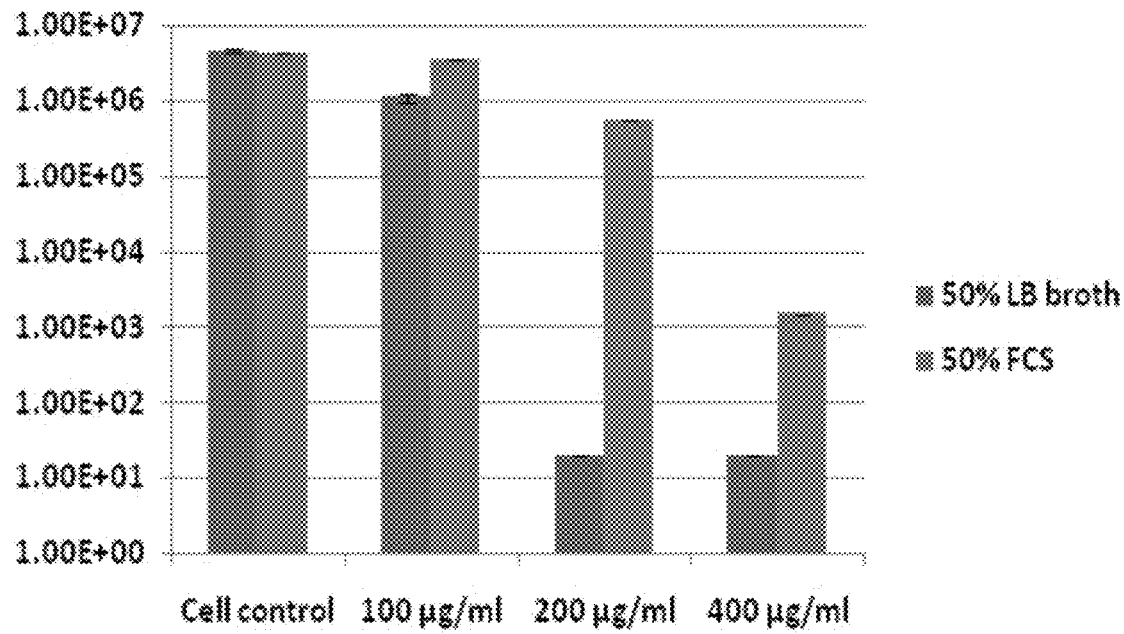
FIG. 6 shows Dose ranging activity of P601 on *A. baumannii* in FCS.

Result: 3 log cell killing obtained in 50% FCS with 400 µg/mL of P601 and 5 log cell-killing obtained in 50% LB broth with 200 and 400 µg/mL. Inference: The fusion protein P601 kills *A. baumannii* in 50% FCS (FIG. 6).

6. MIC of P601 on *Acinetobacter baumannii*:

MIC was determined using a modified Clinical and Laboratory Standards Institute (CLSI) broth microdilution procedure on *A. baumannii* strain HER1401 in Cation-adjusted Mueller Hinton Broth (CA-MHB) and 50% FCS. Wells of a 96-well polystyrene plated were coated with 0.5% BSA for 1 hour at 37° C. and each well were inoculated with 5×$10^5$ cell s/mL *A. baumannii*. A positive control for growth which is devoid of P601 was included in the assay. Microtiter plates were incubated at 35° C. for 18-20 hrs. The endpoint for this assay was complete inhibition of growth at the end of incubation as determined by colorless wells after addition of Iodonitro tetrazolium (INT) dye. For this assay, P601 buffered in 10 mM Sodium acetate pH 4.0 and 20 mM HEPES pH 7.0 were used.

TABLE D3

MIC of P601 on *A. baumanni*

| Sl. No. | Protein | CA-MHB (µg/ml) | FCS (µg/ml) |
|---|---|---|---|
| 1 | P601 (SA pH 4) | 250 | 250 |
| 2 | P601 (HEPES pH 7) | >500 | >335 |

Example 3: Construct P617 (WLBU2 Fused to Phi29 Endolysin FL at N-Terminal)

Sequence of the construct has the WLBU2 fused to the N-terminus of the full length phi29 endolysin with a 6×His purification tag (SEQ ID NO: 9):

```
                                               (SEQ ID NO: 25)
ATGCGTCGTT GGGTTCGTCG TGTTCGTCGT TGGGTTCGTC

GTGTTGTTCG TGTTGTTCGT CGTTGGGTTC

GTCGTGGCTC CGGATCGGCT TCTGGGCAAA TTTCACAAGC

GGGTATCAAC TTAATTAAGA GCTTTGAGGG

TTTACAACTG AAAGCATATA AAGCTGTTCC GACTGAGAAG

CATTACACCA TTGGTTACGG TCATTACGGT

TCCGATGTTT CACCTAGGCA GGTTATCACT GCTAAACAGG

CTGAAGACAT GTTGCGTGAT GATGTGCAGG

CTTTTGTGGA TGGTGTAAAT AAAGCATTAA AAGTATCTGT

CACCCAAAAT CAATTTGATG CACTTGTCTC
```

```
-continued
ATTCGCTTAC AACGTTGGGT TAGGGCTTT CAGGTCTTCT

TCTCTACTGG AATACTTGAA TGAAGGAAGA

ACAGCTCTAG CGGCGGCTGA ATTCCCTAAA TGGAATAAGT

CAGGCGGTAA AGTTTATCAA GGGTTGATTA

ACCGTAGAGC ACAGGAGCAA GCCTTGTTTA ATAGTGGAAC

ACCTAAAAAT GTTTCACGTG AACATCGTC

TACTAAAACG ACACCTAAGT ATAAGGTGAA GAGTGGTGAC

AACCTTACTA AAATCGCTAA AAAGCATAAT

ACAACGGTTG CTACTTTGTT GAAGTTGAAT CCGAGTATCA

AAGACCCGAA CATGATTAGA GTTGGACAAA

CAATAAATGT TACAGGTAGC GGCGGCAAAA CACATAAGGT

GAAAAGTGGT GACACACTCA GTAAAATTGC

CGTTGATAAC AAAACGACTG TGAGTAGATT GATGAGTCTA

AACCCTGAAA TTACGAATCC AAATCATATA

AAAGTAGGTC AAACAATTAG ATTAAGTCTC GAGCACCACC

ACCACCACCA CTAA
```

Amino Acid Sequence:

```
                                               (SEQ ID NO: 26)
MRRWVRRVRR WVRRVVRVVR RWVRRGSGSA SGQISQAGIN

LIKSFEGLQL KAYKAVPTEK HYTIGYGHYG SDVSPRQVIT

AKQAEDMLRD DVQAFVDGVN KALKVSVTQN QFDALVSFAY

NVGLGAFRSS SLLEYLNEGR TALAAAEFPK WNKSGGKVYQ

GLINRRAQEQ ALFNSGTPKN VSRGTSSTKT TPKYKVKSGD

NLTKIAKKHN TTVATLLKLN PSIKDPNMIR VGQTINVTGS

GGKTHKVKSG DTLSKIAVDN KTTVSRLMSL NPEITNPNHI

KVGQTIRLSL EHHHHHH
```

Molecular weight: 32762.48

Theoretical pI: 10.74

Domains in P617: WLBU2 (2-25; RRWV . . . (SEQ ID NO: 27) to . . . WVRR (SEQ ID NO: 28)); Phi29 endolysin (33-289; QISQ . . . (SEQ ID NO: 29) to . . . IRLS (SEQ ID NO: 30)); 6x His (SEQ ID NO: 9) (290-297; LEHHHHHH (SEQ ID NO: 31))

Introduction:

P617 is a chimeric fusion of WLBU2 peptide with Phi29 endolysin. Phi29 endolysin is a natural fusion of a lysozyme domain with tandem LysM domains. This construct will have an outer membrane penetrating motif at the N-terminus and a membrane traversing domain at the C-terminus, LysM domain. Construction of a triple fusion containing the WLBU2 peptide, lysozyme domain, and LysM domains were done to determine if this triple fusion would be more soluble and potent in biological fluids and able to kill Gram-negative pathogens.

1. Generating WLBU2-Phi29 Endolysin Fusion (Cloning Strategy):

WLBU2 was fused to the 5' end of the Phi29 full-length coding region by a PCR based method introducing appropriate cloning sites and the chimeric DNA sequence without a stop codon was cloned into E. coli expression vector pET26b as an NdeI-XhoI fragment, for expression of the chimeric protein as a C-terminal 6x-His tag (SEQ ID NO: 9) fusion. E. coli transformants were screened by PCR, plasmid DNA isolated from the positive clones and presence of the insert confirmed by restriction digestion analysis. The plasmids released the expected DNA fragment of ~900 bp, demonstrating that the cloning was successful. The clones were then confirmed by DNA sequencing of the target fusion gene in the plasmids. DNA sequence of Clone #3 was confirmed and designated as pGDC 617.

Protein expression: Protein expression was performed by introducing the plasmids into E. coli ER2566, growing the E. coli transformants in LB medium until absorbance at 600 nm reached ~0.8-1.0 and inducing the recombinant protein expression by addition of IPTG to final concentration of 1 mM. The induction was done at 37° C., 200 rpm for 4 hours. After 4 hours of IPTG induction, the induced whole cell lysate samples were analyzed on a 12% acrylamide gel. A hyperexpressed protein of ~33 kDa was observed on the acrylamide gel demonstrating that the fusion protein was successfully expressed in E. coli ER2566 cells.

Sub-cellular localization: The induced E. coli cultures were pelleted by centrifugation at 13,000 rpm for 10 minutes and the spent media was discarded. The cell pellet was resuspended in 20 mM Sodium phosphate buffer pH 7.0 and sonicated to disrupt the cells. After sonication cycle, the samples are centrifuged to separate the supernatant, which represent the soluble fraction of the cells, from the pellet, which represent the inclusion bodies (IB). The supernatant and the pellet fraction were analyzed on a 12% acrylamide gel, stained with coomassie brilliant blue (CBB) stain and visualized. The P617 protein of 33 kDa was in the pellet fraction of the cells indicating formation of insoluble inclusion bodies. P617 forms inclusion bodies upon hyperexpression in E. coli.

2. Purification and Refolding of P617:

Purification of P617: P617 forms inclusion bodies on expression E. coli. P617 was solubilized, purified and refolded from the inclusion bodies to get soluble protein. Inclusion bodies were solubilized in Buffer A (6M Guanidine hydrochloride in 100 mM $NaH_2PO_4$, 100 mM TrisCl, pH 8.0) and protein was purified by Ni-NTA chromatography. The solubilized inclusion bodies were clarified by centrifugation at 13,000 rpm for 10 minutes and the clarified sample was loaded on a Ni-NTA agarose column which was pre-equilibrated with Buffer B. After the loading is completed, the column was washed with 10 column volumes (CV) of buffer B and the bound protein was eluted with step gradient of Buffer B containing 50, 100, and 300 mM imidazole. Appropriate fractions were collected and analyzed on a 12% acrylamide gel. Most of the P617 was eluted in 100 mM imidazole and the purified protein was 90% homogeneous.

Refolding of the P617: The 100 mM imidazole fractions containing P617 was dialyzed for 16 hrs against 10 mM Sodium acetate buffer, pH 4.0, to refold the protein by slowly removing the urea. A fraction of the refolded protein was dialyzed against 10 mM HEPES pH 7.0 buffer. After dialysis, P617 buffered at pH 4.0 and pH 7.0 were analyzed on a 12% acrylamide gel and the refolded proteins were 90-95% homogeneous. These proteins were used for further activity testing to determine their antibacterial activity.

3. Activity of Purified P617: Two Assays were Done to Determine the Activity of the Purified, Refolded P617.

a) OD fall assay: The catalytic activity of the Phi29 lysozyme CD was determined by OD fall assay using chloroform treated P. aeruginosa cells as substrate. 50 µg/ml of purified P617 and a positive control protein, P203 were used in this assay. An active protein by OD fall assay also suggests the correct refolding of the Phi29 lysozyme CD.

Figure 7:
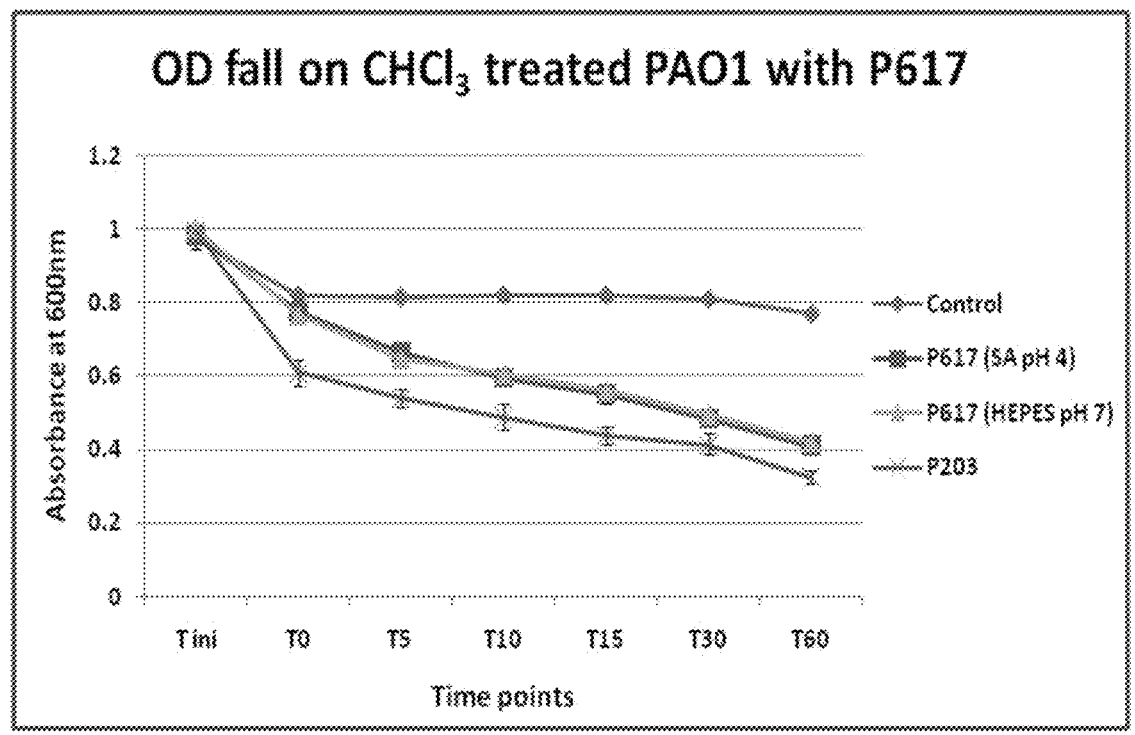
FIG. 7 shows Catalytic activity of P617 on CHCl3 treated PA01.

Result: The purified P617 is catalytically active in both buffers, as observed by the OD fall obtained. Inference: P617 was catalytically active (FIG. 7).

b) CFU drop assay: The antibacterial activities of P617 in both buffers were tested against P. aeruginosa strain PA01 by using the CFU drop assay. ~$10^6$ cells/mL of PA01 in buffer and buffer containing saline was treated with 200 µg/mL (6.2 µM) of P617, incubated at 37° C. for 2 hours and enumerated remaining number of viable cells.

Figure 8:
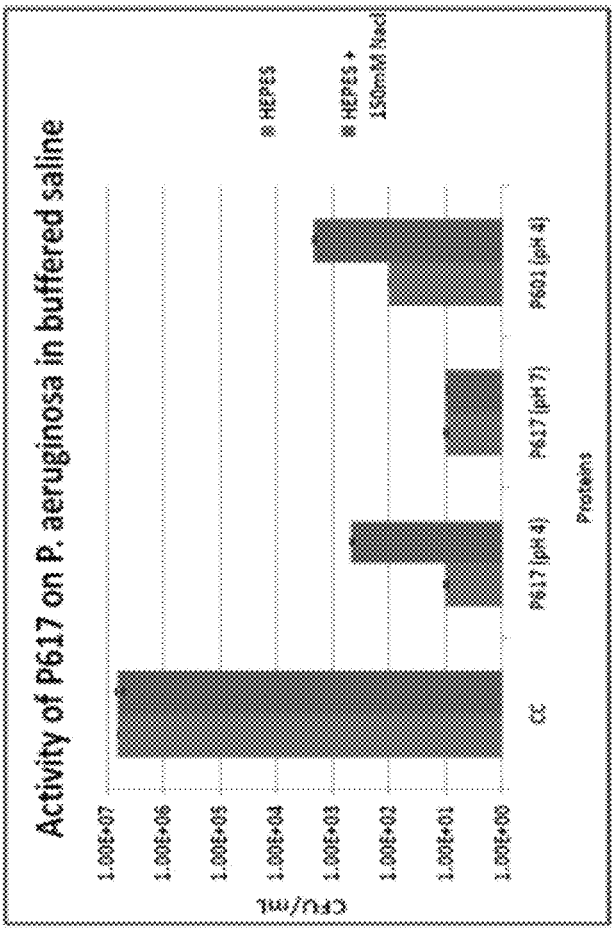
FIG. 8 shows Bactericidal activity of P617 on *P. aeruginosa* PA01.

Result: 4-5 log cell killing obtained in both buffer and saline. Inference: The fusion protein P617 kills P. aeruginosa efficiently in both buffer and buffered saline (FIG. 8).

4. Activity of Purified P617 on Acinetobacter baumannii:

For this assay, P617 in 10 mM Sodium acetate pH 6.0 and 20 mM HEPES pH 7.0 were used and the assay was done in Cation-adjusted Mueller Hinton Broth (CA-MHB). CA-MHB was used because it is the media recommended by CLSI for testing MIC and MBC of antibiotics. $10^6$ cells/mL of A. baumannii strain HER1401 in CA-MHB medium was treated with 10, 25, 50, and 100 µg/mL corresponding to 0.39, 0.775, 1.55, and 3.1 µM of P617, incubated at 37° C. for 2 hours and determined cell-killing by enumerating remaining number of viable cells by dilution plating on LB plates followed by incubation at 37° C. for 16-18 hrs.

Figure 9:
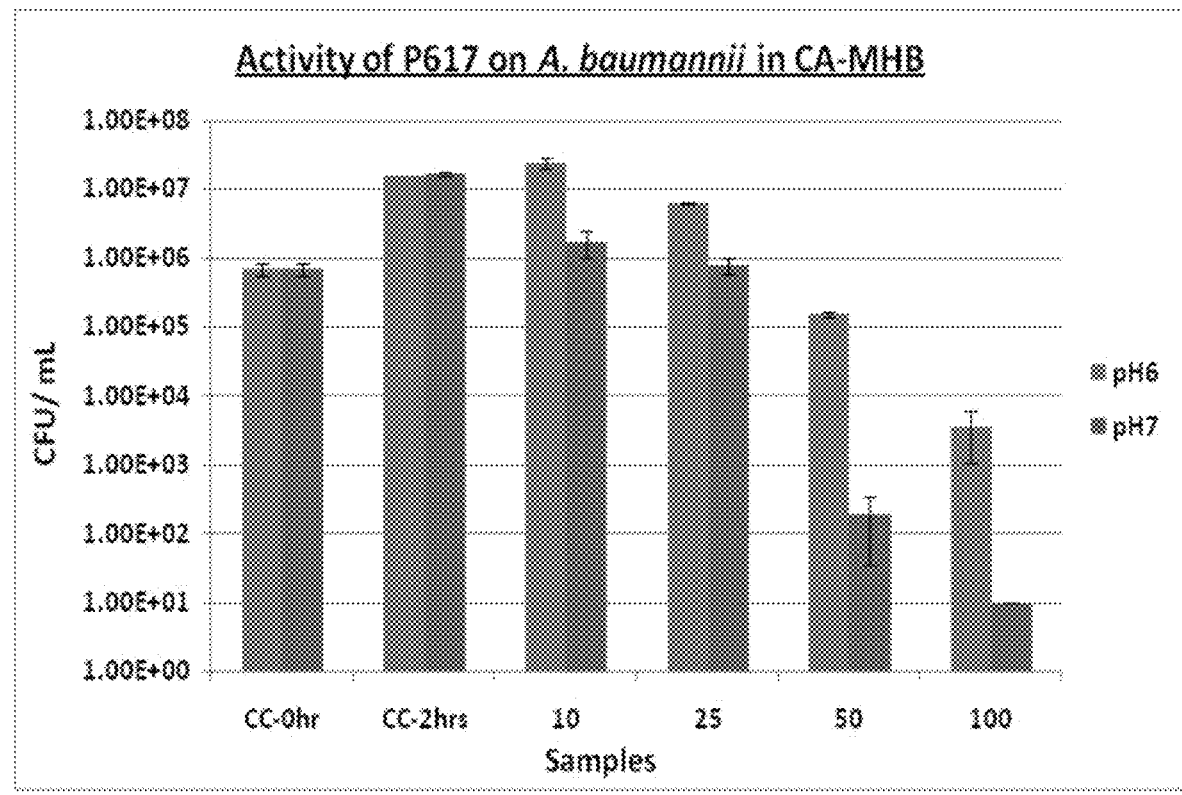
FIG. 9 shows Dose ranging activity of P617 on *A. baumannii* in CA-MHB media.

Result: P617 buffered in both buffer skilled cells at 50-100 µg/mL with >3 log cell killing obtained with protein buffered at pH 7.0 (FIG. 9).

5. Activity of Purified P617 on E. coli:

P617 in 10 mM Sodium acetate pH 6.0 and 20 mM HEPES pH 7.0 were used and the assay was done in Cation-adjusted Mueller Hinton Broth (CA-MHB). $10^6$ cells/mL of E. coli strain B5500 in CA-MHB medium was treated with 10, 25, 50, and 100 µg/mL corresponding to 0.39, 0.775, 1.55, and 3.1 µM of P617, incubated at 37° C. for 2 hours and determined cell-killing by enumerating remaining number of viable cells by dilution plating on LB plates followed by incubation at 37° C. for 16-18 hrs.

Figure 10:
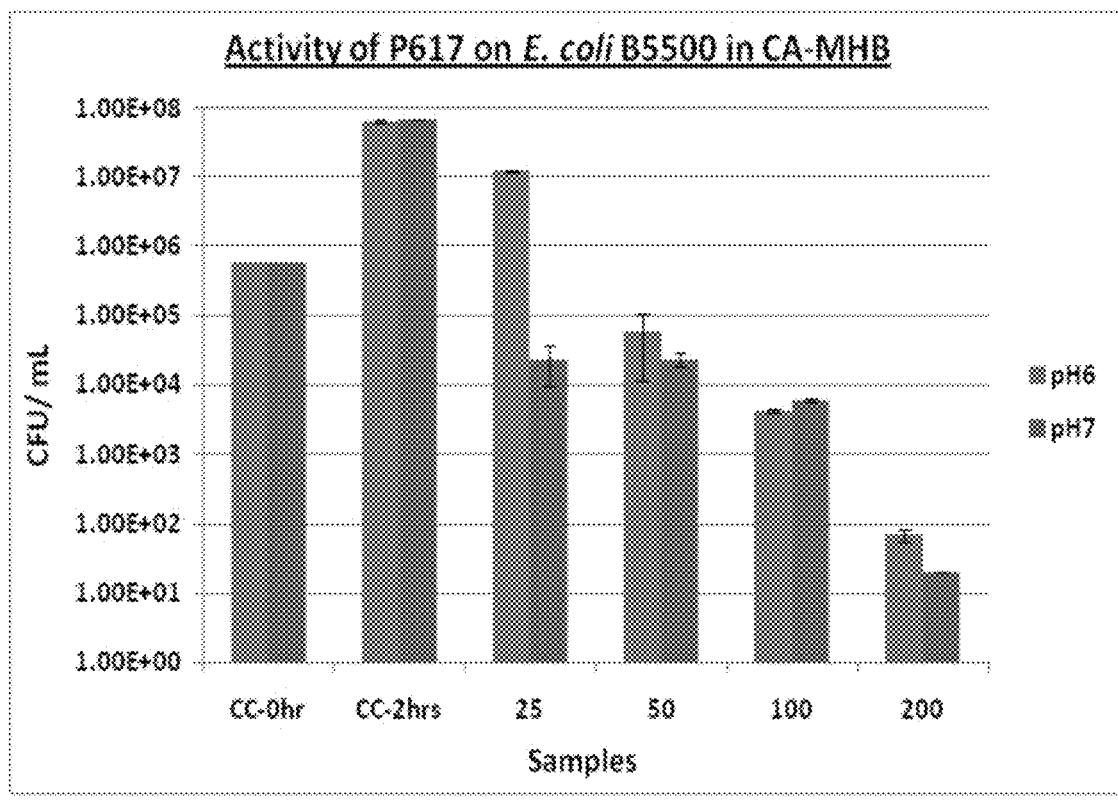
FIG. 10 shows Dose ranging activity of P617 on *E. coli* in CA-MHB media.

P617 buffered in both buffer skilled cells with 2 logs kill obtained with 100 µg/mL and 4 log cell killing obtained with 200 µg/mL of the protein (FIG. 10).

6. Activity of Purified P617 on Pseudomonas aeruginosa:

P617 in 10 mM Sodium acetate pH 6.0 and 20 mM HEPES pH 7.0 were used and the assay was done in Cation-adjusted Mueller Hinton Broth (CA-MHB). $10^6$ cells/mL of P. aeruginosa strain PA01 in CA-MHB medium was treated with 100, 200, and 400 µg/mL corresponding to 3.1, 6.2, and 12.4 µM of P617, incubated at 37° C. for 2 hours and determined cell-killing by enumerating remaining number of viable cells by dilution plating on LB plates followed by incubation at 37° C. for 16-18 hrs.

Figure 11:
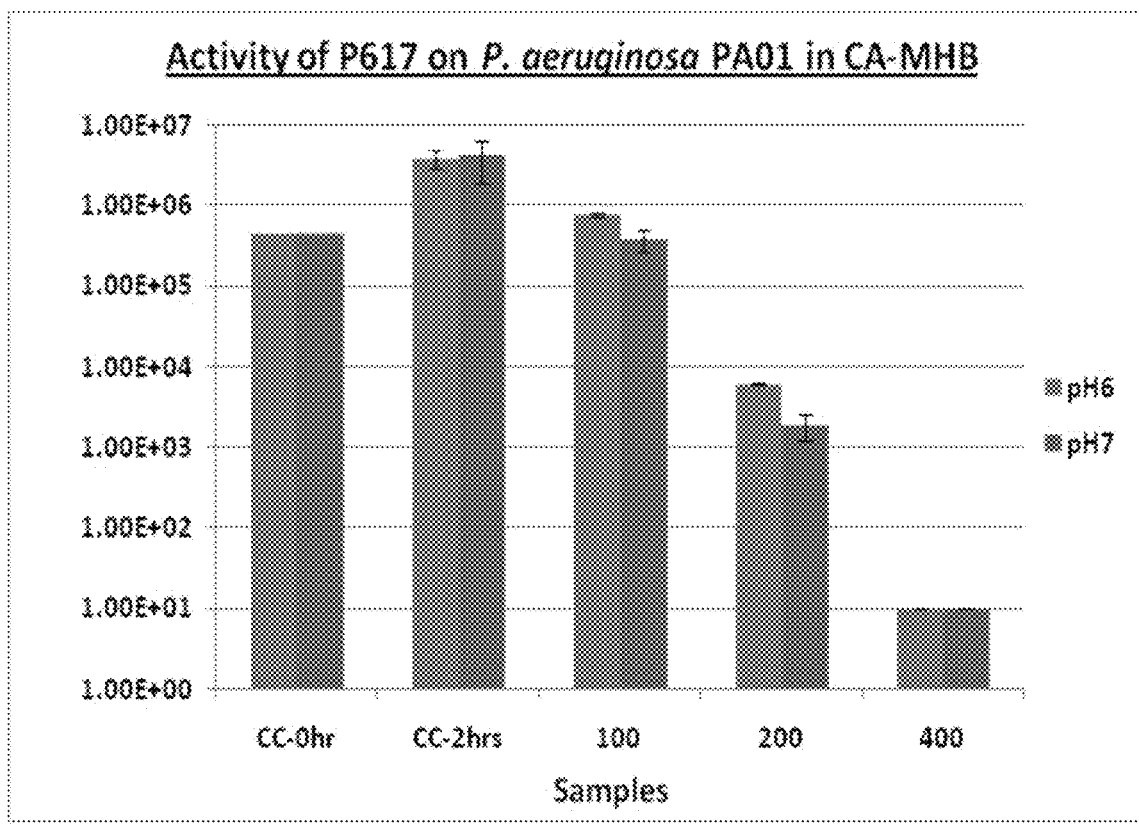
FIG. 11 shows Dose ranging activity of P617 on *P. aeruginosa* in CA-MHB media.

P617 buffered in both buffers killed cells with 2 logs kill obtained with 200 µg/mL and 4.5 logs cell killing obtained 400 µg/mL of the purified protein (FIG. 11).

7. Activity of Purified P617 on K. pneumoniae:

P617 in 10 mM Sodium acetate pH 4.0 and 20 mM HEPES pH 7.0 were used and the assay was done in Cation-adjusted Mueller Hinton Broth (CA-MHB). $10^6$ cells/mL of *K. pneumoniae* strain NDM-1 in CA-MHB was treated with 50, 100, 200, and 400 µg/mL corresponding to 1.6, 3.1, 6.2, and 12.4 µM of P617, incubated at 37° C. for 2 hours and determined cell-killing by enumerating remaining number of viable cells by dilution plating on LB plates followed by incubation at 37° C. for 16-18 hrs.

Figure 12:
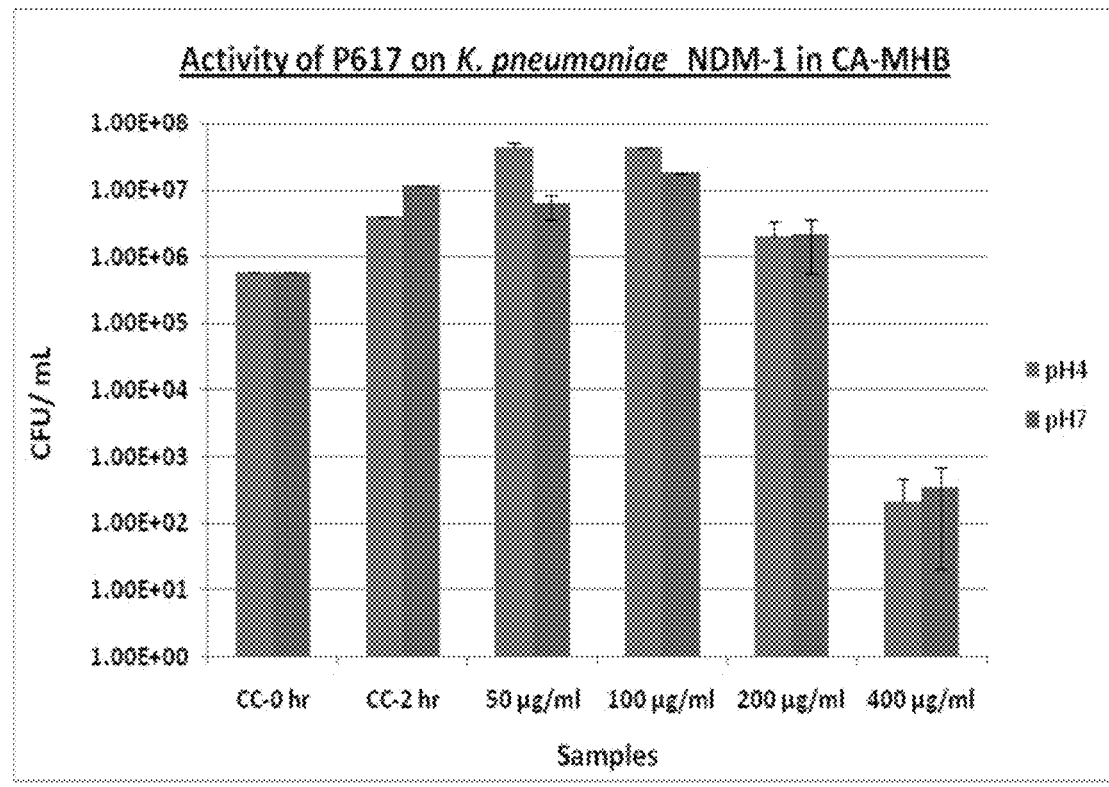
FIG. 12 shows Dose ranging activity of P617 on *K. pneumoniae* in CA-MHB media.

Result: P617 buffered in both buffers killed cells with 3 logs kill obtained with 400 µg/mL of the protein (FIG. 12).

8. MIC of P617 in Growth Media on *Acinetobacter baumannii*:

MIC was determined using a modified Clinical and Laboratory Standards Institute (CLSI) broth microdilution procedure on *A. baumannii* strain HER1401 in Cation-adjusted Mueller Hinton Broth (CA-MHB media). A 10-point MIC was set up in microtitre plates in duplicates with two-fold dilutions starting at 400 µg/mL (12.5 Wells of a 96-well polystyrene plated were coated with 0.5% BSA for 1 hour at 37° C. and each well were inoculated with 5×10$^5$ cells/mL *A. baumannii*. A positive control for growth which is devoid of P617 was included in the assay. Microtiter plates were incubated at 35° C. for 18-20 hrs. The endpoint for this assay was complete inhibition of growth at the end of incubation as determined by colorless wells after addition of Iodonitro tetrazolium (INT) dye. For this assay, P617 buffered in 10 mM Sodium acetate pH 4.0, 10 mM Sodium acetate pH 5.0, 10 mM Sodium acetate pH 6.0 and 20 mM HEPES pH 7.0 were used.

TABLE D4

MIC of P617 on *A. baumannii* in media

| SI. No. | Protein | CA-MHB (µg/mL) |
| --- | --- | --- |
| 1 | P617 (SA pH 4) | 200 |
| 2 | P617 (SA pH 5) | 200 |
| 3 | P617 (SA pH 6) | 200 |
| 2 | P617 (HEPES pH 7) | 200 |

Result: MIC was obtained at 6 µM (200 µg/mL) of P617 in all buffers indicating that the protein is active (Table D4).

9. MIC of P617 in Fetal Calf Serum (FCS) on *Acinetobacter baumannii*:

MIC was determined using a modified Clinical and Laboratory Standards Institute (CLSI) broth microdilution method on *A. baumannii* strain HER1401 in 50% FCS. A 10-point MIC was set up in microtitre plates in duplicates with two-fold dilutions starting at 400 µg/mL (12.5 Wells of a 96-well polystyrene plated were coated with 0.5% BSA for 1 hour at 37° C. and each well were inoculated with 5×10$^5$ cells/mL *A. baumannii*. A positive control for growth which is devoid of P617 was included in the assay. Microtiter plates were incubated at 35° C. for 18-20 hrs. The endpoint for this assay was complete inhibition of growth at the end of incubation as determined by colorless wells after addition of Iodonitro tetrazolium (INT) dye. For this assay, P617 buffered in 10 mM Sodium acetate pH 4.0, 10 mM Sodium acetate pH 5.0, 10 mM Sodium acetate pH 6.0, and 20 mM HEPES pH 7.0 were used.

TABLE D5

MIC of P617 on *A. baumannii* in FCS

| SI. No. | Protein | 50% FCS (µg/mL) |
| --- | --- | --- |
| 1 | P617 (SA pH 4) | 400 |
| 2 | P617 (SA pH 5) | >400 |

TABLE D5-continued

MIC of P617 on *A. baumannii* in FCS

| SI. No. | Protein | 50% FCS (µg/mL) |
| --- | --- | --- |
| 3 | P617 (SA pH 6) | >400 |
| 2 | P617 (HEPES pH 7) | >400 |

Result: MIC of P617 was obtained only with pH 4.0 buffered protein in 50% FCS at 12.5 µM (400 µg/mL) (Table D5).

10. Bactericidal Activity of P617 on *Acinetobacter baumannii* FCS:

P617 demonstrated cell killing activity in growth media such as LB and CA-MHB medium. And further, the MIC of P617 on *A. baumannii* was also determined to be 200 µg/mL in CA-MHB and 400 µg/mL in 50% FCS. In this experiment the cell killing activity of P617 in 50% FCS was determined.

For this assay, P617 refolded in 10 mM Sodium acetate pH 4.0 was used and the assay was done in 50% FCS. ~10$^6$ cells/mL of *A. baumannii* strain HER1401 in FCS was treated with 100, 200, and 400 µg/mL of P617, incubated at 37° C. for 2 hours and enumerated remaining number of viable cells.

Figure 13:
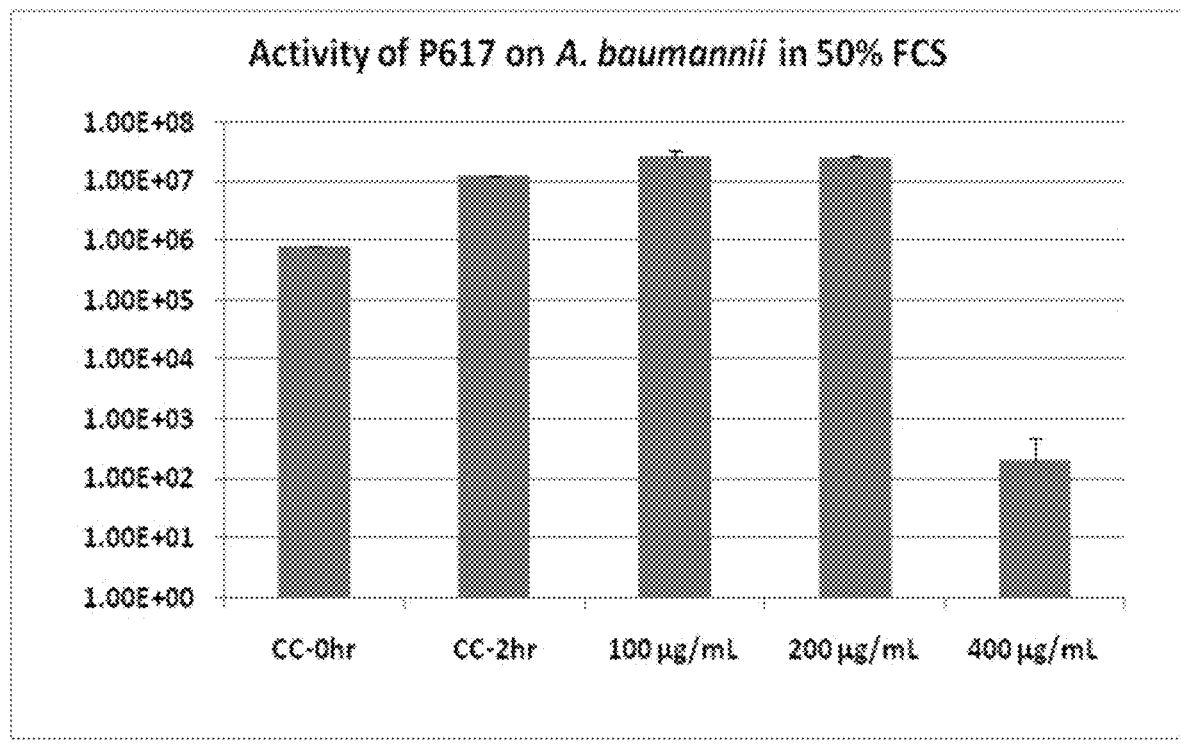
FIG. 13 shows Dose ranging activity of P617 on *A. baumannii* in FCS.

Result: 4 log cell killing obtained in 50% FCS with 400 µg/mL of P617. Inference: The fusion protein P617 kills *A. baumannii* in 50% FCS (FIG. 13).

11. Improving Solubility of P617 in Growth Media:

Previously we observed that the P617 precipitates in LB media and it is more soluble in CA-MHB. This experiment was done to figure out if we could improve the solubility of P617 by addition of solubilizing/stabilizing agents and whether improved solubility would result in improved cell killing activity in serum.

L-arginine is a well studied solubilizing agent for improving solubility of recombinant proteins and monoclonal antibodies (Golovanov, et al. (2004). Since P617 easily precipitates out in LB media, we evaluated the utility of L-arginine in improving P617 solubility in this media.

To study this, a protein precipitation assay was performed by incubating 20 µg of P617 buffered in 10 mM Sodium acetate pH 4.0 and 20 mM HEPES pH 7.0 in 50% LB at 37° C. for 2 hours with and without 200 mM L-arginine. Following incubation, the mix was spun at 13,000 rpm for 10 minutes to pellet any precipitate, the supernatants and pellets were analyzed on a 15% acrylamide gel.

Result: P617 at pH 4 and 7 completely precipitated in LB and is localized in the pellet fraction. However, P617 remained soluble with addition of L-Arginine at 200 mM. Inference: L-Arginine aids protein solubility in LB medium.

12. Antibacterial Activity of P617 on *A. baumannii* in LB with and without L-Arginine:

L-Arginine aids in improving solubility of P617. To determine whether the improved solubility translates to improved antibacterial activity, cell killing activity of P617 was done in LB with and without supplementation of 200 mM L-Arginine. For this assay, P617 refolded in 10 mM Sodium acetate pH 4.0 and dialyzed against 10 mM Sodium acetate pH 4.0 and 20 mM HEPES pH 7.0 were used and the assay was done in LB medium. 10$^6$ cells/mL of *A. baumannii* strain HER1401 in LB medium was treated with 100 and 200 µg/mL corresponding to 3.1 and 6.2 µM of P617, incubated at 37° C. for 2 hours. In another set, similar cell numbers and protein amounts were supplemented with 200 mm L-Arginine and treated as before. Antibacterial activity was determined by enumerating remaining number of viable cells by dilution plating on LB plates followed by incubation at 37° C. for 16-18 hrs.

Figure 2:
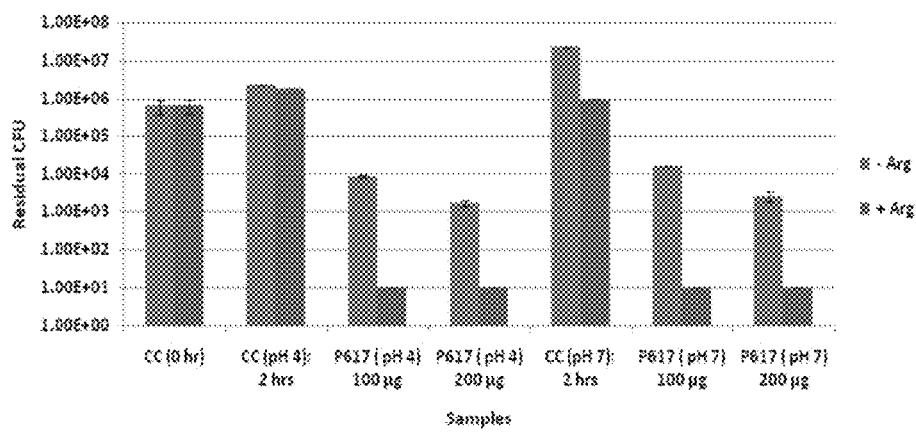
FIG. 2 shows Bactericidal activity of P617 on *A. baumannii* in LB with and without L-Arginine.

Result: L-Arginine at 200 mM improves the antibacterial activity of P617 in LB media. Inference: L-Arginine improves solubility of P617 and subsequently improves its antibacterial activity (FIG. 2).

13. Antibacterial Activity of P617 on *P. aeruginosa* in LB with and without L-Arginine:

For this assay, P617 refolded in 10 mM Sodium acetate pH 4.0 and dialyzed against 10 mM Sodium acetate pH 4.0 and 20 mM HEPES pH 7.0 were used and the assay was done in LB medium. $10^6$ cells/mL of *P. aeruginosa* strain PA01 in LB medium was treated with 100 and 200 µg/mL corresponding to 3.1 and 6.2 µM of P617, incubated at 37° C. for 2 hours. In another set similar cell numbers and protein amounts were supplemented with 200 mM L-Arginine and treated as before. Antibacterial activity was determined by enumerating remaining number of viable cells by dilution plating on LB plates followed by incubation at 37° C. for 16-18 hrs.

Figure 3:
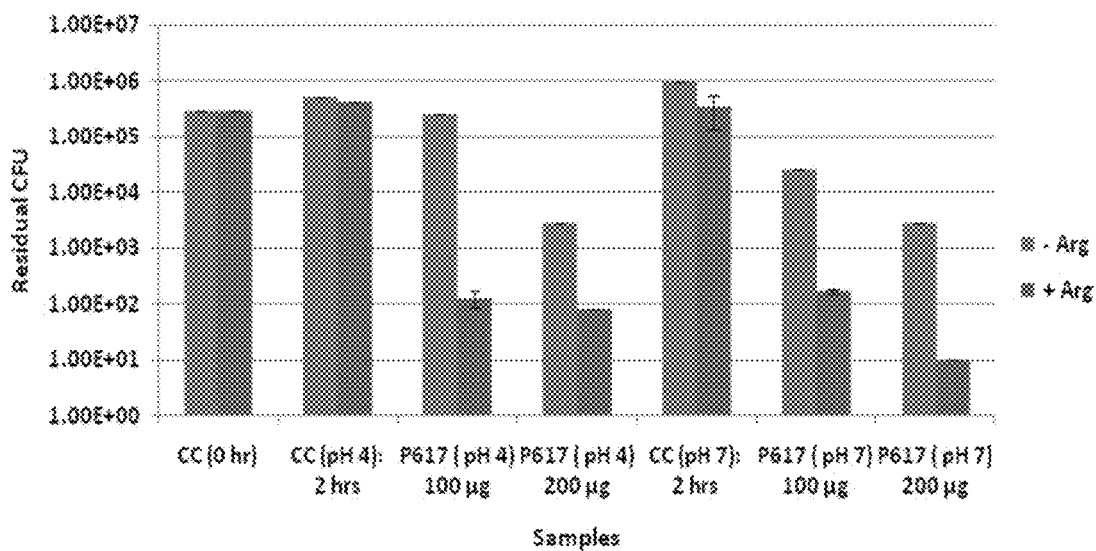
FIG. 3 shows Bactericidal activity of P617 on *P. aeruginosa* in LB with and without L-Arginine.

Result: L-Arginine at 200 mM improves the antibacterial activity of P617 on *P. aeruginosa* in LB media. Inference: L-Arginine improves solubility of P617 and subsequently improves its antibacterial activity (FIG. 3).

14. Activity of P617 on *A. baumannii* Interstitial Fluid (IF):

P617 demonstrated cell killing activity in LB and CA-MHB growth media. And further, it also demonstrated antibacterial activity against *A. baumannii* in 50% FCS. Interstitial fluid is another important biological fluid that is present in the spaces between the cells of the tissues. Formed by filtration through the blood capillaries, it is drained away as lymph. It closely resembles blood plasma in composition but contains less amount of protein. In this experiment the cell killing activity of P617 in Interstitial Fluid (IF) was determined. Since we figured that L-Arginine aids antibacterial activity of P617, this assay was set up with and without L-Arginine.

For this assay, P617 refolded in 10 mM Sodium acetate pH 4.0 was used and the assay was done in IF. ~$10^6$ cells/mL of *A. baumannii* strain HER1401 in IF was treated with 50, 100, and 200 µg/mL of P617, incubated at 37° C. for 2 hours and enumerated remaining number of viable cells.

Figure 14:
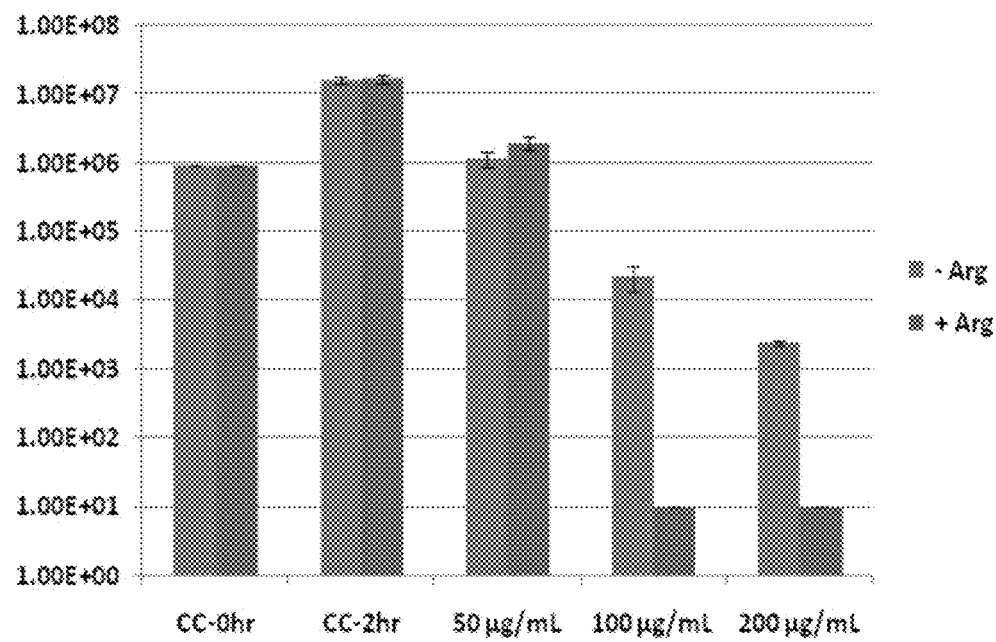
FIG. 14 shows Bactericidal activity of P617 on *A. baumannii* in IF with and without L-Arginine.

Result: P617 kills *A. baumannii* in IF with >3 logs cell killing obtained with 100 µg/mL in the presence of L-Arginine. L-Arginine aids antibacterial activity in IF. Inference: P617 demonstrates potent antibacterial activity in IF (FIG. 14).

Example 4: Construct P340: (6×his (SEQ ID NO: 9)-Phi29 Phage Lysozyme-LysM-RRR-BPI TMD-RRR)

DNA Sequence P340:

```
                                      (SEQ ID NO: 32)
ATGCATCATC ATCATCATCA TCAAATTTCA CAAGCGGGTA

TCAACTTAAT TAAGAGCTTT GAGGGTTTAC

AACTGAAAGC ATATAAAGCT GTTCCGACTG AGAAGCATTA

CACCATTGGT TACGGTCATT ACGGTTCCGA

TGTTTCACCT AGGCAGGTTA TCACTGCTAA ACAGGCTGAA
```

```
                      -continued
GACATGTTGC GTGATGATGT GCAGGCTTTT

GTGGATGGTG TAAATAAAGC ATTAAAAGTA TCTGTCACCC

AAAATCAATT TGATGCCTTG TCTCATTCGC

TTACAACGTT GGGTTAGGGG CTTTCAGGTC TTCTTCTCTA

CTGGAATACT TGAATGAAGG AAGAACAGCT

CTAGCGGCGG CTGAATTCCC TAAATGGAAT AAGTCAGGCG

GTAAAGTTTA TCAAGGGTTG ATTAACCGTA

GAGCACAGGA GCAAGCCTTG TTTAATAGTG GAACACCTAA

AAATGTTTCA CGTGGAACAT CGTCTACTAA

AACGACACCT AAGTATAAGG TGAAGAGTGG TGACAACCTT

ACTAAAATCG CTAAAAAGCA TAATACAACG

GTTGCTACTT TGTTGAAGTT GAATCCGAGT ATCAAAGACC

CGAACATGAT TAGAGTTGGA CAAACAATAA

ATGTTACAGG TAGCGGCGGC AAAACACATA AGGTGAAAAG

TGGTGACACA CTCAGTAAAA TTGCCGTTGA

TAACAAAACG ACTGTGAGTA GATTGATGAG TCTAAACCCT

GAAATTACGA ATCCAAATCA TATAAAAGTA

GGTCAAACAA TTAGATTAAG TAAGCTTCGC CGTCGCGCGT

CCCTGATGGT GCTGGTCGCC ATAGGCACCG

CCGTGACAGC GGCCGTCAAC CCTGGCGTCG TGGTCAGGCG

CCGTCGCTGA
```

Nucleotide P340:

Phi29 catalytic domain: 22 to 468 from sequence NC 011048.1:15457-16233:Phi29 catalytic domain: 1 to 450. Lys M: 469 to 792. BPI TMD: 807 to 879.

Amino Acid Sequence:

```
                                      (SEQ ID NO: 33)
MHHHHHHQIS QAGINLIKSF EGLQLKAYKA VPTEKHYTIG

YGHYGSDVSP RQVITAKQAE

DMLRDDVQAF VDGVNKALKV SVTQNQFDAL VSFAYNVGLG

AFRSSSLLEY LNEGRTALAA

AEFPKWNKSG GKVYQGLINR RAQEQALFNS GTPKNVSRGT

SSTKTTPKYK VKSGDNLTKI

AKKHNTTVAT LLKLNPSIKD PNMIRVGQTI NVTGSGGKTH

KVKSGDTLSK IAVDNKTTVS

RLMSLNPEIT NPNHIKVGQT IRLSKLRRRA SLMVLVAIGT

AVTAAVNPGV VVRRRR
```

Vector sequence along with 6X His tag (SEQ ID NO: 9) (1-7; MHHHHHH (SEQ ID NO: 34));

Lysozyme domain (8-156; QISQA... (SEQ ID NO: 35) to ...TPKNV (SEQ ID NO: 36));

LysM domain (157-264; SRGT... (SEQ ID NO: 37)
to ...TIRLS (SEQ ID NO: 38));

RRR linkers (267-269 and 294-296);

BPI TMD Peptide (270-293; ASLM... (SEQ ID NO: 39)
to ...PGVVVR (SEQ ID NO: 40))

Figure 15:
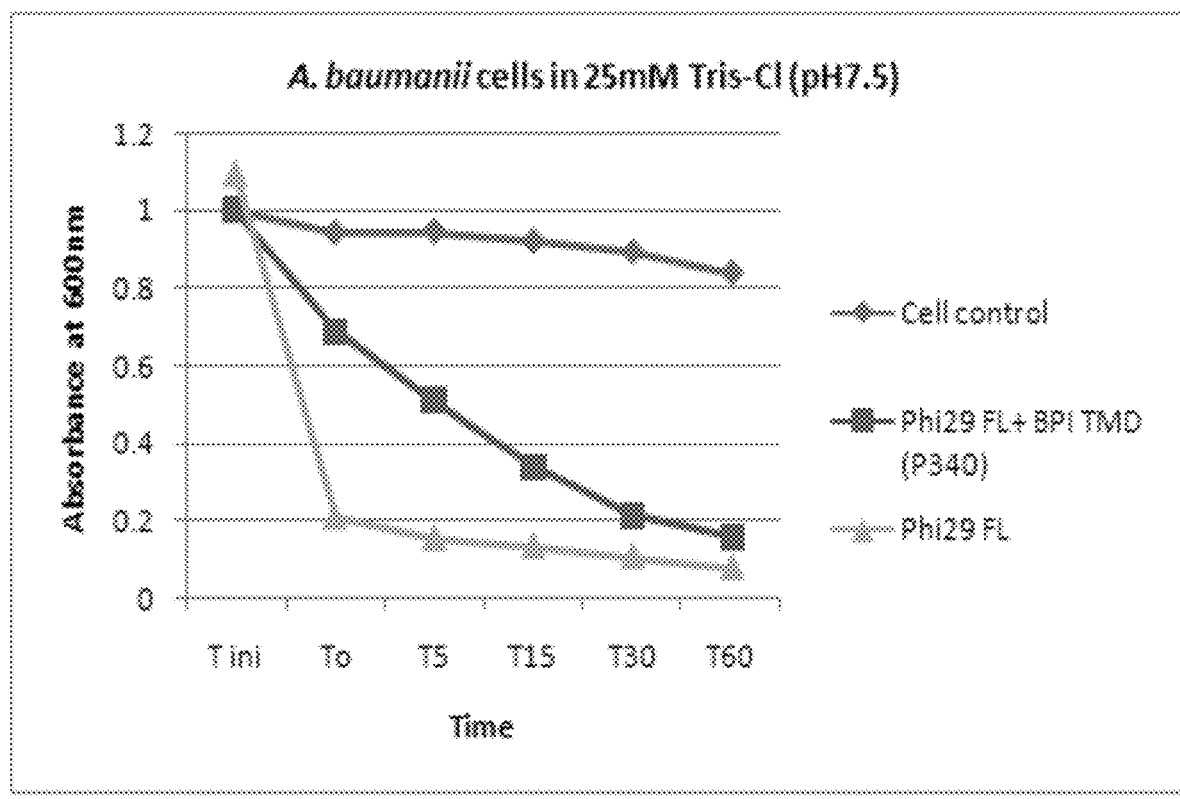
FIG. 15 shows OD fall assay of Phi29FL (P340) 30.
Figure 16A:
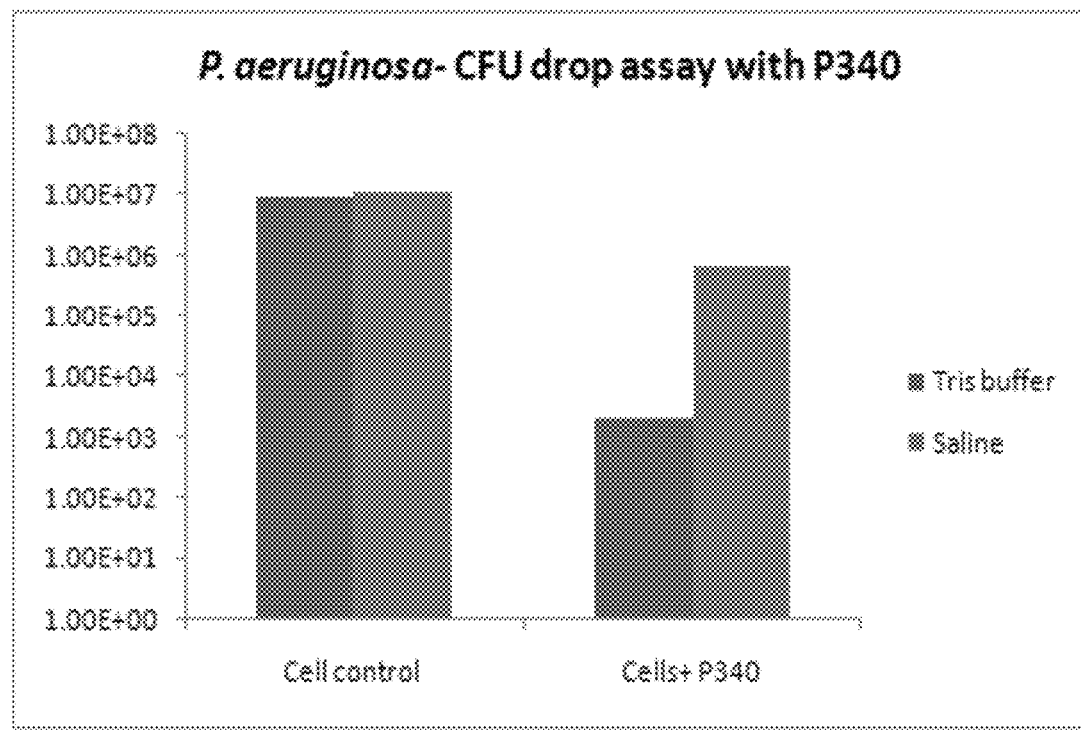
FIGS. 16A-16D shows The protein P340 kills *P. aeruginosa. A. baumannii*, and *E. coli* efficiently in both physiological buffer and buffered saline, and *K. pneumoniae* in buffer.
Figure 16B:
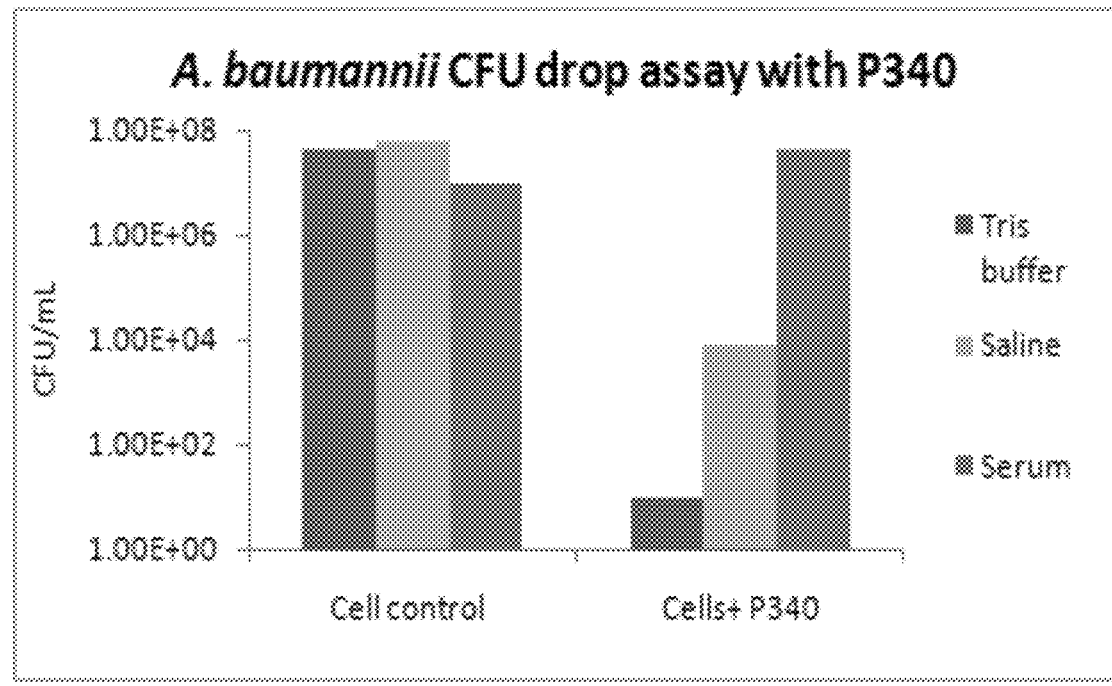
Figure 16C:
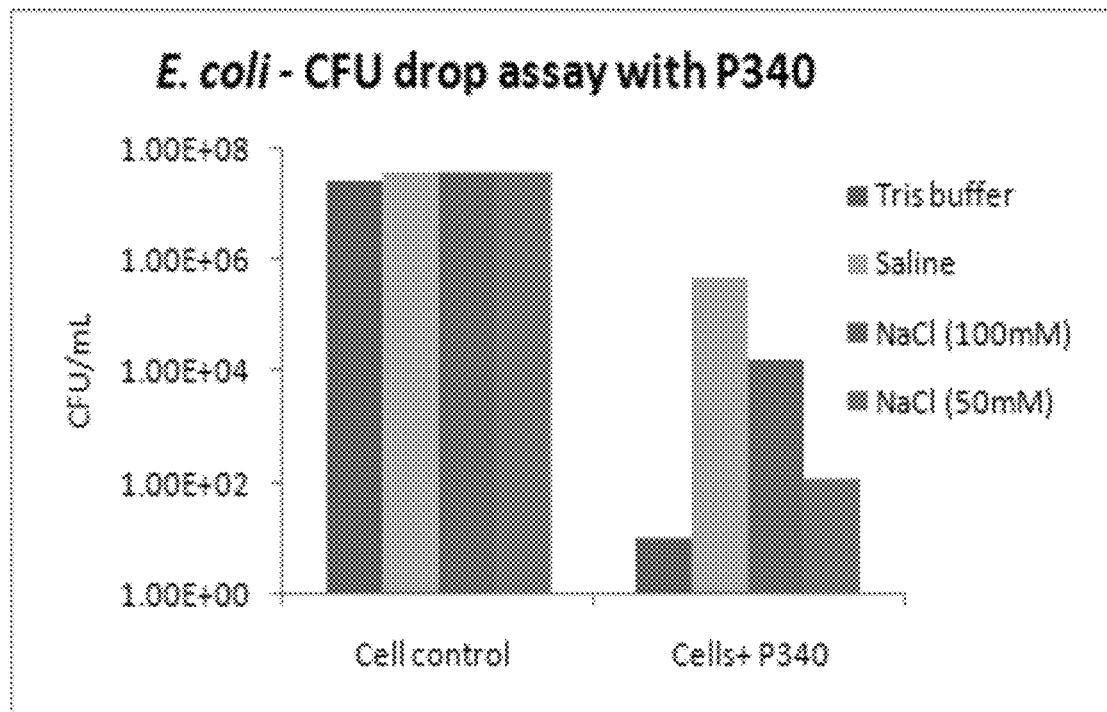
Figure 16D:
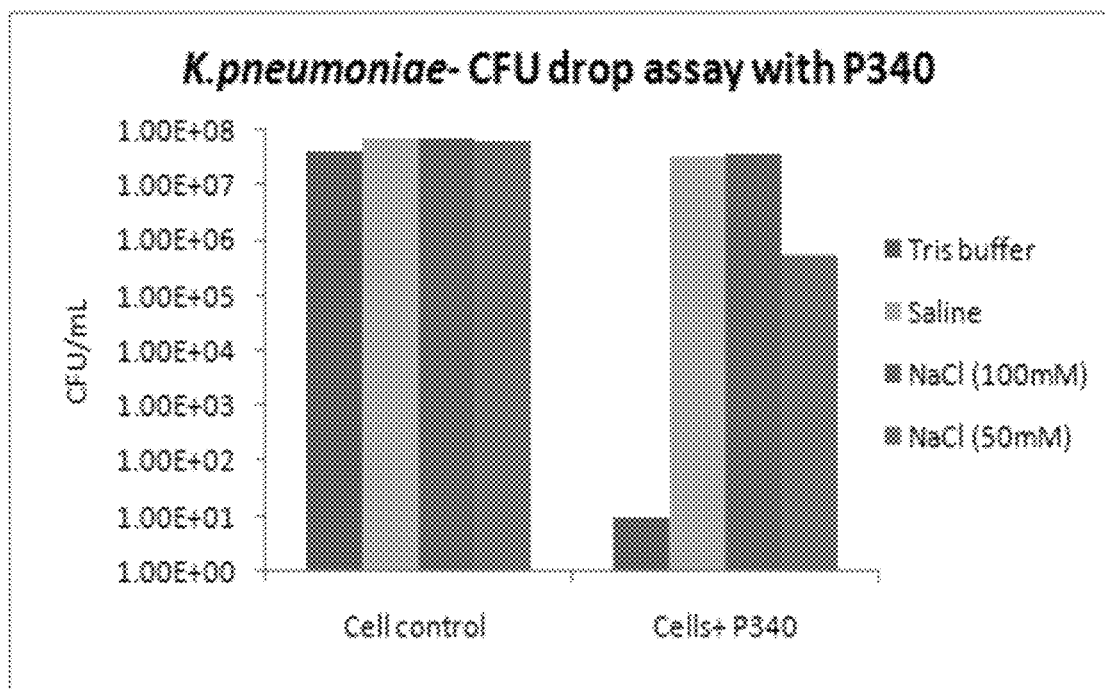
Figure 17A:
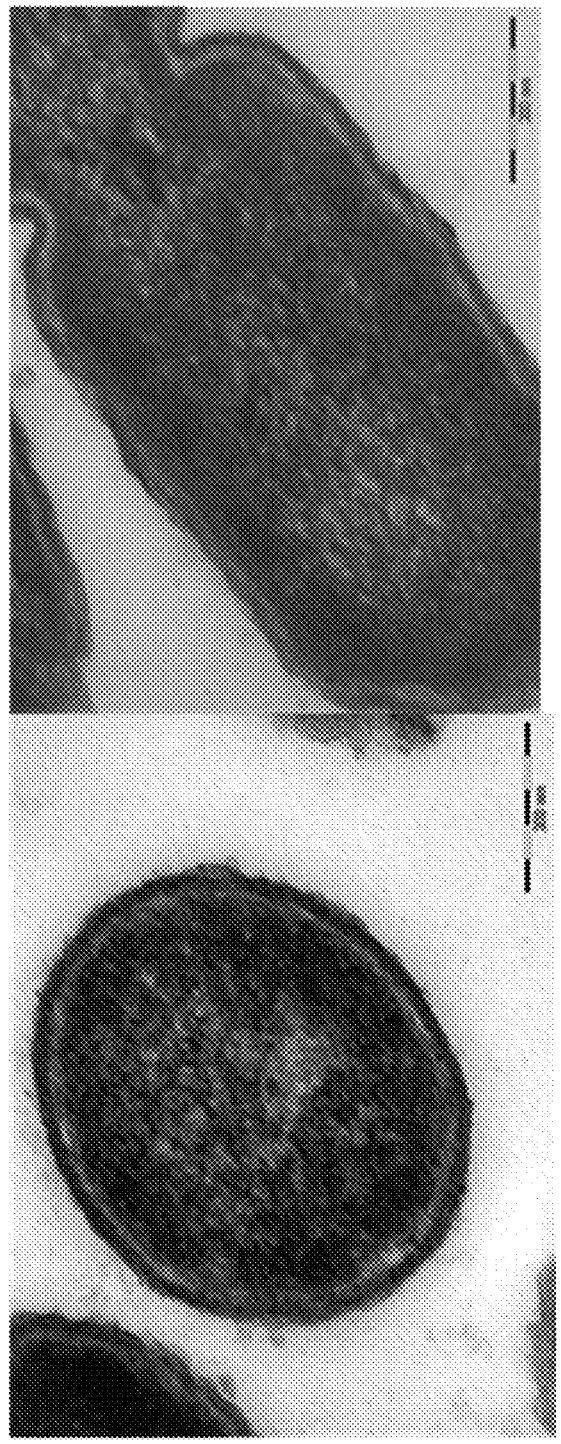
FIGS. 17A-17B—FIG. 17A shows untreated cells showed normal morphology.
Figure 17B:
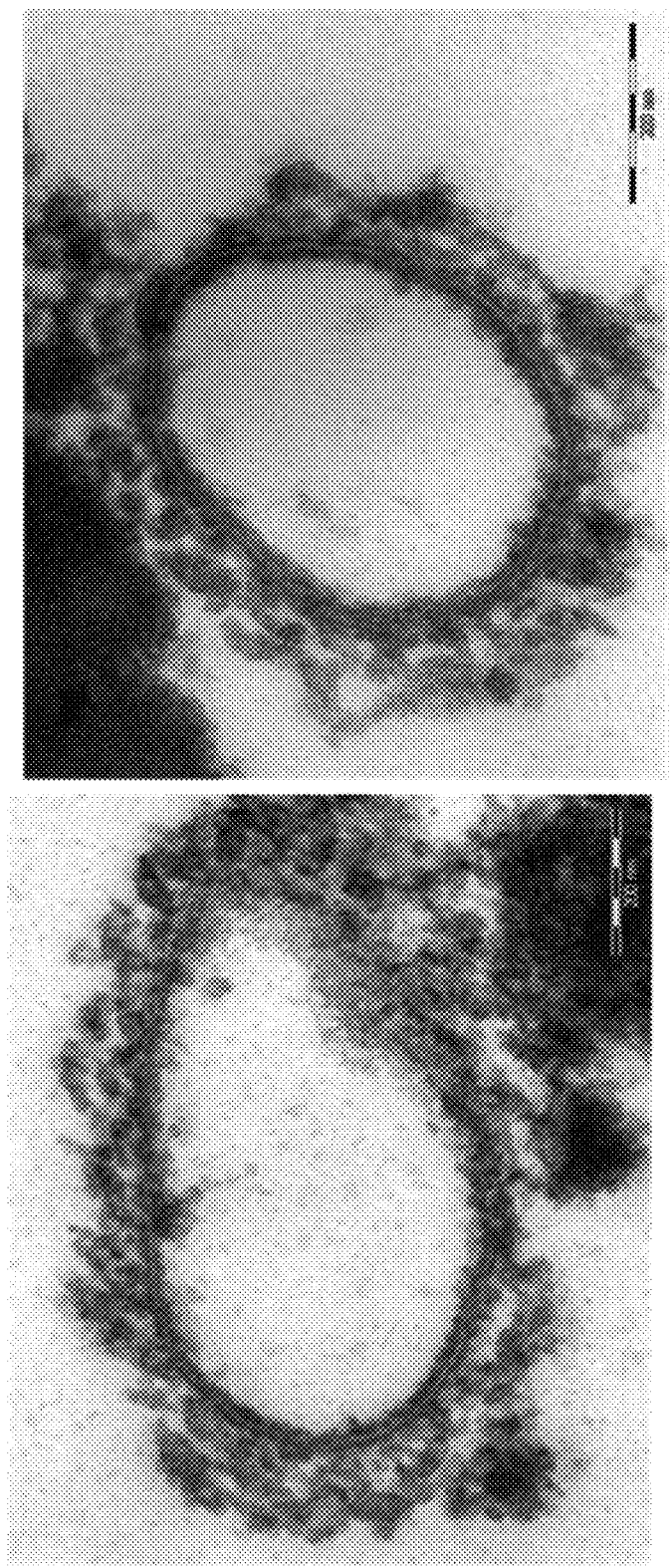

From sequence ID YP_002004544: Phi29 catalytic domain: 1 to 150
LysM: 151 to 258
From sequence ID NP 001716: BPI TMD: 16 to 39
Introduction
The BPI TMD with RRR flanks was first cloned into pET21b as Hind III/XhoI. The phi 29 endolysin gene was then cloned upstream of the BPI TMD segment at NdeI/XhoI sites to generate a fusion construct. The forward primer for amplification of Phi29 endolysin included a 6×-His tag (SEQ ID NO: 9) to aid protein purification.
Test protein expression was performed in *E. coli* C43 (DE3) by inducing with 1 mM IPTG at 37° C. for 4 hours induced at OD600 of 2.0
1. Purification and Refolding of P340:
Protein expression was done in *E. coli* C43 (DE3) by inducing with 1 mM IPTG at 37° C. at 2.0 OD for 4 hours. Induced cell pellet was resuspended in buffer, sonicated to lyse the cells, separated supernatant and pellet by centrifugation at 10,000 rpm. Protein purification was done from the inclusion bodies. Inclusion bodies were solubilized in 6M Guanidium hydrochloride and protein was purified by Ni-NTA chromatography.
2. Activity of Purified P340:
Two assays were done to determine the activity of the purified, refolded P340.
a. OD Fall Assay:
The catalytic activity of the Phi29 lysozyme was determined by OD fall assay using chloroform treated *P. aeruginosa* cells as substrate. 50 µg/ml of purified P340 and a positive control protein Phi29 Lysozyme-LysM (Phi29 FL) were used in this assay. An active protein by OD fall assay will also suggest the correct refolding of the Phi29 lysozyme.
Result: The purified P340 is catalytically active as observed by the OD fall obtained (FIG. 15).
b. CFU Drop Assay:
The antibacterial activity of P340 was tested against *P. aeruginosa, A. baumannii, E. coli,* and *K. pneumoniae* by using the CFU drop assay. ~$10^7$ cells of cells in the respective assay condition (buffer, buffer containing saline) was treated with 250 µg/ml of P340, incubated at 37° C. for 2 hours and enumerated remaining number of viable cells. The experiment was set up in duplicates and the results tabulated as average of duplicates.
Assay Conditions: reaction volume: 200 µl; buffer: 25 mM Tris-Cl pH 7.5 and 25 mM Tris-Cl pH 7.5+saline; duration: 2 hours @ 37° C., 200 rpm; protein: 250 µg/ml
Result: Killing observed in both buffer and saline in *P. aeruginosa, A. baumannii,* and *E. coli*
Inference: The protein P340 kills *P. aeruginosa. A. baumannii,* and *E. coli* efficiently in both physiological buffer and buffered saline, and *K. pneumoniae* in buffer (FIGS. 16A-16D).
3. Electron Microscopy:
Electron microscopy was done with *P. aeruginosa* PAO1 cells treated with protein P340.
Inference: Untreated cells showed normal morphology (FIG. 17A).
Inference: Cells treated with P340 appeared to be bacterial ghosts that contained intact bacterial envelope, devoid of cytoplasmic contents (FIG. 17B).

Example 5: Construct P603 (WLBU2-Link-Phi29 Lysozyme-his)

Introduction
WLBU2 is a modified antimicrobial peptide (AMP) derived from the AMP LL37 (Berthony Deslouches, et al. (2005) *Antimicrobial Agents & Chemotherapy*, p. 3208-3216). A unique feature of this peptide is its activity in human biological fluids (serum and blood) compared to LL37.
The phage genome of a *Bacillus subtilis* Phage Phi29 encodes an endolysin that comprises of a lysozyme and LysM domains. The lysozyme domain is responsible for the degradation of peptidoglycan. The strategy was to fuse the AMP WLBU2 to Phi29 lysozyme to evaluate its activity.
DNA Sequence of pGDC 603 (564 Bases):

(SEQ ID NO: 41)
ATGCGTCGTT GGGTTCGTCG TGTTCGTCGT

TGGGTTCGTC GTGTTGTTCG TGTTGTTCGT

CGTTGGGTTC GTCGTGGCTC CGGATCGGCT

TCTGGGCAAA TTTCACAAGC GGGTATCAAC

TTAATTAAGA GCTTTGAGGG TTTACAACTG

AAAGCATATA AAGCTGTTCC GACTGAGAAG

CATTACACCA TTGGTTACGG TCATTACGGT

TCCGATGTTT CACCTAGGCA GGTTATCACT

GCTAAACAGG CTGAAGACAT GTTGCGTGAT

GATGTGCAGG CTTTTGTGGA TGGTGTAAAT

AAAGCATTAA AAGTATCTGT CACCCAAAAT

CAATTTGATG CACTTGTCTC ATTCGCTTAC

AACGTTGGGT TAGGGGCTTT CAGGTCTTCT

TCTCTACTGG AATACTTGAA TGAAGGAAGA

ACAGCTCTAG CGGCGGCTGA ATTCCCTAAA

TGGAATAAGT CAGGCGGTAA AGTTTATCAA

GGGTTGATTA ACCGTAGAGC ACAGGAGCAA

GCCTTGTTTA ATAGTGGAAC ACCTAAAAAT

GTTCACCACC ACCACCACCA CTAA

Amino Acid Sequence of P603:

(SEQ ID NO: 42)
MRRWVRRVRR WVRRVVRVVR RWVRRGSGSA SGQISQAGIN

LIKSFEGLQL KAYKAVPTEK HYTIGYGHYG SDVSPRQVIT

AKQAEDMLRD DVQAFVDGVN KALKVSVTQN QFDALVSFAY

NVGLGAFRSS SLLEYLNEGR TALAAAEFPK WNKSGGKVYQ

GLINRRAQEQ ALFNSGTPKN VHHHHHH segments: WLBU2 Peptide 2-25; Phi29 lysozyme 33-181
Theoretical pI/Mw: 10.71/21171.08

2. Cloning of P603

WLBU2 was fused to the 5' end of the Phi29 lysozyme coding region by a PCR based method introducing appropriate cloning sites and the chimeric DNA sequence without a stop codon was cloned into *E. coli* expression vector pET26b as an NdeI-XhoI fragment, for expression of the chimeric protein as a C-terminal 6x-His tag (SEQ ID NO: 9) fusion.

*E. coli* transformants were screened by PCR, plasmid DNA isolated from the positive clones and presence of the insert confirmed by restriction digestion analysis.

3. Expression and Purification of P603

Test protein expression was performed in *E. coli* ER2566 by inducing with 1 mM IPTG at 37° C. for 4 hours.

Protein expression was done in *E. coli* ER2566 by inducing with 1 mM IPTG at 37° C. for 4 hours. Induced cell pellet was resuspended in buffer, sonicated to lyse the cells, separated supernatant and pellet by centrifugation at 10,000 rpm. Protein purification was done from the inclusion bodies. Inclusion bodies were solubilized in 6M Guanidium hydrochloride and protein was purified by Ni-NTA chromatography.

The purified fractions were refolded by step wise dialysis to remove the denaturant and finally the protein was dialyzed against 20 mM HEPES pH 7.0. The final concentration post dialysis was 0.76 mg/ml.

4. Activity of Purified P603:

Two assays were done to determine the activity of the purified, refolded P603.

a) OD Fall Assay:

The catalytic activity of the Phi29 lysozyme was determined by OD fall assay using chloroform treated *P. aeruginosa* cells as substrate. 50 µg/ml of purified P603 and a positive control protein P203 were used in this assay. An active protein by OD fall assay will also suggest the correct refolding of the Phi29 lysozyme.

Figure 18:
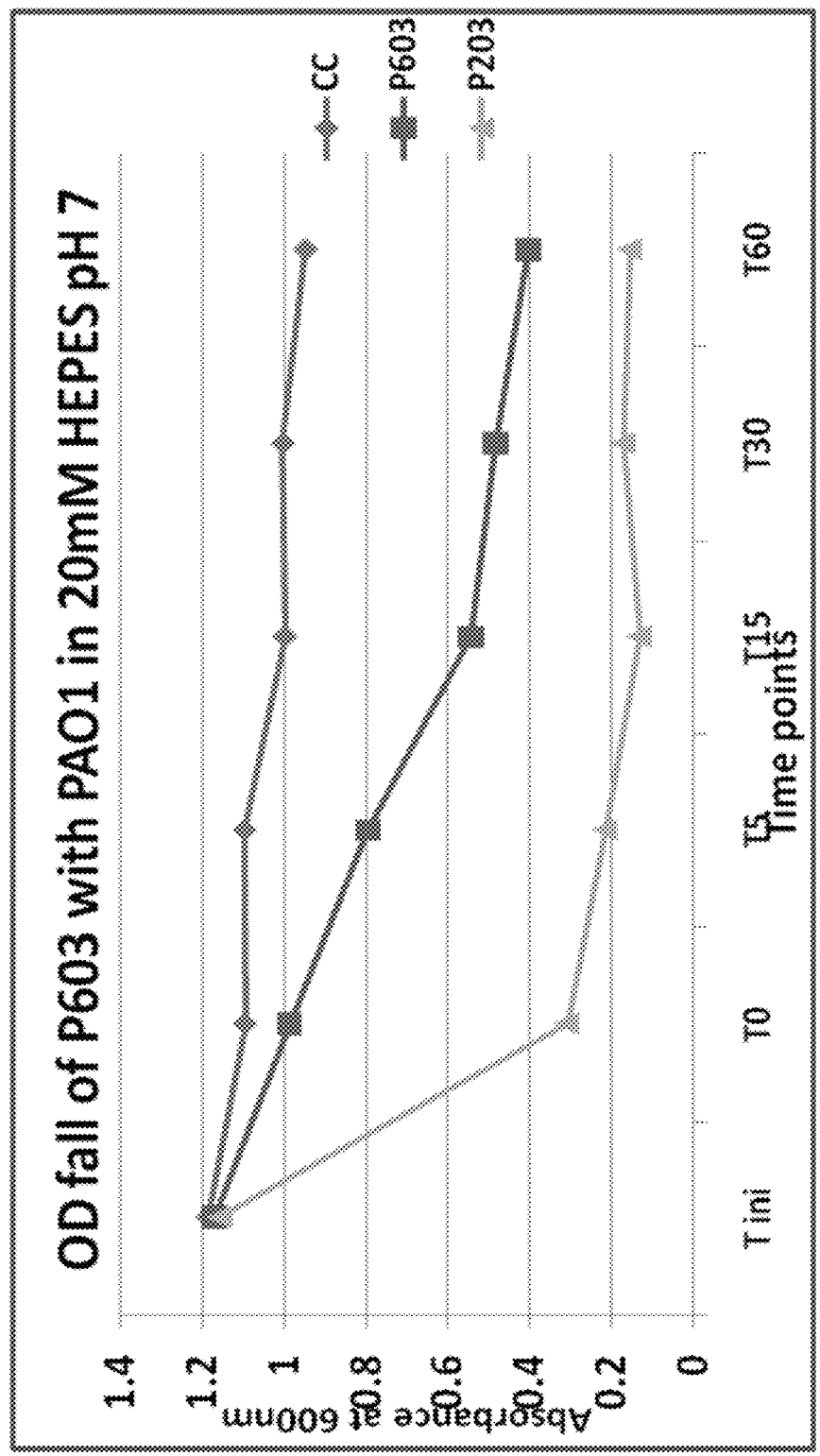
FIG. 18 shows the purified P603 is catalytically active as observed by the OD fall obtained.

Result: The purified P603 is catalytically active as observed by the OD fall obtained (FIG. 18).

b) CFU Drop Assay:

The antibacterial activity of P603 was tested against *P. aeruginosa* strain PA01 by using the CFU drop assay. ~$10^7$ cells of PA01 in buffer, buffer containing saline, FBS, LB medium was treated with 250 µg/ml of P603, incubated at 37° C. for 2 hours and enumerated remaining number of viable cells.

Assay Conditions: reaction volume: 200 ul; buffer: HEPES pH 7.0 and HEPES pH 7.0+saline; duration: 2 hours @ 37° C., 200 rpm; protein: 250 µg/ml.

Figure 19:
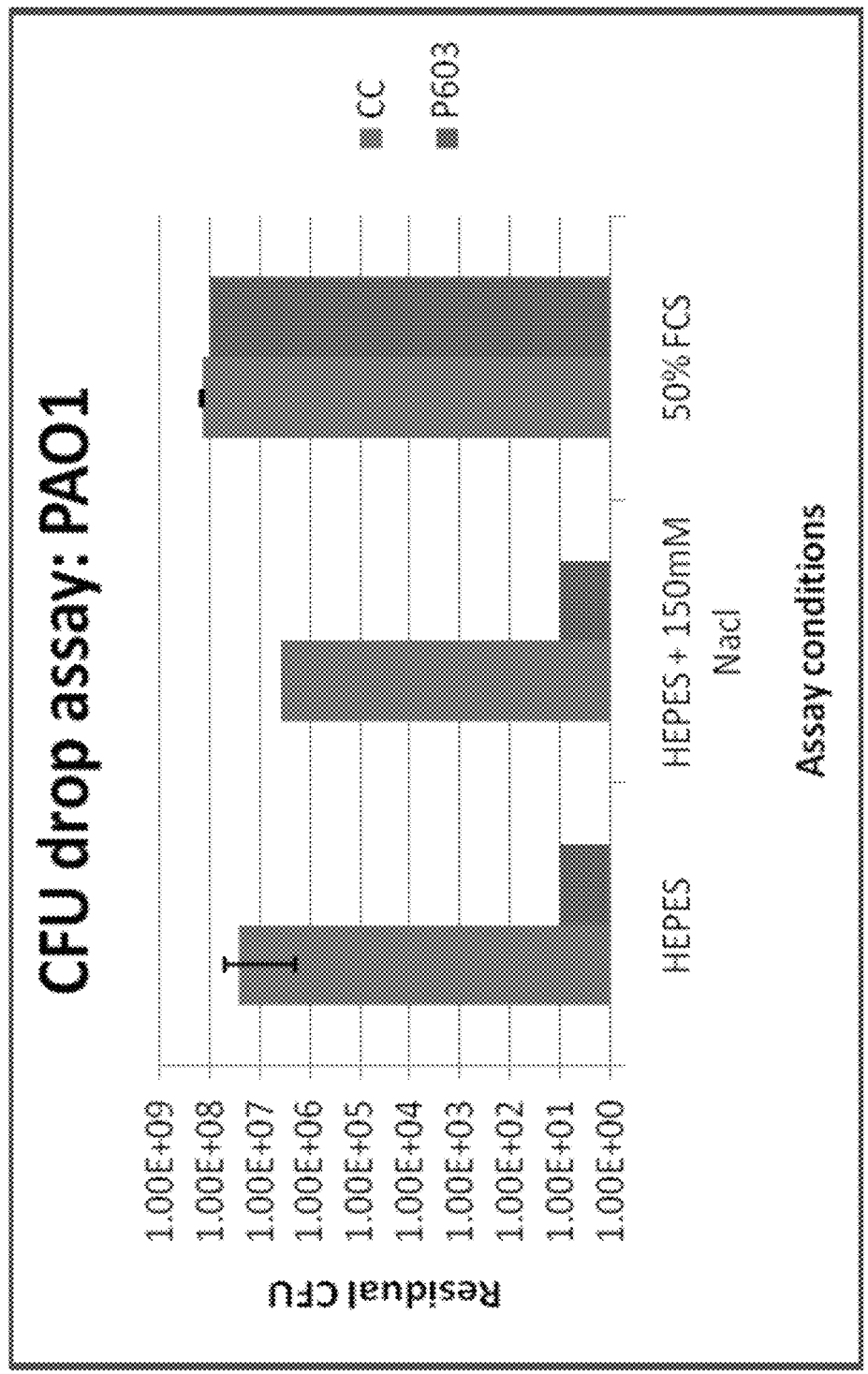
FIG. 19 shows the fusion protein P603 kills *P. aeruginosa* efficiently in both physiological buffer and buffered saline. However, in 50% serum P603 was not active.

Result: ~6 log cell killing obtained in both buffer and saline (FIG. 19).

Inference: The fusion protein P603 kills *P. aeruginosa* efficiently in both physiological buffer and buffered saline. However, in 50% serum P603 was not active.

c) Dose Response:

Dose response was done in buffered saline with varying protein concentrations as indicated below on *P. aeruginosa* PAO1 cells.

Figure 20:
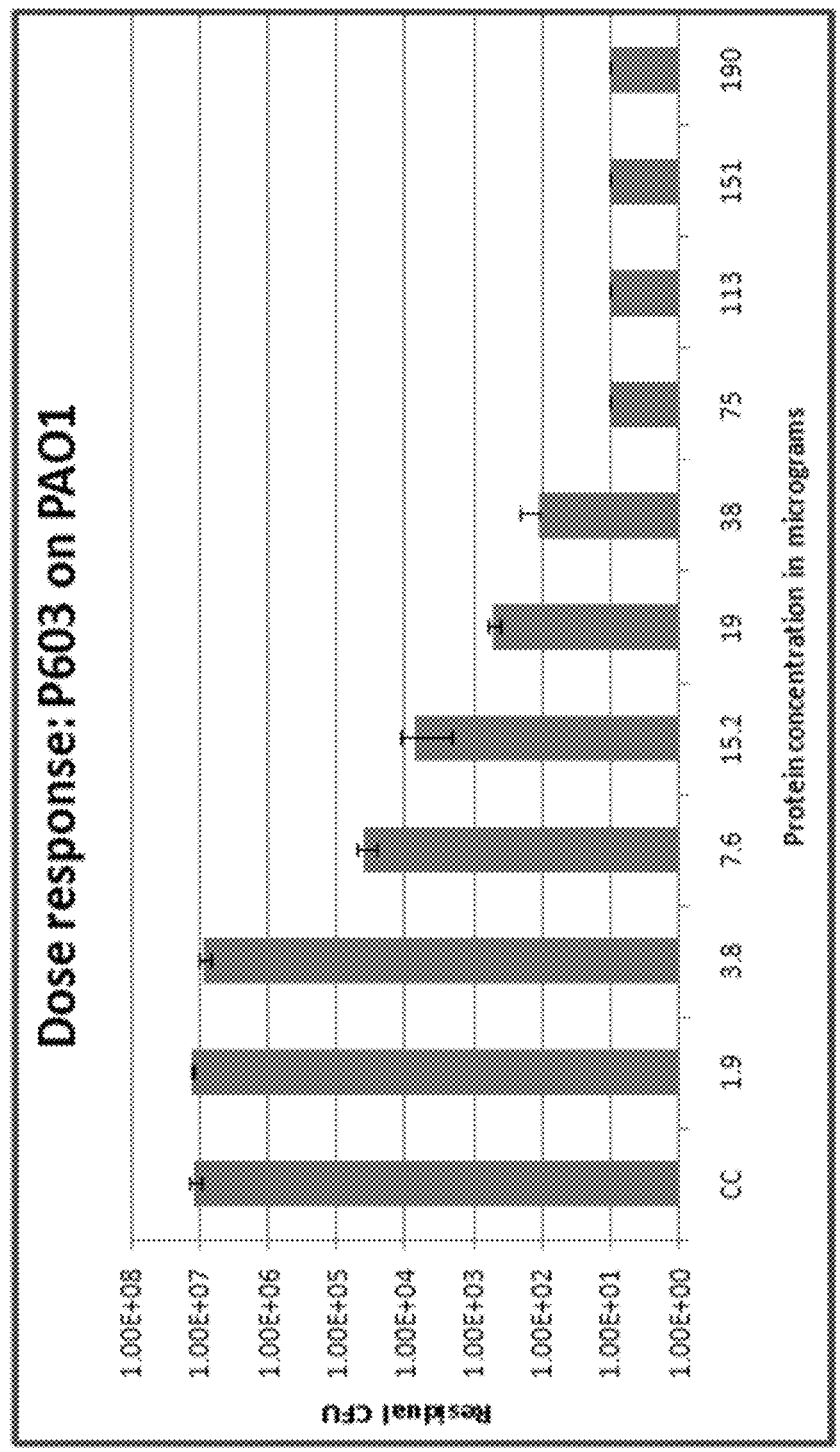
FIG. 20 shows P603 exhibits dose response. Significant cell-killing observed with 7.6 µg/mL of the protein.

Assay Conditions: reaction volume: 200 µl; buffer: HEPES pH 7.0 and HEPES pH 7.0+saline; duration: 2 hours @ 37° C., 200 rpm; protein: 1.9 µg/ml to 190 µg/ml Result: P603 exhibits dose response. Significant cell-killing observed with 7.6 µg/mL of the protein (FIG. 20).

Example 6: P594 (WLBU2-Linker-GP36-his)

DNA Sequence of pGDC 594 (765 Bases):

(SEQ ID NO: 43)
```
ATGCGTCGTT GGGTTCGTCG TGTTCGTCGT
TGGGTTCGTC GTGTTGTTCG TGTTGTTCGT
CGTTGGGTTC GTCGTGGCTC CGGATCGGCT
TCTGGGGGTG TGGCCCTGGA CCGCACGCGG
GTTGATCCCC AGGCAGTCGG CAACGAGGTG
CTCAAGCGCA ACGCGGATAA GCTGAATGCG
ATGCGGGGCG CCGAGTACGG TGCCAACGTC
AAGGTCAGCG GCACGGACAT TCGCATGAAC
GGGGGTAACA GTGCCGGCAT GCTGAAGCAG
GACGTGTTCA ACTGGCGGAA GGAACTGGCT
CAGTTCGAGG CTTACCGAGG GGAGGCGTAT
AAGGATGCCG ATGGTTATAG TGTGGGCCTG
GGGCATTACC TGGGCAGTGG CAATGCTGGG
GCAGGTACTA CAGTCACGCC TGAGCAAGCC
GCGCAGTGGT TCGCCGAGGA CACCGACCGC
GCACTCGACC AGGGTGTGAG GTTGGCCGAC
GAGCTGGGCG TTACGAACAA TGCCTCTATC
CTGGGATTGG CCGGTATGGC CTTCCAGATG
GGCGAAGGAC GTGCCCGGCA GTTCCGTAAC
ACCTTCCAGG CGATCAAGGA TCGCAACAAG
GAAGCCTTCG AGGCTGGTGT GCGAAACAGC
AAGTGGTACA CGCAGACGCC CAACCGGGCC
GAGGCATTCA TCAAGCGCAT GGCGCCCCAC
TTCGATACAC CGAGTCAAAT CGGTGTCGAT
TGGTACAGCG CCGCAACAGC GGAGCACCAC
CACCACCACC ACTGA
```

Amino Acid Sequence of P594:

(SEQ ID NO: 44)
```
MRRWVRRVRR WVRRVVRVVR RWVRRGSGSA SGGVALDRTR
VDPQAVGNEV LKRNADKLNA MRGAEYGANV KVSGTDIRMN
GGNSAGMLKQ DVFNWRKELA QFEAYRGEAY KDADGYSVGL
GHYLGSGNAG AGTTVTPEQA AQWFAEDTDR ALDQGVRLAD
ELGVTNNASI LGLAGMAFQM GEGRARQFRN TFQAIKDRNK
EAFEAGVRNS KWYTQTPNRA EAFIKRMAPH FDTPSQIGVD
WYSAATAEHH HHHH
```

Segments: WLBU2 Peptide 2-25; GP36 CD 33-248
Theoretical pI/Mw: 10.21/28388.74

1. Introduction:

WLBU2 was fused to the 5' end of the Gp36 CD coding region by a PCR based method introducing appropriate cloning sites and the chimeric DNA sequence without a stop codon was cloned into *E. coli* expression vector pET26b as an NdeI-XhoI fragment, for expression of the chimeric protein as a C-terminal 6×-His tag (SEQ ID NO: 9) fusion. *E. coli* transformants were screened by PCR, plasmid DNA isolated from the positive clones and presence of the insert confirmed by restriction digestion analysis.

2. Protein Expression Studies: Test protein expression was performed in *E. coli* ER2566 by inducing with 1 mM IPTG at 37° C. for 4 hours.

3. Purification and Refolding of P594:
Protein expression was done in *E. coli* ER2566 by inducing with 1 mM IPTG at 37° C. for 4 hours. Induced cell pellet was resuspended in buffer, sonicated to lyse the cells, separated supernatant and pellet by centrifugation at 10,000 rpm. Protein purification was done from the inclusion bodies. Inclusion bodies were solubilized in 6M Guanidium hydrochloride and protein was purified by Ni-NTA chromatography.

Refolding:
The purified fractions were refolded by step wise dialysis to remove the denaturant and finally the protein is dialyzed against 20 mM HEPES pH 7.0. Protein precipitation was observed during dialysis and almost 50% of the protein was precipitated. The remaining amount of soluble protein was concentrated using a 10 kDa Vivaspin concentrators to a final concentration of 1.1 mg/ml.

Figure 21:
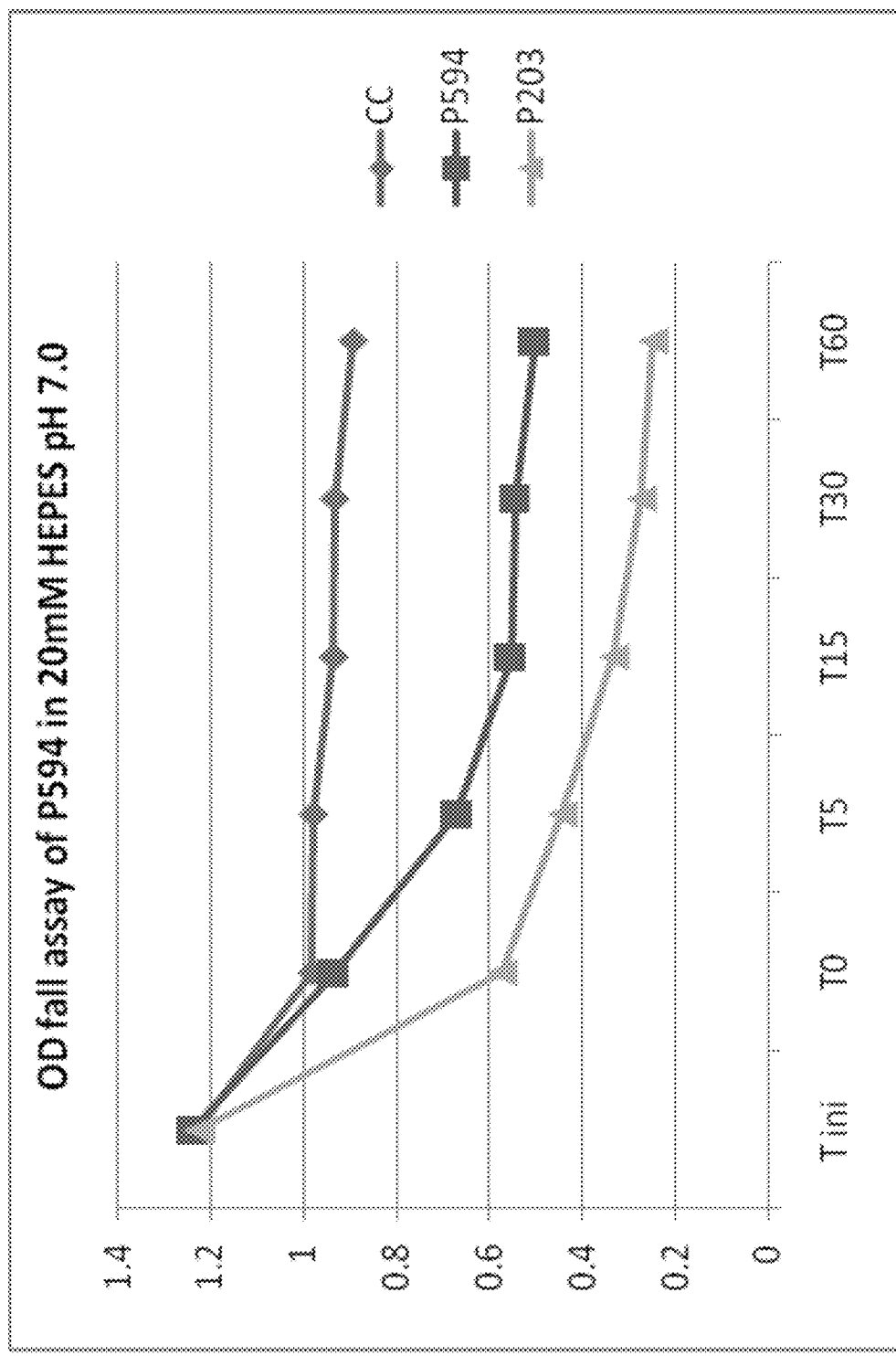
FIG. 21 shows the purified P594 is catalytically active as observed by the OD fall obtained.
Figure 22:
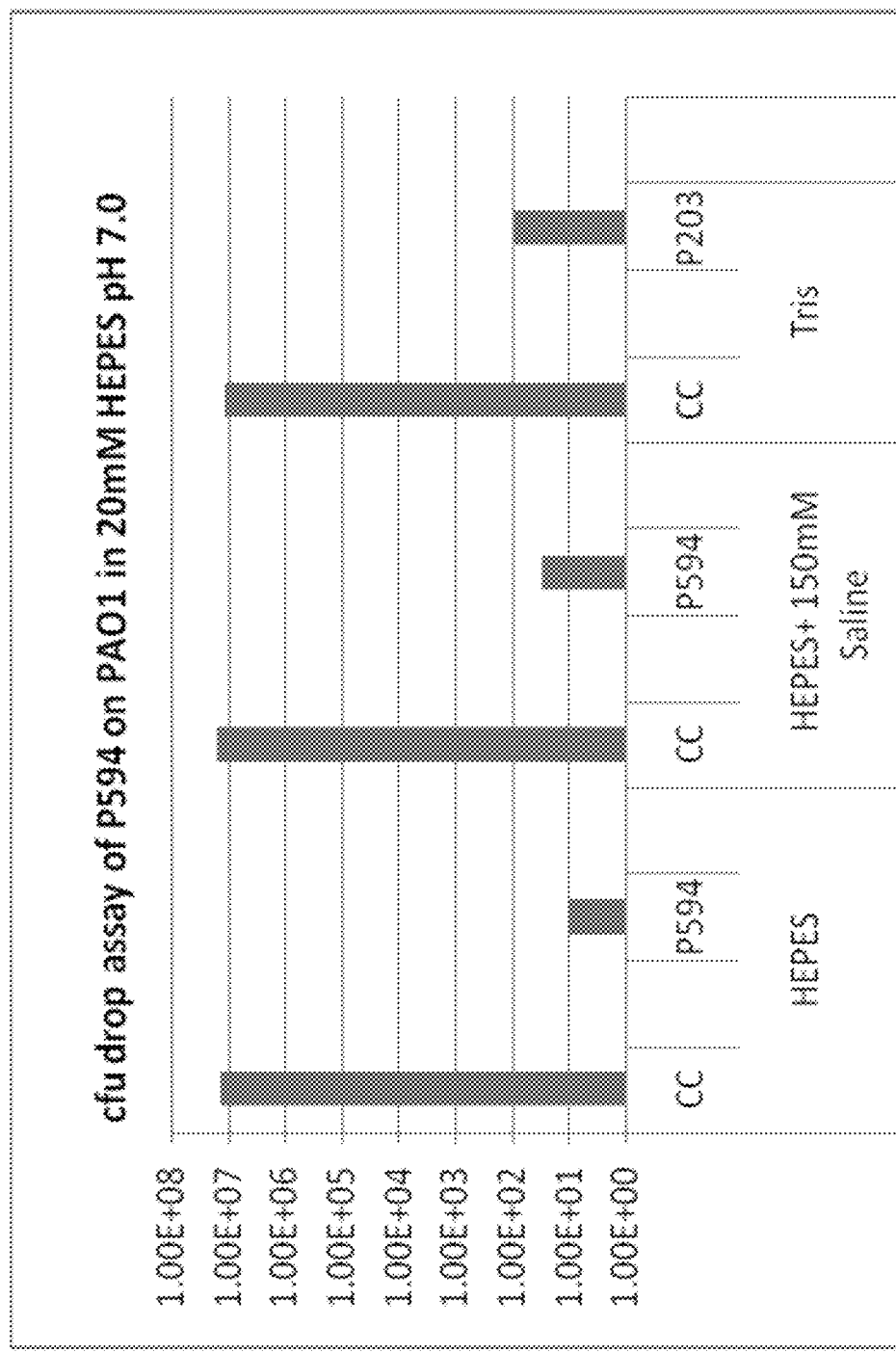
FIG. 22 shows 6 log cell killing obtained in both buffer and saline.
Figure 23:
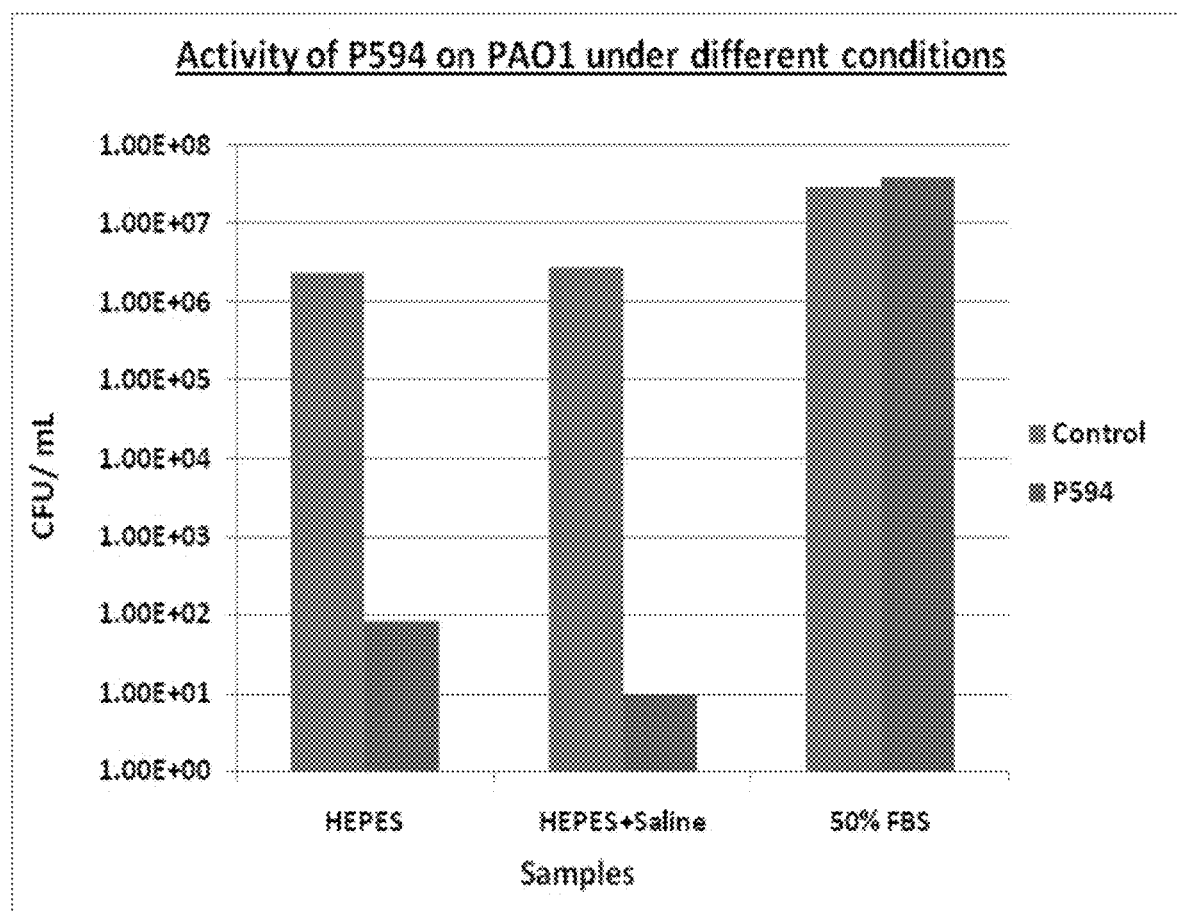
FIG. 23 shows P594 killed cells in both buffer and saline with more than 6 log reduction in cfu. However, in 50% serum P594 was not active.
Figure 24:
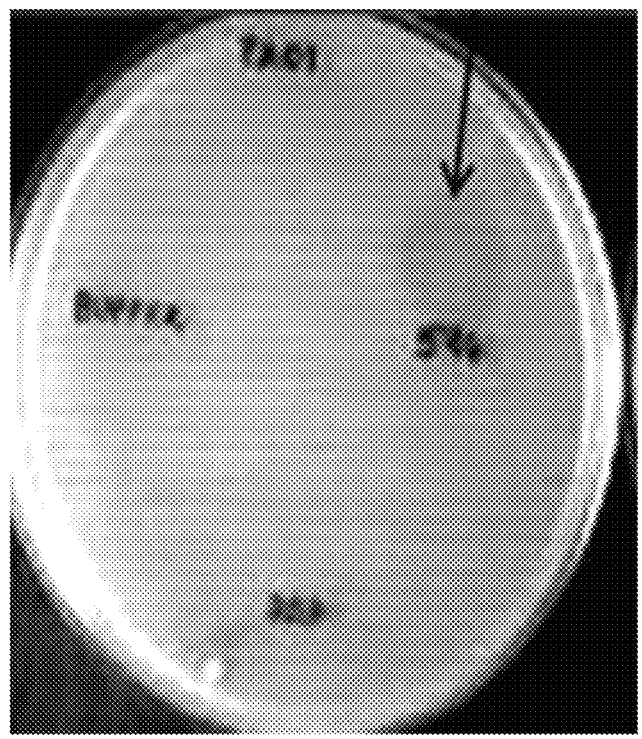
FIG. 24 shows an inhibition zone was observed on lawn of PA01 with P594.

4. Activity of Purified P594:
Two assays were done to determine the activity of the purified, refolded P594.

a) OD Fall Assay:
The catalytic activity of the Gp36 CD was determined by OD fall assay using chloroform treated *P. aeruginosa* cells as substrate. 50 µg/ml of purified P594 and a positive control protein P203 were used in this assay. An active protein by OD fall assay will also suggest the correct refolding of the Gp36 CD.
Result: The purified P594 is catalytically active as observed by the OD fall obtained (FIG. 21).

b) CFU Drop Assay:
The antibacterial activity of P594 was tested against *P. aeruginosa* strain PA01 by using the CFU drop assay. ~$10^7$ cells of PA01 in buffer, buffer containing saline, FBS, LB medium was treated with 250 µg/ml of P594, incubated at 37° C. for 2 hours and enumerated remaining number of viable cells.
Assay Conditions: reaction volume: 200 µl; buffer: HEPES pH 7.0 and HEPES pH 7.0+saline; duration: 2 hours @ 37° C., 200 rpm; protein: 250 µg/ml
Result: 6 log cell killing obtained in both buffer and saline (FIG. 22).
Inference: The fusion protein P594 kills *P. aeruginosa* efficiently in both physiological buffer and buffered saline.

c) CFU Drop Assay in Serum:
In addition to the cell-killing assay in buffer and buffered saline, the ability of P594 to kill *P. aeruginosa* cells in serum was determined by CFU drop assay in 50% Fetal Bovine Serum (FBS).
Result: P594 killed cells in both buffer and saline with more than 6 log reduction in cfu. However, in 50% serum P594 was not active (FIG. 23).

d) Lawn inhibition assay:
10 µg of P594 was spotted on *P. aeruginosa* strain PA01, incubated at 37° C. for 16-18 hrs.
Result: An inhibition zone was observed on lawn of PA01 with P594 (FIG. 24).

Figure 25:
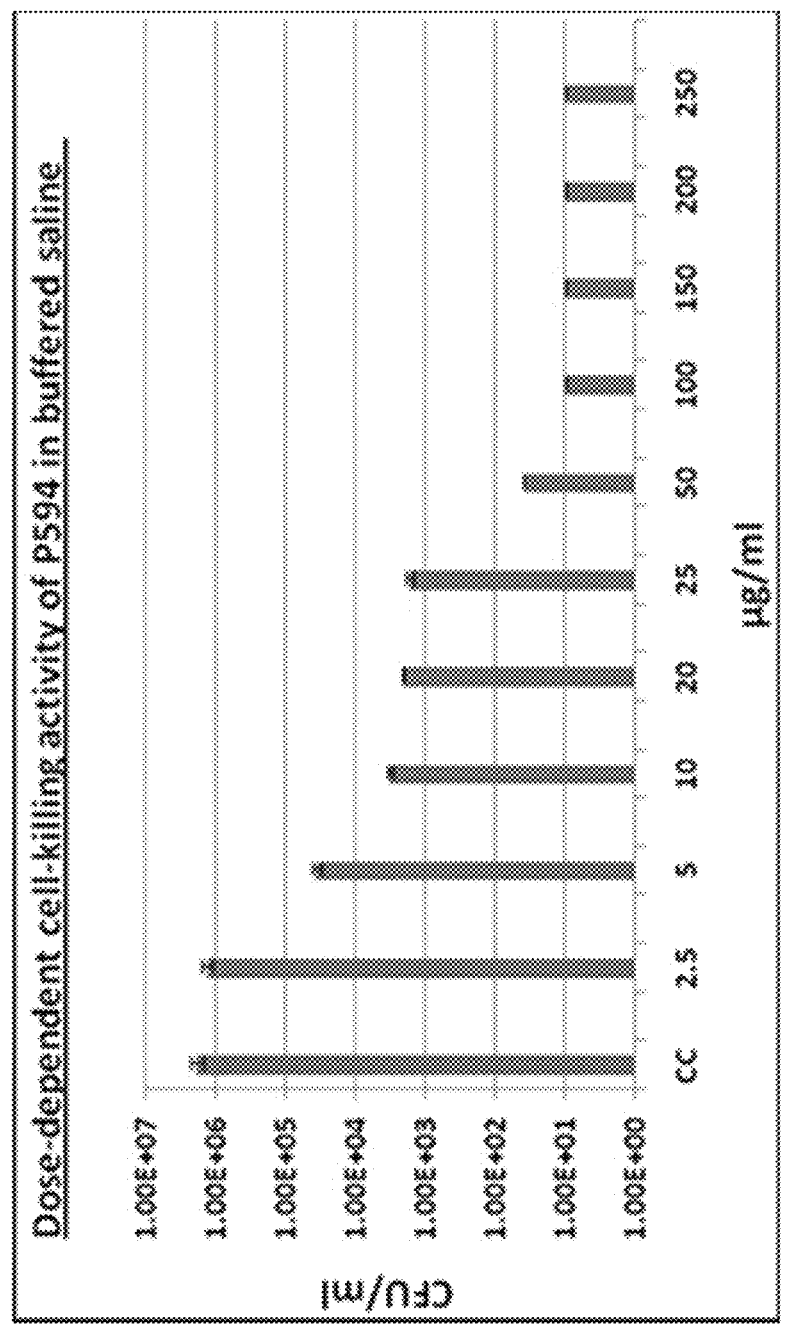
FIG. 25 shows 1 log cell-killing was obtained with even 5 µg/mL and >3 log reduction obtained with 25 µg/mL.

7. Dose Dependent Cell-Killing Activity of P594 in Saline:
P594 was found to precipitate in buffered saline and serum. However, the cell-killing activity of P594 was maintained in buffered saline while it was inactive in serum. Amount of protein remaining in soluble form in saline might be sufficient to kill PA01 cells in buffered saline. To determine minimum amounts of protein sufficient for cell-killing activity, a dose depended assay was done with *P. aeruginosa* PA01 cells.
Result: ~1 log cell-killing was obtained with even 5 µg/mL and >3 log reduction obtained with 25 µg/mL (FIG. 25).
Inference: A clear dose-depended cell-killing is observed with 3 logs reduction in CFU obtained with 10 µg/mL and saturation observed with >50 µg/mL of the protein. The low amounts of protein sufficient for cell-killing clearly demonstrated the potent activity of P594.

Figure 26:
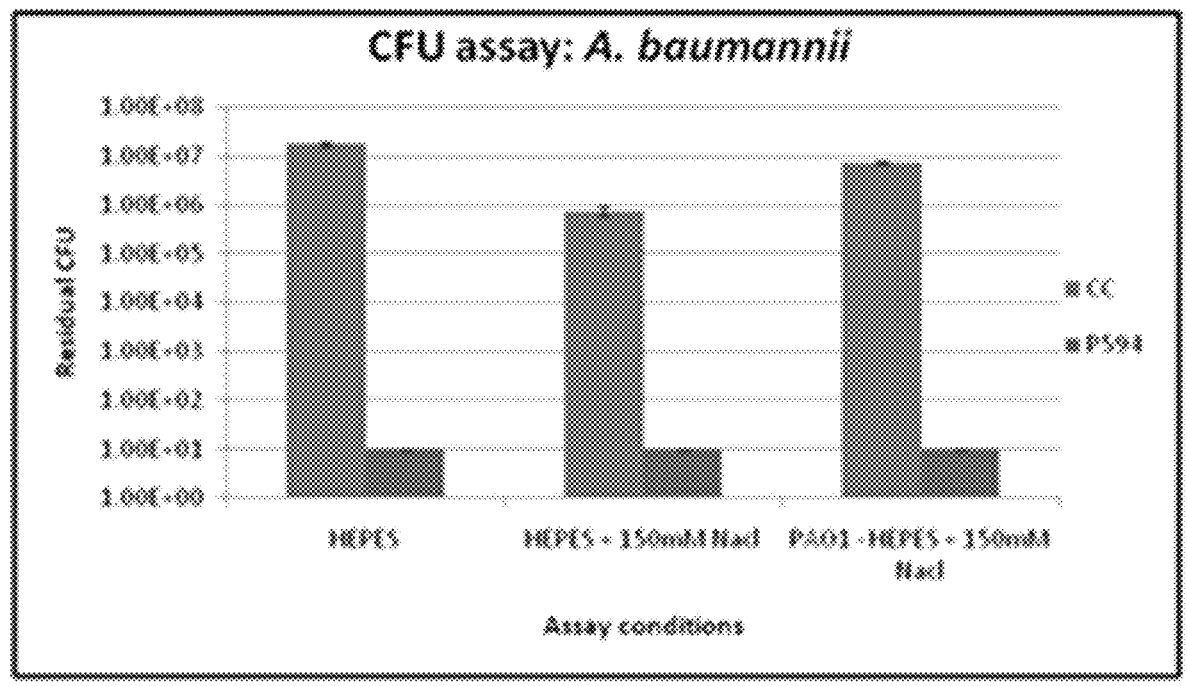
FIG. 26 shows P594 is bactericidal on *A. baumannii* in buffer and saline

8. Activity of P594 on *Acinetobacter baumannii*:
Another Gram-negative bacteria that causes serious infection is *A. baumannii*. The antibacterial activity of P594 was tested against *A. baumannii* strain HER1401 by using the CFU drop assay. ~$10^7$ cells of HER1401 in buffer and buffer containing saline was treated with 250 µg/ml of P594, incubated at 37° C. for 2 hours and enumerated remaining number of viable cells.
Result: P594 is bactericidal on *A. baumannii* in buffer and saline (FIG. 26).

Example 7: P663 (WLBU Variant-P203 Fusion)

DNA Sequence of pGDC663:

(SEQ ID NO: 45)
ATGCGTCGTT GGGTTCGTCG TGTTCGTCGT

TGGGTTCGTC GTGTTGTTCG

TGTTGTTCGT CGTGCTTCTG GGGGTGTGGC

CCTGGACCGC ACGCGGGTTG

ATCCCCAGGC AGTCGGCAAC GAGGTGCTCA

AGCGCAACGC GGATAAGCTG

AATGCGATGC GGGGCGCCGA GTACGGTGCC

AACGTCAAGG TCAGCGGCAC

GGACATTCGC ATGAACGGGG GTAACAGTGC

CGGCATGCTG AAGCAGGACG

TGTTCAACTG GCGGAAGGAA CTGGCTCAGT

TCGAGGCTTA CCGAGGGGAG

GCGTATAAGG ATGCCGATGG TTATAGTGTG

GGCCTGGGGC ATTACCTGGG

CAGTGGCAAT GCTGGGGCAG GTACTACAGT

CACGCCTGAG CAAGCCGCGC

AGTGGTTCGC CGAGGACACC GACCGCGCAC

TCGACCAGGG TGTGAGGTTG

GCCGACGAGC TGGGCGTTAC GTACAATGCC

TCTATCCTGG GATTGGCCGG

TATGGCCTTC CAGATGGGCG AAGGACGTGC

-continued

```
CCGGCAGTTC CGTAACACCT

TCCAGGCGAT CAAGGATCGC AACAAGGAAG

CCTTCGAGGC TGGTGTGCGA

AACAGCAAGT GGTACACGCA GACGCCCAAC

CGGGCCGAGG CATTCATCAA

GCGCATGGCG CCCCACTTCG ATACACCGAG

TCAAATCGGT GTCGATTGGT

ACAGCGCCGC AACAGCGGAG AAGCTTTCAC

GTGGAACATC GTCTACTAAA

ACGACACCTA AGTATAAGGT GAAGAGTGGT

GACAACCTTA CTAAAATCGC

TAAAAAGCAT AATACAACGG TTGCTACTTT

GTTGAAGTTG AATCCGAGTA

TCAAAGACCC GAACATGATT AGAGTTGGAC

AAACAATAAA TGTTACAGGT

AGCGGCGGCA AAACACATAA GGTGAAAAGT

GGTGACACAC TCAGTAAAAT

TGCCGTTGAT AACAAAACGA CTGTGAGTAG

ATTGATGAGT CTAAACCCTG

AAATTACGAA TCCAAATCAT ATAAAAGTAG

GTCAAACAAT TAGATTAAGT

CTCGAGCACC ACCACCACCA CCACTGA
```

WLBU2 Peptide: 1st base to 63d base; GP36 lysozyme: 73d base to 720th base; LysM: 727th base to 1050th base; 6×-His tag (SEQ ID NO: 9): 1057th base to 1074th base Amino Acid Sequence:

```
                                    (SEQ ID NO: 46)
MRRWVRRVRR WVRRVRVVR RASGGVALDR

TRVDPQAVGN EVLKRNADKL NAMRGAEYGA

NVKVSGTDIR MNGGNSAGML KQDVFNWRKE

LAQFEAYRGE AYKDADGYSV GLGHYLGSGN

AGAGTTVTPE QAAQWFAEDT DRALDQGVRL

ADELGVTYNA SILGLAGMAF QMGEGRARQF

RNTFQAIKDR NKEAFEAGVR NSKWYTQTPN

RAEAFIKRMA PHFDTPSQIG VDWYSAATAE

KLSRGTSSTK TTPKYKVKSG DNLTKIAKKH

NTTVATLLKL NPSIKDPNMI RVGQTINVTG

SGGKTHKVKS GDTLSKIAVD NKTTVSRLMS

LNPEITNPNH IKVGQTIRLS LEHHHHHH
```

WLBU2 Peptide: 1st aa to 20th aa; GP36 lysozyme: 25th aa to 240th aa; LysM: 243d aa to 350th aa; 6×-His tag (SEQ ID NO: 9): 353d aa to 358th aa Theoretical pI/Mw: 10.25/39626.84

Introduction

P663 is a chimeric triple fusion of WLBU peptide variant with GP36 lysozyme derived from *P. aeruginosa* phage P134 and LysM domain. This construct has the variant of antimicrobial peptide WLBU2 which serves as outer membrane penetrating motif at the N-terminus and a membrane traversing domain at the C-terminus, LysM domain. The fusion of GP36 lysozyme and LysM is referred to as P203. Although LysM domains are reported to bind to bacterial peptidoglycan, they have not been reported to possess or exhibit Gram-negative bacterial outer membrane penetrating or traversing function. However, we found that LysM domains could bind to outer membrane of Gram-negative bacteria. Construction of a triple fusion containing the WLBU2 peptide, lysozyme domain and LysM domains were done to determine if this triple fusion would be more soluble in biological fluids and able to kill Gram-negative pathogens.

1. Generating WLBU2-P203 Fusion (Cloning Strategy):

WLBU2 variant was fused to the 5' end of the GP36 lysozyme coding region by a PCR based method introducing appropriate cloning sites and the chimeric DNA sequence without a stop codon was cloned into *E. coli* expression vector pET26b as an NdeI-XhoI fragment, for expression of the chimeric protein as a C-terminal 6×-His tag (SEQ ID NO: 9) fusion. *E. coli* transformants were screened by PCR, plasmid DNA isolated from the positive clones and presence of the insert confirmed by restriction digestion analysis.

2. Expression and Purification:

Test protein expression was performed in *E. coli* ER2566 by inducing with 1 mM IPTG at 37° C. for 4 hours. The expected size of fusion protein is 39 kDa.

Protein expression was done in *E. coli* ER2566 by inducing with 1 mM IPTG at 37° C. for 4 hours. Induced cell pellet was resuspended in buffer, sonicated to lyse the cells, separated supernatant and pellet by centrifugation at 10,000 rpm. Protein purification was done from the inclusion bodies. Inclusion bodies were solubilized in 6M Guanidium hydrochloride and protein was purified by Ni-NTA chromatography.

3. Refolding of the P663:

P663 was dialyzed against 10 mM Na-Acetate buffer, pH 4.0, to remove the denaturant and to refold the protein.

Figure 27:
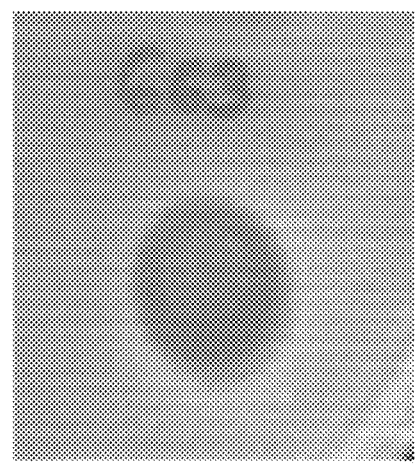
FIG. 27 shows lawn inhibition on *A. baumannii*.
Figure 28:
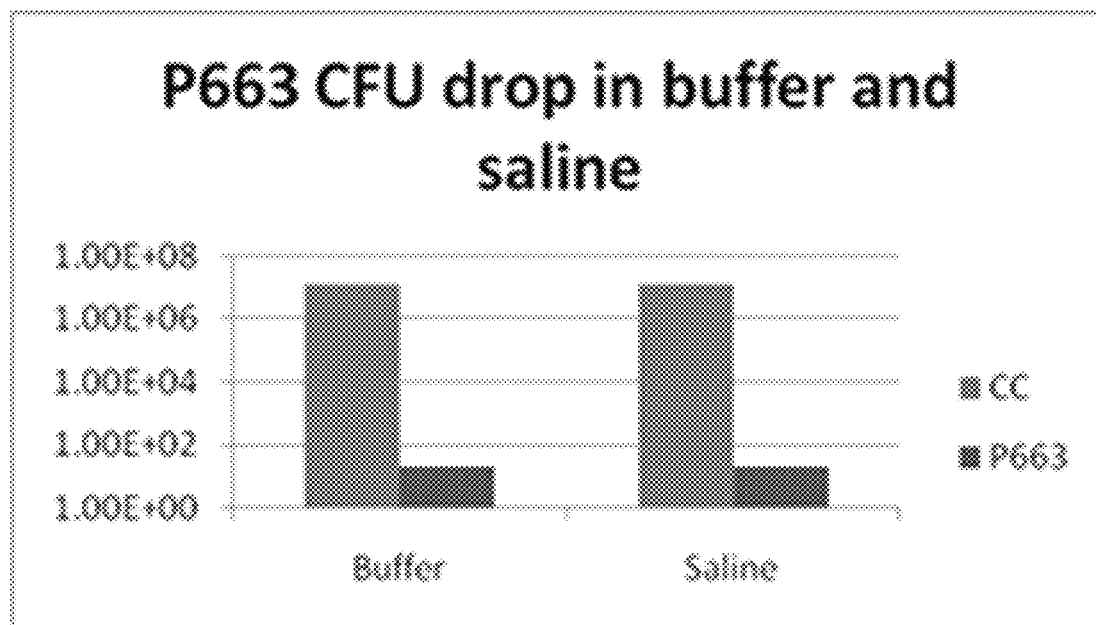
FIG. 28 shows P663 gives 6 logs killing in Buffer and buffer+saline at 100 µg/mL Inference: The fusion protein P663 kills *A. baumannii* efficiently in both buffer and buffered saline.

4. Activity of Purified P663:

Assays were done to determine the activity of the purified, refolded P663.

a) Lawn Inhibition Assay:

10 μg of P663 spotted on *A. baumannii* ATCC19606 lawn, shows lawn inhibition (FIG. 27).

b) CFU Drop Assay:

The antibacterial activity of P663 in both buffer and saline were tested against *A. baumannii* strain ATCC19606 by using the CFU drop assay. Briefly, $10^6$ cells/mL of *A. baumannii* in buffer and buffer containing saline were treated with 100 μg/mL of P663, incubated at 37° C. for 2 hours and enumerated remaining number of viable cells. Result: P663 gives 6 logs killing in Buffer and buffer+saline at 100 μg/mL Inference: The fusion protein P663 kills *A. baumannii* efficiently in both buffer and buffered saline (FIG. 28).

c) Activity of Purified P663 on *Acinetobacter baumannii* in MHB:

P663 dialyzed against 10 mM Sodium acetate pH 4.0 was used and the assay was done in Mueller Hinton Broth (MHB media). CA-MHB was used because it is the media recommended by CLSI for testing MIC and MBC of antibiotics. $10^6$ cells/mL of *A. baumannii* strain ATCC19606 in MHB medium was treated with 100 and 200 μg/mL of P663, incubated at 37° C. for 2 hours and determined cell-killing by enumerating remaining number of viable cells by dilution plating on LB plates followed by incubation at 37° C. for 16-18 hrs.

Figure 29:
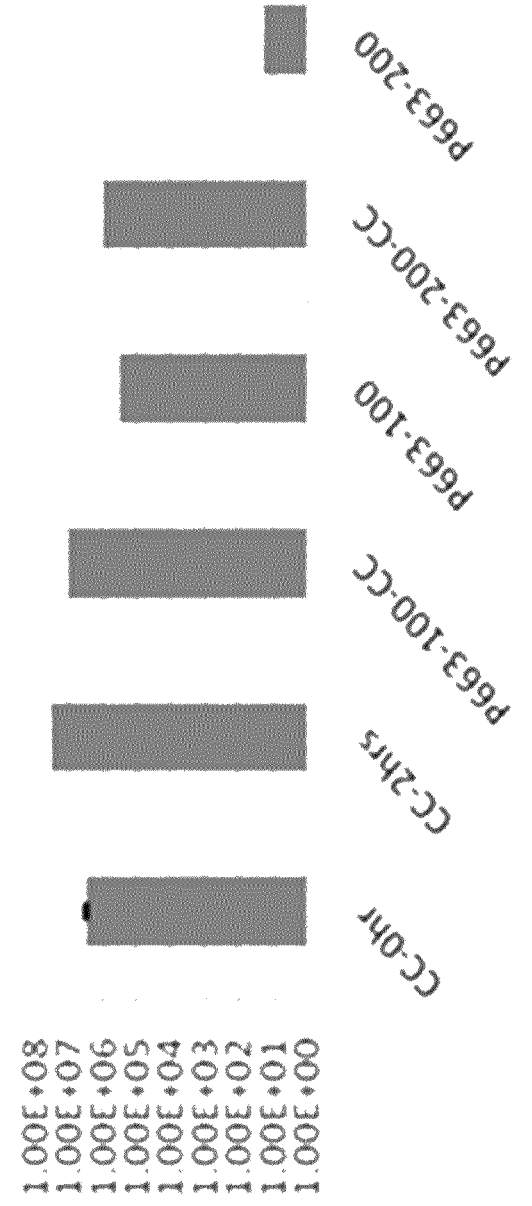
FIG. 29 shows P663 killed cells at 100-200 µg/mL with 3-5 log cell killing

Result: P663 killed cells at 100-200 µg/mL with 3-5 log cell killing (FIG. 29).

d) Activity of P663 on *Acinetobacter baumannii* in 50% Fetal Calf Serum (FCS):

The assay was done in 50% FCS with remaining volume made up with Mueller Hinton Broth (MHB media). $10^6$ cells/mL of *A. baumannii* strain ATCC19606 in MHB medium was treated with 25, 50, 100, and 200 µg/mL of P663, incubated at 37° C. for 2 hours and determined cell-killing by enumerating remaining number of viable cells by dilution plating on LB plates followed by incubation at 37° C. for 16-18 hrs.

Figure 30:
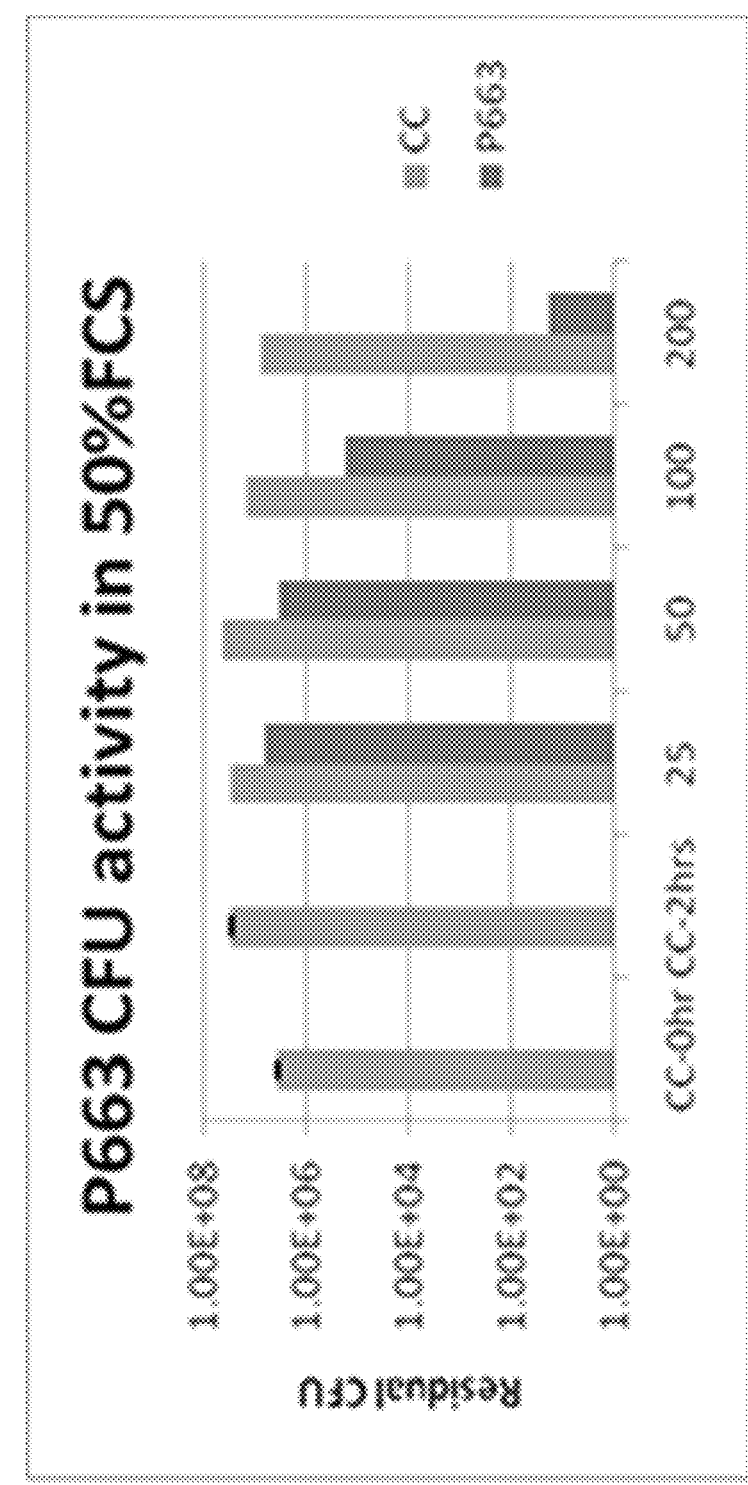
FIG. 30 shows P663 exhibits dose dependent killing in 50% FCS. 5 logs killing with 200 µg/mL

Result: P663 exhibits dose dependent killing in 50% FCS. 5 logs killing with 200 µg/mL (FIG. 30).

e) Activity of P663 on *P. aeruginosa* PA01 in 50% Fetal Calf Serum (FCS and Interstitial Fluid):

The assay was done in 50% FCS and interstitial fluid with remaining volume made up with Mueller Hinton Broth (MHB media). $10^6$ cells/mL of *A. baumannii* strain ATCC19606 was treated with 250 µg/mL of P663, incubated at 37° C. for 2 hours and determined cell-killing by enumerating remaining number of viable cells by dilution plating on LB plates followed by incubation at 37° C. for 16-18 hrs.

Figure 31:
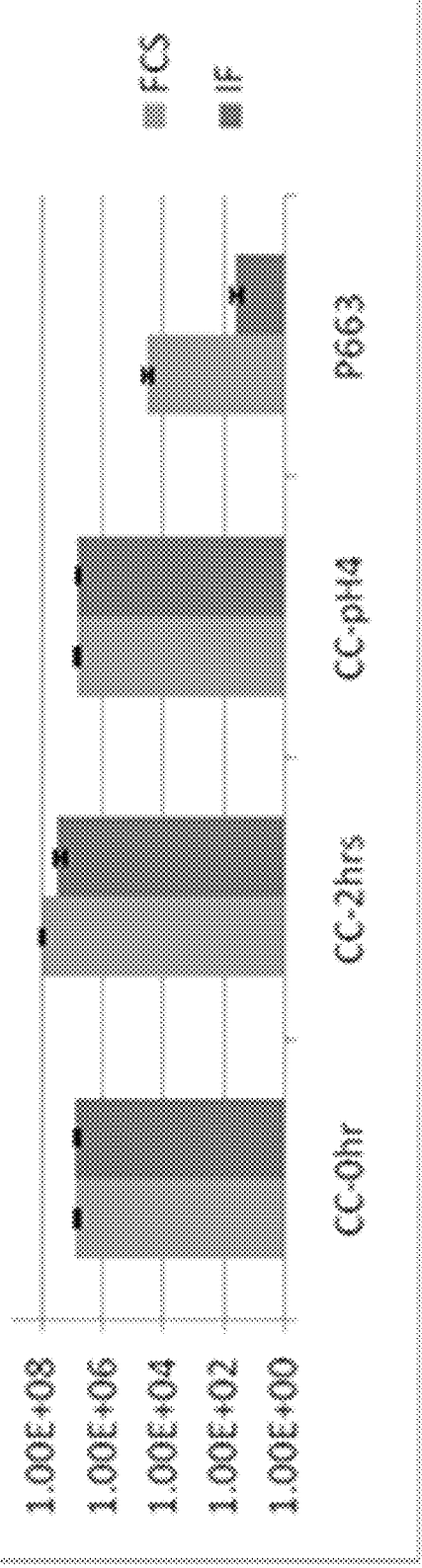
FIG. 31 shows P663 exhibits killing in 50% FCS (2.5 logs) and IF (5 logs) killing at 250 µg/mL on *P. aeruginosa* PAO1.

Result: P663 exhibits killing in 50% FCS (2.5 logs) and IF (5 logs) killing at 250 µg/mL on *P. aeruginosa* PAO1 (FIG. 31).

MIC of P663 in Growth Media (MHB and Serum) on *Acinetobacter baumannii*:

MIC was determined using a modified Clinical and Laboratory Standards Institute (CLSI) broth microdilution procedure on *A. baumannii* strain HER1401 in Cation-adjusted Mueller Hinton Broth (CA-MHB media) and FCS. A 10-point MIC was set up in microtitre plates in duplicates with two fold dilutions starting at 245 µg/mL. Wells of a 96-well polystyrene plated were coated with 0.5% BSA for 1 hour at 37° C. and each well were inoculated with $5 \times 10^5$ cells/mL *A. baumannii*. A positive control for growth which is devoid of P663 was included in the assay. Microtiter plates were incubated at 35° C. for 18-20 hrs. The endpoint for this assay was complete inhibition of growth at the end of incubation as determined by colorless wells after addition of Iodonitro tetrazolium (INT) dye.

TABLE D6

| | MIC of P663 in media A.baumannii | | |
|---|---|---|---|
| SI. No. | Protein | CA-MHB (µg/mL) | FCS (µg/mL) |
| 1 | P663 | 61 | 122 |

Result: MIC was obtained at 61 µg/ml in MHB and 122 µg/mL in FCS (Table D6).

Example 8: P664 (WLBU 2-Rigid Linker-P203 Fusion)

DNA Sequence of pGDC664:

(SEQ ID NO: 47)
```
ATGCGTCGTT GGGTTCGTCG TGTTCGTCGT
TGGGTTCGTC GTGTTGTTCG
TGTTGTTCGT CGTTGGGTTC GTCGTgaagc
cgctgccaag Caggcggccg
ctaaaGGTGT GGCCCTGGAC CGCACGCGGG
TTGATCCCCA GGCAGTCGGC
AACGAGGTGC TCAAGCGCAA CGCGGATAAG
CTGAATGCGA TGCGGGCGC
CGAGTACGGT GCCAACGTCA AGGTCAGCGG
CACGGACATT CGCATGAACG
GGGGTAACAG TGCCGGCATG CTGAAGCAGG
ACGTGTTCAA CTGGCGGAAG
GAACTGGCTC AGTTCGAGGC TTACCGAGGG
GAGGCGTATA AGGATGCCGA
TGGTTATAGT GTGGGCCTGG GGCATTACCT
GGGCAGTGGC AATGCTGGGG
CAGGTACTAC AGTCACGCCT GAGCAAGCCG
CGCAGTGGTT CGCCGAGGAC
ACCGACCGCG CACTCGACCA GGGTGTGAGG
TTGGCCGACG AGCTGGGCGT
TACGAACAAT GCCTCTATCC TGGGATTGGC
CGGTATGGCC TTCCAGATGG
GCGAAGGACG TGCCCGGCAG TTCCGTAACA
CCTTCCAGGC GATCAAGGAT
CGCAACAAGG AAGCCTTCGA GGCTGGTGTG
CGAAACAGCA AGTGGTACAC
GCAGACGCCC AACCGGGCCG AGGCATTCAT
CAAGCGCATG GCGCCCCACT
TCGATACACC GAGTCAAATC GGTGTCGATT
GGTACAGCGC CGCAACAGCG
GAGAAGCTTT CACGTGGAAC ATCGTCTACT
AAAACGACAC CTAAGTATAA
GGTGAAGAGT GGTGACAACC TTACTAAAAT
CGCTAAAAAG CATAATACAA
CGGTTGCTAC TTTGTTGAAG TTGAATCCGA
GTATCAAAGA CCCGAACATG
ATTAGAGTTG GACAAACAAT AAATGTTACA
```

-continued

```
GGTAGCGGCG GCAAAACACA

TAAGGTGAAA AGTGGTGACA CACTCAGTAA

AATTGCCGTT GATAACAAAA

CGACTGTGAG TAGATTGATG AGTCTAAACC

CTGAAATTAC GAATCCAAAT

CATATAAAAG TAGGTCAAAC AATTAGATTA

AGTCTCGAGC ACCACCACCA CCACCACTGA
``` segments: WLBU2 Peptide: 1st base to 75th base; rigid linker: 76th base to 105th base; GP36 lysozyme: 106th base to 753d base; LysM: 760th base to 1083d base; 6x-His tag (SEQ ID NO: 9): 1090th base to 1107th base
Amino Acid Sequence:

```
                                    (SEQ ID NO: 48)
MRRWVRRVRR WVRRVVRVVR RWVRREAAAK

QAAAKGVALD RTRVDPQAVG NEVLKRNADK

LNAMRGAEYG ANVKVSGTDI RMNGGNSAGM

LKQDVFNWRK ELAQFEAYRG EAYKDADGYS

VGLGHYLGSG NAGAGTTVTP EQAAQWFAED

TDRALDQGVR LADELGVTNN ASILGLAGMA

FQMGEGRARQ FRNTFQAIKD RNKEAFEAGV

RNSKWYTQTP NRAEAFIKRM APHFDTPSQI

DVDWYSAATA EKLSRGTSST KTTPKYKVKS

GDNLTKIAKK HNTTVATLLK LNPSIKDPNM

IRVGQTINVT GSGGKTHKVK SGDTLSKIAV

DNKTTVSRLM SLNPEITNPN HIKVGQTIRL

Figure 32:
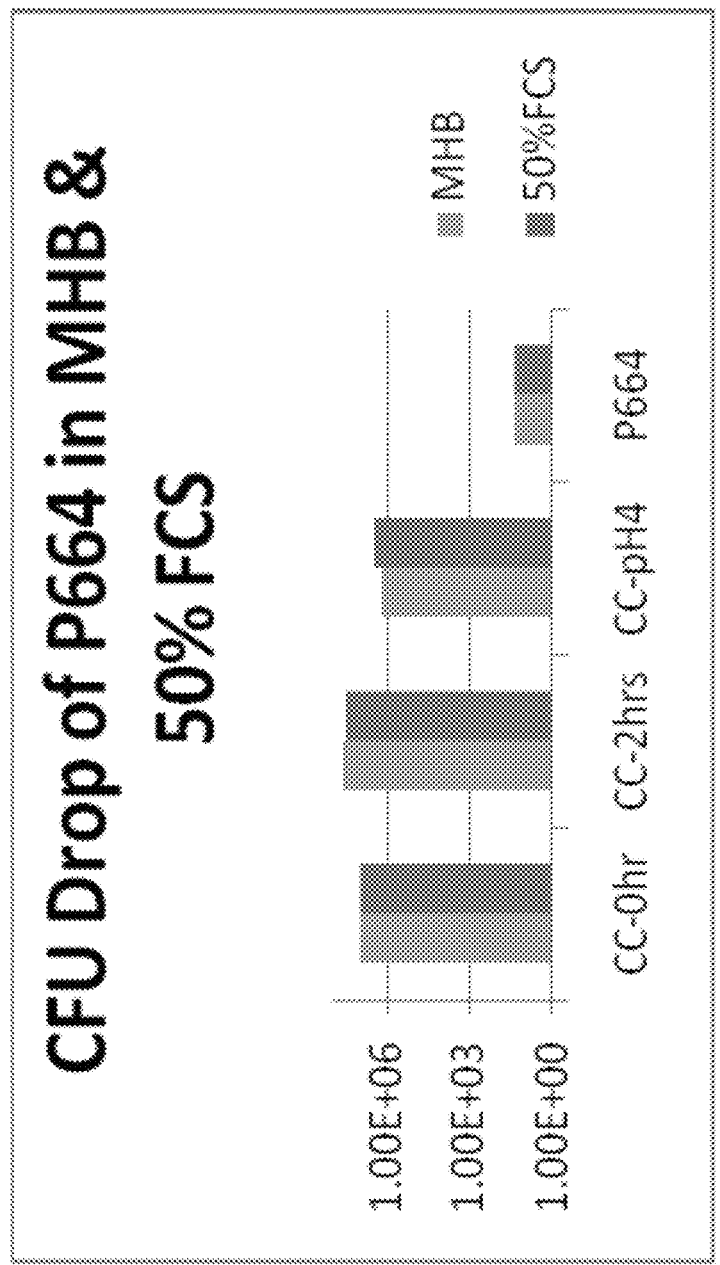
FIG. 32 shows P664 killed cells at 150 µg/mL with 5 log cell killing in MHB and 50% FCS

SLEHHHHHH
``` segments: WLBU2 Peptide: 1st aa to 25th aa; rigid linker: 26th aa to 35th aa; GP36 lysozyme: 36th aa to 251st aa; LysM: 254th aa to 361st aa; 6x-His tag (SEQ ID NO: 9): 364th aa to 369th aa
Theoretical pI/Mw: 10.32/40958.38
1. Generating WLBU2-Phi29 Endolysin Fusion (Cloning Strategy):
WLBU2 was fused to the 5' end of the GP36 lysozyme coding region by a PCR based method introducing appropriate cloning sites and the chimeric DNA sequence without a stop codon was cloned into E. coli expression vector pET26b as an NdeI-XhoI fragment, for expression of the chimeric protein as a C-terminal 6x-His tag (SEQ ID NO: 9) fusion. E. coli transformants were screened by PCR, plasmid DNA isolated from the positive clones and presence of the insert confirmed by restriction digestion analysis.
Test protein expression was performed in E. coli ER2566 by inducing with 1 mM IPTG at 37° C. for 4 hours. The expected size of fusion protein is 41 kDa.
DNA sequence of clone was confirmed and glycerol stocks made and designated as pGDC 664.
Protein expression was done in E. coli ER2566 by inducing with 1 mM IPTG at 37° C. for 4 hours. Induced cell pellet was resuspended in buffer, sonicated to lyse the cells, separated supernatant and pellet fraction by centrifugation at 10,000 rpm. Protein purification was done from the inclusion bodies. Inclusion bodies were solubilized in 6M Guanidium hydrochloride and protein was purified by Ni-NTA chromatography.
P664 was dialyzed against 10 mM Na-Acetate buffer, pH 4.0, to remove the denaturant and to refold the protein. Protein was purified to >95% homogeneity.
4. Activity of Purified P664:
Assays were done to determine the activity of the purified, refolded P664.
CFU Drop Assay:
Activity of Purified P664 on Acinetobacter baumannii in MHB and 50% FCS:
P664 dialyzed against 10 mM Sodium acetate pH 4.0 was used and the assay was done in Mueller Hinton Broth (MHB media) and 50% FCS. $10^6$ cells/mL of A. baumannii strain ATCC19606 was treated with 150 µg/mL of P664, incubated at 37° C. for 2 hours and determined cell-killing by enumerating remaining number of viable cells by dilution plating on LB plates followed by incubation at 37° C. for 16-18 hrs.
Result: P664 killed cells at 150 µg/mL with 5 log cell killing in MHB and 50% FCS (FIG. 32).
5. MIC of P664 in Growth Media (MHB and Serum) on Acinetobacter baumannii:
MIC was determined using a modified Clinical and Laboratory Standards Institute (CLSI) broth microdilution procedure on A. baumannii strain HER1401 in Mueller Hinton Broth (MHB media) and FCS. A 10-point MIC was set up in microtitre plates in duplicates with two fold dilutions starting at 165 µg/mL. Wells of a 96-well polystyrene plated were coated with 0.5% BSA for 1 hour at 37° C. and each well were inoculated with $5 \times 10^5$ cells/mL A. baumannii. A positive control for growth which is devoid of P664 was included in the assay. Microtiter plates were incubated at 35° C. for 18-20 hrs. The endpoint for this assay was complete inhibition of growth at the end of incubation as determined by colorless wells after addition of Iodonitro tetrazolium (INT) dye. For this assay, P664 buffered in 10 mM Sodium acetate (SA) pH 4.0 was used.

TABLE D7

| MIC of P664 in media | | |
| --- | --- | --- |
| SI. No. | Protein | MHB (µg/mL) FCS (µg/mL) |
| 1 | P664 | 41     83 |

Result: MIC was obtained at 41 µg/ml in MHB and 83 µg/mL in FCS (Table D7).

Example 9: P671 (6xHis (SEQ ID NO: 9)-Phi29FL-Flexible Linker-WLBU2)

DNA Sequence:

```
                                    (SEQ ID NO: 49)
ATGCACCATC ACCATCACCA TCAAATTTCA

CAAGCGGGTA TCAACTTAAT

TAAGAGCTTT GAGGGTTTAC AACTGAAAGC

ATATAAAGCT GTTCCGACTG

AGAAGCATTA CACCATTGGT TACGGTCATT

ACGGTTCCGA TGTTTCACCT
```

-continued

```
AGGCAGGTTA TCACTGCTAA ACAGGCTGAA

GACATGTTGC GTGATGATGT

GCAGGCTTTT GTGGATGGTG TAAATAAAGC

ATTAAAAGTA TCTGTCACCC

AAAATCAATT TGATGCACTT GTCTCATTCG

CTTACAACGT TGGGTTAGGG

GCTTTCAGGT CTTCTTCTCT ACTGGAATAC

TTGAATGAAG GAAGAACAGC

TCTAGCGGCG GCTGAATTCC CTAAATGGAA

TAAGTCAGGC GGTAAAGTTT

ATCAAGGGTT GATTAACCGT AGAGCACAGG

AGCAAGCCTT GTTTAATAGT

GGAACACCTA AAAATGTTTC ACGTGGAACA

TCGTCTACTA AAACGACACC

TAAGTATAAG GTGAAGAGTG GTGACAACCT

TACTAAAATC GCTAAAAAGC

ATAATACAAC GGTTGCTACT TTGTTGAAGT

TGAATCCGAG TATCAAAGAC

CCGAACATGA TTAGAGTTGG ACAAACAATA

AATGTTACAG GTAGCGGCGG

CAAAACACAT AAGGTGAAAA GTGGTGACAC

ACTCAGTAAA ATTGCCGTTG

ATAACAAAAC GACTGTGAGT AGATTGATGA

GTCTAAACCC TGAAATTACG

AATCCAAATC ATATAAAAGT AGGTCAAACA

ATTAGATTAA GTGGCTCCGG

ATCGGCTTCT GGGCGTCGTT GGGTTCGTCG

CGTGCGTCGC TGGGTGCGTC

GTGTTGTTCG TGTTGTTCGT CGTTGGGTTC

GTCGTTGA
``` segments: 6×-His tag (SEQ ID NO: 9): 1st base to 21st base; Phi29 Lysozyme: 22d base to 468th base; LysM: 469th base to 792d base; Flexible linker: 793d base to 813th base; WLBU2 Peptide: 814th base to 885th base Amino Acid Sequence:

```
                                        (SEQ ID NO: 50)
MHHHHHHQIS QAGINLIKSF EGLQLKAYKA

VPTEKHYTIG YGHYGSDVSP RQVITAKQAE

DMLRDDVQAF VDGVNKALKV SVTQNQFDAL

VSFAYNVGLG AFRSSSLLEY LNEGRTALAA

AEFPKWNKSG GKVYQGLINR RAQEQALFNS

GTPKNVSRGT SSTKTTPKYK VKSGDNLTKI

AKKHNTTVAT LLKLNPSIKD PNMIRVGQTI

NVTGSGGKTH KVKSGDTLSK IAVDNKTTVS

RLMSLNPEIT NPNHIKVGQT IRLSGSGSAS

GRRWVRRVRR WVRRVVRVVR RWVRR
``` segments: 6×-His tag (SEQ ID NO: 9): 1st aa to 7th aa; Phi29 lysozyme: 8th aa to 156th aa; LysM: 157th aa to 264th aa; Flexible linker: 265th aa to 271st aa; WLBU2 Peptide: 272d aa to 295th aa Theoretical pI/Mw: 10.74/32762.48

Example 10: SMAP29-Flexible Linker-Phi29 FL-6×his (SEQ ID NO: 9)

DNA Sequence:

```
                                        (SEQ ID NO: 51)
ATGAGGGGAC TTCGAAGACT GGGTAGGAAG

ATAGCACATG GTGTGAAGAA

GTATGGCCCA ACTGTTCTCC GAATAATCAG

AATAGCTGGG GGCTCCGGAT

CGGCTTCTGG GCAAATTTCA CAAGCGGGTA

TCAACTTAAT TAAGAGCTTT

GAGGGTTTAC AACTGAAAGC ATATAAAGCT

GTTCCGACTG AGAAGCATTA

CACCATTGGT TACGGTCATT ACGGTTCCGA

TGTTTCACCT AGGCAGGTTA

TCACTGCTAA ACAGGCTGAA GACATGTTGC

GTGATGATGT GCAGGCTTTT

GTGGATGGTG TAAATAAAGC ATTAAAAGTA

TCTGTCACCC AAAATCAATT

TGATGCACTT GTCTCATTCG CTTACAACGT

TGGGTTAGGG GCTTTCAGGT

CTTCTTCTCT ACTGGAATAC TTGAATGAAG

GAAGAACAGC TCTAGCGGCG

GCTGAATTCC CTAAATGGAA TAAGTCAGGC

GGTAAAGTTT ATCAAGGGTT

GATTAACCGT AGAGCACAGG AGCAAGCCTT

GTTTAATAGT GGAACACCTA

AAAATGTTTC ACGTGGAACA TCGTCTACTA

AAACGACACC TAAGTATAAG

GTGAAGAGTG GTGACAACCT TACTAAAATC

GCTAAAAAGC ATAATACAAC

GGTTGCTACT TTGTTGAAGT TGAATCCGAG

TATCAAAGAC CCGAACATGA
```

-continued

```
TTAGAGTTGG ACAAACAATA AATGTTACAG

GTAGCGGCGG CAAAACACAT

AAGGTGAAAA GTGGTGACAC ACTCAGTAAA

ATTGCCGTTG ATAACAAAAC

GACTGTGAGT AGATTGATGA GTCTAAACCC

TGAAATTACG AATCCAAATC

ATATAAAAGT AGGTCAAACA ATTAGATTAA

GTCTCGAGCA CCATCACCAT CACCATTGA
``` segments: SMAP Peptide: 1st base to 90th base; Flexible linker: 91st base to 111th base; Phi29 Lysozyme: 112th base to 558th base; LysM: 559th base to 882d base; 6×-His tag (SEQ ID NO: 9): 889th base to 906th base Amino Acid Sequence:

```
                                (SEQ ID NO: 52)
MRGLRRLGRK IAHGVKKYGP TVLRIIRIAG

GSGSASGQIS QAGINLIKSF EGLQLKAYKA

VPTEKHYTIG YGHYGSDVSP RQVITAKQAE

DMLRDDVQAF VDGVNKALKV SVTQNQFDAL

VSFAYNVGLG AFRSSSLLEY LNEGRTALAA

AEFPKWNKSG GKVYQGLINR RAQEQALFNS

GTPKNVSRGT SSTKTTPKYK VKSGDNLTKI

AKKHNTTVAT LLKLNPSIKD PNMIRVGQTI

NVTGSGGKTH KVKSGDTLSK IAVDNKTTVS

RLMSLNPEIT NPNHIKVGQT IRLSLEHHHH HH
``` segments: SMAP Peptide: 1st aa to 30th aa; Flexible linker: 31st aa to 37th aa; Phi29 Lysozyme: 38th aa to 186th aa; LysM: 187th aa to 294th aa; 6×-His tag (SEQ ID NO: 9): 297th aa to 302d aa Theoretical pI/Mw: 10.32/32618.33

Example 11: SMAP29-Flexible Linker-P203-6×his (SEQ ID NO: 9)

DNA Sequence:

```
                                (SEQ ID NO: 53)
ATGAGGGGAC TTCGAAGACT GGGTAGGAAG

ATAGCACATG GTGTGAAGAA

GTATGGCCCA ACTGTTCTCC GAATAATCAG

AATAGCTGGG GGCTCCGGAT

CGGCTTCTGG GGGTGTGGCC CTGGACCGCA

CGCGGGTTGA TCCCCAGGCA

GTCGGCAACG AGGTGCTCAA GCGCAACGCG

GATAAGCTGA ATGCGATGCG

GGGCGCCGAG TACGGTGCCA ACGTCAAGGT

CAGCGGCACG GACATTCGCA

TGAACGGGGG TAACAGTGCC GGCATGCTGA

AGCAGGACGT GTTCAACTGG

CGGAAGGAAC TGGCTCAGTT CGAGGCTTAC

CGAGGGGAGG CGTATAAGGA

TGCCGATGGT TATAGTGTGG GCCTGGGGCA

TTACCTGGGC AGTGGCAATG

CTGGGGCAGG TACTACAGTC ACGCCTGAGC

AAGCCGCGCA GTGGTTCGCC

GAGGACACCG ACCGCGCACT CGACCAGGGT

GTGAGGTTGG CCGACGAGCT

GGGCGTTACG AACAATGCCT CTATCCTGGG

ATTGGCCGGT ATGGCCTTCC

AGATGGGCGA AGGACGTGCC CGGCAGTTCC

GTAACACCTT CCAGGCGATC

AAGGATCGCA ACAAGGAAGC CTTCGAGGCT

GGTGTGCGAA ACAGCAAGTG

GTACACGCAG ACGCCCAACC GGGCCGAGGC

ATTCATCAAG CGCATGGCGC

CCCACTTCGA TACACCGAGT CAAATCGGTG

TCGATTGGTA CAGCGCCGCA

ACAGCGGAGA AGCTTTCACG TGGAACATCG

TCTACTAAAA CGACACCTAA

GTATAAGGTG AAGAGTGGTG ACAACCTTAC

TAAAATCGCT AAAAAGCATA

ATACAACGGT TGCTACTTTG TTGAAGTTGA

ATCCGAGTAT CAAAGACCCG

AACATGATTA GAGTTGGACA ACAATAAAT

GTTACAGGTA GCGGCGGCAA

AACACATAAG GTGAAAAGTG GTGACACACT

CAGTAAAATT GCCGTTGATA

ACAAAACGAC TGTGAGTAGA TTGATGAGTC

TAAACCCTGA AATTACGAAT

CCAAATCATA TAAAAGTAGG TCAAACAATT

AGATTAAGTC TCGAGCACCA

CCACCACCAC CACTGA
``` segments: SMAP Peptide: 1st base to 90th base; Flexible linker: 91st base to 111th base; GP36 Lysozyme: 112th base to 765th base; LysM: 766th base to 1089th base; 6×-His tag (SEQ ID NO: 9): 1096th base to 1113th base Amino Acid Sequence:

```
                                        (SEQ ID NO: 54)
MRGLRRLGRK IAHGVKKYGP TVLRIIRIAG GSGSASGGVA

LDRTRVDPQA VGNEVLKRNA DKLNAMRGAE YGANVKVSGT

DIRMNGGNSA GMLKQDVFNW RKELAQFEAY RGEAYKDADG

YSVGLGHYLG SGNAGAGTTV TPEQAAQWFA EDTDRALDQG

VRLADELGVT NNASILGLAG MAFQMGEGRA RQFRNTFQAI

KDRNKEAFEA GVRNSKWYTQ TPNRAEAFIK RMAPHFDTPS

QIGVDWYSAA TAEKLSRGTS STKTTPKYKV KSGDNLTKIA

KKHNTTVATL LKLNPSIKDP NMIRVGQTIN VTGSGGKTHK

VKSGDTLSKI AVDNKTTVSR LMSLNPEITN PNHIKVGQTI

RLSLEHHHHH
``` segments: SMAP Peptide: 1st aa to 30th aa; Flexible linker: 31st aa to 37th aa; GP36 Lysozyme: 38th aa to 253d aa; LysM: 256th aa to 363d aa; 6×-His tag (SEQ ID NO: 9): 366th aa to 371st aa
Theoretical pI/Mw: 10.12/40077.32

Example 12: WLBU2-Rigid Linker-LysM

DNA Sequence:

```
                                        (SEQ ID NO: 55)
ATGCGTCGTT GGGTTCGTCG TGTTCGTCGT TGGGTTCGTC

GTGTTGTTCG TGTTGTTCGT CGTTGGGTTC GTCGTGAAGC

CGCTGCCAAG GAGGCGGCCG CTAAATCACG TGGAACATCG

TCTACTAAAA CGACACCTAA GTATAAGGTG AAGAGTGGTG

ACAACCTTAC TAAAATCGCT AAAAAGCATA ATACAACGGT

TGCTACTTTG TTGAAGTTGA ATCCGAGTAT CAAAGACCCG

AACATGATTA GAGTTGGACA ACAATAAAT GTTACAGGTA

GCGGCGGCAA ACACATAAG GTGAAAAGTG GTGACACACT

CAGTAAAATT GCCGTTGATA ACAAAACGAC TGTGAGTAGA

TTGATGAGTC TAAACCCTGA ATTACGAAT CCAAATCATA

TAAAAGTAGG TCAAACAATT AGATTAAGTC TCGAGCACCA

CCACCACCAC CACTGA
``` segments: WLBU2 Peptide: 1st base to 70th base; Rigid linker: 71st base to 105th base; LysM: 106th base to 429th base; 6×-His tag (SEQ ID NO: 9): 436th base to 453d base
Amino Acid Sequence:

```
                                        (SEQ ID NO: 56)
MRRWVRRVRR WVRRVVRVVR RWVRREAAAK EAAAKSRGTS

STKTTPKYKV KSGDNLTKIA KKHNTTVATL LKLNPSIKDP

NMIRVGQTIN VTGSGGKTHK VKSGDTLSKI AVDNKTTVSR

LMSLNPEITN PNHIKVGQTI RLSLEHHHHH H
``` segments: WLBU2 Peptide: 1st aa to 25th aa; Rigid linker: 26th aa base to 35th aa; LysM: 36th aa to 143d aa; 6×-His tag (SEQ ID NO: 9): 146th aa to 151st aa
Theoretical pI/Mw: 11.8/17.1

Example 13: WLBU2-Rigid Linker-Phi29FL

DNA Sequence:

```
                                        (SEQ ID NO: 57)
ATGCGTCGTT GGGTTCGTCG CGTGCGTCGC TGGGTGCGTC

GTGTTGTTCG TGTTGTTCGT CGTTGGGTTC GTCGTGAAGC

CGCTGCCAAG GAGGCGGCCG CTAAACAAAT TTCACAAGCG

GGTATCAACT TAATTAAGAG CTTTGAGGGT TTACAACTGA

AAGCATATAA AGCTGTTCCG ACTGAGAAGC ATTACACCAT

TGGTTACGGT CATTACGGTT CCGATGTTTC ACCTAGGCAG

GTTATCACTG CTAAACAGGC TGAAGACATG TTGCGTGATG

ATGTGCAGGC TTTTGTGGAT GGTGTAAATA AAGCATTAAA

AGTATCTGTC ACCCAAAATC AATTTGATGC ACTTGTCTCA

TTCGCTTACA ACGTTGGGTT AGGGGCTTTC AGGTCTTCTT

CTCTACTGGA ATACTTGAAT GAAGGAAGAA CAGCTCTAGC

GGCGGCTGAA TTCCCTAAAT GGAATAAGTC AGGCGGTAAA

GTTTATCAAG GGTTGATTAA CCGTAGAGCA CAGGAGCAAG

CCTTGTTTAA TAGTGGAACA CCTAAAAATG TTTCACGTGG

AACATCGTCT ACTAAAACGA CACCTAAGTA TAAGGTGAAG

AGTGGTGACA ACCTTACTAA AATCGCTAAA AAGCATAATA

CAACGGTTGC TACTTTGTTG AAGTTGAATC CGAGTATCAA

AGACCCGAAC ATGATTAGAG TTGGACAAAC AATAAATGTT

ACAGGTAGCG GCGGCAAAAC ACATAAGGTG AAAAGTGGTG

ACACACTCAG TAAAATTGCC GTTGATAACA AAACGACTGT

GAGTAGATTG ATGAGTCTAA ACCCTGAAAT TACGAATCCA

AATCATATAA AAGTAGGTCA AACAATTAGA TTAAGTC

TCGAGCACCA CCACCACCAC CACTGA
``` segments: WLBU2 Peptide: 1st base to 70th base; rigid linker: 71st base to 552d base; Phi29 lysozyme: 106th base to 552d base; LysM: 553d base to 876th base; 6×-His tag (SEQ ID NO: 9): 883d base to 900th base Amino Acid Sequence:

```
                                        (SEQ ID NO: 58)
MRRWVRRVRR WVRRVVRVVR RWVRREAAAK EAAAKQISQA

GINLIKSFEG LQLKAYKAVP TEKHYTIGYG HYGSDVSPRQ

VITAKQAEDM LRDDVQAFVD GVNKALKVSV TQNQFDALVS

FAYNVGLGAF RSSSLLEYLN EGRTALAAAE FPKWNKSGGK

VYQGLINRRA QEQALFNSGT PKNVSRGTSS TKTTPKYKVK

SGDNLTKIAK KHNTTVATLL KLNPSIKDPN MIRVGQTINV

TGSGGKTHKV KSGDTLSKIA VDNKTTVSRL MSLNPEITNP

NHIKVGQTIR LSLEHHHHH
``` segments: WLBU2 Peptide: 1st aa to 25th aa; rigid linker: 26th aa to 35th aa; Phi29 lysozyme: 36th aa to 184th aa; LysM: 185th aa to 292d aa; 6×-His tag (SEQ ID NO: 9): 295th aa to 300th aa
Theoretical pI/Mw: 10.62/32377.22

Example 14: P630 (WLBU 2-Flexible Linker-LysM Domain Fusion)

DNA sequence of pGDC630:

```
                                          (SEQ ID NO: 59)
ATGCGTCGTT GGGTTCGTCG TGTTCGTCGT TGGGTTCGTC

GTGTTGTTCG TGTTGTTCGT CGTTGGGTTC GTCGTGGCTC

CGGATCGGCT TCTGGGTCAC GTGGAACATC GTCTACTAAA

ACGACACCTA AGTATAAGGT GAAGAGTGGT GACAACCTTA

CTAAAATCGC TAAAAAGCAT AATACAACGG TTGCTACTTT

GTTGAAGTTG AATCCGAGTA TCAAAGACCC GAACATGATT

AGAGTTGGAC AAACAATAAA TGTTACAGGT AGCGGCGGCA

AAACACATAA GGTGAAAAGT GGTGACACAC TCAGTAAAAT

TGCCGTTGAT AACAAAACGA CTGTGAGTAG ATTGATGAGT

CTAAACCCTG AAATTACGAA TCCAAATCAT ATAAAAGTAG

GTCAAACAAT TAGATTAAGT CTCGAGCACC ACCACCACCA

CCACTGA
``` segments: WLBU2 Peptide: 1st base to 75th base; Flexible linker: 76th base to 96th base; LysM: 97th base to 420th base; 6×-His tag (SEQ ID NO: 9): 427th base to 447th base
Amino Acid Sequence:

```
                                          (SEQ ID NO: 60)
MRRWVRRVRR WVRRVVRVVR RWVRRGSGSA SGSRGTSSTK

TTKYKVKSGD NTKAKKHNTT VATKNSKDNM RVGTNVTGSG

GKTHKVKSGD TSKAVDNKTT VSRMSNTNNH KVGTRSHHHH

Figure 33:
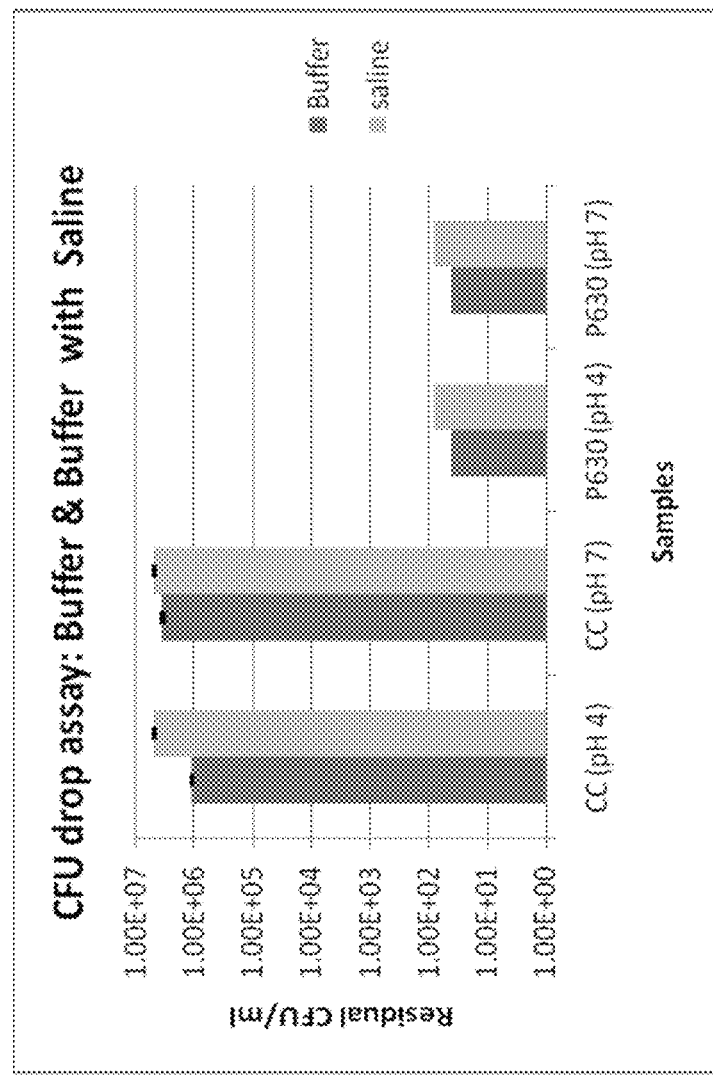
FIG. 33 shows P630 gives 5 logs killing in Buffer and 4 logs killing in buffer+saline at 100 µg/mL.
Figure 34:
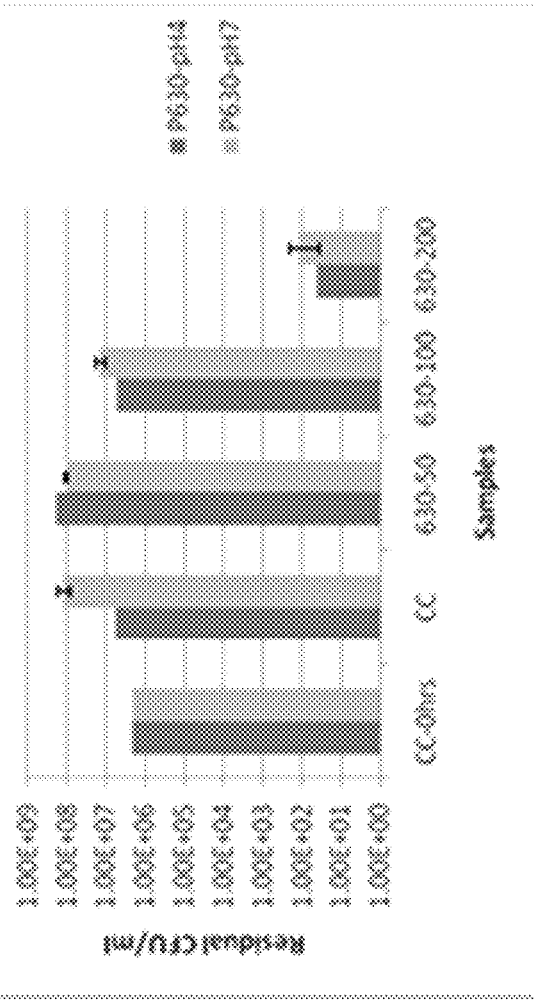
FIG. 34 shows P630 exhibits activity in LB at 200 µg/mL.

HH
``` segments: WLBU2 Peptide: 1st aa to 25th aa; Flexible linker: 26th aa to 32d aa; LysM: 33d aa to 116th aa; 6×-His tag (SEQ ID NO: 9): 117th aa to 122d aa
Theoretical pI/Mw: 12.27/13.7
Introduction
A chimeric fusion of WLBU2 peptide fused to LysM was constructed. This construct has the antimicrobial peptide WLBU2 which serves as outer membrane penetrating motif at the N-terminus and a membrane traversing domain, LysM domain at the C terminus. Although LysM domains are reported to bind to bacterial peptidoglycan, they have not been reported to possess or exhibit Gram-negative bacterial outer membrane penetrating or traversing function. However, we found that LysM domains could bind to outer membrane of Gram-negative bacteria. Construction of a fusion of WLBU2 peptide to LysM connected with a flexible linker were done to determine if this double fusion would be more soluble in biological fluids and able to kill Gram-negative pathogens.
1. Generating WLBU2-LysM Fusion (Cloning Strategy):
WLBU2 variant was fused to the 5' end of LysM coding region by a PCR based method introducing appropriate cloning sites and the chimeric DNA sequence without a stop codon was cloned into E. coli expression vector pET26b as an NdeI-XhoI fragment, for expression of the chimeric protein as a C-terminal 6×-His tag (SEQ ID NO: 9) fusion. E. coli transformants were screened by PCR, plasmid DNA isolated from the positive clones and presence of the insert confirmed by restriction digestion analysis.
2.
Test protein expression was performed in E. coli ER2566 by inducing with 1 mM IPTG at 37° C. for 4 hours. The expected size of fusion protein is 13 kDa.
3. Purification and Refolding of P630:
Protein expression was done in E. coli ER2566 by inducing with 1 mM IPTG at 37° C. for 4 hours. Induced cell pellet was resuspended in buffer, sonicated to lyse the cells, separated supernatant and pellet by centrifugation at 10,000 rpm. Protein purification was done from the inclusion bodies. Inclusion bodies were solubilized in 6M Guanidium hydrochloride and protein was purified by Ni-NTA chromatography.
P630 was dialyzed against 10 mM Na-Acetate buffer (pH 4) and 20 mM HEPES (pH 7) to remove the denaturant and to refold the protein.
4. CFU Drop Assay:
The antibacterial activity of P630 in both buffer and saline were tested against A. baumannii strain ATCC19606 by using the CFU drop assay. Briefly, $10^6$ cells/mL of A. baumannii in buffer and buffer containing saline were treated with 100 μg/mL of P630, incubated at 37° C. for 2 hours and enumerated remaining number of viable cells.
Result: P630 gives 5 logs killing in Buffer and 4 logs killing in buffer+saline at 100 μg/mL (FIG. 33).
Inference: The fusion protein P630 kills A. baumannii efficiently in both buffer and buffered saline.
5. Dose Response:
Dose response was done in buffered saline with varying protein concentrations as indicated below on A. baumannii cells.
Assay Conditions: Reaction volume: 200 ul; protein storage: 10 mM Sodium acetate pH 4 and 20 mM HEPES pH 7; assay condition: 50% LB; duration: 2 hours @ 37° C., 200 rpm; protein: 50, 100, and 200 μg/ml.
Result: P630 exhibits activity in LB at 200 μg/mL (FIG. 34).
6. MIC of P630 in Growth Media on Acinetobacter baumannii and Pseudomonas aeruginosa:
MIC was determined using a modified Clinical and Laboratory Standards Institute (CLSI) broth microdilution procedure on A. baumannii strain HER1401 and P. aeruginosa strain PA01in Cation-adjusted Mueller Hinton Broth (CA-MHB media). A 10-point MIC was set up in microtitre plates in duplicates with two fold dilutions starting at 450 μg/mL. Wells of a 96-well polystyrene plated were coated with 0.5% BSA for 1 hour at 37° C. and each well were inoculated with $5×10^5$ cells/mL A. baumannii and P. aeruginosa. A positive control for growth which is devoid of P630 was included in the assay. Microtiter plates were incubated at 35° C. for 18-20 hrs. The endpoint for this assay was complete inhibition of growth at the end of incubation as determined by colorless wells after addition of Iodonitro tetrazolium (INT) dye.

TABLE D8

| Bacteria | P630 | MHB-2 (μg/mL) |
| --- | --- | --- |
| A. baumannii HER1401 | pH4 | 112.5 |
|  | pH7 | 112.5 |

TABLE D8-continued

| Bacteria | P630 | MHB-2 (μg/mL) |
|---|---|---|
| *P. aeruginosa* PA01 | pH4 | 112.5 |
| | pH7 | 112.5 |

Result: MIC was obtained at 112 μg/ml in MHB for both *A. baumannii* and *P. aeruginosa* (Table D8).

Example 15: Additional Constructs; SEQ IDs

1. P191 (10×-His Tag (SEQ ID NO: 24)+LysM Domain):

```
                                        (SEQ ID NO: 5)
MGHHHHHHHH HHSSGHIEGR HMSRGTSSTK TTPKYKVKSG

DNLTKIAKKH NTTVATLLKL NPSIKDPNMI RVGQTINVTG

SGGKTHKVKS GDTLSKIAVD NKTTVSRLMS LNPEITNPNH

IKVGQTIRLS

Vector sequence along with 10X His tag (SEQ ID NO: 24) (1-22; MGH . . . to . . . GRHM (SEQ ID NO: 61)); LysM domain (23-130; SRGT . . .

(SEQ ID NO: 37) to . . . TIRLS (SEQ ID NO: 38))

Lys M: 23 to 130 from sequence ID YP_002004544:

LysM; amino acids 151 to 258
```

Vector sequence along with 10×His tag (SEQ ID NO: 24) (1-22; MGH . . . to . . . GRHM (SEQ ID NO: 61)); LysM domain (23-130; SRGT . . . (SEQ ID NO: 37) to . . . TIRLS (SEQ ID NO: 38)) Lys M: 23 to 130 from sequence ID YP_002004544:LysM; amino acids 151 to 258 DNA sequence P191:

```
                                       (SEQ ID NO: 62)
ATGGGCCATC ATCATCATCA TCATCATCAT CATCACAGCA

GCGGCCATAT CGAAGGTCGT CATATGTCAC GTGGAACATC

GTCTACTAAA ACGACACCTA AGTATAAGGT GAAGAGTGGT

GACAACCTTA CTAAAATCGC TAAAAAGCAT AATACAACGG

TTGCTACTTT GTTGAAGTTG AATCCGAGTA TCAAAGACCC

GAACATGATT AGAGTTGGAC AAACAATAAA TGTTACAGGT

AGCGGCGGCA AAACACATAA GGTGAAAAGT GGTGACACAC

TCAGTAAAAT TGCCGTTGAT AACAAAACGA CTGTGAGTAG

ATTGATGAGT CTAAACCCTG AAATTACGAA TCCAAATCAT

ATAAAAGTAG GTCAAACAAT TAGATTAAGT TGACTCGAG
```

Nucleotide: P191
Lys M: 67 to 390
Cloning strategy: The DNA segment encoding the LysM domain was PCR amplified using specific primers and the PCR product was digested with NdeI-XhoI restriction enzyme and cloned into the expression vector pET16b at the NdeI/XhoI sites. The final protein includes a 10×-His Tag (SEQ ID NO: 24) at the N-terminus of the protein along with the vector sequence that follows the translational start.

2. P199 (Phi29 Endolysin+6×His Tag (SEQ ID NO: 9)):

```
                                          (SEQ ID NO: 63)
MQISQAGINL IKSFEGLQLK AYKAVPTEKH YTIGYGHYGS

DVSPRQVITA KQAEDMLRDD VQAFVDGVNK ALKVSVTQNQ

FDALVSFAYN VGLGAFRSSS LLEYLNEGRT ALAAAEFPKW

NKSGGKVYQG LINRRAQEQA LFNSGTPKNV SRGTSSTKTT

PKYKVKSGDN LTKIAKKHNT TVATLLKLNP SIKDPNMIRV

GQIINVIGSG GKTHKVKSGD TLSKIAVDNK TTVSRLMSLN

PEITNPNHIK VGQTIRLSLE HHHHHH

Lysozyme domain (1-150; MQIS . . . (SEQ ID NO: 64)

to . . . PKNV (SEQ ID NO: 65)) from sequence ID

YP_002004544: Phi29 catalytic domain: 1 to 150.

LysM domain (151-258; SRGT . . . (SEQ ID NO: 37)

to . . . IRLS (SEQ ID NO: 30)). Vector sequence along with 6X His tag (SEQ ID NO: 9) (259-266;

LEHHHHHH (SEQ ID NO: 31))
```

DNA sequence P199:

```
                                        (SEQ ID NO: 66)
ATGCAAATTT CACAAGCGGG TATCAACTTA ATTAAGAGCT

TTGAGGGTTT ACAACTGAAA GCATATAAAG CTGTTCCGAC

TGAGAAGCAT TACACCATTG GTTACGGTCA TTACGGTTCC

GATGTTTCAC CTAGGCAGGT TATCACTGCT AAACAGGCTG

AAGACATGTT GCGTGATGAT GTGCAGGCTT TTGTGGATGG

TGTAAATAAA GCATTAAAAG TATCTGTCAC CCAAAATCAA

TTTGATGCAC TTGTCTCATT CGCTTACAAC GTTGGGTTAG

GGCTTTCAG GTCTTCTTCT CTACTGGAAT ACTTGAATGA

AGGAAGAACA GCTCTAGCGG CGGCTGAATT CCCTAAATGG

AATAAGTCAG GCGGTAAAGT TTATCAAGGG TTGATTAACC

GTAGAGCACA GGAGCAAGCC TTGTTTAATA GTGGAACACC

TAAAAATGTT TCACGTGGAA CATCGTCTAC TAAAACGACA

CCTAAGTATA AGGTGAAGAG TGGTGACAAC CTTACTAAAA

TCGCTAAAAA GCATAATACA ACGGTTGCTA CTTTGTTGAA

GTTGAATCCG AGTATCAAAG ACCCGAACAT GATTAGAGTT

GGACAAACAA TAAATGTTAC AGGTAGCGGC GGCAAAACAC

ATAAGGTGAA AAGTGGTGAC ACACTCAGTA AAATTGCCGT

TGATAACAAA ACGACTGTGA GTAGATTGAT GAGTCTAAAC

CCTGAAATTA CGAATCCAAA TCATATAAAA GTAGGTCAAA

CAATTAGATT AAGTCTCGAG CACCACCACC ACCACCACTG

A
```

Nucleotide: P199:
Phi29 catalytic domain: 1 to 450. Lys M: 451 to 774.
Cloning strategy: The gene encoding the phi29 endolysin was PCR amplified from the genomic DNA of the phage phi29 using gene specific primers. The resultant PCR product was cloned using sites NdeI/XhoI into the pET21b vector. The reverse primer was designed without a stop codon so that the vector encoded 6×-His tag (SEQ ID NO: 9) would be included in the expressed protein.

3. P203 (GP36 CD+LysM Domain+6×His Tag (SEQ ID NO: 9)):

(SEQ ID NO: 67)
MGVALDRTRV DPQAVGNEVL KRNADKLNAM RGAEYGANVK

VSGTDIRMNG GNSAGMLKQD VFNWRKELAQ FEAYRGEAYK

DADGYSVGLG HYLGSGNAGA GTTVTPEQAA QWFAEDTDRA

LDQGVRLADE LGVTNNASIL GLAGMAFQMG EGRARQFRNT

FQAIKDRNKE AFEAGVRNSK WYTQTPNRAE AFIKRMAPHF

DTPSQIGVDW YSAATAEKLS RGTSSTKTTP KYKVKSGDNL

TKIAKKHNTT VATLLKLNPS IKDPNMIRVG QTINVTGSGG

KTHKVKSGDT LSKIAVDNKT TVSRLMSLNP EITNPNHIKV

GQTIRLSLEK LAAALEHHHH HH

GP36 CD (1-219; MGVA . . . (SEQ ID NO: 68) to . . . AEKL (SEQ ID NO: 69)) was from in-house sequenced phage, sequence not deposited in Genbank. LysM domain (220-327; SRGT . . . (SEQ ID NO: 37) to . . . IRLS (SEQ ID NO: 30)) from sequence ID YP_002004544: LysM; amino acids 151 to 258. Vector sequence along with 6X His tag (SEQ ID NO: 9) (328-342; LEK . . . to . . . HHHHHH (SEQ ID NO: 9))

DNA Sequence P203:

(SEQ ID NO: 70)
ATGGGTGTGG CCCTGGACCG CACGCGGGTT GATCCCCAGG

CAGTCGGCAA CGAGGTGCTC AAGCGCAACG CGGATAAGCT

GAATGCGATG CGGGGCGCCG AGTACGGTGC CAACGTCAAG

GTCAGCGGCA CGGACATTCG CATGAACGGG GGTAACAGTG

CCGGCATGCT GAAGCAGGAC GTGTTCAACT GGCGGAAGGA

ACTGGCTCAG TTCGAGGCTT ACCGAGGGGA GGCGTATAAG

GATGCCGATG GTTATAGTGT GGGCCTGGGG CATTACCTGG

GCAGTGGCAA TGCTGGGGCA GGTACTACAG TCACGCCTGA

GCAAGCCGCG CAGTGGTTCG CCGAGGACAC CGACCGCGCA

CTCGACCAGG GTGTGAGGTT GGCCGACGAG CTGGGCGTTA

CGAACAATGC CTCTATCCTG GGATTGGCCG GTATGGCCTT

CCAGATGGGC GAAGGACGTG CCCGGCAGTT CCGTAACACC

TTCCAGGCGA TCAAGGATCG CAACAAGGAA GCCTTCGAGG

CTGGTGTGCG AAACAGCAAG TGGTACACGC AGACGCCCAA

CCGGGCCGAG GCATTCATCA AGCGCATGGC GCCCCACTTC

GATACACCGA GTCAAATCGG TGTCGATTGG TACAGCGCCG

CAACAGCGGA GAAGCTTTCA CGTGGAACAT CGTCTACTAA

AACGACACCT AAGTATAAGG TGAAGAGTGG TGACAACCTT

ACTAAAATCG CTAAAAAGCA TAATACAACG GTTGCTACTT

TGTTGAAGTT GAATCCGAGT ATCAAAGACC CGAACATGAT

TAGAGTTGGA CAAACAATAA ATGTTACAGG TAGCGGCGGC

AAAACACATA AGGTGAAAAG TGGTGACACA CTCAGTAAAA

TTGCCGTTGA TAACAAAACG ACTGTGAGTA GATTGATGAG

TCTAAACCCT GAAATTACGA ATCCAAATCA TATAAAAGTA

GGTCAAACAA TTAGATTAAG TCTCGAGAAG CTTGCGGCCG

CACTCGAGCA CCACCACCAC CACCACTGA

Nucleotide: P203

GP36 CD: 1 to 657 from in-house sequenced phage, sequence not deposited in Genbank. Lys M: 658 to 981.

Cloning strategy: The GP36 CD was PCR amplified and cloned without stop codon at the NdeI/Hind III site into pET21b. To pET21b-GP36 CD clone, the LysM domain from phi29 endolysin was cloned without a stop codon at Hind III site thereby fusing it to the C-terminal of the GP36 CD. The protein expressed from this construct will have a 6×-His tag (SEQ ID NO: 9) at its C-terminal.

4. P340 (6×His Tag (SEQ ID NO: 9)+Phi29 Endolysin+RRR BPI TMD RRR):

(SEQ ID NO: 33)
MHHHHHHQIS QAGINLIKSF EGLQLKAYKA VPTEKHYTIG

YGHYGSDVSP RQVITAKQAE DMLRDDVQAF VDGVNKALKV

SVTQNQFDAL VSFAYNVGLG AFRSSSLLEY LNEGRTALAA

AEFPKWNKSG GKVYQGLINR RAQEQALFNS GTPKNVSRGT

SSTKTTPKYK VKSGDNLTKI AKKHNTTVAT LLKLNPSIKD

PNMIRVGQTI NVTGSGGKTH KVKSGDTLSK IAVDNKTTVS

RLMSLNPEIT NPNHIKVGQT IRLSKLRRRA SLMVLVAIGT

AVTAAVNPGV VVRRRR

Vector sequence along with 6X His tag (SEQ ID NO: 9) (1-7; MHHHHHH (SEQ ID NO: 34)); Lysozyme domain (8-156; QISQ . . . (SEQ ID NO: 29) to . . . PKNV (SEQ ID NO: 65)); LysM domain (157-264; SRGT . . . (SEQ ID NO: 37) to . . . IRLS (SEQ ID NO: 30)); RRR linkers (267-269 and 294-296); BPI TMD Peptide (270-293; ASLM . . . (SEQ ID NO: 39) to . . . VVVR (SEQ ID NO: 71))

From sequence ID YP_002004544
Phi29 catalytic domain; amino acids 1 to 150
LysM; amino acids 151 to 258
From sequence ID NP 001716
BPI TMD; amino acids 16 to 39

DNA sequence P340:

(SEQ ID NO: 72)
ATGCATCATC ATCATCATCA TCAAATTTCA CAAGCGGGTA

TCAACTTAAT TAAGAGCTTT GAGGGTTTAC AACTGAAAGC

ATATAAAGCT GTTCCGACTG AGAAGCATTA CACCATTGGT

TACGGTCATT ACGGTTCCGA TGTTTCACCT AGGCAGGTTA

TCACTGCTAA ACAGGCTGAA GACATGTTGC GTGATGATGT

GCAGGCTTTT GTGGATGGTG TAAATAAAGC ATTAAAAGTA

TCTGTCACCC AAAATCAATT TGATGCACTT GTCTCATTCG

CTTACAACGT TGGGTTAGGG GCTTTCAGGT CTTCTTCTCT

ACTGGAATAC TTGAATGAAG AAGAACAGC TCTAGCGGCG

GCTGAATTCC CTAAATGGAA TAAGTCAGGC GGTAAAGTTT

ATCAAGGGTT GATTAACCGT AGAGCACAGG AGCAAGCCTT

GTTTAATAGT GGAACACCTA AAAATGTTTC ACGTGGAACA

TCGTCTACTA AAACGACACC TAAGTATAAG GTGAAGAGTG

GTGACAACCT TACTAAAATC GCTAAAAAGC ATAATACAAC

GGTTGCTACT TTGTTGAAGT TGAATCCGAG TATCAAAGAC

CCGAACATGA TTAGAGTTGG ACAAACAATA AATGTTACAG

GTAGCGGCGG CAAAACACAT AAGGTGAAAA GTGGTGACAC

ACTCAGTAAA ATTGCCGTTG ATAACAAAAC GACTGTGAGT

AGATTGATGA GTCTAAACCC TGAAATTACG AATCCAAATC

ATATAAAGT AGGTCAAACA ATTAGATTAA GTAAGCTTCG

CCGTCGCGCG TCCCTGATGG TGCTGGTCGC CATAGGCACC

GCCGTGACAG CGGCCGTCAA CCCTGGCGTC GTGGTCAGGC

GCCGTCGCTG A

Nucleotide P340:
Phi29 catalytic domain: 22 to 468. Lys M: 469 to 792. BPI TMD: 807 to 879.
Cloning strategy: The BPI TMD with RRR flanks was first cloned into pET21b as Hind III/XhoI. The phi 29 endolysin gene was then cloned upstream of the BPI TMD segment at NdeI/XhoI sites to generate a fusion construct. The forward primer for amplification of Phi29 endolysin included a 6×-His tag (SEQ ID NO: 9) to aid protein purification.
5. P526 (GP36 CD+LysM Domain+LBP Peptide+6×His Tag (SEQ ID NO: 9)):

(SEQ ID NO: 73)
MHHHHHHGVA LDRTRVDPQA VGNEVLKRNA DKLNAMRGAE

YGANVKVSGT DIRMNGGNSA GMLKQDVFNW RKELAQFEAY

RGEAYKDADG YSVGLGHYLG SGNAGAGTTV TPEQAAQWFA

EDTDRALDQG VRLADELGVT NNASTLGLAG MAFQMGEGRA

RQFRNTFQAI KDRNKEAFEA GVRNSKWYTQ TPNRAEAFIK

RMAPHFDTPS QIGVDWYSAA TAEKLSRGTS STKTTPKYKV

KSGDNLTKIA KKHNTTVATL LKLNPSIKDP NMIRVGQTIN

VTGSGGKTHK VKSGDTLSKI AVDNKTTVSR LMSLNPEITN

PNHIKVGQTI RLSLEKLAAA GSGSASGSDS SIRVQGRWKV

RASFFKLQGS FDVSVKG

Vector sequence along 6X His tag (SEQ ID NO: 9)
(1- 7; MHHHHHHH (SEQ ID NO: 74)); GP36 CD (8-225;
GVAL . . . (SEQ ID NO: 75) to . . . AEKL (SEQ ID
NO: 69)); LysM domain (226- 333; SRGTS . . . (SEQ
ID NO: 76) to . . . IRLS (SEQ ID NO: 30)); Linker
(341- 347; GSGSASG (SEQ ID NO: 77)); LBP Peptide
(348-377; SDSS . . . (SEQ ID NO: 78) to . . . SVKG
(SEQ ID NO: 79))

GP36 CD was from in house sequenced phage, sequence not deposited in Genbank.
From sequence ID YP_002004544: LysM: amino acids 151 to 258.
From sequence ID AAH22256: LBP peptide amino acids 106 to 135.
DNA Sequence P526:

(SEQ ID NO: 80)
ATGCACCATC ACCATCACCA TGGTGTGGCC CTGGACCGCA

CGCGGGTTGA TCCCCAGGCA GTCGGCAACG AGGTGCTCAA

GCGCAACGCG GATAAGCTGA ATGCGATGCG GGGCGCCGAG

TACGGTGCCA ACGTCAAGGT CAGCGGCACG GACATTCGCA

TGAACGGGGG TAACAGTGCC GGCATGCTGA AGCAGGACGT

GTTCAACTGG CGGAAGGAAC TGGCTCAGTT CGAGGCTTAC

CGAGGGGAGG CGTATAAGGA TGCCGATGGT TATAGTGTGG

GCCTGGGGCA TTACCTGGGC AGTGGCAATG CTGGGGCAGG

TACTACAGTC ACGCCTGAGC AAGCCGCGCA GTGGTTCGCC

GAGGACACTG ACCGCGCACT CGACCAGGGT GTGAGGTTGG

CCGACGAGCT GGGCGTTACG AACAATGCCT CTACCCTGGG

ATTGGCCGGT ATGGCCTTCC AGATGGGCGA AGGACGTGCC

CGGCAGTTCC GTAACACCTT CCAGGCGATC AAGGATCGCA

ACAAGGAAGC CTTCGAGGCT GGTGTGCGAA ACAGCAAGTG

GTACACGCAG ACGCCCAACC GGGCCGAGGC ATTCATCAAG

CGCATGGCGC CCCACTTCGA TACACCGAGT CAAATCGGTG

TCGATTGGTA CAGCGCCGCA ACAGCGGAGA AGCTTTCACG

TGGAACATCG TCTACTAAAA CGACACCTAA GTATAAGGTG

AAGAGTGGTG ACAACCTTAC TAAAATCGCT AAAAAGCATA

ATACAACGGT TGCTACTTTG TTGAAGTTGA ATCCGAGTAT

CAAAGACCCG AACATGATTA GAGTTGGACA GACAATAAAT

GTTACAGGTA GCGGCGGCAA AACACATAAG GTGAAAAGTG

GTGACACACT CAGTAAAATT GCCGTTGATA ACAAAACGAC

TGTGAGTAGA TTGATGAGTC TAAACCCTGA AATTACGAAT

```
CCAAATCATA TAAAAGTAGG TCAAACAATT AGATTAAGTC

TTGAGAAACT TGCGGCCGCA GGCTCCGGAT CGGCTTCTGG

GTCCGACTCC TCCATCCGGG TCCAGGGCCG TTGGAAGGTG

CGCGCGTCAT TCTTCAAACT GCAGGGCTCC TTCGATGTCA

GTGTCAAGGG CTGA
```

Nucleotide: P526
GP36 CD: 22 to 675, from in-house sequenced phage, sequence not deposited in Genbank.
Lys M: 676 to 999; LBP peptide: 1041 to 1134.
Cloning strategy: The LBP peptide along with a flexible GS linker was fused to the C-terminus of P203 (GP36-LysM) by using long primers designed to add LBP, in two sequential rounds of PCR amplification. DNA segment coding for 6x-His tag (SEQ ID NO: 9) was incorporated in the forward primer itself. This fusion construct was cloned into NdeI/XhoI site in pET26b vector.
6. P549 (10x-His Tag (SEQ ID NO: 24)+LysM Domain+LBP):

```
                                         (SEQ ID NO: 81)
MGHHHHHHHH HHSSGHIEGR HMSRGTSSTK TTPKYKVKSG

DNLTKIAKKH NTTVATLLKL NPSIKDPNMI RVGQIINVIG

SGGKTHKVKS GDTLSKIAVD NKTTVSRLMS LNPEITNPNH

IKVGQTIRLS LEKLAAAGSG AGSGSDSSIR VQGRWKVRAS

FFKLQGSFDV SVKG

Vector sequence along with 10X His tag (SEQ ID NO: 24) (1-22; MGHH . . . (SEQ ID NO: 82)

to . . . GRHM (SEQ ID NO: 61)); LysM domain (23-130; SRGT . . . (SEQ ID NO: 37) to IRLS (SEQ ID NO: 30)); Linker (138-144; GSGAGSG (SEQ ID NO: 83)); LBP Peptide (145-174; SDSS . . . (SEQ ID NO: 78) to . . . SVKG (SEQ ID NO: 79))
```

From sequence ID YP_002004544:LysM; amino acids 151 to 258
From sequence ID AAH22256: LBP peptide amino acids 106 to 135
DNA sequence P549:

```
                                         (SEQ ID NO: 84)
ATGGGCCATC ATCATCATCA TCATCATCAT CATCACAGCA

GCGGCCATAT CGAAGGTCGT CATATGTCAC GTGGAACATC

GTCTACTAAA ACGACACCTA AGTATAAGGT GAAGAGTGGT

GACAACCTTA CTAAAATCGC TAAAAAGCAT AATACAACGG

TTGCTACTTT GTTGAAGTTG AATCCGAGTA TCAAAGACCC

GAACATGATT AGAGTTGGAC AAACAATAAA TGTTACAGGT

AGCGGCGGCA AAACACATAA GGTGAAAAGT GGTGACACAC

TCAGTAAAAT TGCCGTTGAT AACAAAACGA CTGTGAGTAG

ATTGATGAGT CTAAACCCTG AAATTACGAA TCCAAATCAT
```

```
ATAAAAGTAG GTCAAACAAT TAGATTAAGT CTTGAGAAAC

TTGCGGCCGC AGGCTCCGGA TCGGCTTCTG GGTCCGACTC

CTCCATCCGG GTCCAGGGCC GTTGGAAGGT GCGCGCGTCA

TTCTTCAAAC TGCAGGGCTC CTTCGATGTC AGTGTCAAGG

GCTGA
```

Nucleotide: P549
Lys M: 67 to 390; LBP peptide: 351 to 440
Cloning strategy: The LBP peptide along with a flexible GS linker was fused to the C-terminal end of LysM by using primers designed to add LBP, in two sequential rounds of PCR amplification. The resulting LysM-LBP fusion PCR product was cloned at NdeI/XhoI site in pET16b vector giving it a 10×His tag (SEQ ID NO: 24) at the N-terminus.
7. P601 (WLBU2+GP36 CD+LysM Domain+6×His Tag (SEQ ID NO: 9)):

```
                                         (SEQ ID NO: 7)
MRRWVRRVRR WVRRVVRVVR RWVRRGSGSA SGGVALDRTR

VDPQAVGNEV LKRNADKLNA MRGAEYGANV KVSGTDIRMN

GGNSAGMLKQ DVFNWRKELA QFEAYRGEAY KDADGYSVGL

GHYLGSGNAG AGTTVTPEQA AQWFAEDTDR ALDQGVRLAD

ELGVTNNASI LGLAGMAFQM GEGRARQFRN TFQAIKDRNK

EAFEAGVRNS KWYTQTPNRA EAFIKRMAPH FDTPSQIGVD

WYSAATAEKL SRGTSSTKTT PKYKVKSGDN LTKIAKKHNT

TVATLLKLNP SIKDPNMIRV GQTINVTGSG GKTHKVKSGD

TLSKIAVDNK TTVSRLMSLN PEITNPNHIK VGQTIRLSLE

HHHHHH

WLBU2 peptide (2-25; RRW . . . to . . . WVRR (SEQ ID NO: 28)); Linker (26-32; GSGSASG (SEQ ID

NO: 77)); GP36 CD (33-250; GVAL . . . (SEQ ID NO:

75) to . . . AEKL (SEQ ID NO: 69)); LysM domain (251-358; SRGT . . . (SEQ ID NO: 37) to . . .

IRLS (SEQ ID NO: 30)); Vector sequence along 6X

His tag (SEQ ID NO: 9) (359-366; LEHHHHHH (SEQ ID NO: 31))
```

DNA Sequence P601:

```
                                         (SEQ ID NO: 86)
ATGCGTCGTT GGGTTCGTCG TGTTCGTCGT TGGGTTCGTC

GTGTTGTTCG TGTTGTTCGT CGTTGGGTTC GTCGTGGCTC

CGGATCGGCT TCTGGGGGTG TGGCCCTGGA CCGCACGCGG

GTTGATCCCC AGGCAGTCGG CAACGAGGTG CTCAAGCGCA

ACGCGGATAA GCTGAATGCG ATGCGGGGCG CCGAGTACGG

TGCCAACGTC AAGGTCAGCG GCACGGACAT TCGCATGAAC

GGGGGTAACA GTGCCGGCAT GCTGAAGCAG GACGTGTTCA

ACTGGCGGAA GGAACTGGCT CAGTTCGAGG CTTACCGAGG
```

-continued

```
GGAGGCGTAT AAGGATGCCG ATGGTTATAG TGTGGGCCTG
GGGCATTACC TGGGCAGTGG CAATGCTGGG GCAGGTACTA
CAGTCACGCC TGAGCAAGCC GCGCAGTGGT TCGCCGAGGA
CACCGACCGC GCACTCGACC AGGGTGTGAG GTTGGCCGAC
GAGCTGGGCG TTACGAACAA TGCCTCTATC CTGGGATTGG
CCGGTATGGC CTTCCAGATG GGCGAAGGAC GTGCCCGGCA
GTTCCGTAAC ACCTTCCAGG CGATCAAGGA TCGCAACAAG
GAAGCCTTCG AGGCTGGTGT GCGAAACAGC AAGTGGTACA
CGCAGACGCC CAACCGGGCC GAGGCATTCA TCAAGCGCAT
GGCGCCCCAC TTCGATACAC CGAGTCAAAT CGGTGTCGAT
TGGTACAGCG CCGCAACAGC GGAGAAGCTT TCACGTGGAA
CATCGTCTAC TAAAACGACA CCTAAGTATA AGGTGAAGAG
TGGTGACAAC CTTACTAAAA TCGCTAAAAA GCATAATACA
ACGGTTGCTA CTTTGTTGAA GTTGAATCCG AGTATCAAAG
ACCCGAACAT GATTAGAGTT GGACAAACAA TAAATGTTAC
AGGTAGCGGC GGCAAAACAC ATAAGGTGAA AAGTGGTGAC
ACACTCAGTA AAATTGCCGT TGATAACAAA ACGACTGTGA
GTAGATTGAT GAGTCTAAAC CCTGAAATTA CGAATCCAAA
TCATATAAAA GTAGGTCAAA CAATTAGATT AAGTCTCGAG
CACCACCACC ACCACCACTG A
```

Nucleotide: P601:
WLBU2: 4 to 75, de novo designed peptide. GP36 CD: 97 to 750, from in house sequenced phage, sequence not deposited in Genbank. Lys M: 751 to 1074.
Cloning strategy: The WLBU2 peptide along with a flexible linker was fused to the N-terminus of P203 using PCR primer designed to add WLBU2, in two sequential rounds of amplification. The PCR product was cloned as NdeI/XhoI into pET26b vector. The reverse primer for the PCR amplification used was without a stop codon so that the fusion protein would be expressed as a C-terminal 6×His tag (SEQ ID NO: 9) fusion.
8. P617 (WLBU2+Phi29 Endolysin+6×His Tag (SEQ ID NO: 9)):

```
                                    (SEQ ID NO: 26)
MRRWVRRVRR WVRRVVRVVR RWVRRGSGSA SGQISQAGIN

LIKSFEGLQL KAYKAVPTEK HYTIGYGHYG SDVSPRQVIT

AKQAEDMLRD DVQAFVDGVN KALKVSVTQN QFDALVSFAY

NVGLGAFRSS SLLEYLNEGR TALAAAEFPK WNKSGGKVYQ

GLINRRAQEQ ALFNSGTPKN VSRGTSSTKT TPKYKVKSGD

NLTKIAKKHN TTVATLLKLN PSIKDPNMIR VGQIINVIGS

GGKTHKVKSG DTLSKIAVDN KTTVSRLMSL NPEITNPNHI

KVGQTIRLSL EHHHHHH
```

WLBU2 peptide (2-25; RRWV . . . (SEQ ID NO: 27) to . . . WVRR (SEQ ID NO: 28)) de novo designed peptide from ID YP_002004544; Linker (26-32; GSGSASG (SEQ ID NO: 77)); Lysozyme domain (33-181; QISQ . . . (SEQ ID NO: 29) to . . . PKNV (SEQ ID NO: 65)); LysM domain (182-289; SRGT . . . (SEQ ID NO: 37) to . . . IRLS (SEQ ID NO: 30)); Vector sequence along 6X His tag (SEQ ID NO: 9) (290-297; LEHHHHHH (SEQ ID NO: 31))

DNA Sequence P617:

```
                                    (SEQ ID NO: 25)
ATGCGTCGTT GGGTTCGTCG TGTTCGTCGT TGGGTTCGTC
GTGTTGTTCG TGTTGTTCGT CGTTGGGTTC GTCGTGGCTC
CGGATCGGCT TCTGGGCAAA TTTCACAAGC GGGTATCAAC
TTAATTAAGA GCTTTGAGGG TTTACAACTG AAAGCATATA
AAGCTGTTCC GACTGAGAAG CATTACACCA TTGGTTACGG
TCATTACGGT TCCGATGTTT CACCTAGGCA GGTTATCACT
GCTAAACAGG CTGAAGACAT GTTGCGTGAT GATGTGCAGG
CTTTTGTGGA TGGTGTAAAT AAAGCATTAA AAGTATCTGT
CACCCAAAAT CAATTTGATG CACTTGTCTC ATTCGCTTAC
AACGTTGGGT TAGGGGCTTT CAGGTCTTCT TCTCTACTGG
AATACTTGAA TGAAGGAAGA ACAGCTCTAG CGGCGGCTGA
ATTCCCTAAA TGGAATAAGT CAGGCGGTAA AGTTTATCAA
GGGTTGATTA ACCGTAGAGC ACAGGAGCAA GCCTTGTTTA
ATAGTGGAAC ACCTAAAAAT GTTTCACGTG GAACATCGTC
TACTAAAACG ACACCTAAGT ATAAGGTGAA GAGTGGTGAC
AACCTTACTA AAATCGCTAA AAAGCATAAT ACAACGGTTG
CTACTTTGTT GAAGTTGAAT CCGAGTATCA AAGACCCGAA
CATGATTAGA GTTGGACAAA CAATAAATGT TACAGGTAGC
GGCGGCAAAA CACATAAGGT GAAAAGTGGT GACACACTCA
GTAAAATTGC CGTTGATAAC AAAACGACTG TGAGTAGATT
GATGAGTCTA AACCCTGAAA TTACGAATCC AAATCATATA
AAAGTAGGTC AAACAATTAG ATTAAGTCTC GAGCACCACC
ACCACCACCA CTAA
```

Nucleotide P617:
WLBU2: 4 to 75. Phi29 catalytic domain: 97 to 543. Lys M: 544 to 867.
Cloning strategy: The WLBU2 peptide along with a flexible linker was fused to the N-terminus of phi29 endolysin (P199) using PCR primers designed to add WLBU2, in two sequential rounds of amplification. The PCR product was cloned as NdeI/XhoI into pET26b vector. The reverse primer for the PCR amplification used was without a stop codon so that the fusion protein would be expressed as a C-terminal 6×His tag (SEQ ID NO: 9) fusion.

9. P630 (WLBU2+LysM Domain+6×His Tag (SEQ ID NO: 9)):

(SEQ ID NO: 87)
MRRWVRRVRR WVRRVVRVVR RWVRRGSGSA SGSRGTSSTK

TTPKYKVKSG DNLTKIAKKH NTTVATLLKL NPSIKDPNMI

RVGQTINVTG SGGKTHKVKS GDTLSKIAVD NKTTVSRLMS

LNPEITNPNH IKVGQTIRLSLEHHHHHH

WLBU2 peptide (2-25; RRWV . . . (SEQ ID NO: 27) to . . . WVRR (SEQ ID NO: 28)); Linker (26-32; GSGSASG (SEQ ID NO: 77)); LysM domain (33-140; SRGT . . . (SEQ ID NO: 37) to . . . IRLS (SEQ ID NO: 30)); Vector sequence along 6X His tag (SEQ ID NO: 9) (141-148; LEHHHHHH (SEQ ID NO: 31))

DNA Sequence P630:

(SEQ ID NO: 59)
ATGCGTCGTT GGGTTCGTCG TGTTCGTCGT TGGGTTCGTC

GTGTTGTTCG TGTTGTTCGT CGTTGGGTTC GTCGTGGCTC

CGGATCGGCT TCTGGGTCAC GTGGAACATC GTCTACTAAA

ACGACACCTA AGTATAAGGT GAAGAGTGGT GACAACCTTA

CTAAAATCGC TAAAAAGCAT AATACAACGG TTGCTACTTT

GTTGAAGTTG AATCCGAGTA TCAAAGACCC GAACATGATT

AGAGTTGGAC AAACAATAAA TGTTACAGGT AGCGGCGGCA

AAACACATAA GGTGAAAAGT GGTGACACAC TCAGTAAAAT

TGCCGTTGAT AACAAAACGA CTGTGAGTAG ATTGATGAGT

CTAAACCCTG AAATTACGAA TCCAAATCAT ATAAAAGTAG

GTCAAACAAT TAGATTAAGT CTCGAGCACC ACCACCACCA

CCACTGA

Nucleotide: P630
WLBU2: 4 to 75; Lys M: 97 to 420
WLBU2: de novo designed peptide, from sequence ID NC_011048.1:15457-16233. Lys M: 451 to 777.
Cloning strategy: The WLBU2 peptide along with a flexible linker was fused to the N terminus of LysM domain from phi29 endolysin using PCR primers designed to add WLBU2, in two sequential rounds of amplification. The PCR product was cloned as NdeI/XhoI into pET26b vector. The reverse primer for the PCR amplification used was without a stop codon so that the fusion protein would be expressed as a C-terminal 6×His tag (SEQ ID NO: 9) fusion.

10. P634 (WLBU2+GP36 CD+LysM Domain+LBP Peptide+6×His tag (SEQ ID NO: 9)):

(SEQ ID NO: 88)
MGHHHHHHHH HHSSGHIEGR HMRRWVRRVR RWVRRVVRVV

RRWVRRGSGS ASGGVALDRT RVDPQAVGNE VLKRNADKLN

AMRGAEYGAN VKVSGTDIRM NGGNSAGMLK QDVFNWRKEL

AQFEAYRGEA YKDADGYSVG LGHYLGSGNA GAGTTVTPEQ

AAQWFAEDTD RALDQGVRLA DELGVTNNAS TLGLAGMAFQ

MGEGRARQFR NTFQAIKDRN KEAFEAGVRN SKWYTQTPNR

AEAFIKRMAP HFDTPSQIGV DWYSAATAEK LSRGTSSTKT

TPKYKVKSGD NLTKIAKKHN TTVATLLKLN PSIKDPNMIR

VGQTINVTGS GGKTHKVKSG DTLSKIAVDN KTTVSRLMSL

NPEITNPNHI KVGQTIRLSL EKLAAAGSGS ASGSDSSIRV

QGRWKVRASF FKLQGSFDVS VKG

Vector sequence along 6X His tag (SEQ ID NO: 9) (1-22; MGHH . . . (SEQ ID NO: 82) to . . . IEGRHM (SEQ ID NO: 89)); WLBU2 peptide (23-46; RRWVR . . . (SEQ ID NO: 90) to . . . RWVRR (SEQ ID NO: 91)); Linker (47-53; GSGSASG (SEQ ID NO: 77)); GP36 CD (54-271; SVALDR . . . (SEQ ID NO: 92) to TAEKL (SEQ ID NO: 93)); LysM domain (272-379; SRGTS . . . (SEQ ID NO: 76) to . . . QTIRLS (SEQ ID NO: 94)); Linker (387-393; SGSASG (SEQ ID NO: 95)); LBP Peptide (394-423; SDSSI . . . (SEQ ID NO: 96) to . . . DVSVKG (SEQ ID NO: 97));

Source of different segments: WLBU2 de novo synthesized peptide; GP36 CD from in-house sequenced phage, sequence not deposited in Genbank; LysM, from sequence ID YP_002004544 amino acids 151 to 258; LBP peptide, from sequence ID AAH22256, amino acids 106 to 135.

DNA effluence P614

(SEQ ID NO: 98)
ATGGGCCATC ATCATCATCA TCATCATCAT CATCACAGCA

GCGGCCATAT CGAAGGTCGT CATATGCGTC GTTGGGTTCG

TCGTGTTCGT CGTTGGGTTC GTCGTGTTGT TCGTGTTGTT

CGTCGTTGGG TTCGTCGTGG CTCCGGATCG GCTTCTGGGG

GTGTGGCCCT GGACCGCACG CGGGTTGATC CCCAGGCAGT

CGGCAACGAG GTGCTCAAGC GCAACGCGGA TAAGCTGAAT

GCGATGCGGG GCGCCGAGTA CGGTGCCAAC GTCAAGGTCA

GCGGCACGGA CATTCGCATG AACGGGGGTA ACAGTGCCGG

CATGCTGAAG CAGGACGTGT TCAACTGGCG GAAGGAACTG

GCTCAGTTCG AGGCTTACCG AGGGGAGGCG TATAAGGATG

CCGATGGTTA TAGTGTGGGC CTGGGGCATT ACCTGGGCAG

TGGCAATGCT GGGGCAGGTA CTACAGTCAC GCCTGAGCAA

GCCGCGCAGT GGTTCGCCGA GGACACTGAC CGCGCACTCG

ACCAGGGTGT GAGGTTGGCC GACGAGCTGG GCGTTACGAA

CAATGCCTCT ACCCTGGGAT TGGCCGGTAT GGCCTTCCAG

ATGGGCGAAG GACGTGCCCG GCAGTTCCGT AACACCTTCC

```
AGGCGATCAA GGATCGCAAC AAGGAAGCCT TCGAGGCTGG

TGTGCGAAAC AGCAAGTGGT ACACGCAGAC GCCCAACCGG

GCCGAGGCAT TCATCAAGCG CATGGCGCCC CACTTCGATA

CACCGAGTCA AATCGGTGTC GATTGGTACA GCGCCGCAAC

AGCGGAGAAG CTTTCACGTG GAACATCGTC TACTAAAACG

ACACCTAAGT ATAAGGTGAA GAGTGGTGAC AACCTTACTA

AAATCGCTAA AAAGCATAAT ACAACGGTTG CTACTTTGTT

GAAGTTGAAT CCGAGTATCA AAGACCCGAA CATGATTAGA

GTTGGACAGA CAATAAATGT TACAGGTAGC GGCGGCAAAA

CACATAAGGT GAAAAGTGGT GACACACTCA GTAAAATTGC

CGTTGATAAC AAAACGACTG TGAGTAGATT GATGAGTCTA

AACCCTGAAA TTACGAATCC AAATCATATA AAAGTAGGTC

AAACAATTAG ATTAAGTCTT GAGAAACTTG CGGCCGCAGG

CTCCGGATCG GCTTCTGGGT CCGACTCCTC CATCCGGGTC

CAGGGCCGTT GGAAGGTGCG CGCGTCATTC TTCAAACTGC

AGGGCTCCTT CGATGTCAGT GTCAAGGGCT GA
```

Nucleotide: P634
Segments: WLBU2: 67 to 138; GP36 CD: 160 to 813 from in-house sequenced phage, sequence not deposited in Genbank; Lys M: 814 to 1158 from sequence ID YP_002004544; LBP peptide: 1180 to 1272 from sequence BC022256.

Cloning strategy: The WLBU2 peptide along with a flexible linker was fused to the N-terminus of P526 using PCR primers designed to add WLBU2, in two sequential rounds of amplification. The fusion PCR product was cloned as NdeI/XhoI into pET16b vector for expression as N-terminal 10×-His tag (SEQ ID NO: 24) fusion protein.

TABLE D9

Activity screening of constructs

| Sl. no | Construct # | Domains in the construct | Localization in E. coli | Catalytic activity | Bactericidal activity (CFU reduction assay) |
|---|---|---|---|---|---|
| 1 | P191 | LysM | Soluble | | Active |
| 2 | P199 | Phi29 CD-LysM (WT endolysin) | Soluble | Active | Active |
| 3 | P203 | GP36 CD-LysM | Soluble | Active | Active |
| 4 | P340 | Phi29CD-LysM-BPI SS | IB | Active | Active |
| 5 | P358 | P340-BPI SS (V232E, V234D, I236K) | IB | Active | Active |
| 6 | P366 | Phi29 endolysin + LysM | Soluble | Active | Active |
| 7 | P375 | PhiKZ GP144 + LysM | Soluble | Active | Active |
| 8 | P377 | P340 (GS Linker) | IB | Active | Active |
| 9 | P378 | P203 (Kan clone) | Soluble | Active | Active |
| 10 | P380 | P378 (D289K, D297K in LysM) | Soluble | Active | Active |
| 11 | P502 | PhiKZ GP181 Lysozyme + LysM | Soluble | Active | Active |
| 12 | P509 | GP36 CD-LysM-9X KR | IB | Active | Active |
| 13 | P512 | Phi6 P5 + LysM | Soluble | Active | Active |
| 14 | P513 | BP7 Lysozyme + LysM | Soluble | Active | Active |
| 15 | P526 | GP36 CD-LysM-Linker-LBP peptide | IB | Active | Active |
| 16 | P534 | GP36 CD-LysM-Sushi peptide | IB | Active | Active |
| 17 | P539 | BP7 Lysozyme + LysM + LBP peptide | IB | Active | Active |
| 18 | P540 | Phi29 endolysin + LBP peptide | IB | Active | Active |
| 19 | P549 | LysM-Linker-LBP peptide | IB | Active | Active |
| 20 | P601 | WLBU2-Linker-GP36 CD-LysM | IB | Active | Active |
| 21 | P617 | WLBU2-Linker-Phi29 CD-LysM | IB | Active | Active |
| 22 | P630 | WLBU2-Linker-LysM | IB | | Active |
| 23 | P634 | WLBU2-GP36 CD-LysM-LBP peptide | IB | Active | Active |
| 24 | P663 | WLBU variant-Rigid Linker-GP36 CD-LysM | IB | Active | Active |
| 25 | P664 | WLBU2-Rigid Linker-GP36 CD-LysM | IB | Active | Active |

The chimeric constructs described herein can thus be tested for binding to a target bacteria. Described here are various assays for whether the construct (with LysMTD) reaches the peptidoglycan layer. SDS-PAGE can be used to detect binding of the protein to cells. For example, $10^7$ cells are treated with a suitable amount of protein for approximately 2 hours. Then the cells are pelleted by centrifugation and the amount of protein in the supernatant is examined on SDS-PAGE and stained. The protein is labeled as adsorbed to cells, if the intensity of the protein before the adsorption to cells is higher than the one after adsorption, the difference is likely to be due to cell binding. Binding can also be detected using, e.g., confocal imaging to detect changes to the bacterial OM upon exposure to a chimeric construct. Fluorescent tags or luciferase can also be used, as will be recognized by one of skill.

What is claimed is:

1. A chimeric polypeptide, said chimeric polypeptide decreases the rate of growth of a Gram-negative bacterium, comprising:
   (i) a LysM polypeptide segment exhibiting at least about 70% identity to SEQ ID NO: 2 and permitting the chimeric polypeptide access to the periplasmic space of the Gram-negative bacterium; and
   (ii) a second polypeptide acting in the periplasmic space to decrease the rate of growth of the Gram-negative bacterium.

2. The chimeric polypeptide of claim 1, wherein said decreased rate of growth results in decrease in population of said Gram-negative bacterium.

3. The chimeric polypeptide of claim 1, wherein said second polypeptide comprises a sequence derived from a polypeptide from an organism different from the origin of said LysM polypeptide.

4. The chimeric polypeptide of claim 1, wherein said Gram-negative bacterium is from a genus selected from *Klebsiella, Acinetobacter, Pseudomonas,* or *Escherichia*.

5. The chimeric polypeptide of claim 1, wherein said LysM polypeptide segment exhibits at least about 80% or 90% identity to SEQ ID NO: 2.

6. The chimeric polypeptide of claim 1, wherein said second polypeptide is derived from: (a) a phage endolysin; (b) a phage structure associated muralytic enzyme (ectolysin); (c) a lipopolysachharide binding protein (LBP); (d) an AntiMicrobial Peptide (AMP); or (e) a bactericidal permeability increasing protein (BPI).

7. The chimeric polypeptide of claim 1, wherein said second polypeptide comprises 6xHis or a segment from Gene Product 36-Catalytic Domain (GP36CD), phi29 endolysin, Bactericidal Permeability Increasing Protein-Transmembrane Domain (BPI TMD), Lipopolysaccharide Binding Protein (LBP), WLBU2, phiKZ, Gene Product 144 (GP144), Gene Product 181 (GP181) lysozyme, phi6 P5, BP7 lysozyme, or SUSHI peptide.

8. A composition comprising the chimeric polypeptide of claim 1 and a pharmaceutically acceptable excipient, carrier, or buffer or another antimicrobial agent.

9. A method of reducing the growth rate of a Gram-negative bacterium, said method comprising contacting said Gram-negative bacterium with said chimeric polypeptide of claim 1.

10. A method of reducing the population of a Gram-negative bacterium, said method comprising contacting said Gram-negative bacterium with said chimeric polypeptide of claim 1.

11. A chimeric polypeptide, said chimeric polypeptide accesses the periplasmic space of a Gram-negative bacterium from outside of the cell, comprising:
    (i) a LysM polypeptide segment exhibiting at least about 70% identity to SEQ ID NO: 2 and permitting the chimeric polypeptide access to the periplasmic space of the Gram-negative bacterium; and
    (ii) a second polypeptide acting in the periplasmic space to decrease the rate of growth of the Gram-negative bacterium.

12. The chimeric polypeptide of claim 11, wherein at least some portion of said chimeric polypeptide accesses the periplasmic space of said Gram-negative bacterium; said access of said chimeric polypeptide results in a decrease in rate of growth of said Gram-negative bacterium.

13. The chimeric polypeptide of claim 11, wherein said second polypeptide comprises a sequence derived from a polypeptide from an organism different from the origin of said LysM polypeptide.

14. The chimeric polypeptide of claim 11, wherein said Gram-negative bacterium is from a genus selected from *Klebsiella, Acinetobacter, Pseudomonas,* or *Escherichia*.

15. The chimeric polypeptide of claim 11, wherein said LysM polypeptide segment exhibits at least about 80% or 90% identity to SEQ ID NO: 2.

16. The chimeric polypeptide of claim 11, wherein said second polypeptide is derived from: (a) a phage endolysin; (b) a phage structure associated muralytic enzyme (ectolysin); (c) a lipopolysachharide binding protein (LBP); (d) an AntiMicrobial Peptide (AMP); or (e) a bactericidal permeability increasing protein (BPI).

17. The chimeric polypeptide of claim 11, wherein said second polypeptide comprises 6xHis or a segment from Gene Product 36-Catalytic Domain (GP36CD), phi29 endolysin, Bactericidal Permeability Increasing Protein-Transmembrane Domain (BPI TMD), Lipopolysaccharide Binding Protein (LBP), WLBU2, phiKZ, Gene Product 144 (GP144), Gene Product 181 (GP181) lysozyme, phi6 P5, BP7 lysozyme, or SUSHI peptide.

18. A composition of the chimeric polypeptide of claim 11 and a pharmaceutically acceptable excipient, carrier, or buffer or another antimicrobial agent.

19. A method of reducing the growth rate of a Gram-negative bacterium, said method comprising contacting said Gram-negative bacterium with said chimeric polypeptide of claim 11.

20. A method of reducing the population of a Gram-negative bacterium, said method comprising contacting said Gram-negative bacterium with said chimeric polypeptide of claim 11.

* * * * *

SEQUENCE LISTING

```
<160> NUMBER OF SEQ ID NOS: 99

<210> SEQ ID NO 1
<211> LENGTH: 324
<212> TYPE: DNA
<213> ORGANISM: Bacillus phage phi29

<400> SEQUENCE: 1
tcacgtggaa catcgtctac taaaacgaca cctaagtata aggtgaagag tggtgacaac      60
cttactaaaa tcgctaaaaa gcataataca acggttgcta ctttgttgaa gttgaatccg     120
agtatcaaag acccgaacat gattagagtt ggacaaacaa taaatgttac aggtagcggc     180
ggcaaaacac ataaggtgaa aagtggtgac acactcagta aaattgccgt tgataacaaa     240
acgactgtga gtagattgat gagtctaaac cctgaaatta cgaatccaaa tcatataaaa     300
gtaggtcaaa caattagatt aagt                                            324

<210> SEQ ID NO 2
<211> LENGTH: 108
<212> TYPE: PRT
<213> ORGANISM: Bacillus phage phi29

<400> SEQUENCE: 2

Ser Arg Gly Thr Ser Ser Thr Lys Thr Thr Pro Lys Tyr Lys Val Lys
  1               5                  10                  15

Ser Gly Asp Asn Leu Thr Lys Ile Ala Lys Lys His Asn Thr Thr Val
                 20                  25                  30

Ala Thr Leu Leu Lys Leu Asn Pro Ser Ile Lys Asp Pro Asn Met Ile
             35                  40                  45

Arg Val Gly Gln Thr Ile Asn Val Thr Gly Ser Gly Gly Lys Thr His
         50                  55                  60

Lys Val Lys Ser Gly Asp Thr Leu Ser Lys Ile Ala Val Asp Asn Lys
 65                  70                  75                  80

Thr Thr Val Ser Arg Leu Met Ser Leu Asn Pro Glu Ile Thr Asn Pro
                 85                  90                  95

Asn His Ile Lys Val Gly Gln Thr Ile Arg Leu Ser
                100                 105

<210> SEQ ID NO 3
<211> LENGTH: 777
<212> TYPE: DNA
<213> ORGANISM: Bacillus phage phi29

<400> SEQUENCE: 3
atgcaaattt cacaagcggg tatcaactta attaagagct ttgagggttt acaactgaaa      60
gcatataaag ctgttccgac tgagaagcat tacaccattg gttacggtca ttacggttcc    120
gatgtttcac ctaggcaggt tatcactgct aaacaggctg aagacatgtt gcgtgatgat    180
gtgcaggctt ttgtggatgg tgtaaataaa gcattaaaag tatctgtcac ccaaaatcaa    240
tttgatgcac ttgtctcatt cgcttacaac gttgggttag gggctttcag gtcttcttct    300
```

-continued

```
ctactggaat acttgaatga aggaagaaca gctctagcgg cggctgaatt ccctaaatgg      360
aataagtcag gcggtaaagt ttatcaaggg ttgattaacc gtagagcaca ggagcaagcc      420
ttgtttaata gtggaacacc taaaaatgtt tcacgtggaa catcgtctac taaaacgaca      480
cctaagtata aggtgaagag tggtgacaac cttactaaaa tcgctaaaaa gcataataca      540
acggttgcta ctttgttgaa gttgaatccg agtatcaaag acccgaacat gattagagtt      600
ggacaaacaa taaatgttac aggtagcggc ggcaaaacac ataaggtgaa aagtggtgac      660
acactcagta aaattgccgt tgataacaaa acgactgtga gtagattgat gagtctaaac      720
cctgaaatta cgaatccaaa tcatataaaa gtaggtcaaa caattagatt aagttga       777
```

<210> SEQ ID NO 4
<211> LENGTH: 258
<212> TYPE: PRT
<213> ORGANISM: Bacillus phage phi29

<400> SEQUENCE: 4

```
Met Gln Ile Ser Gln Ala Gly Ile Asn Leu Ile Lys Ser Phe Glu Gly
1               5                   10                  15

Leu Gln Leu Lys Ala Tyr Lys Ala Val Pro Thr Glu Lys His Tyr Thr
                20                  25                  30

Ile Gly Tyr Gly His Tyr Gly Ser Asp Val Ser Pro Arg Gln Val Ile
            35                  40                  45

Thr Ala Lys Gln Ala Glu Asp Met Leu Arg Asp Asp Val Gln Ala Phe
        50                  55                  60

Val Asp Gly Val Asn Lys Ala Leu Lys Val Ser Val Thr Gln Asn Gln
65                  70                  75                  80

Phe Asp Ala Leu Val Ser Phe Ala Tyr Asn Val Gly Leu Gly Ala Phe
                85                  90                  95

Arg Ser Ser Ser Leu Leu Glu Tyr Leu Asn Glu Gly Arg Thr Ala Leu
            100                 105                 110

Ala Ala Ala Glu Phe Pro Lys Trp Asn Lys Ser Gly Gly Lys Val Tyr
        115                 120                 125

Gln Gly Leu Ile Asn Arg Arg Ala Gln Glu Gln Ala Leu Phe Asn Ser
    130                 135                 140

Gly Thr Pro Lys Asn Val Ser Arg Gly Thr Ser Ser Thr Lys Thr Thr
145                 150                 155                 160

Pro Lys Tyr Lys Val Lys Ser Gly Asp Asn Leu Thr Lys Ile Ala Lys
                165                 170                 175

Lys His Asn Thr Thr Val Ala Thr Leu Leu Lys Leu Asn Pro Ser Ile
            180                 185                 190

Lys Asp Pro Asn Met Ile Arg Val Gly Gln Thr Ile Asn Val Thr Gly
        195                 200                 205

Ser Gly Gly Lys Thr His Lys Val Lys Ser Gly Asp Thr Leu Ser Lys
    210                 215                 220

Ile Ala Val Asp Asn Lys Thr Thr Val Ser Arg Leu Met Ser Leu Asn
225                 230                 235                 240

Pro Glu Ile Thr Asn Pro Asn His Ile Lys Val Gly Gln Thr Ile Arg
                245                 250                 255

Leu Ser
```

<210> SEQ ID NO 5
<211> LENGTH: 130
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 5

```
Met Gly His His His His His His His His Ser Ser Gly His
1               5                   10                  15

Ile Glu Gly Arg His Met Ser Arg Gly Thr Ser Ser Thr Lys Thr Thr
            20                  25                  30

Pro Lys Tyr Lys Val Lys Ser Gly Asp Asn Leu Thr Lys Ile Ala Lys
        35                  40                  45

Lys His Asn Thr Thr Val Ala Thr Leu Leu Lys Leu Asn Pro Ser Ile
    50                  55                  60

Lys Asp Pro Asn Met Ile Arg Val Gly Gln Thr Ile Asn Val Thr Gly
65                  70                  75                  80

Ser Gly Gly Lys Thr His Lys Val Lys Ser Gly Asp Thr Leu Ser Lys
                85                  90                  95

Ile Ala Val Asp Asn Lys Thr Thr Val Ser Arg Leu Met Ser Leu Asn
                100                 105                 110

Pro Glu Ile Thr Asn Pro Asn His Ile Lys Val Gly Gln Thr Ile Arg
            115                 120                 125

Leu Ser
    130
```

<210> SEQ ID NO 6
<211> LENGTH: 1101
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
atgcgtcgtt gggttcgtcg tgttcgtcgt tgggttcgtc gtgttgttcg tgttgttcgt        60
cgttgggttc gtcgtggctc cggatcggct tctgggggtg tggccctgga ccgcacgcgg       120
gttgatcccc aggcagtcgg caacgaggtg ctcaagcgca acgcggataa gctgaatgcg       180
atgcggggcg ccgagtacgg tgccaacgtc aaggtcagcg gcacggacat tcgcatgaac       240
gggggtaaca gtgccggcat gctgaagcag gacgtgttca actggcggaa ggaactggct       300
cagttcgagg cttaccgagg ggaggcgtat aaggatgccg atggttatag tgtgggcctg       360
gggcattacc tgggcagtgg caatgctggg caggtactca gtcacgcc tgagcaagcc         420
gcgcagtggt tcgccgagga caccgaccgc gcactcgacc agggtgtgag gttggccgac       480
gagctgggcg ttacgaacaa tgcctctatc ctgggattgg ccgtatggc cttccagatg        540
ggcgaaggac gtgcccggca gttccgtaac accttccagg cgatcaagga tcgcaacaag       600
gaagccttcg aggctggtgt gcgaaacagc aagtggtaca cgcagacgcc caaccgggcc       660
gaggcattca tcaagcgcat ggcgccccac ttcgatacac cgagtcaaat cggtgtcgat       720
tggtacagcg ccgcaacagc ggagaagctt tcacgtggaa catcgtctac taaaacgaca       780
cctaagtata aggtgaagag tggtgacaac cttactaaaa tcgctaaaaa gcataataca       840
acggttgcta ctttgttgaa gttgaatccg agtatcaaag acccgaacat gattagagtt       900
ggacaaacaa taaatgttac aggtagcggc ggcaaaacac ataaggtgaa aagtggtgac       960
acactcagta aaattgccgt tgataacaaa acgactgtga gtagattgat gagtctaaac      1020
```

```
cctgaaatta cgaatccaaa tcatataaaa gtaggtcaaa caattagatt aagtctcgag    1080
caccaccacc accaccactg a                                              1101
```

<210> SEQ ID NO 7
<211> LENGTH: 366
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Met Arg Arg Trp Val Arg Arg Val Arg Arg Trp Val Arg Arg Val Val
1               5                   10                  15

Arg Val Val Arg Arg Trp Val Arg Arg Gly Ser Gly Ser Ala Ser Gly
            20                  25                  30

Gly Val Ala Leu Asp Arg Thr Arg Val Asp Pro Gln Ala Val Gly Asn
        35                  40                  45

Glu Val Leu Lys Arg Asn Ala Asp Lys Leu Asn Ala Met Arg Gly Ala
    50                  55                  60

Glu Tyr Gly Ala Asn Val Lys Val Ser Gly Thr Asp Ile Arg Met Asn
65                  70                  75                  80

Gly Gly Asn Ser Ala Gly Met Leu Lys Gln Asp Val Phe Asn Trp Arg
                85                  90                  95

Lys Glu Leu Ala Gln Phe Glu Ala Tyr Arg Gly Glu Ala Tyr Lys Asp
            100                 105                 110

Ala Asp Gly Tyr Ser Val Gly Leu Gly His Tyr Leu Gly Ser Gly Asn
        115                 120                 125

Ala Gly Ala Gly Thr Thr Val Thr Pro Glu Gln Ala Ala Gln Trp Phe
    130                 135                 140

Ala Glu Asp Thr Asp Arg Ala Leu Asp Gln Gly Val Arg Leu Ala Asp
145                 150                 155                 160

Glu Leu Gly Val Thr Asn Asn Ala Ser Ile Leu Gly Leu Ala Gly Met
                165                 170                 175

Ala Phe Gln Met Gly Glu Gly Arg Ala Arg Gln Phe Arg Asn Thr Phe
            180                 185                 190

Gln Ala Ile Lys Asp Arg Asn Lys Glu Ala Phe Glu Ala Gly Val Arg
        195                 200                 205

Asn Ser Lys Trp Tyr Thr Gln Thr Pro Asn Arg Ala Glu Ala Phe Ile
    210                 215                 220

Lys Arg Met Ala Pro His Phe Asp Thr Pro Ser Gln Ile Gly Val Asp
225                 230                 235                 240

Trp Tyr Ser Ala Ala Thr Ala Glu Lys Leu Ser Arg Gly Thr Ser Ser
                245                 250                 255

Thr Lys Thr Thr Pro Lys Tyr Lys Val Lys Ser Gly Asp Asn Leu Thr
            260                 265                 270

Lys Ile Ala Lys Lys His Asn Thr Thr Val Ala Thr Leu Leu Lys Leu
        275                 280                 285

Asn Pro Ser Ile Lys Asp Pro Asn Met Ile Arg Val Gly Gln Thr Ile
    290                 295                 300

Asn Val Thr Gly Ser Gly Gly Lys Thr His Lys Val Lys Ser Gly Asp
305                 310                 315                 320

Thr Leu Ser Lys Ile Ala Val Asp Asn Lys Thr Thr Val Ser Arg Leu
                325                 330                 335

Met Ser Leu Asn Pro Glu Ile Thr Asn Pro Asn His Ile Lys Val Gly
```

```
                    340                 345                 350
Gln Thr Ile Arg Leu Ser Leu Glu His His His His His His
            355                 360                 365

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Thr Ala Glu
1

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
1               5

<210> SEQ ID NO 10
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Arg Trp Val Arg Arg Val Arg Arg Trp Val Arg Arg Val Val Arg
1               5                   10                  15

Val Val Arg Arg Trp Val Arg Arg
            20

<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Leu Leu Arg Lys Gly Gly Glu Lys Ile Gly Glu Lys Leu Lys Lys
1               5                   10                  15

Ile Gly Gln Lys Ile Lys Asn Phe Phe Gln Lys Leu Val Pro Gln Pro
            20                  25                  30

Glu Gln

<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12
```

```
His Ala Glu His Lys Val Lys Ile Gly Val Glu Gln Lys Tyr Gly Gln
1               5                   10                  15

Phe Pro Gln Gly Thr Glu Val Thr Tyr Thr Cys Ser Gly Asn Tyr Phe
            20                  25                  30

Leu Met

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Lys Lys Thr Arg Lys Arg Leu Lys Lys Ile Gly Lys Val Leu Lys
1               5                   10                  15

Trp Ile

<210> SEQ ID NO 14
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Trp Lys Leu Phe Lys Lys Ile Gly Ile Gly Ala Val Leu Lys Val
1               5                   10                  15

Leu Thr Thr Gly Leu Pro Ala Leu Ile Ser
            20                  25

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Arg Arg Arg Arg Ser Val Gln Trp Cys Ala
1               5                   10

<210> SEQ ID NO 16
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 17
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 17

Ile Leu Arg Trp Pro Trp Trp Pro Trp Arg Arg Lys
1               5                   10

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Phe Cys Trp Tyr Val Cys Tyr Arg Asn Gly Val Arg Val Cys Tyr
1               5                   10                  15

Arg Arg Cys Asn
            20

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser Asp Ser Ser Ile Arg Val Gln Gly Arg Trp Lys Val Arg Ala Ser
1               5                   10                  15

Phe Phe Lys Leu Gln Gly Ser Phe Asp Val Ser Val Lys Gly
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Pro Arg Arg Arg Arg Ser Ser Ser Arg Pro Val Arg Arg Arg Arg Arg
1               5                   10                  15

Pro Arg Val Ser Arg Arg Arg Arg Arg Gly Gly Arg Arg Arg Arg
            20                  25                  30

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Asn Asn Arg Pro Val Tyr Ile Pro Gln Pro Arg Pro Pro His Pro
1               5                   10                  15

Arg Leu

<210> SEQ ID NO 22
<211> LENGTH: 29
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 22

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Gly Gly Gly
1               5

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 24

His His His His His His His His His His
1               5                   10

<210> SEQ ID NO 25
<211> LENGTH: 894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atgcgtcgtt gggttcgtcg tgttcgtcgt tgggttcgtc gtgttgttcg tgttgttcgt      60
cgttgggttc gtcgtggctc cggatcggct tctgggcaaa tttcacaagc gggtatcaac     120
ttaattaaga gctttgaggg tttacaactg aaagcatata aagctgttcc gactgagaag     180 cattcacca ttggttacgg tcattacggt tccgatgttt cacctaggca ggttatcact      240
gctaaacagg ctgaagacat gttgcgtgat gatgtgcagg cttttgtgga tggtgtaaat     300
aaagcattaa aagtatctgt cacccaaaat caatttgatg cacttgtctc attcgcttac     360
aacgttgggt taggggcttt caggtcttct tctctactgg aatacttgaa tgaaggaaga     420
acagctctag cggcggctga attccctaaa tggaataagt caggcggtaa agtttatcaa     480
gggttgatta ccgtagagc acaggagcaa gccttgttta atagtggaac acctaaaaat      540
gtttcacgtg gaacatcgtc tactaaaacg acacctaagt ataaggtgaa gagtggtgac     600
aaccttacta aaatcgctaa aaagcataat acaacggttg ctactttgtt gaagttgaat     660
ccgagtatca agacccgaa catgattaga gttggacaaa caataaatgt tacaggtagc      720
ggcggcaaaa cacataaggt gaaaagtggt gacacactca gtaaaattgc cgttgataac     780
aaaacgactg tgagtagatt gatgagtcta aaccctgaaa ttacgaatcc aaatcatata     840
aaagtaggtc aaacaattag attaagtctc gagcaccacc accaccacca ctaa    894

<210> SEQ ID NO 26
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Arg Arg Trp Val Arg Val Arg Arg Trp Val Arg Val Val
1               5                   10                  15

Arg Val Val Arg Arg Trp Val Arg Arg Gly Ser Gly Ser Ala Ser Gly
            20                  25                  30

Gln Ile Ser Gln Ala Gly Ile Asn Leu Ile Lys Ser Phe Glu Gly Leu
        35                  40                  45

Gln Leu Lys Ala Tyr Lys Ala Val Pro Thr Glu Lys His Tyr Thr Ile
    50                  55                  60

Gly Tyr Gly His Tyr Gly Ser Asp Val Ser Pro Arg Gln Val Ile Thr
65                  70                  75                  80

Ala Lys Gln Ala Glu Asp Met Leu Arg Asp Val Gln Ala Phe Val
                85                  90                  95

Asp Gly Val Asn Lys Ala Leu Lys Val Ser Val Thr Gln Asn Gln Phe
            100                 105                 110

Asp Ala Leu Val Ser Phe Ala Tyr Asn Val Gly Leu Gly Ala Phe Arg
        115                 120                 125

Ser Ser Ser Leu Leu Glu Tyr Leu Asn Glu Gly Arg Thr Ala Leu Ala
130                 135                 140

Ala Ala Glu Phe Pro Lys Trp Asn Lys Ser Gly Gly Lys Val Tyr Gln
145                 150                 155                 160

Gly Leu Ile Asn Arg Arg Ala Gln Glu Gln Ala Leu Phe Asn Ser Gly
                165                 170                 175

Thr Pro Lys Asn Val Ser Arg Gly Thr Ser Ser Thr Lys Thr Thr Pro
            180                 185                 190

Lys Tyr Lys Val Lys Ser Gly Asp Asn Leu Thr Lys Ile Ala Lys Lys
        195                 200                 205

His Asn Thr Thr Val Ala Thr Leu Leu Lys Leu Asn Pro Ser Ile Lys
    210                 215                 220

Asp Pro Asn Met Ile Arg Val Gly Gln Thr Ile Asn Val Thr Gly Ser
225                 230                 235                 240

Gly Gly Lys Thr His Lys Val Lys Ser Gly Asp Thr Leu Ser Lys Ile
                245                 250                 255

Ala Val Asp Asn Lys Thr Thr Val Ser Arg Leu Met Ser Leu Asn Pro
            260                 265                 270

Glu Ile Thr Asn Pro Asn His Ile Lys Val Gly Gln Thr Ile Arg Leu
        275                 280                 285

Ser Leu Glu His His His His His His
290                 295

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Arg Trp Val
1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Val Arg Arg
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Ile Ser Gln
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Arg Leu Ser
1

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Glu His His His His His His
1               5

<210> SEQ ID NO 32
<211> LENGTH: 890
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atgcatcatc atcatcatca tcaaatttca caagcgggta tcaacttaat taagagcttt      60
gagggtttac aactgaaagc atataaagct gttccgactg agaagcatta caccattggt     120
tacggtcatt acggttccga tgtttcacct aggcaggtta tcactgctaa acaggctgaa     180

```
gacatgttgc gtgatgatgt gcaggctttt gtggatggtg taaataaagc attaaaagta    240
tctgtcaccc aaaatcaatt tgatgccttg tctcattcgc ttacaacgtt gggttagggg    300
ctttcaggtc ttcttctcta ctggaatact tgaatgaagg aagaacagct ctagcggcgg    360
ctgaattccc taaatggaat aagtcaggcg gtaaagttta tcaagggttg attaaccgta    420
gagcacagga gcaagccttg tttaatagtg gaacacctaa aaatgtttca cgtggaacat    480
cgtctactaa aacgacacct aagtataagg tgaagagtgg tgacaacctt actaaaatcg    540
ctaaaaagca taatacaacg gttgctactt tgttgaagtt gaatccgagt atcaaagacc    600
cgaacatgat tagagttgga caaacaataa atgttacagg tagcggcggc aaaacacata    660
aggtgaaaag tggtgacaca ctcagtaaaa ttgccgttga taacaaaacg actgtgagta    720
gattgatgag tctaaaccct gaaattacga atccaaatca tataaaagta ggtcaaacaa    780
ttagattaag taagcttcgc cgtcgcgcgt ccctgatggt gctggtcgcc ataggcaccg    840
ccgtgacagc ggccgtcaac cctggcgtcg tggtcaggcg ccgtcgctga              890
```

```
<210> SEQ ID NO 33
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met His His His His His His Gln Ile Ser Gln Ala Gly Ile Asn Leu
1               5                   10                  15

Ile Lys Ser Phe Glu Gly Leu Gln Leu Lys Ala Tyr Lys Ala Val Pro
            20                  25                  30

Thr Glu Lys His Tyr Thr Ile Gly Tyr Gly His Tyr Gly Tyr Ser Asp Val
        35                  40                  45

Ser Pro Arg Gln Val Ile Thr Ala Lys Gln Ala Glu Asp Met Leu Arg
    50                  55                  60

Asp Asp Val Gln Ala Phe Val Asp Gly Val Asn Lys Ala Leu Lys Val
65                  70                  75                  80

Ser Val Thr Gln Asn Gln Phe Asp Ala Leu Val Ser Phe Ala Tyr Asn
                85                  90                  95

Val Gly Leu Gly Ala Phe Arg Ser Ser Leu Leu Glu Tyr Leu Asn
            100                 105                 110

Glu Gly Arg Thr Ala Leu Ala Ala Glu Phe Pro Lys Trp Asn Lys
            115                 120                 125

Ser Gly Gly Lys Val Tyr Gln Gly Leu Ile Asn Arg Arg Ala Gln Glu
    130                 135                 140

Gln Ala Leu Phe Asn Ser Gly Thr Pro Lys Asn Val Ser Arg Gly Thr
145                 150                 155                 160

Ser Ser Thr Lys Thr Thr Pro Lys Tyr Lys Val Lys Ser Gly Asp Asn
                165                 170                 175

Leu Thr Lys Ile Ala Lys Lys His Asn Thr Thr Val Ala Thr Leu Leu
            180                 185                 190

Lys Leu Asn Pro Ser Ile Lys Asp Pro Asn Met Ile Arg Val Gly Gln
        195                 200                 205

Thr Ile Asn Val Thr Gly Ser Gly Gly Lys Thr His Lys Val Lys Ser
    210                 215                 220

Gly Asp Thr Leu Ser Lys Ile Ala Val Asp Asn Lys Thr Thr Val Ser
225                 230                 235                 240
```

```
Arg Leu Met Ser Leu Asn Pro Glu Ile Thr Asn Pro Asn His Ile Lys
            245                 250                 255

Val Gly Gln Thr Ile Arg Leu Ser Lys Leu Arg Arg Arg Ala Ser Leu
            260                 265                 270

Met Val Leu Val Ala Ile Gly Thr Ala Val Thr Ala Ala Val Asn Pro
        275                 280                 285

Gly Val Val Arg Arg Arg
    290             295

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met His His His His His His
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ile Ser Gln Ala
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Pro Lys Asn Val
1               5

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Arg Gly Thr
1

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38
```

Thr Ile Arg Leu Ser
1               5

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Ser Leu Met
1

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Gly Val Val Val Arg
1               5

<210> SEQ ID NO 41
<211> LENGTH: 564
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
atgcgtcgtt gggttcgtcg tgttcgtcgt tgggttcgtc gtgttgttcg tgttgttcgt      60
cgttgggttc gtcgtggctc cggatcggct tctgggcaaa tttcacaagc gggtatcaac     120
ttaattaaga gctttgaggg tttacaactg aaagcatata agctgttcc gactgagaag      180 cattacacca ttggttacgg tcattacggt tccgatgttt cacctaggca ggttatcact     240
gctaaacagg ctgaagacat gttgcgtgat gatgtgcagg cttttgtgga tggtgtaaat     300
aaagcattaa aagtatctgt cacccaaaat caatttgatg cacttgtctc attcgcttac     360
aacgttgggt tagggctttt caggtcttct tctctactgg aatacttgaa tgaaggaaga     420
acagctctag cggcggctga attccctaaa tggaataagt caggcggtaa agtttatcaa     480
gggttgatta accgtagagc acaggagcaa gccttgttta atagtggaac acctaaaaat     540
gttcaccacc accaccacca ctaa                                            564

<210> SEQ ID NO 42
<211> LENGTH: 187
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Arg Arg Trp Val Arg Arg Val Arg Arg Trp Val Arg Arg Val Val
1               5                   10                  15

Arg Val Val Arg Arg Trp Val Arg Arg Gly Ser Gly Ser Ala Ser Gly
            20                  25                  30

```
Gln Ile Ser Gln Ala Gly Ile Asn Leu Ile Lys Ser Phe Glu Gly Leu
        35                  40                  45

Gln Leu Lys Ala Tyr Lys Ala Val Pro Thr Glu Lys His Tyr Thr Ile
 50                  55                  60

Gly Tyr Gly His Tyr Gly Ser Asp Val Ser Pro Arg Gln Val Ile Thr
 65                  70                  75                  80

Ala Lys Gln Ala Glu Asp Met Leu Arg Asp Asp Val Gln Ala Phe Val
                85                  90                  95

Asp Gly Val Asn Lys Ala Leu Lys Val Ser Val Thr Gln Asn Gln Phe
            100                 105                 110

Asp Ala Leu Val Ser Phe Ala Tyr Asn Val Gly Leu Gly Ala Phe Arg
        115                 120                 125

Ser Ser Ser Leu Leu Glu Tyr Leu Asn Glu Gly Arg Thr Ala Leu Ala
130                 135                 140

Ala Ala Glu Phe Pro Lys Trp Asn Lys Ser Gly Gly Lys Val Tyr Gln
145                 150                 155                 160

Gly Leu Ile Asn Arg Arg Ala Gln Glu Gln Ala Leu Phe Asn Ser Gly
                165                 170                 175

Thr Pro Lys Asn Val His His His His His
            180                 185

<210> SEQ ID NO 43
<211> LENGTH: 765
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
atgcgtcgtt gggttcgtcg tgttcgtcgt tgggttcgtc gtgttgttcg tgttgttcgt      60
cgttgggttc gtcgtggctc cggatcggct tctgggggtg tggccctgga ccgcacgcgg     120
gttgatcccc aggcagtcgg caacgaggtg ctcaagcgca acgcggataa gctgaatgcg     180
atgcggggcg ccgagtacgg tgccaacgtc aaggtcagcg gcacggacat tcgcatgaac     240
gggggtaaca gtgccggcat gctgaagcag gacgtgttca ctggcggaa ggaactggct      300 cagttcgagg cttaccgagg ggaggcgtat aaggatgccg atggttatag tgtgggcctg     360
gggcattacc tgggcagtgg caatgctggg gcaggtacta cagtcacgcc tgagcaagcc     420
gcgcagtggt tcgccgagga caccgaccgc gcactcgacc agggtgtgag gttggccgac     480
gagctgggcg ttacgaacaa tgcctctatc ctgggattgg ccggtatggc cttccagatg     540
ggcgaaggac gtgcccggca gttccgtaac accttccagg cgatcaagga tcgcaacaag     600
gaagccttcg aggctggtgt gcgaaacagc aagtggtaca cgcagacgcc caaccgggcc     660
gaggcattca tcaagcgcat ggcgccccac ttcgatacac cgagtcaaat cggtgtcgat     720
tggtacagcg ccgcaacagc ggagcaccac caccaccacc actga                    765

<210> SEQ ID NO 44
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44
```

```
Met Arg Arg Trp Val Arg Val Arg Trp Val Arg Val Val
1               5                   10                  15

Arg Val Val Arg Trp Val Arg Gly Ser Gly Ser Ala Ser Gly
            20                  25                  30

Gly Val Ala Leu Asp Arg Thr Arg Val Asp Pro Gln Ala Val Gly Asn
        35                  40                  45

Glu Val Leu Lys Arg Asn Ala Asp Lys Leu Asn Ala Met Arg Gly Ala
50                  55                  60

Glu Tyr Gly Ala Asn Val Lys Val Ser Gly Thr Asp Ile Arg Met Asn
65                  70                  75                  80

Gly Gly Asn Ser Ala Gly Met Leu Lys Gln Asp Val Phe Asn Trp Arg
                85                  90                  95

Lys Glu Leu Ala Gln Phe Glu Ala Tyr Arg Gly Glu Ala Tyr Lys Asp
                100                 105                 110

Ala Asp Gly Tyr Ser Val Gly Leu Gly His Tyr Leu Gly Ser Gly Asn
            115                 120                 125

Ala Gly Ala Gly Thr Thr Val Thr Pro Glu Gln Ala Ala Gln Trp Phe
130                 135                 140

Ala Glu Asp Thr Asp Arg Ala Leu Asp Gln Gly Val Arg Leu Ala Asp
145                 150                 155                 160

Glu Leu Gly Val Thr Asn Asn Ala Ser Ile Leu Gly Leu Ala Gly Met
                165                 170                 175

Ala Phe Gln Met Gly Glu Gly Arg Ala Arg Gln Phe Arg Asn Thr Phe
                180                 185                 190

Gln Ala Ile Lys Asp Arg Asn Lys Glu Ala Phe Glu Ala Gly Val Arg
            195                 200                 205

Asn Ser Lys Trp Tyr Thr Gln Thr Pro Asn Arg Ala Glu Ala Phe Ile
210                 215                 220

Lys Arg Met Ala Pro His Phe Asp Thr Pro Ser Gln Ile Gly Val Asp
225                 230                 235                 240

Trp Tyr Ser Ala Ala Thr Ala Glu His His His His His His
                245                 250
```

<210> SEQ ID NO 45
<211> LENGTH: 1077
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 45

```
atgcgtcgtt gggttcgtcg tgttcgtcgt tgggttcgtc gtgttgttcg tgttgttcgt     60
cgtgcttctg ggggtgtggc cctggaccgc acgcgggttg atccccaggc agtcggcaac    120
gaggtgctca gcgcaacgc ggataagctg aatgcgatgc ggggcgccga gtacggtgcc     180
aacgtcaagg tcagcggcac ggacattcgc atgaacgggg gtaacagtgc cggcatgctg    240
aagcaggacg tgttcaactg gcggaaggaa ctggctcagt tcgaggctta ccgaggggag    300
gcgtataagg atgccgatgg ttatagtgtg ggcctggggc attacctggg cagtggcaat    360
gctggggcag gtactacagt cacgcctgag caagccgcgc agtggttcgc cgaggacacc    420
gaccgcgcac tcgaccaggg tgtgaggttg gccgacgagc tgggcgttac gtacaatgcc    480
tctatcctgg gattgccggg tatggccttc cagatgggcg aaggacgtgc ccggcagttc    540
cgtaacacct tccaggcgat caaggatcgc aacaaggaag ccttcgaggc tggtgtgcga    600
```

```
aacagcaagt ggtacacgca gacgcccaac cgggccgagg cattcatcaa gcgcatggcg    660
ccccacttcg atacaccgag tcaaatcggt gtcgattggt acagcgccgc aacagcggag    720
aagctttcac gtggaacatc gtctactaaa acgacaccta agtataaggt gaagagtggt    780
gacaacctta ctaaaatcgc taaaaagcat aatacaacgg ttgctacttt gttgaagttg    840
aatccgagta tcaaagaccc gaacatgatt agagttggac aaacaataaa tgttacaggt    900
agcggcggca aaacacataa ggtgaaaagt ggtgacacac tcagtaaaat tgccgttgat    960
aacaaaacga ctgtgagtag attgatgagt ctaaaccctg aaattacgaa tccaaatcat   1020
ataaaagtag gtcaaacaat tagattaagt ctcgagcacc accaccacca ccactga      1077
```

<210> SEQ ID NO 46
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Arg Arg Trp Val Arg Val Arg Arg Trp Val Arg Arg Val
1               5                   10                  15

Arg Val Val Arg Arg Ala Ser Gly Gly Val Ala Leu Asp Arg Thr Arg
                20                  25                  30

Val Asp Pro Gln Ala Val Gly Asn Glu Val Leu Lys Arg Asn Ala Asp
            35                  40                  45

Lys Leu Asn Ala Met Arg Gly Ala Glu Tyr Gly Ala Asn Val Lys Val
        50                  55                  60

Ser Gly Thr Asp Ile Arg Met Asn Gly Gly Asn Ser Ala Gly Met Leu
65                  70                  75                  80

Lys Gln Asp Val Phe Asn Trp Arg Lys Glu Leu Ala Gln Phe Glu Ala
                85                  90                  95

Tyr Arg Gly Glu Ala Tyr Lys Asp Ala Asp Gly Tyr Ser Val Gly Leu
            100                 105                 110

Gly His Tyr Leu Gly Ser Gly Asn Ala Gly Ala Gly Thr Thr Val Thr
        115                 120                 125

Pro Glu Gln Ala Ala Gln Trp Phe Ala Glu Asp Thr Asp Arg Ala Leu
    130                 135                 140

Asp Gln Gly Val Arg Leu Ala Asp Glu Leu Gly Val Thr Tyr Asn Ala
145                 150                 155                 160

Ser Ile Leu Gly Leu Ala Gly Met Ala Phe Gln Met Gly Glu Gly Arg
                165                 170                 175

Ala Arg Gln Phe Arg Asn Thr Phe Gln Ala Ile Lys Asp Arg Asn Lys
            180                 185                 190

Glu Ala Phe Glu Ala Gly Val Arg Asn Ser Lys Trp Tyr Thr Gln Thr
        195                 200                 205

Pro Asn Arg Ala Glu Ala Phe Ile Lys Arg Met Ala Pro His Phe Asp
    210                 215                 220

Thr Pro Ser Gln Ile Gly Val Asp Trp Tyr Ser Ala Ala Thr Ala Glu
225                 230                 235                 240

Lys Leu Ser Arg Gly Thr Ser Ser Thr Lys Thr Pro Lys Tyr Lys
                245                 250                 255

Val Lys Ser Gly Asp Asn Leu Thr Lys Ile Ala Lys His Asn Thr
            260                 265                 270

Thr Val Ala Thr Leu Leu Lys Leu Asn Pro Ser Ile Lys Asp Pro Asn

```
              275                 280                 285
Met Ile Arg Val Gly Gln Thr Ile Asn Val Thr Gly Ser Gly Gly Lys
            290                 295                 300

Thr His Lys Val Lys Ser Gly Asp Thr Leu Ser Lys Ile Ala Val Asp
305                 310                 315                 320

Asn Lys Thr Thr Val Ser Arg Leu Met Ser Leu Asn Pro Glu Ile Thr
                325                 330                 335

Asn Pro Asn His Ile Lys Val Gly Gln Thr Ile Arg Leu Ser Leu Glu
            340                 345                 350

His His His His His His
        355
```

<210> SEQ ID NO 47
<211> LENGTH: 1110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
atgcgtcgtt gggttcgtcg tgttcgtcgt tgggttcgtc gtgttgttcg tgttgttcgt      60
cgttgggttc gtcgtgaagc cgctgccaag caggcggccg ctaaaggtgt ggccctggac     120
cgcacgcggg ttgatcccca ggcagtcggc aacgaggtgc tcaagcgcaa gcggataag     180 ctgaatgcga tgcggggcgc cgagtacggt gccaacgtca aggtcagcgg cacggacatt     240
cgcatgaacg ggggtaacag tgccggcatg ctgaagcagg acgtgttcaa ctggcggaag     300
gaactggctc agttcgaggc ttaccgaggg gaggcgtata aggatgccga tggttatagt     360
gtgggcctgg gcattaccct gggcagtggc aatgctgggg caggtactac agtcacgcct     420
gagcaagccg cgcagtggtt cgccgaggac accgaccgcg cactcgacca gggtgtgagg     480
ttggccgacg agctgggcgt tacgaacaat gcctctatcc tgggattggc cggtatggcc     540
ttccagatgg gcgaaggacg tgcccggcag ttccgtaaca ccttccaggc gatcaaggat     600
cgcaacaagg aagccttcga ggctggtgtg cgaaacagca gtggtacac gcagacgccc      660 aaccgggccg aggcattcat caagcgcatg gcgccccact tcgataccc gagtcaaatc      720 ggtgtcgatt ggtacagcgc cgcaacagcg gagaagcttt cacgtggaac atcgtctact     780
aaaacgacac taagtataa ggtgaagagt ggtgacaacc ttactaaaat cgctaaaaag      840
cataatacaa cggttgctac tttgttgaag ttgaatccga gtatcaaaga cccgaacatg     900
attagagttg acaaacaat aaatgttaca ggtagcggcg gcaaaacaca taaggtgaaa      960
agtggtgaca cactcagtaa aattgccgtt gataacaaaa cgactgtgag tagattgatg    1020
agtctaaacc ctgaaattac gaatccaaat catataaaag taggtcaaac aattagatta    1080
agtctcgagc accaccacca ccaccactga                                     1110
```

<210> SEQ ID NO 48
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Met Arg Arg Trp Val Arg Arg Val Arg Arg Trp Val Arg Arg Val Val
1               5                   10                  15
```

Arg Val Val Arg Arg Trp Val Arg Arg Glu Ala Ala Ala Lys Gln Ala
            20                  25                  30

Ala Ala Lys Gly Val Ala Leu Asp Arg Thr Arg Val Asp Pro Gln Ala
        35                  40                  45

Val Gly Asn Glu Val Leu Lys Arg Asn Ala Asp Lys Leu Asn Ala Met
 50                  55                  60

Arg Gly Ala Glu Tyr Gly Ala Asn Val Lys Val Ser Gly Thr Asp Ile
 65                  70                  75                  80

Arg Met Asn Gly Gly Asn Ser Ala Gly Met Leu Lys Gln Asp Val Phe
                85                  90                  95

Asn Trp Arg Lys Glu Leu Ala Gln Phe Glu Ala Tyr Arg Gly Glu Ala
            100                 105                 110

Tyr Lys Asp Ala Asp Gly Tyr Ser Val Gly Leu Gly His Tyr Leu Gly
        115                 120                 125

Ser Gly Asn Ala Gly Ala Gly Thr Thr Val Thr Pro Glu Gln Ala Ala
130                 135                 140

Gln Trp Phe Ala Glu Asp Thr Asp Arg Ala Leu Asp Gln Gly Val Arg
145                 150                 155                 160

Leu Ala Asp Glu Leu Gly Val Thr Asn Asn Ala Ser Ile Leu Gly Leu
                165                 170                 175

Ala Gly Met Ala Phe Gln Met Gly Glu Gly Arg Ala Arg Gln Phe Arg
            180                 185                 190

Asn Thr Phe Gln Ala Ile Lys Asp Arg Asn Lys Glu Ala Phe Glu Ala
        195                 200                 205

Gly Val Arg Asn Ser Lys Trp Tyr Thr Gln Thr Pro Asn Arg Ala Glu
 210                 215                 220

Ala Phe Ile Lys Arg Met Ala Pro His Phe Asp Thr Pro Ser Gln Ile
225                 230                 235                 240

Asp Val Asp Trp Tyr Ser Ala Ala Thr Ala Glu Lys Leu Ser Arg Gly
                245                 250                 255

Thr Ser Ser Thr Lys Thr Thr Pro Lys Tyr Lys Val Lys Ser Gly Asp
            260                 265                 270

Asn Leu Thr Lys Ile Ala Lys Lys His Asn Thr Thr Val Ala Thr Leu
        275                 280                 285

Leu Lys Leu Asn Pro Ser Ile Lys Asp Pro Asn Met Ile Arg Val Gly
290                 295                 300

Gln Thr Ile Asn Val Thr Gly Ser Gly Gly Lys Thr His Lys Val Lys
305                 310                 315                 320

Ser Gly Asp Thr Leu Ser Lys Ile Ala Val Asp Asn Lys Thr Thr Val
                325                 330                 335

Ser Arg Leu Met Ser Leu Asn Pro Glu Ile Thr Asn Pro Asn His Ile
            340                 345                 350

Lys Val Gly Gln Thr Ile Arg Leu Ser Leu Glu His His His His His
        355                 360                 365

His

<210> SEQ ID NO 49
<211> LENGTH: 888
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
atgcaccatc accatcacca tcaaatttca caagcgggta tcaacttaat taagagcttt      60
gagggtttac aactgaaagc atataaagct gttccgactg agaagcatta caccattggt     120
tacggtcatt acggttccga tgtttcacct aggcaggtta tcactgctaa acaggctgaa     180
gacatgttgc gtgatgatgt gcaggctttt gtggatggta taaataaagc attaaaagta     240
tctgtcaccc aaaatcaatt tgatgcactt gtctcattcg cttacaacgt tgggttaggg     300
gctttcaggt cttcttctct actggaatac ttgaatgaag gaagaacagc tctagcggcg     360
gctgaattcc ctaaatggaa taagtcaggc ggtaaagttt atcaagggtt gattaaccgt     420
agagcacagg agcaagcctt gtttaatagt ggaacaccta aaaatgtttc acgtggaaca     480
tcgtctacta aaacgacacc taagtataag gtgaagagtg gtgacaacct tactaaaatc     540
gctaaaaagc ataatacaac ggttgctact ttgttgaagt tgaatccgag tatcaaagac     600
ccgaacatga ttagagttgg acaaacaata aatgttacag gtagcggcgg caaaacacat     660
aaggtgaaaa gtggtgacac actcagtaaa attgccgttg ataacaaaac gactgtgagt     720
agattgatga gtctaaaccc tgaaattacg aatccaaatc atataaagt aggtcaaaca      780 attagattaa gtggctccgg atcggcttct gggcgtcgtt gggttcgtcg cgtgcgtcgc     840
tgggtgcgtc gtgttgttcg tgttgttcgt cgttgggttc gtcgttga                 888
```

<210> SEQ ID NO 50
<211> LENGTH: 295
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met His His His His His His Gln Ile Ser Gln Ala Gly Ile Asn Leu
1               5                   10                  15

Ile Lys Ser Phe Glu Gly Leu Gln Leu Lys Ala Tyr Lys Ala Val Pro
            20                  25                  30

Thr Glu Lys His Tyr Thr Ile Gly Tyr Gly His Tyr Gly Ser Asp Val
        35                  40                  45

Ser Pro Arg Gln Val Ile Thr Ala Lys Gln Ala Glu Asp Met Leu Arg
    50                  55                  60

Asp Asp Val Gln Ala Phe Val Asp Gly Val Asn Lys Ala Leu Lys Val
65                  70                  75                  80

Ser Val Thr Gln Asn Gln Phe Asp Ala Leu Val Ser Phe Ala Tyr Asn
                85                  90                  95

Val Gly Leu Gly Ala Phe Arg Ser Ser Ser Leu Leu Glu Tyr Leu Asn
            100                 105                 110

Glu Gly Arg Thr Ala Leu Ala Ala Ala Glu Phe Pro Lys Trp Asn Lys
        115                 120                 125

Ser Gly Gly Lys Val Tyr Gln Gly Leu Ile Asn Arg Arg Ala Gln Glu
    130                 135                 140

Gln Ala Leu Phe Asn Ser Gly Thr Pro Lys Asn Val Ser Arg Gly Thr
145                 150                 155                 160

Ser Ser Thr Lys Thr Thr Pro Lys Tyr Lys Val Lys Ser Gly Asp Asn
                165                 170                 175

Leu Thr Lys Ile Ala Lys Lys His Asn Thr Thr Val Ala Thr Leu Leu
            180                 185                 190

Lys Leu Asn Pro Ser Ile Lys Asp Pro Asn Met Ile Arg Val Gly Gln

```
                195                 200                 205
Thr Ile Asn Val Thr Gly Ser Gly Gly Lys Thr His Lys Val Lys Ser
    210                 215                 220

Gly Asp Thr Leu Ser Lys Ile Ala Val Asp Asn Lys Thr Thr Val Ser
225                 230                 235                 240

Arg Leu Met Ser Leu Asn Pro Glu Ile Thr Asn Pro Asn His Ile Lys
                245                 250                 255

Val Gly Gln Thr Ile Arg Leu Ser Gly Ser Gly Ser Ala Ser Gly Arg
            260                 265                 270

Arg Trp Val Arg Val Arg Arg Trp Val Arg Arg Val Val Arg Val
                275                 280                 285

Val Arg Arg Trp Val Arg Arg
            290                 295

<210> SEQ ID NO 51
<211> LENGTH: 909
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
atgaggggac ttcgaagact gggtaggaag atagcacatg gtgtgaagaa gtatggccca      60
actgttctcc gaataatcag aatagctggg ggctccggat cggcttctgg gcaaatttca     120
caagcgggta tcaacttaat taagagcttt gagggtttac aactgaaagc atataaagct     180
gttccgactg agaagcatta ccccattggt tacggtcatt acggttccga tgtttcacct     240
aggcaggtta tcactgctaa acaggctgaa gacatgttgc gtgatgatgt gcaggctttt     300
gtggatggtg taaataaagc attaaaagta tctgtcaccc aaaatcaatt tgatgcactt     360
gtctcattcg cttacaacgt tgggttaggg gctttcaggt cttcttctct actggaatac     420
ttgaatgaag gaagaacagc tctagcggcg gctgaattcc taaatggaa taagtcaggc     480
ggtaaagttt atcaagggtt gattaaccgt agagcacagg agcaagcctt gtttaatagt     540
ggaacaccta aaaatgtttc acgtggaaca tcgtctacta aaacgacacc taagtataag     600
gtgaagagtg gtgacaacct tactaaaatc gctaaaaagc ataatacaac ggttgctact     660
ttgttgaagt tgaatccgag tatcaaagac ccgaacatga ttagagttgg acaaacaata     720
aatgttacag gtagcggcgg caaaacacat aaggtgaaaa gtggtgacac actcagtaaa     780
attgccgttg ataacaaaac gactgtgagt agattgatga gtctaaaccc tgaaattacg     840
aatccaaatc atataaaagt aggtcaaaca attagattaa gtctcgagca ccatcaccat     900
caccattga                                                             909

<210> SEQ ID NO 52
<211> LENGTH: 302
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30
```

Gly Ser Ala Ser Gly Gln Ile Ser Gln Ala Gly Ile Asn Leu Ile Lys
        35                  40                  45

Ser Phe Glu Gly Leu Gln Leu Lys Ala Tyr Lys Ala Val Pro Thr Glu
    50                  55                  60

Lys His Tyr Thr Ile Gly Tyr Gly His Tyr Gly Ser Asp Val Ser Pro
65                  70                  75                  80

Arg Gln Val Ile Thr Ala Lys Gln Ala Glu Asp Met Leu Arg Asp Asp
                85                  90                  95

Val Gln Ala Phe Val Asp Gly Val Asn Lys Ala Leu Lys Val Ser Val
            100                 105                 110

Thr Gln Asn Gln Phe Asp Ala Leu Val Ser Phe Ala Tyr Asn Val Gly
        115                 120                 125

Leu Gly Ala Phe Arg Ser Ser Ser Leu Leu Glu Tyr Leu Asn Glu Gly
    130                 135                 140

Arg Thr Ala Leu Ala Ala Ala Glu Phe Pro Lys Trp Asn Lys Ser Gly
145                 150                 155                 160

Gly Lys Val Tyr Gln Gly Leu Ile Asn Arg Arg Ala Gln Glu Gln Ala
                165                 170                 175

Leu Phe Asn Ser Gly Thr Pro Lys Asn Val Ser Arg Gly Thr Ser Ser
            180                 185                 190

Thr Lys Thr Thr Pro Lys Tyr Lys Val Lys Ser Gly Asp Asn Leu Thr
        195                 200                 205

Lys Ile Ala Lys Lys His Asn Thr Thr Val Ala Thr Leu Leu Lys Leu
    210                 215                 220

Asn Pro Ser Ile Lys Asp Pro Asn Met Ile Arg Val Gly Gln Thr Ile
225                 230                 235                 240

Asn Val Thr Gly Ser Gly Gly Lys Thr His Lys Val Lys Ser Gly Asp
                245                 250                 255

Thr Leu Ser Lys Ile Ala Val Asp Asn Lys Thr Thr Val Ser Arg Leu
            260                 265                 270

Met Ser Leu Asn Pro Glu Ile Thr Asn Pro Asn His Ile Lys Val Gly
        275                 280                 285

Gln Thr Ile Arg Leu Ser Leu Glu His His His His His His
    290                 295                 300

<210> SEQ ID NO 53
<211> LENGTH: 1116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
atgaggggac ttcgaagact gggtaggaag atagcacatg gtgtgaagaa gtatggccca      60
actgttctcc gaataatcag aatagctggg ggctccggat cggcttctgg gggtgtggcc     120
ctggaccgca cgcgggttga tccccaggca gtcggcaacg aggtgctcaa gcgcaacgcg     180
gataagctga atgcgatgcg gggcgccgag tacggtgcca acgtcaaggt cagcggcacg     240
gacattcgca tgaacggggg taacagtgcc ggcatgctga agcaggacgt gttcaactgg     300
cggaaggaac tggctcagtt cgaggcttac cgaggggagg cgtataagga tgccgatggt     360
tatagtgtgg gcctggggca ttacctgggc agtggcaatg ctggggcagg tactacagtc     420
acgcctgagc aagccgcgca gtggttcgcc gaggacaccg accgcgcact cgaccagggt     480

```
gtgaggttgg ccgacgagct gggcgttacg aacaatgcct ctatcctggg attggccggt    540
atggccttcc agatgggcga aggacgtgcc cggcagttcc gtaacacctt ccaggcgatc    600
aaggatcgca acaaggaagc cttcgaggct ggtgtgcgaa acagcaagtg gtacacgcag    660
acgcccaacc gggccgaggc attcatcaag cgcatggcgc cccacttcga tacaccgagt    720
caaatcggtg tcgattggta cagcgccgca acagcggaga agctttcacg tggaacatcg    780
tctactaaaa cgacacctaa gtataaggtg aagagtggtg acaaccttac taaaatcgct    840
aaaaagcata atacaacggt tgctactttg ttgaagttga atccgagtat caaagacccg    900
aacatgatta gagttggaca acaataaat gttacaggta gcggcggcaa acacataag     960 gtgaaaagtg gtgacacact cagtaaaatt gccgttgata acaaaacgac tgtgagtaga   1020
ttgatgagtc taaaccctga aattacgaat ccaaatcata taaaagtagg tcaaacaatt   1080
agattaagtc tcgagcacca ccaccaccac cactga                             1116
```

<210> SEQ ID NO 54
<211> LENGTH: 371
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Gly Ser Ala Ser Gly Gly Val Ala Leu Asp Arg Thr Arg Val Asp Pro
        35                  40                  45

Gln Ala Val Gly Asn Glu Val Leu Lys Arg Asn Ala Asp Lys Leu Asn
    50                  55                  60

Ala Met Arg Gly Ala Glu Tyr Gly Ala Asn Val Lys Val Ser Gly Thr
65                  70                  75                  80

Asp Ile Arg Met Asn Gly Gly Asn Ser Ala Gly Met Leu Lys Gln Asp
                85                  90                  95

Val Phe Asn Trp Arg Lys Glu Leu Ala Gln Phe Glu Ala Tyr Arg Gly
            100                 105                 110

Glu Ala Tyr Lys Asp Ala Asp Gly Tyr Ser Val Gly Leu Gly His Tyr
        115                 120                 125

Leu Gly Ser Gly Asn Ala Gly Ala Gly Thr Thr Val Thr Pro Glu Gln
    130                 135                 140

Ala Ala Gln Trp Phe Ala Glu Asp Thr Asp Arg Ala Leu Asp Gln Gly
145                 150                 155                 160

Val Arg Leu Ala Asp Glu Leu Gly Val Thr Asn Asn Ala Ser Ile Leu
                165                 170                 175

Gly Leu Ala Gly Met Ala Phe Gln Met Gly Glu Gly Arg Ala Arg Gln
            180                 185                 190

Phe Arg Asn Thr Phe Gln Ala Ile Lys Asp Arg Asn Lys Glu Ala Phe
        195                 200                 205

Glu Ala Gly Val Arg Asn Ser Lys Trp Tyr Thr Gln Thr Pro Asn Arg
    210                 215                 220

Ala Glu Ala Phe Ile Lys Arg Met Ala Pro His Phe Asp Thr Pro Ser
225                 230                 235                 240

Gln Ile Gly Val Asp Trp Tyr Ser Ala Ala Thr Ala Glu Lys Leu Ser
```

```
                    245                 250                 255
Arg Gly Thr Ser Ser Thr Lys Thr Thr Pro Lys Tyr Lys Val Lys Ser
            260                 265                 270

Gly Asp Asn Leu Thr Lys Ile Ala Lys Lys His Asn Thr Thr Val Ala
        275                 280                 285

Thr Leu Leu Lys Leu Asn Pro Ser Ile Lys Asp Pro Asn Met Ile Arg
    290                 295                 300

Val Gly Gln Thr Ile Asn Val Thr Gly Ser Gly Lys Thr His Lys
305                 310                 315                 320

Val Lys Ser Gly Asp Thr Leu Ser Lys Ile Ala Val Asp Asn Lys Thr
                325                 330                 335

Thr Val Ser Arg Leu Met Ser Leu Asn Pro Glu Ile Thr Asn Pro Asn
            340                 345                 350

His Ile Lys Val Gly Gln Thr Ile Arg Leu Ser Leu Glu His His
        355                 360                 365

His His His
    370

<210> SEQ ID NO 55
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atgcgtcgtt gggttcgtcg tgttcgtcgt tgggttcgtc gtgttgttcg tgttgttcgt      60
cgttgggttc gtcgtgaagc cgctgccaag gaggcggccg ctaaatcacg tggaacatcg     120
tctactaaaa cgacacctaa gtataaggtg aagagtggtg acaaccttac taaaatcgct     180
aaaaagcata tacaacggtt gctactttg ttgaagttga atccgagtat caaagacccg      240
aacatgatta gagttggaca acaataaat gttacaggta gcggcggcaa acacataag      300 gtgaaaagtg gtgacacact cagtaaaatt gccgttgata caaaaacgac tgtgagtaga     360
ttgatgagtc taaaccctga aattacgaat ccaaatcata taaagtagg tcaaacaatt      420 agattaagtc tcgagcacca ccaccaccac cactga                                456

<210> SEQ ID NO 56
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Arg Arg Trp Val Arg Arg Val Arg Arg Trp Val Arg Arg Val Val
1               5                   10                  15

Arg Val Val Arg Arg Trp Val Arg Arg Glu Ala Ala Lys Glu Ala
            20                  25                  30

Ala Ala Lys Ser Arg Gly Thr Ser Ser Thr Lys Thr Thr Pro Lys Tyr
        35                  40                  45

Lys Val Lys Ser Gly Asp Asn Leu Thr Lys Ile Ala Lys Lys His Asn
    50                  55                  60

Thr Thr Val Ala Thr Leu Leu Lys Leu Asn Pro Ser Ile Lys Asp Pro
65                  70                  75                  80
```

```
Asn Met Ile Arg Val Gly Gln Thr Ile Asn Val Thr Gly Ser Gly Gly
             85                  90                  95

Lys Thr His Lys Val Lys Ser Gly Asp Thr Leu Ser Lys Ile Ala Val
        100                 105                 110

Asp Asn Lys Thr Thr Val Ser Arg Leu Met Ser Leu Asn Pro Glu Ile
    115                 120                 125

Thr Asn Pro Asn His Ile Lys Val Gly Gln Thr Ile Arg Leu Ser Leu
    130                 135                 140

Glu His His His His His His
145                 150

<210> SEQ ID NO 57
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
atgcgtcgtt gggttcgtcg cgtgcgtcgc tgggtgcgtc gtgttgttcg tgttgttcgt      60
cgttgggttc gtcgtgaagc cgctgccaag gaggcggccg ctaaacaaat ttcacaagcg     120
ggtatcaact taattaagag ctttgagggt tacaactga aagcatataa agctgttccg     180
actgagaagc attacaccat tggttacggt cattacggtt ccgatgtttc acctaggcag     240
gttatcactg ctaaacaggc tgaagacatg ttgcgtgatg atgtgcaggc ttttgtggat     300
ggtgtaaata aagcattaaa agtatctgtc acccaaaatc aatttgatgc acttgtctca     360
ttcgcttaca acgttgggtt aggggctttc aggtcttctt ctctactgga atacttgaat     420
gaaggaagaa cagctctagc ggcggctgaa ttccctaaat ggaataagtc aggcggtaaa     480
gtttatcaag ggttgattaa ccgtagagca caggagcaag ccttgtttaa tagtggaaca     540
cctaaaaatg tttcacgtgg aacatcgtct actaaaacga cacctaagta taaggtgaag     600
agtggtgaca accttactaa atcgctaaaa agcataata caacggttgc tactttgttg      660
aagttgaatc cgagtatcaa agacccgaac atgattagag ttggacaaac aataaatgtt     720
acaggtagcg gcggcaaaac acataaggtg aaaagtggtg acacactcag taaaattgcc     780
gttgataaca aaacgactgt gagtagattg atgagtctaa accctgaaat tacgaatcca     840
aatcatataa agtaggtca acaattaga ttaagtctcg agcaccacca ccaccaccac       900
tga                                                                    903

<210> SEQ ID NO 58
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Arg Arg Trp Val Arg Arg Val Arg Arg Trp Val Arg Val Val
1                5                  10                  15

Arg Val Val Arg Arg Trp Val Arg Arg Glu Ala Ala Lys Glu Ala
             20                  25                  30

Ala Ala Lys Gln Ile Ser Gln Ala Gly Ile Asn Leu Ile Lys Ser Phe
        35                  40                  45

Glu Gly Leu Gln Leu Lys Ala Tyr Lys Ala Val Pro Thr Glu Lys His
```

```
                 50                  55                  60
Tyr Thr Ile Gly Tyr Gly His Tyr Gly Ser Asp Val Ser Pro Arg Gln
 65                  70                  75                  80

Val Ile Thr Ala Lys Gln Ala Glu Asp Met Leu Arg Asp Val Gln
                 85                  90                  95

Ala Phe Val Asp Gly Val Asn Lys Ala Leu Lys Val Ser Val Thr Gln
                100                 105                 110

Asn Gln Phe Asp Ala Leu Val Ser Phe Ala Tyr Asn Val Gly Leu Gly
            115                 120                 125

Ala Phe Arg Ser Ser Ser Leu Leu Glu Tyr Leu Asn Glu Gly Arg Thr
        130                 135                 140

Ala Leu Ala Ala Ala Glu Phe Pro Lys Trp Asn Lys Ser Gly Lys
145                 150                 155                 160

Val Tyr Gln Gly Leu Ile Asn Arg Arg Ala Gln Glu Gln Ala Leu Phe
                165                 170                 175

Asn Ser Gly Thr Pro Lys Asn Val Ser Arg Gly Thr Ser Ser Thr Lys
            180                 185                 190

Thr Thr Pro Lys Tyr Lys Val Lys Ser Gly Asp Asn Leu Thr Lys Ile
        195                 200                 205

Ala Lys Lys His Asn Thr Thr Val Ala Thr Leu Leu Lys Leu Asn Pro
    210                 215                 220

Ser Ile Lys Asp Pro Asn Met Ile Arg Val Gly Gln Thr Ile Asn Val
225                 230                 235                 240

Thr Gly Ser Gly Gly Lys Thr His Lys Val Lys Ser Gly Asp Thr Leu
                245                 250                 255

Ser Lys Ile Ala Val Asp Asn Lys Thr Thr Val Ser Arg Leu Met Ser
            260                 265                 270

Leu Asn Pro Glu Ile Thr Asn Pro Asn His Ile Lys Val Gly Gln Thr
        275                 280                 285

Ile Arg Leu Ser Leu Glu His His His His His
    290                 295                 300

<210> SEQ ID NO 59
<211> LENGTH: 447
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
atgcgtcgtt gggttcgtcg tgttcgtcgt tgggttcgtc gtgttgttcg tgttgttcgt    60
cgttgggttc gtcgtggctc cggatcggct tctgggtcac gtggaacatc gtctactaaa   120
acgacaccta agtataaggt gaagagtggt gacaacctta ctaaaatcgc taaaaagcat   180
aatacaacgg ttgctacttt gttgaagttg aatccgagta tcaaagaccc gaacatgatt   240
agagttggac aaacaataaa tgttacaggt agcggcggca aaacacataa ggtgaaaagt   300
ggtgacacac tcagtaaaat tgccgttgat aacaaaacga ctgtgagtag attgatgagt   360
ctaaaccctg aaattacgaa tccaaatcat ataaaagtag gtcaaacaat tagattaagt   420
ctcgagcacc accaccacca ccactga                                       447

<210> SEQ ID NO 60
<211> LENGTH: 122
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 60

Met Arg Arg Trp Val Arg Arg Val Arg Arg Trp Val Arg Arg Val Val
1               5                   10                  15

Arg Val Val Arg Arg Trp Val Arg Arg Gly Ser Gly Ser Ala Ser Gly
            20                  25                  30

Ser Arg Gly Thr Ser Ser Thr Lys Thr Thr Lys Tyr Lys Val Lys Ser
        35                  40                  45

Gly Asp Asn Thr Lys Ala Lys Lys His Asn Thr Thr Val Ala Thr Lys
    50                  55                      60

Asn Ser Lys Asp Asn Met Arg Val Gly Thr Asn Val Thr Gly Ser Gly
65                  70                  75                  80

Gly Lys Thr His Lys Val Lys Ser Gly Asp Thr Ser Lys Ala Val Asp
                85                  90                  95

Asn Lys Thr Thr Val Ser Arg Met Ser Asn Thr Asn Asn His Lys Val
                100                 105                 110

Gly Thr Arg Ser His His His His His His
            115                 120

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Arg His Met
1

<210> SEQ ID NO 62
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
atgggccatc atcatcatca tcatcatcat catcacagca gcggccatat cgaaggtcgt     60
catatgtcac gtggaacatc gtctactaaa acgacaccta agtataaggt gaagagtggt    120
gacaacctta ctaaaatcgc taaaaagcat aatacaacgg ttgctacttt gttgaagttg    180
aatccgagta tcaaagaccc gaacatgatt agagttggac aaacaataaa tgttacaggt    240
agcggcggca aaacacataa ggtgaaaagt ggtgacacac tcagtaaaat tgccgttgat    300
aacaaaacga ctgtgagtag attgatgagt ctaaaccctg aaattacgaa tccaaatcat    360
ataaaagtag gtcaaacaat tagattaagt tgactcgag                          399

<210> SEQ ID NO 63
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63
```

```
Met Gln Ile Ser Gln Ala Gly Ile Asn Leu Ile Lys Ser Phe Glu Gly
1               5                   10                  15

Leu Gln Leu Lys Ala Tyr Lys Ala Val Pro Thr Glu Lys His Tyr Thr
            20                  25                  30

Ile Gly Tyr Gly His Tyr Gly Ser Asp Val Ser Pro Arg Gln Val Ile
        35                  40                  45

Thr Ala Lys Gln Ala Glu Asp Met Leu Arg Asp Val Gln Ala Phe
    50                  55                  60

Val Asp Gly Val Asn Lys Ala Leu Lys Val Ser Val Thr Gln Asn Gln
65                  70                  75                  80

Phe Asp Ala Leu Val Ser Phe Ala Tyr Asn Val Gly Leu Gly Ala Phe
                85                  90                  95

Arg Ser Ser Ser Leu Leu Glu Tyr Leu Asn Glu Gly Arg Thr Ala Leu
                100                 105                 110

Ala Ala Ala Glu Phe Pro Lys Trp Asn Lys Ser Gly Lys Val Tyr
            115                 120                 125

Gln Gly Leu Ile Asn Arg Arg Ala Gln Glu Gln Ala Leu Phe Asn Ser
    130                 135                 140

Gly Thr Pro Lys Asn Val Ser Arg Gly Thr Ser Ser Thr Lys Thr Thr
145                 150                 155                 160

Pro Lys Tyr Lys Val Lys Ser Gly Asp Asn Leu Thr Lys Ile Ala Lys
                165                 170                 175

Lys His Asn Thr Thr Val Ala Thr Leu Leu Lys Leu Asn Pro Ser Ile
            180                 185                 190

Lys Asp Pro Asn Met Ile Arg Val Gly Gln Thr Ile Asn Val Thr Gly
            195                 200                 205

Ser Gly Gly Lys Thr His Lys Val Lys Ser Gly Asp Thr Leu Ser Lys
    210                 215                 220

Ile Ala Val Asp Asn Lys Thr Thr Val Ser Arg Leu Met Ser Leu Asn
225                 230                 235                 240

Pro Glu Ile Thr Asn Pro Asn His Ile Lys Val Gly Gln Thr Ile Arg
                245                 250                 255

Leu Ser Leu Glu His His His His His
        260                 265

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Met Gln Ile Ser
1

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Pro Lys Asn Val
1
```

<210> SEQ ID NO 66
<211> LENGTH: 801
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

```
atgcaaattt cacaagcggg tatcaactta attaagagct ttgagggttt acaactgaaa      60
gcatataaag ctgttccgac tgagaagcat tacaccattg ttacggtca ttacggttcc     120
gatgtttcac ctaggcaggt tatcactgct aaacaggctg aagacatgtt gcgtgatgat     180
gtgcaggctt ttgtggatgg tgtaaataaa gcattaaaag tatctgtcac ccaaaatcaa     240
tttgatgcac ttgtctcatt cgcttacaac gttgggttag gggctttcag gtcttcttct     300
ctactggaat acttgaatga aggaagaaca gctctagcgg cggctgaatt ccctaaatgg     360
aataagtcag gcggtaaagt ttatcaaggg ttgattaacc gtagagcaca ggagcaagcc     420
ttgtttaata gtggaacacc taaaaatgtt tcacgtggaa catcgtctac taaaacgaca     480
cctaagtata aggtgaagag tggtgacaac cttactaaaa tcgctaaaaa gcataataca     540
acggttgcta ctttgttgaa gttgaatccg agtatcaaag acccgaacat gattagagtt     600
ggacaaacaa taaatgttac aggtagcggc ggcaaaacac ataaggtgaa aagtggtgac     660
acactcagta aaattgccgt tgataacaaa cgactgtga gtagattgat gagtctaaac     720
cctgaaatta cgaatccaaa tcatataaaa gtaggtcaaa caattagatt aagtctcgag     780
caccaccacc accaccactg a                                                801
```

<210> SEQ ID NO 67
<211> LENGTH: 342
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

```
Met Gly Val Ala Leu Asp Arg Thr Arg Val Asp Pro Gln Ala Val Gly
1               5                   10                  15
Asn Glu Val Leu Lys Arg Asn Ala Asp Lys Leu Asn Ala Met Arg Gly
            20                  25                  30
Ala Glu Tyr Gly Ala Asn Val Lys Val Ser Gly Thr Asp Ile Arg Met
        35                  40                  45
Asn Gly Gly Asn Ser Ala Gly Met Leu Lys Gln Asp Val Phe Asn Trp
    50                  55                  60
Arg Lys Glu Leu Ala Gln Phe Glu Ala Tyr Arg Gly Glu Ala Tyr Lys
65                  70                  75                  80
Asp Ala Asp Gly Tyr Ser Val Gly Leu Gly His Tyr Leu Gly Ser Gly
                85                  90                  95
Asn Ala Gly Ala Gly Thr Thr Val Thr Pro Glu Gln Ala Ala Gln Trp
            100                 105                 110
Phe Ala Glu Asp Thr Asp Arg Ala Leu Asp Gln Gly Val Arg Leu Ala
        115                 120                 125
Asp Glu Leu Gly Val Thr Asn Asn Ala Ser Ile Leu Gly Leu Ala Gly
    130                 135                 140
Met Ala Phe Gln Met Gly Glu Gly Arg Ala Arg Gln Phe Arg Asn Thr
```

```
            145                 150                 155                 160
        Phe Gln Ala Ile Lys Asp Arg Asn Lys Glu Ala Phe Glu Ala Gly Val
                        165                 170                 175
        Arg Asn Ser Lys Trp Tyr Thr Gln Thr Pro Asn Arg Ala Glu Ala Phe
                        180                 185                 190
        Ile Lys Arg Met Ala Pro His Phe Asp Thr Pro Ser Gln Ile Gly Val
                        195                 200                 205
        Asp Trp Tyr Ser Ala Ala Thr Ala Glu Lys Leu Ser Arg Gly Thr Ser
                210                 215                 220
        Ser Thr Lys Thr Thr Pro Lys Tyr Lys Val Lys Ser Gly Asp Asn Leu
        225                 230                 235                 240
        Thr Lys Ile Ala Lys Lys His Asn Thr Thr Val Ala Thr Leu Leu Lys
                        245                 250                 255
        Leu Asn Pro Ser Ile Lys Asp Pro Asn Met Ile Arg Val Gly Gln Thr
                        260                 265                 270
        Ile Asn Val Thr Gly Ser Gly Gly Lys Thr His Lys Val Lys Ser Gly
                        275                 280                 285
        Asp Thr Leu Ser Lys Ile Ala Val Asp Asn Lys Thr Thr Val Ser Arg
                290                 295                 300
        Leu Met Ser Leu Asn Pro Glu Ile Thr Asn Pro Asn His Ile Lys Val
        305                 310                 315                 320
        Gly Gln Thr Ile Arg Leu Ser Leu Glu Lys Leu Ala Ala Ala Leu Glu
                        325                 330                 335
        His His His His His His
                        340

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Met Gly Val Ala
1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Glu Lys Leu
1

<210> SEQ ID NO 70
<211> LENGTH: 1029
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
atgggtgtgg ccctggaccg cacgcgggtt gatccccagg cagtcggcaa cgaggtgctc        60
```

```
aagcgcaacg cggataagct gaatgcgatg cggggcgccg agtacggtgc caacgtcaag      120
gtcagcggca cggacattcg catgaacggg ggtaacagtg ccggcatgct gaagcaggac      180
gtgttcaact ggcggaagga actggctcag ttcgaggctt accgagggga ggcgtataag      240
gatgccgatg gttatagtgt gggcctgggg cattacctgg gcagtggcaa tgctggggca      300
ggtactacag tcacgcctga gcaagccgcg cagtggttcg ccgaggacac cgaccgcgca      360
ctcgaccagg gtgtgaggtt ggccgacgag ctgggcgtta cgaacaatgc ctctatcctg      420
ggattggccg gtatggcctt ccagatgggc gaaggacgtg cccggcagtt ccgtaacacc      480
ttccaggcga tcaaggatcg caacaaggaa gccttcgagg ctggtgtgcg aaacagcaag      540
tggtacacgc agacgcccaa ccgggccgag gcattcatca agcgcatggc gccccacttc      600
gatacaccga gtcaaatcgg tgtcgattgg tacagcgccg caacagcgga gaagctttca      660
cgtggaacat cgtctactaa aacgacacct aagtataagg tgaagagtgg tgacaacctt      720
actaaaatcg ctaaaaagca taatacaacg gttgctactt tgttgaagtt gaatccgagt      780
atcaaagacc cgaacatgat tagagttgga caaacaataa atgttacagg tagcggcggc      840
aaaacacata aggtgaaaag tggtgacaca ctcagtaaaa ttgccgttga taacaaaacg      900
actgtgagta gattgatgag tctaaaccct gaaattacga atccaaatca tataaaagta      960
ggtcaaacaa ttagattaag tctcgagaag cttgcggccg cactcgagca ccaccaccac     1020
caccactga                                                             1029
```

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Val Val Val Arg
1

<210> SEQ ID NO 72
<211> LENGTH: 891
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

```
atgcatcatc atcatcatca tcaaatttca caagcgggta tcaacttaat taagagcttt       60
gagggtttac aactgaaagc atataaagct gttccgactg agaagcatta caccattggt      120
tacggtcatt acggttccga tgtttcacct aggcaggtta tcactgctaa acaggctgaa      180
gacatgttgc gtgatgatgt gcaggctttt gtggatggta taaataaagc attaaaagta      240
tctgtcaccc aaaatcaatt tgatgcactt gtctcattcg cttacaacgt tgggttaggg      300
gctttcaggt cttcttctct actggaatac ttgaatgaag gaagaacagc tctagcggcg      360
gctgaattcc ctaaatggaa taagtcaggc ggtaaagttt atcaagggtt gattaaccgt      420
agagcacagg agcaagcctt gtttaatagt ggaacaccta aaaatgtttc acgtggaaca      480
tcgtctacta aaacgacacc taagtataag gtgaagagtg gtgacaacct tactaaaatc      540
gctaaaaagc ataatacaac ggttgctact ttgttgaagt tgaatccgag tatcaaagac      600
```

```
ccgaacatga ttagagttgg acaaacaata aatgttacag gtagcggcgg caaaacacat    660
aaggtgaaaa gtggtgacac actcagtaaa attgccgttg ataacaaaac gactgtgagt    720
agattgatga gtctaaaccc tgaaattacg aatccaaatc atataaaagt aggtcaaaca    780
attagattaa gtaagcttcg ccgtcgcgcg tccctgatgg tgctggtcgc cataggcacc    840
gccgtgacag cggccgtcaa ccctggcgtc gtggtcaggc gccgtcgctg a             891
```

<210> SEQ ID NO 73
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met His His His His His His Gly Val Ala Leu Asp Arg Thr Arg Val
1               5                   10                  15

Asp Pro Gln Ala Val Gly Asn Glu Val Leu Lys Arg Asn Ala Asp Lys
            20                  25                  30

Leu Asn Ala Met Arg Gly Ala Glu Tyr Gly Ala Asn Val Lys Val Ser
        35                  40                  45

Gly Thr Asp Ile Arg Met Asn Gly Gly Asn Ser Ala Gly Met Leu Lys
    50                  55                  60

Gln Asp Val Phe Asn Trp Arg Lys Glu Leu Ala Gln Phe Glu Ala Tyr
65                  70                  75                  80

Arg Gly Glu Ala Tyr Lys Asp Ala Asp Gly Tyr Ser Val Gly Leu Gly
                85                  90                  95

His Tyr Leu Gly Ser Gly Asn Ala Gly Ala Gly Thr Thr Val Thr Pro
            100                 105                 110

Glu Gln Ala Ala Gln Trp Phe Ala Glu Asp Thr Asp Arg Ala Leu Asp
        115                 120                 125

Gln Gly Val Arg Leu Ala Asp Glu Leu Gly Val Thr Asn Asn Ala Ser
    130                 135                 140

Thr Leu Gly Leu Ala Gly Met Ala Phe Gln Met Gly Glu Gly Arg Ala
145                 150                 155                 160

Arg Gln Phe Arg Asn Thr Phe Gln Ala Ile Lys Asp Arg Asn Lys Glu
                165                 170                 175

Ala Phe Glu Ala Gly Val Arg Asn Ser Lys Trp Tyr Thr Gln Thr Pro
            180                 185                 190

Asn Arg Ala Glu Ala Phe Ile Lys Arg Met Ala Pro His Phe Asp Thr
        195                 200                 205

Pro Ser Gln Ile Gly Val Asp Trp Tyr Ser Ala Thr Ala Glu Lys
    210                 215                 220

Leu Ser Arg Gly Thr Ser Ser Thr Lys Thr Thr Pro Lys Tyr Lys Val
225                 230                 235                 240

Lys Ser Gly Asp Asn Leu Thr Lys Ile Ala Lys His Asn Thr Thr
                245                 250                 255

Val Ala Thr Leu Leu Lys Leu Asn Pro Ser Ile Lys Asp Pro Asn Met
            260                 265                 270

Ile Arg Val Gly Gln Thr Ile Asn Val Thr Gly Ser Gly Gly Lys Thr
        275                 280                 285

His Lys Val Lys Ser Gly Asp Thr Leu Ser Lys Ile Ala Val Asp Asn
    290                 295                 300

Lys Thr Thr Val Ser Arg Leu Met Ser Leu Asn Pro Glu Ile Thr Asn

```
            305                 310                 315                 320
Pro Asn His Ile Lys Val Gly Gln Thr Ile Arg Leu Ser Leu Glu Lys
                325                 330                 335

Leu Ala Ala Gly Ser Gly Ser Ala Ser Gly Ser Asp Ser Ser Ile
            340                 345                 350

Arg Val Gln Gly Arg Trp Lys Val Arg Ala Ser Phe Phe Lys Leu Gln
                355                 360                 365

Gly Ser Phe Asp Val Ser Val Lys Gly
    370                 375

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Met His His His His His His His
1               5

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Val Ala Leu
1

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Arg Gly Thr Ser
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Ser Gly Ser Ala Ser Gly
1               5

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 78

Ser Asp Ser Ser
1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Val Lys Gly
1

<210> SEQ ID NO 80
<211> LENGTH: 1134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
atgcaccatc accatcacca tggtgtggcc ctggaccgca cgcgggttga tccccaggca      60
gtcggcaacg aggtgctcaa gcgcaacgcg gataagctga atgcgatgcg gggcgccgag     120
tacggtgcca acgtcaaggt cagcggcacg gacattcgca tgaacggggg taacagtgcc     180
ggcatgctga agcaggacgt gttcaactgg cggaaggaac tggctcagtt cgaggcttac     240
cgaggggagg cgtataagga tgccgatggt tatagtgtgg gcctggggca ttacctgggc     300
agtggcaatg ctggggcagg tactacagtc acgcctgagc aagccgcgca gtggttcgcc     360
gaggacactg accgcgcact cgaccagggt gtgaggttgg ccgacgagct gggcgttacg     420
aacaatgcct ctaccctggg attggccggt atggccttcc agatgggcga aggacgtgcc     480
cggcagttcc gtaacaccct tccaggcgat caaggatcgc acaaggaagc cttcgaggct     540
ggtgtgcgaa acagcaagtg gtacacgcag acgcccaacc gggccgaggc attcatcaag     600
cgcatggcgc cccacttcga tacaccgagt caaatcggtg tcgattggta cagcgccgca     660
acagcggaga agctttcacg tggaacatcg tctactaaaa cgacacctaa gtataaggtg     720
aagagtggtg acaaccttac taaaatcgct aaaaagcata atacaacggt tgctactttg     780
ttgaagttga atccgagtat caaagacccg aacatgatta gagttggaca gacaataaat     840
gttacaggta gcggcggcaa aacacataag gtgaaaagtg gtgacacact cagtaaaatt     900
gccgttgata acaaaacgac tgtgagtaga ttgatgagtc taaaccctga aattacgaat     960
ccaaatcata taaaagtagg tcaaacaatt agattaagtc ttgagaaact gcggccgca     1020
ggctccggat cggcttctgg gtccgactcc tccatccggg tccagggccg ttggaaggtg    1080
cgcgcgtcat tcttcaaact gcagggctcc ttcgatgtca gtgtcaaggg ctga          1134
```

<210> SEQ ID NO 81
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Met Gly His His His His His His His His Ser Ser Gly His
1               5                   10                  15

Ile Glu Gly Arg His Met Ser Arg Gly Thr Ser Thr Lys Thr Thr
            20                  25                  30

Pro Lys Tyr Lys Val Lys Ser Gly Asp Asn Leu Thr Lys Ile Ala Lys
        35                  40                  45

Lys His Asn Thr Thr Val Ala Thr Leu Leu Lys Leu Asn Pro Ser Ile
    50                  55                  60

Lys Asp Pro Asn Met Ile Arg Val Gly Gln Thr Ile Asn Val Thr Gly
65                  70                  75                  80

Ser Gly Gly Lys Thr His Lys Val Lys Ser Gly Asp Thr Leu Ser Lys
                85                  90                  95

Ile Ala Val Asp Asn Lys Thr Thr Val Ser Arg Leu Met Ser Leu Asn
                100                 105                 110

Pro Glu Ile Thr Asn Pro Asn His Ile Lys Val Gly Gln Thr Ile Arg
            115                 120                 125

Leu Ser Leu Glu Lys Leu Ala Ala Ala Gly Ser Gly Ala Gly Ser Gly
        130                 135                 140

Ser Asp Ser Ser Ile Arg Val Gln Gly Arg Trp Lys Val Arg Ala Ser
145                 150                 155                 160

Phe Phe Lys Leu Gln Gly Ser Phe Asp Val Ser Val Lys Gly
                165                 170
```

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Met Gly His His
1

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Gly Ser Gly Ala Gly Ser Gly
1               5

<210> SEQ ID NO 84
<211> LENGTH: 525
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84
atgggccatc atcatcatca tcatcatcat catcacagca gcggccatat cgaaggtcgt    60
catatgtcac gtggaacatc gtctactaaa acgacaccta agtataaggt gaagagtggt   120
gacaacctta ctaaaatcgc taaaaagcat aatacaacgg ttgctacttt gttgaagttg   180
aatccgagta tcaaagaccc gaacatgatt agagttggac aaacaataaa tgttacaggt   240

```
agcggcggca aaacacataa ggtgaaaagt ggtgacacac tcagtaaaat tgccgttgat    300
aacaaaacga ctgtgagtag attgatgagt ctaaaccctg aaattacgaa tccaaatcat    360
ataaaagtag gtcaaacaat tagattaagt cttgagaaac ttgcggccgc aggctccgga    420
tcggcttctg ggtccgactc ctccatccgg gtccagggcc gttggaaggt gcgcgcgtca    480
ttcttcaaac tgcagggctc cttcgatgtc agtgtcaagg gctga                   525
```

<210> SEQ ID NO 85
<211> LENGTH: 8
<212> TYPE: PRT
<213> ORGANISM: Bacillus phage phi29

<400> SEQUENCE: 85

Val Gly Gln Thr Ile Arg Leu Ser
1               5

<210> SEQ ID NO 86
<211> LENGTH: 1101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86

```
atgcgtcgtt gggttcgtcg tgttcgtcgt tgggttcgtc gtgttgttcg tgttgttcgt     60
cgttgggttc gtcgtggctc cggatcggct tctgggggtg tggccctgga ccgcacgcgg    120
gttgatcccc aggcagtcgg caacgaggtg ctcaagcgca acgcggataa gctgaatgcg    180
atgcggggcg ccgagtacgg tgccaacgtc aaggtcagcg gcacggacat tcgcatgaac    240
gggggtaaca gtgccggcat gctgaagcag gacgtgttca ctggcggaa ggaactggct     300 cagttcgagg cttaccgagg ggaggcgtat aaggatgccg atggttatag tgtgggcctg    360
gggcattacc tgggcagtgg caatgctggg gcaggtacta cagtcacgcc tgagcaagcc    420
gcgcagtggt tcgccgagga caccgaccgc gcactcgacc agggtgtgag gttggccgac    480
gagctgggcg ttacgaacaa tgcctctatc ctgggattgg ccggtatggc cttccagatg    540
ggcgaaggac gtgccggca gttccgtaac accttccagg cgatcaagga tcgcaacaag    600
gaagccttcg aggctggtgt gcgaaacagc aagtggtaca cgcagacgcc caaccgggcc    660
gaggcattca tcaagcgcat ggcgcccac ttcgatacac cgagtcaaat cggtgtcgat     720
tggtacagcg ccgcaacagc ggagaagctt tcacgtggaa catcgtctac taaaacgaca    780
cctaagtata aggtgaagag tggtgacaac cttactaaaa tcgctaaaaa gcataataca    840
acggttgcta ctttgttgaa gttgaatccg agtatcaaag acccgaacat gattagagtt    900
ggacaaacaa taaatgttac aggtagcggc ggcaaaacac ataaggtgaa aagtggtgac    960
acactcagta aaattgccgt tgataacaaa acgactgtga gtagattgat gagtctaaac   1020
cctgaaatta cgaatccaaa tcatataaaa gtaggtcaaa caattagatt aagtctcgag   1080
caccaccacc accaccactg a                                             1101
```

<210> SEQ ID NO 87
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Met Arg Arg Trp Val Arg Arg Val Arg Trp Val Arg Val Val
1               5                   10                  15

Arg Val Arg Arg Trp Val Arg Arg Gly Ser Gly Ser Ala Ser Gly
                20                  25                  30

Ser Arg Gly Thr Ser Ser Thr Lys Thr Thr Pro Lys Tyr Lys Val Lys
            35                  40                  45

Ser Gly Asp Asn Leu Thr Lys Ile Ala Lys Lys His Asn Thr Thr Val
50                      55                  60

Ala Thr Leu Leu Lys Leu Asn Pro Ser Ile Lys Asp Pro Asn Met Ile
65                  70                  75                  80

Arg Val Gly Gln Thr Ile Asn Val Thr Gly Ser Gly Lys Thr His
                85                  90                  95

Lys Val Lys Ser Gly Asp Thr Leu Ser Lys Ile Ala Val Asp Asn Lys
                100                 105                 110

Thr Thr Val Ser Arg Leu Met Ser Leu Asn Pro Glu Ile Thr Asn Pro
            115                 120                 125

Asn His Ile Lys Val Gly Gln Thr Ile Arg Leu Ser Leu Glu His His
        130                 135                 140

His His His His
145
```

<210> SEQ ID NO 88
<211> LENGTH: 423
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

```
Met Gly His His His His His His His His Ser Ser Gly His
1               5                   10                  15

Ile Glu Gly Arg His Met Arg Arg Trp Val Arg Val Arg Trp
                20                  25                  30

Val Arg Val Val Arg Val Val Arg Arg Trp Val Arg Gly Ser
            35                  40                  45

Gly Ser Ala Ser Gly Val Ala Leu Asp Arg Thr Arg Val Asp Pro
50                      55                  60

Gln Ala Val Gly Asn Glu Val Leu Lys Arg Asn Ala Asp Lys Leu Asn
65                  70                  75                  80

Ala Met Arg Gly Ala Glu Tyr Gly Ala Asn Val Lys Val Ser Gly Thr
                85                  90                  95

Asp Ile Arg Met Asn Gly Gly Asn Ser Ala Gly Met Leu Lys Gln Asp
                100                 105                 110

Val Phe Asn Trp Arg Lys Glu Leu Ala Gln Phe Glu Ala Tyr Arg Gly
            115                 120                 125

Glu Ala Tyr Lys Asp Ala Asp Gly Tyr Ser Val Gly Leu Gly His Tyr
        130                 135                 140

Leu Gly Ser Gly Asn Ala Gly Ala Gly Thr Thr Val Thr Pro Glu Gln
145                 150                 155                 160

Ala Ala Gln Trp Phe Ala Glu Asp Thr Asp Arg Ala Leu Asp Gln Gly
                165                 170                 175

Val Arg Leu Ala Asp Glu Leu Gly Val Thr Asn Asn Ala Ser Thr Leu
            180                 185                 190
```

Gly Leu Ala Gly Met Ala Phe Gln Met Gly Glu Gly Arg Ala Arg Gln
         195                 200                 205

Phe Arg Asn Thr Phe Gln Ala Ile Lys Asp Arg Asn Lys Glu Ala Phe
210                 215                 220

Glu Ala Gly Val Arg Asn Ser Lys Trp Tyr Thr Gln Thr Pro Asn Arg
225                 230                 235                 240

Ala Glu Ala Phe Ile Lys Arg Met Ala Pro His Phe Asp Thr Pro Ser
                245                 250                 255

Gln Ile Gly Val Asp Trp Tyr Ser Ala Ala Thr Ala Glu Lys Leu Ser
                260                 265                 270

Arg Gly Thr Ser Ser Thr Lys Thr Thr Pro Lys Tyr Lys Val Lys Ser
                275                 280                 285

Gly Asp Asn Leu Thr Lys Ile Ala Lys Lys His Asn Thr Thr Val Ala
    290                 295                 300

Thr Leu Leu Lys Leu Asn Pro Ser Ile Lys Asp Pro Asn Met Ile Arg
305                 310                 315                 320

Val Gly Gln Thr Ile Asn Val Thr Gly Ser Gly Lys Thr His Lys
                325                 330                 335

Val Lys Ser Gly Asp Thr Leu Ser Lys Ile Ala Val Asn Lys Thr
                340                 345                 350

Thr Val Ser Arg Leu Met Ser Leu Asn Pro Glu Ile Thr Asn Pro Asn
    355                 360                 365

His Ile Lys Val Gly Gln Thr Ile Arg Leu Ser Leu Glu Lys Leu Ala
    370                 375                 380

Ala Ala Gly Ser Gly Ser Ala Ser Gly Ser Asp Ser Ser Ile Arg Val
385                 390                 395                 400

Gln Gly Arg Trp Lys Val Arg Ala Ser Phe Phe Lys Leu Gln Gly Ser
                405                 410                 415

Phe Asp Val Ser Val Lys Gly
            420

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ile Glu Gly Arg His Met
1               5

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Arg Trp Val Arg
1               5

<210> SEQ ID NO 91
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 91

Arg Trp Val Arg Arg
1               5

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Val Ala Leu Asp Arg
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Ala Glu Lys Leu
1               5

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Thr Ile Arg Leu Ser
1               5

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Gly Ser Ala Ser Gly
1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Asp Ser Ser Ile
1               5
```

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

Asp Val Ser Val Lys Gly
1               5

<210> SEQ ID NO 98
<211> LENGTH: 1272
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98

| | | | | | |
|---|---|---|---|---|---|
| atgggccatc | atcatcatca | tcatcatcat | catcacagca | gcggccatat | cgaaggtcgt | 60 |
| catatgcgtc | gttgggttcg | tcgtgttcgt | cgttgggttc | gtcgtgttgt | tcgtgttgtt | 120 |
| cgtcgttggg | ttcgtcgtgg | ctccggatcg | gcttctgggg | gtgtggccct | ggaccgcacg | 180 |
| cgggttgatc | cccaggcagt | cggcaacgag | gtgctcaagc | gcaacgcgga | taagctgaat | 240 |
| gcgatgcggg | gcgccgagta | cggtgccaac | gtcaaggtca | gcggcacgga | cattcgcatg | 300 |
| aacggggta | acagtgccgg | catgctgaag | caggacgtgt | tcaactggcg | gaaggaactg | 360 |
| gctcagttcg | aggcttaccg | aggggaggcg | tataaggatg | ccgatggtta | tagtgtgggc | 420 |
| ctggggcatt | acctgggcag | tgcaatgct | ggggcaggta | ctacagtcac | gcctgagcaa | 480 |
| gccgcgcagt | ggttcgccga | ggacactgac | cgcgcactcg | accagggtgt | gaggttggcc | 540 |
| gacgagctgg | gcgttacgaa | caatgcctct | accctgggat | tggccggtat | ggccttccag | 600 |
| atgggcgaag | acgtgcccg | gcagttccgt | aacaccttcc | aggcgatcaa | ggatcgcaac | 660 |
| aaggaagcct | tcgaggctgg | tgtgcgaaac | agcaagtggt | acacgcagac | gcccaaccgg | 720 |
| gccgaggcat | tcatcaagcg | catggcgccc | cacttcgata | caccgagtca | atcggtgtc | 780 |
| gattggtaca | gcgccgcaac | agcggagaag | ctttcacgtg | gaacatcgtc | tactaaaacg | 840 |
| acacctaagt | ataaggtgaa | gagtggtgac | aaccttacta | aaatcgctaa | aaagcataat | 900 |
| acaacggttg | ctactttgtt | gaagttgaat | ccgagtatca | aagacccgaa | catgattaga | 960 |
| gttggacaga | caataaatgt | tacaggtagc | ggcggcaaaa | cacataaggt | gaaaagtggt | 1020 |
| gacacactca | gtaaaattgc | cgttgataac | aaaacgactg | tgagtagatt | gatgagtcta | 1080 |
| aaccctgaaa | ttacgaatcc | aaatcatata | aaagtaggtc | aaacaattag | attaagtctt | 1140 |
| gagaaacttg | cggccgcagg | ctccggatcg | gcttctgggt | ccgactcctc | catccgggtc | 1200 |
| cagggccgtt | ggaaggtgcg | cgcgtcattc | ttcaaactgc | agggctcctt | cgatgtcagt | 1260 |
| gtcaagggct | ga |  |  |  |  | 1272 |

<210> SEQ ID NO 99
<211> LENGTH: 6
<212> TYPE: PRT
<213> ORGANISM: Bacillus phage phi29

```
<400> SEQUENCE: 99

Ser Arg Gly Thr Ser Ser
1               5
```